(12) United States Patent
Pugachev et al.

(10) Patent No.: US 8,815,564 B2
(45) Date of Patent: Aug. 26, 2014

(54) REPLICATION-DEFECTIVE FLAVIVIRUS VACCINES AND VACCINE VECTORS

(75) Inventors: Konstantin V. Pugachev, Natick, MA (US); Alexander A. Rumyantsev, Somerville, MA (US); Maryann Giel-Moloney, Brighton, MA (US); Harold Kleanthous, Westford, MA (US)

(73) Assignee: Sanofi Pasteur Biologics, LLC, Cambridge, MA (US)

( * ) Notice: Subject to any disclaimer, the term of this patent is extended or adjusted under 35 U.S.C. 154(b) by 611 days.

(21) Appl. No.: 12/922,513

(22) PCT Filed: Mar. 16, 2009

(86) PCT No.: PCT/US2009/001666
§ 371 (c)(1),
(2), (4) Date: Dec. 28, 2010

(87) PCT Pub. No.: WO2009/114207
PCT Pub. Date: Sep. 17, 2009

(65) Prior Publication Data
US 2011/0135686 A1     Jun. 9, 2011

Related U.S. Application Data

(60) Provisional application No. 61/069,451, filed on Mar. 14, 2008, provisional application No. 61/092,814, filed on Aug. 29, 2008.

(51) Int. Cl.
*C12N 7/04*      (2006.01)
*A61K 39/12*      (2006.01)

(52) U.S. Cl.
USPC ........................................ 435/236; 424/218.1

(58) Field of Classification Search
None
See application file for complete search history.

(56) References Cited

U.S. PATENT DOCUMENTS

| | | | |
|---|---|---|---|
| 5,830,477 A * | 11/1998 | Lathe et al. | 424/224.1 |
| 6,486,135 B1 | 11/2002 | Li et al. | |
| 6,696,281 B1 * | 2/2004 | Chambers et al. | 435/235.1 |
| 2001/0046499 A1 | 11/2001 | Kantor et al. | |
| 2004/0005542 A1 | 1/2004 | Krempl et al. | |
| 2004/0223979 A1 | 11/2004 | Chambers et al. | |
| 2006/0159704 A1 | 7/2006 | Bonaldo et al. | |
| 2006/0204523 A1 | 9/2006 | Khromykh et al. | |
| 2007/0218078 A1 | 9/2007 | Clarke et al. | |
| 2007/0249032 A1 | 10/2007 | Pang et al. | |
| 2008/0175862 A1 * | 7/2008 | Pugachev et al. | 424/205.1 |

FOREIGN PATENT DOCUMENTS

| | | |
|---|---|---|
| WO | WO 98/37911 A1 | 9/1998 |
| WO | WO 02/102828 A2 | 12/2002 |
| WO | WO 03/046189 A1 | 6/2003 |
| WO | WO 2006/086838 A1 | 8/2006 |
| WO | WO 2007/098267 A2 | 8/2007 |
| WO | WO 2008/137163 A2 | 11/2008 |
| WO | WO 2010/107847 A1 | 9/2010 |

OTHER PUBLICATIONS

U.S. Appl. No. 13/256,565, filed Sep. 14, 2011, Pugachev et al.
International Search Report from International Patent Application No. PCT/US2010/027552, dated May 20, 2010 (date of completion of search) and Jun. 15, 2010 (date of mailing of report).
Written Opinion from International Patent Application No. PCT/US2010/027552, dated May 20, 2010 (date of completion of opinion) and Jun. 15, 2010 (date of mailing of opinion).
International Preliminary Report on Patentability from International Application No. PCT/US09/01666, dated Apr. 25, 2011 (date of completion of report) and Jun. 20, 2011 (date of mailing of report).
Shustov et al., "Production of Pseudoinfectious Yellow Fever Virus with a Two-Component Genome," J. Virology 81:11737-11748, 2007.
International Search Report from International Patent Application No. PCT/US2009/001666, dated Aug. 12, 2009 (date of completion of search) and Sep. 1, 2009 (date of mailing of report).
Written Opinion from International Patent Application No. PCT/US2009/001666, dated Aug. 12, 2009 (date of completion of opinion) and Sep. 1, 2009 (date of mailing of opinion).
Search Report and Written Opinion issued by the Hungarian Intellectual Property Office for Singapore Patent Application No. 201006578-7, dated Jul. 19, 2012.
Bonaldo et al., "The Yellow Fever 17D Vaccine Virus as a Vector for the Expression of Foreign Proteins: Development of New Live Flavivirus Vaccines," Mem. Inst. Oswaldo Cruz. 95:Suppl.1:215-223, 2000.
Bredenbeek et al., "A Recombinant Yellow Fever 17D Vaccine Expressing Lassa Virus Glycoproteins," Virology 345:299-304, 2006.
Hsu et al., "Efficacy of Adenovirus-Vectored Respiratory Syncytial Virus Vaccines in a New Ferret Model," Vaccine 12:607-612, 1994.
Li et al., "Chimeric Influenza Virus Induces Neutralizing Antibodies and Cytotoxic T Cells Against Human Immunodeficiency Virus Type 1," J. Virology 67:6659-6666, 1993.
Martinez-Sobrido et al., "Protection Against Respiratory Syncytial Virus by a Recombinant Newcastle Disease Virus Vector," J. Virology 80:1130-1139, 2006.
McAllister et al., "Recombinant Yellow Fever Viruses are Effective Therapeutic Vaccines for Treatment of Murine Experimental Solid Tumors and Pulmonary Metastases," J. Virology 74:9197-9205, 2000.
Pang et al., "Development of Dengue Virus Replicons Expressing HIV-1 gp120 and other Heterologous Genes: A Potential Future Tool for Dual Vaccination Against Dengue Virus and HIV," BMC Microbiology 1:28(1-9), 2001.
Extended European Search Report from European Patent Application No. 09720269.1, dated Mar. 26, 2012.

\* cited by examiner

*Primary Examiner* — Stacy B. Chen
(74) *Attorney, Agent, or Firm* — Clark & Elbing LLP

(57) ABSTRACT

This invention provides replication-defective flavivirus vaccines and vaccine vectors, and corresponding compositions and methods.

7 Claims, 19 Drawing Sheets

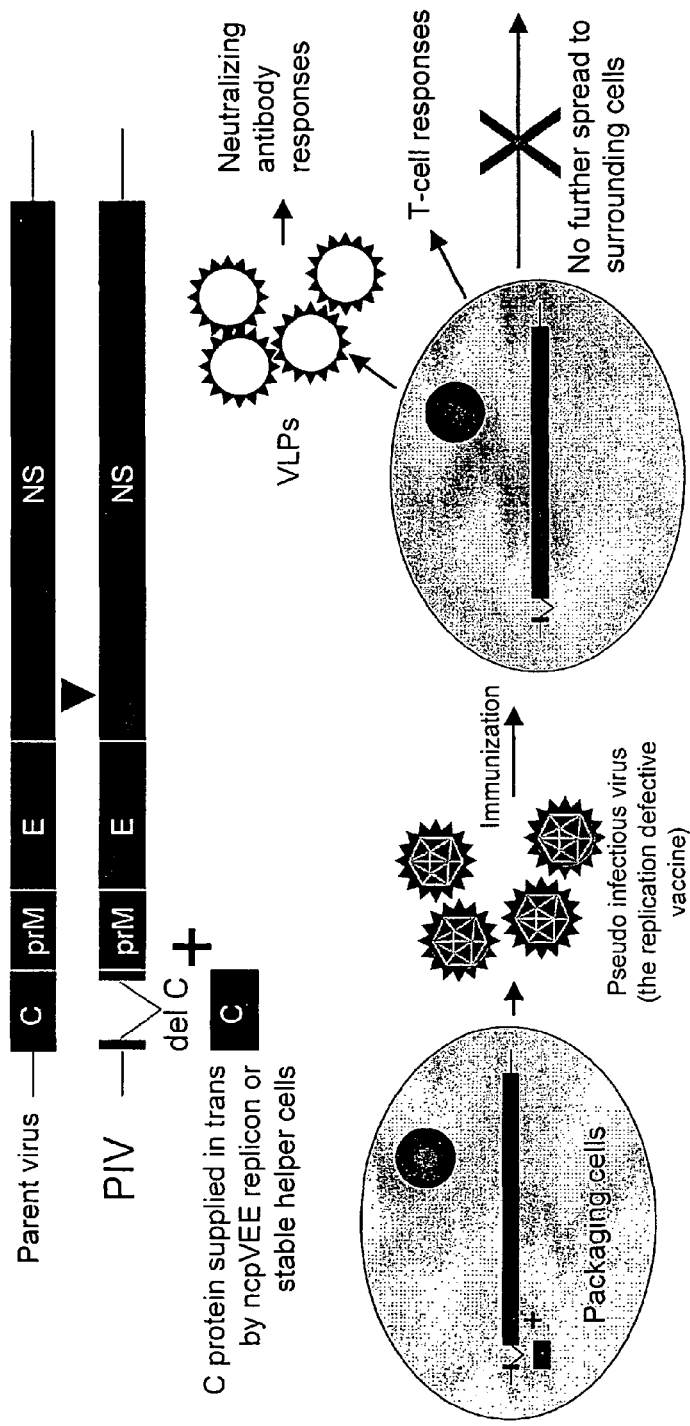

Fig. 2. Principle of two-component PIV (d-PIV; limited spread in vivo)

For recombinant vaccines: foreign immunogen inserted in place of ΔC and/or ΔprM-E, or elsewhere.

Fig. 3. Immunogenicity/efficacy: general experiment design (mice)
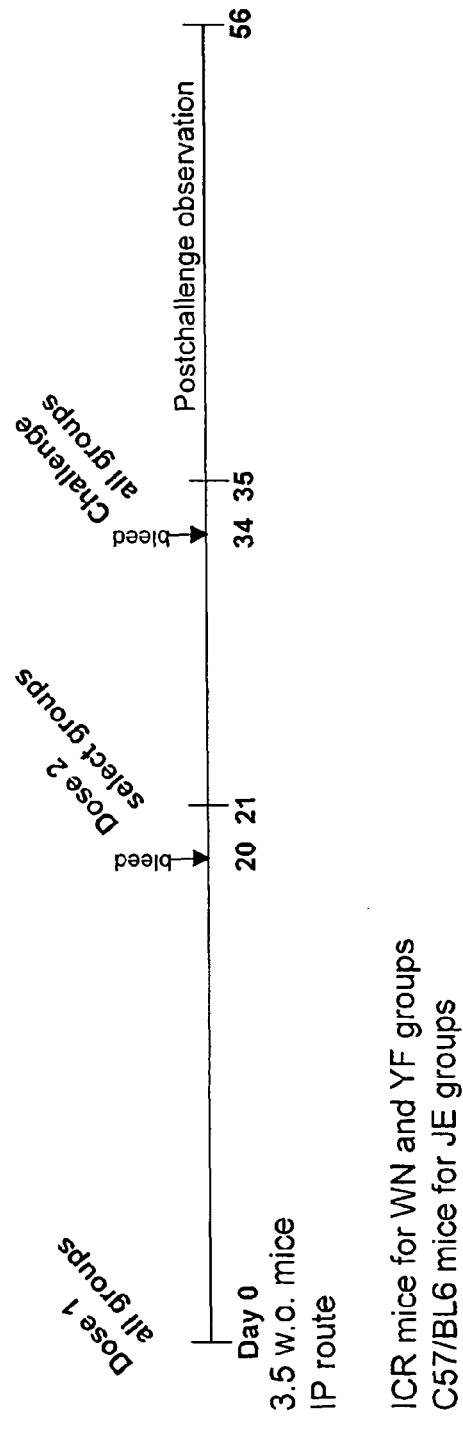

Fig. 4. PIV-WN induces uniform humoral immunity in mice

ICR mice, IP inoculation

Fig. 5. PIV-YF and PIV-WN protect hamsters against post-challenge viremia and morbidity

Fig. 6. YF/TBE viruses

| prM-E genes | P0 virus titer log$_{10}$ PFU/ml | P1 virus titer log$_{10}$ PFU/ml | Immuno-staining mHIAF | Immuno-staining αRSSE |
|---|---|---|---|---|
| TBEV prM-SP (p42) | 7.6 | 7.9 | | <p42 |
| Hypr WNV prM-SP (p45) | 7.1 | 7.4 | | p45> |
| Hypr + dC2 "CΔ3aa" (p59) | 5.6 | 6.5 | | p59> |
| LGT/E5 (p43) | 7.8 | 8.1 | | <p43 |

NOTES:
- p42, p45, p59, and p43 are designations of plasmids
- plaque morphology for p59-derived chimera was determined in a separate titration experiment (not shown; result of immunofluorescence assay shown)

Fig. 7. PIV-WNV/TBE constructs

| prM-E genes | P0 titer log₁₀ FFU/ml | | P1 titer log₁₀ FFU/ml | | Immuno-staining αRSSE mHIAF |
|---|---|---|---|---|---|
| | C helper cells | CprME helper cells | C helper cells | CprME helper cells | |
| Hypr (TBEV signal) (p39) | 7.2 | 6.7 | 6.9 | 77.1 | |
| Hypr (WNV signal) (p40) | 6.7 | 6.0 | 5.9 | 66.9 | |

Fig. 8. Replication kinetics of live YF/TBE and replication defective PIV-WNV/TBE variants in cell substrates Fig. 9. Survival of mice inoculated IC with PIV-TBE and YF/TBE constructs in the neurovirulence test (3.5 week-old ICR mice)

Fig. 10. Survival of mice inoculated IP with PIV-TBE and YF/TBE constructs in a neuroinvasiveness test (3.5 week-old ICR mice)

Fig. 11. Post-TBE-challenge morbidity (weight loss); day 9 post-challenge

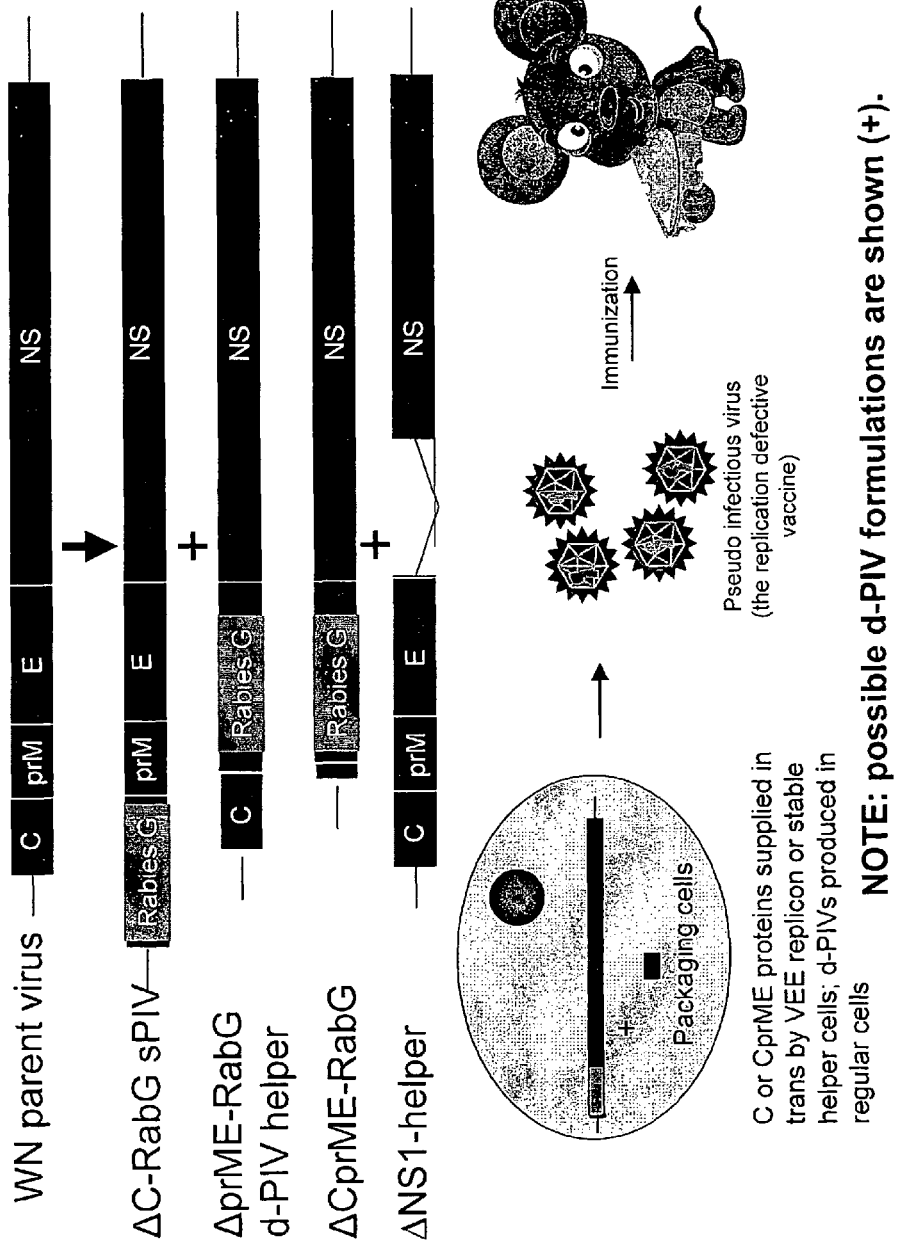

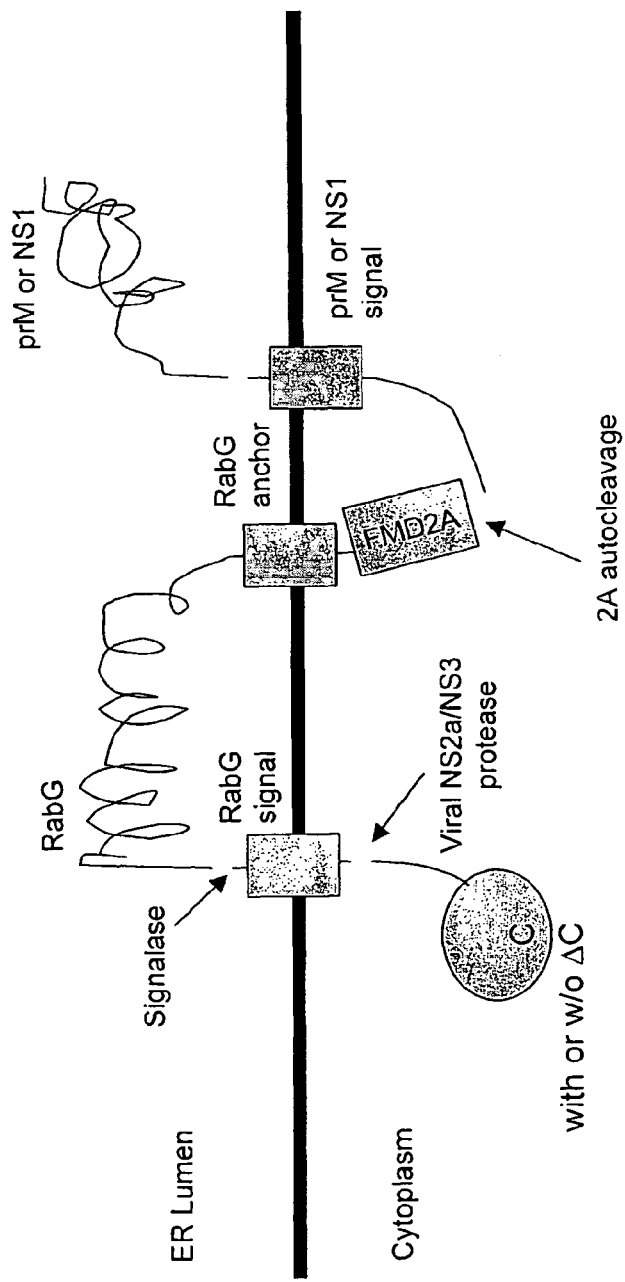
Fig. 13. Schematic representation of insertion designs resulting in viable/expressing constructs (exemplified by rabies G Fig. 14. PIV-WN/Rabies G PIVs: immunofluorescence of transfected cells and growth curves after transfection

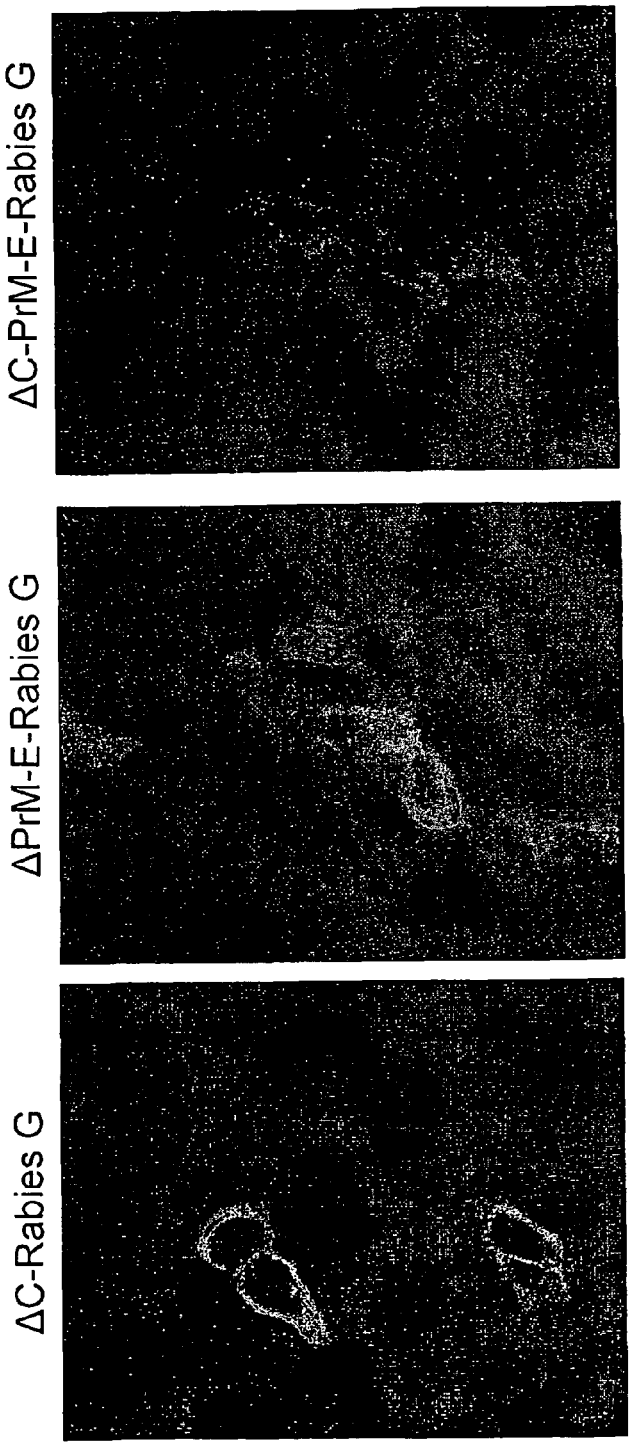
Fig. 15. Efficient expression of RabG on the plasma membrane of Vero cells
MOI 0.1, day 2 post infection, 4% PFA Fixed non-permeabilized
ΔC-Rabies G ΔPrM-E-Rabies G ΔC-PrM-E-Rabies G
1Ab (Abcam) Anti Rabies 1:500 2-3hrs RT, 2Ab Anti-Mouse IgG 1:1000 1hr RT
Images are 40X and exposure time is 40ms

Fig. 16. PIV - Rabies G spread in helper cells, no spread in naïve cells

PIV WN
ΔC - RabG

| Rabies G | prM | E | NS |

Packaging Cell Lines

MOI 0.001 D 4 p.i.

BHK    BHK-C    BHK-CprME

α rabies-G Mab

PIVs spread in helper cells and not naïve cells.
No infectious material in supernatants from BHK cells.

Similarly, VSV G was expressed, and no spread in regular cells (Vero, BHK) was observed and no infectious material detected in the supernatants Fig. 17. Stability of rabies G protein gene in PIV-WN vectors Passages in BHK-C-prM-E helper cells, MOI 0.1; titration in Vero by immunostaining Fig. 18. Comparison of spread in Vero cells of single-component vs. two-component PIV-Rabies variants Fig. 19. Example of expression of full-length RSV F protein (strain A2): immunostaining of helper cells after transfection Control BHK helper cells (WN C-prM-E)

PIV-WNΔprME-RSV F, 3 days post-transfection

Cells stained with anti-RSVF Mab, DAPI

REPLICATION-DEFECTIVE FLAVIVIRUS VACCINES AND VACCINE VECTORS

CROSS-REFERENCE TO RELATED APPLICATIONS

This application is the U.S. national stage filing under 35 U.S.C. §371 of international application PCT/US2009/001666, filed Mar. 16, 2009, which claims benefit of Provisional Application Nos. 61/069,451, filed Mar. 14, 2008 and 61/092,814, filed Aug. 29, 2008.

FIELD OF THE INVENTION

This invention relates to replication-defective flavivirus vaccines and vaccine vectors, and corresponding compositions and methods.

BACKGROUND OF THE INVENTION

Flaviviruses are distributed worldwide and represent a global public health problem. Flaviviruses also have a significant impact as veterinary pathogens. Flavivirus pathogens include yellow fever (YF), dengue types 1-4 (DEN1-4), Japanese encephalitis (JE), West Nile (WN), tick-borne encephalitis (TBE), and other viruses from the TBE serocomplex, such as Kyasanur Forest disease (KFD) and Omsk hemorrhagic fever (OHF) viruses. Vaccines against YF [live attenuated vaccine (LAV) strain 17D], JE [inactivated vaccines (INV) and LAV], and TBE (INV) are available. No licensed human vaccines are currently available against DEN and WN. Veterinary vaccines have been in use including, for example, vaccines against WN in horses (INV, recombinant and live chimeric vaccines), JE (INV and LAV) to prevent encephalitis in horses and stillbirth in pigs in Asia, louping ill flavivirus (INV) to prevent neurologic disease in sheep in the UK, and TBE (INV) used in farm animals in Czech Republic (INV) (Monath and Heinz, Flaviviruses, in Fields et al. Eds., Fields Virology, 3rd Edition, Philadelphia, N.Y., Lippincott-Raven Publishers, 1996, pp. 961-1034).

Tick-borne encephalitis (TBE) is the most important tick-borne viral disease of humans. It is endemic in parts of Europe and Northern Asia, causing more than 10,000 hospitalizations annually, with a case-fatality rate 0.5-1.5% in Europe and 6-40% in Siberia and the Far East. A significant proportion of patients suffer from long-lasting neuropsychiatric sequelae. Inactivated vaccines produced in chick embryo cell cultures have proven effective in preventing the disease. For example, an 86% vaccination coverage of the Austrian population (the highest among European countries) has resulted in an approximately 90% reduction of hospitalized cases (Heinz and Kunz, Arch. Virol. Suppl. 18:201-205, 2004). The inactivated vaccines are expensive and require three inoculations for primary immunization. Periodic boosters (every 2-5 years) are required to maintain immunity. Therefore, a less costly TBE vaccine, which is effective after one-two doses and provides durable, such as life-long immunity (similar to that achieved by YF 17D immunization) is needed, and indeed has been identified by the WHO as a major priority. Development of TBE LAV candidates in the past several decades by means of empirical or rational attenuation of TBE virus parent per se or chimerization of TBE or Langat (LGT, a naturally attenuated flavivirus that is closely related (serologically) to TBE) viruses with dengue 4 virus has faced difficulties due to problems with residual virulence of candidates and/or low immunogenicity/overattenuation (Wright et al., Vaccine 26:882-890, 2008; Maximova et al., J. Virol. 82:5255-5268, 2008; Rumyantsev et al., Vaccine 24:133-143, 2006; Kofler et al., Arch. Virol. Suppl. 18:191-200, 2004; and references therein).

Flaviviruses are small, enveloped, plus-strand RNA viruses transmitted primarily by arthropod vectors (mosquitoes or ticks) to natural hosts, which are primarily vertebrate animals, such as various mammals, including humans, and birds. The flavivirus genomic RNA molecule is about 11,000 nucleotides (nt) in length and encompasses a long open reading frame (ORF) flanked by 5' and 3' untranslated terminal regions (UTRs) of about 120 and 500 nucleotides in length, respectively. The ORF encodes a polyprotein precursor that is cleaved co- and post-translationally to generate individual viral proteins. The proteins are encoded in the order: C-prM/M-E-NS1-NS2A/2B-NS3-NS4A/4B-NS5, where C (core/capsid), prM/M (pre-membrane/membrane), and E (envelope) are the structural proteins, i.e., the components of viral particles, and the NS proteins are non-structural proteins, which are involved in intracellular virus replication. Flavivirus replication occurs in the cytoplasm. Upon infection of cells and translation of genomic RNA, processing of the polyprotein starts with translocation of the prM portion of the polyprotein into the lumen of endoplasmic reticulum (ER) of infected cells, followed by translocation of E and NS1 portions, as directed by the hydrophobic signals for the prM, E, and NS1 proteins. Amino-termini of prM, E, and NS1 proteins are generated by cleavage with cellular signalase, which is located on the luminal side of the ER membrane, and the resulting individual proteins remain carboxy-terminally anchored in the membrane. Most of the remaining cleavages, in the nonstructural region, are carried out by the viral NS2B/NS3 serine protease. The viral protease is also responsible for generating the C-terminus of the mature C protein found in progeny virions. Newly synthesized genomic RNA molecules and the C protein form a dense spherical nucleocapsid, which becomes surrounded by cellular membrane in which the E and prM proteins are embedded. The mature M protein is produced by cleavage of prM shortly prior to virus release by cellular furin or a similar protease. E, the major protein of the envelope, is the principal target for neutralizing antibodies, the main correlate of immunity against flavivirus infection. Virus-specific cytotoxic T-lymphocyte (CTL) response is the other key attribute of immunity. Multiple CD8+ and CD4+ CTL epitopes have been characterized in various flavivirus structural and non-structural proteins. In addition, innate immune responses contribute to both virus clearance and regulating the development of adaptive immune responses and immunologic memory.

In addition to the inactivated (INV) and live-attenuated (LAV) vaccines against flaviviruses discussed above, other vaccine platforms have been developed. One example is based on chimeric flaviviruses that include yellow fever virus capsid and non-structural sequences and prM-E proteins from other flaviviruses, to which immunity is sought. This technology has been used to develop vaccine candidates against dengue (DEN), Japanese encephalitis (JE), West Nile (WN), and St. Louis encephalitis (SLE) viruses (see, e.g., U.S. Pat. Nos. 6,962,708 and 6,696,281). Yellow fever virus-based chimeric flaviviruses have yielded highly promising results in clinical trials.

Another flavivirus vaccine platform is based on the use of pseudoinfectious virus (PIV) technology (Mason et al., Virology 351:432-443, 2006; Shustov et al., J. Virol. 21:11737-11748, 2007; Widman et al., Adv. Virus. Res. 72:77-126, 2008; Suzuki et al., J. Virol. 82:6942-6951, 2008; Suzuki et al., J. Virol. 83:1870-1880, 2009; Ishikawa et al., Vaccine 26:2772-2781, 2008; Widman et al., Vaccine 26:2762-2771, 2008). PIVs are replication-defective viruses attenuated by a deletion(s). Unlike live flavivirus vaccines, they undergo a single round replication in vivo (or optionally limited rounds, for two-component constructs; see below), which may provide benefits with respect to safety. PIVs also do not induce viremia and systemic infection. Further, unlike inactivated vaccines, PIVs mimic whole virus infection, which can result in increased efficacy due to the induction of robust B- and T-cell responses, higher durability of immunity, and decreased dose requirements. Similar to whole viruses, PIV vaccines target antigen-presenting cells, such as dendritic cells, stimulate toll-like receptors (TLRs), and induce balanced Th1/Th2 immunity. In addition, PIV constructs have been shown to grow to high titers in substrate cells, with little or no cytopathic effect (CPE), allowing for high-yield manufacture, optionally employing multiple harvests and/or expansion of infected substrate cells.

The principles of the PIV technology are illustrated in FIGS. 1 and 2. There are two variations of the technology. In the first variation, a single-component pseudoinfectious virus (s-PIV) is constructed with a large deletion in the capsid protein (C), rendering mutant virus unable to form infectious viral particles in normal cells (FIG. 1). The deletion does not remove the first ~20 codons of the C protein, which contain an RNA cyclization sequence, and a similar number of codons at the end of C, which encode a viral protease cleavage site and the signal peptide for prM. The s-PIV can be propagated, e.g., during manufacture, in substrate (helper) cell cultures in which the C protein is supplied in trans, e.g., in stably transfected cells producing the C protein (or a larger helper cassette including C protein), or in cells containing an alphavirus replicon [e.g., a Venezuelan equine encephalitis virus (VEE) replicon] expressing the C protein or another intracellular expression vector expressing the C protein. Following inoculation in vivo, e.g., after immunization, the PIV undergoes a single round of replication in infected cells in the absence of trans-complementation of the deletion, without spread to surrounding cells. The infected cells produce empty virus-like particles (VLPs), which are the product of the prM-E genes in the PIV, resulting in the induction of neutralizing antibody response. A T-cell response should also be induced via MHCI presentation of viral epitopes. This approach has been applied to YF 17D virus and WN viruses and WN/JE and WN/DEN2 chimeric viruses (Mason et al., Virology 351:432-443, 2006; Suzuki et al., J. Virol. 83:1870-1880, 2009; Ishikawa et al., Vaccine 26:2772-2781, 2008; Widman et al., Vaccine 26:2762-2771, 2008; WO 2007/098267; WO 2008/137163).

In the second variation, a two-component PIV (d-PIV) is constructed (FIG. 2). Substrate cells are transfected with two defective viral RNAs, one with a deletion in the C gene and another lacking the prM-E envelope protein genes. The two defective genomes complement each other, resulting in accumulation of two types of PIVs in the cell culture medium (Shustov et al., J. Virol. 21:11737-11748, 2007; Suzuki et al., J. Virol. 82:6942-6951, 2008). Optionally, the two PIVs can be manufactured separately in appropriate helper cell lines and then mixed in a two-component formulation. The latter may offer an advantage of adjusting relative concentrations of the two components, increasing immunogenicity and efficacy. This type of PIV vaccine should be able to undergo a limited spread in vivo due to coinfection of some cells at the site of inoculation with both components. The spread is expected to be self-limiting as there are more cells in tissues than viral particles produced by initially coinfected cells. In addition, a relatively high MOI is necessary for efficient coinfection, and cells outside of the inoculation site are not expected to be efficiently coinfected (e.g., in draining lymph nodes). Cells infected with the ΔC PIV alone produce the highly immunogenic VLPs. Coinfected cells produce the two types of packaged defective viral particles, which also stimulate neutralizing antibodies. The limited infection is expected to result in a stronger neutralizing antibody response and T-cell response compared to s-PIVs. To decrease chances of recombination during manufacture or in vivo, including with circulating flaviviruses, viral sequences can be modified in both s-PIVs and d-PIVs using, e.g., synonymous codon replacements, to reduce nucleotide sequence homologies, and mutating the complementary cyclization 5' and 3' elements.

SUMMARY OF THE INVENTION

The invention provides replication-deficient or defective pseudoinfectious flaviviruses including a flavivirus genome that includes (i) one or more deletions or mutations in nucleotide sequences encoding one or more proteins selected from the group consisting of capsid (C), pre-membrane (prM), envelope (E), non-structural protein 1 (NS1), non-structural protein 3 (NS3), and non-structural protein 5 (NS5), and (ii) sequences encoding one or more heterologous pathogen, cancer, or allergy-related immunogens. For example, the deletion/mutation can be within capsid (C) sequences; pre-membrane (prM) and/or envelope (E) sequences; capsid (C), pre-membrane (prM), and envelope (E) sequences; or non-structural protein 1 (NS1) sequences.

The heterologous immunogen can be, for example, from a pathogen selected from the group consisting of a rabies virus (e.g., a rabies virus G protein epitope), *Borrelia burgdorferi* (e.g., OspA immunogen or an immunogenic fragment thereof), a tick (e.g., a tick saliva protein selected from the group consisting of 64TRP, Isac, and Salp20, or an immunogenic fragment thereof), an influenza virus (e.g., an influenza virus M2, hemaglutinnin (HA), or neuraminidase (NA) epitope, or an immunogenic fragment thereof), a human immunodeficiency virus (e.g., a codon-optimized HIV gag, tat/nef, or gp120 protein, or an immunogenic fragment thereof), a simian immunodeficiency virus, a human papilloma virus (e.g., an HPV16 or HPV18 capsid protein L1 or L2, or an immunogenic fragment thereof), a respiratory syncytial virus (e.g., a respiratory syncytial virus F or G glycoprotein), malaria parasite, and *Mycobacterium tuberculosis* (also see below).

The replication-deficient pseudoinfectious flaviviruses can include sequences encoding a pre-membrane (prM) and/or envelope (E) protein. Further, the replication-deficient pseudoinfectious flavivirus genomes can be selected from those of yellow fever virus, West Nile virus, tick-borne encephalitis virus, Langat virus, Japanese encephalitis virus, dengue virus, and St. Louis encephalitis virus, attenuated strains thereof, and chimeras thereof (also see below). In various examples, the chimeras include pre-membrane (prM) and envelope (E) sequences of a first flavivirus (e.g., a tick-borne encephalitis virus or a Langat virus), and capsid (C) and non-structural sequences of a second, different flavivirus (e.g., a yellow fever, a West Nile, or Langat virus).

The replication-deficient pseudoinfectious flavivirus genomes can be packaged in particles including pre-membrane (prM) and envelope (E) sequences from a flavivirus that is the same or different from that of the genomes. Further, the sequences encoding the heterologous immunogens can be inserted in the place of, or in combination with, the deletion(s) or mutation(s) of the one or more proteins.

The sequences encoding the heterologous immunogens can be inserted in the flavivirus genomes within sequences encoding the envelope (E) protein, within sequences encoding the non-structural 1 (NS1) protein, within sequences encoding the pre-membrane (prM) protein, intergenically between sequences encoding the envelope (E) protein and non-structural protein 1 (NS1), intergenically between non-structural protein 2B (NS2B) and non-structural protein 3 (NS3), and/or as a bicistronic insertion in the 3' untranslated region of the flavivirus genome.

The invention also includes compositions including a first replication-deficient pseudoinfectious flavivirus, as described above, and a second (or further), different replication-deficient pseudoinfectious flavivirus including a genome that includes one or more deletions or mutations in nucleotide sequences encoding one or more proteins selected from the group consisting of capsid (C), pre-membrane (prM), envelope (E), non-structural protein 1 (NS1), non-structural protein 3 (NS3), and non-structural protein 5 (NS5). In these compositions, the one or more proteins encoded by the sequences in which the deletion(s) or mutation(s) occur in the second, different replication-deficient pseudoinfectious flavivirus are different from the one or more proteins encoded by the sequences in which the deletion(s) occur in the first replication-deficient pseudoinfectious flavivirus.

The invention further includes methods of inducing immune responses to an immunogen in a subject, which involves administering to the subject one or more replication-deficient pseudoinfectious flavivirus and/or composition as described herein to the subject. In various examples, the subject is at risk of but does not have an infection by the pathogen or a disease or condition associated with the cancer or allergy-related immunogen. In other examples, the subject has an infection by the pathogen or a disease or condition associated with the cancer or allergy-related immunogen. The invention thus includes prophylactic and therapeutic methods. In these methods, the immunogen can be from, for example, a pathogen selected from the group consisting of a rabies virus, *Borrelia burgdorferi*, a tick, an influenza virus, a human immunodeficiency virus, a simian immunodeficiency virus, a human papilloma virus, a respiratory syncytial virus, malaria parasite, and *Mycobacterium tuberculosis* (also see below). Further, the methods can be for inducing an immune response against a protein encoded by the flavivirus genome, in addition to the source of the immunogen. In various examples, the subject is at risk of but does not have an infection by the flavivirus corresponding to the genome of the pseudoinfectious flavivirus, which includes sequences encoding a flavivirus pre-membrane and/or envelope protein. In other examples, the subject has an infection by the flavivirus corresponding to the genome of the pseudoinfectious flavivirus, which includes sequences encoding a flavivirus pre-membrane and/or envelope protein.

The invention also includes live, attenuated chimeric flaviviruses including a yellow fever virus in which sequences encoding pre-membrane and envelope proteins are replaced with sequences encoding pre-membrane and envelope proteins of a tick-borne encephalitis virus or a Langat virus, and the signal sequence between the capsid and pre-membrane proteins of the chimeric flavivirus includes a hybrid of yellow fever virus and tick-borne encephalitis or Langat virus capsid/pre-membrane signal sequences, or a variant thereof. In various examples, the capsid/pre-membrane signal sequence of the chimeric flavivirus includes yellow fever virus sequences in the amino terminal region and tick-borne encephalitis or Langat virus sequences in the carboxy terminal region (see below).

Further, the invention includes live, attenuated chimeric flaviviruses including a West Nile virus in which sequences encoding pre-membrane and envelope proteins are replaced with sequences encoding pre-membrane and envelope proteins of a tick-borne encephalitis or a Langat virus, and the signal sequence between the capsid and pre-membrane proteins of the chimeric flavivirus includes a tick-borne encephalitis or a Langat virus capsid/pre-membrane signal sequence, or a variant thereof.

The invention also includes pharmaceutical compositions including one or more pseudoinfectious flavivirus, composition, or live, attenuated flavivirus as described herein, and a pharmaceutically acceptable carrier or diluent. Further, the compositions can include an adjuvant.

Also included in the invention are replication-deficient pseudoinfectious flaviviruses including a flavivirus genome including one or more deletion(s) or mutation(s) in nucleotide sequences encoding non-structural protein 1 (NS1), non-structural protein 3 (NS3), or non-structural protein 5 (NS5).

Further, the invention includes nucleic acid molecules corresponding to the genome of a pseudoinfectious flavivirus, or the genome the live, attenuated flavivirus, as described herein, and complements thereof.

The invention also provides methods of making replication-deficient pseudoinfectious flaviviruses as described herein, involving introducing one or more nucleic acid molecules, as described above, into a cell that expresses the protein(s) corresponding to any sequences deleted from the flavivirus genome of the replication-deficient pseudoinfectious flaviviruses. In these methods, the protein can be expressed in the cell from the genome of a second (or further), different, replication-deficient pseudoinfectious flavivirus. In other examples, the protein is expressed from a replicon (e.g., an alphavirus replicon, such as a Venezuelan Equine Encephalitis virus replicon; see below).

The invention also includes compositions containing two or more replication-deficient pseudoinfectious flaviviruses, in which two of the replication-deficient pseudoinfectious flaviviruses are selected from the groups consisting of: (a) a replication-deficient pseudoinfectious flavivirus including a genome containing Japanese encephalitis virus sequences, and a replication-deficient pseudoinfectious flavivirus including a genome containing dengue virus sequences; (b) a replication-deficient pseudoinfectious flavivirus including a genome containing yellow fever virus sequences, and a replication-deficient pseudoinfectious flavivirus including a genome containing dengue virus sequences; and (c) a replication-deficient pseudoinfectious flavivirus including a genome containing tick-borne encephalitis or Langat virus sequences and an inserted sequence encoding a *Borrelia burgdorferi* immunogen, and a replication-deficient pseudoinfectious flavivirus including a genome containing tick-borne encephalitis or Langat virus sequences and an inserted sequence encoding a tick saliva protein immunogen, or a replication-deficient pseudoinfectious flavivirus including a genome containing tick-borne encephalitis or Langat virus sequences and inserted sequences encoding a *Borrelia burgdorferi* immunogen and a tick saliva protein immunogen.

Pharmaceutical compositions including the live, attenuated chimeric flaviviruses described herein are also included in the invention. Further, the invention includes methods of inducing an immune response to tick-borne encephalitis virus or Langat virus in a subject, involving administering to the subject such a pharmaceutical composition. In various examples, the subject does not have but is at risk of developing infection by tick-borne encephalitis virus or Langat virus. In other examples, the subject is infected with tick-borne encephalitis virus or Langat virus.

The invention further includes replication-deficient pseudoinfectious flaviviruses including a flavivirus genome including one or more deletions or mutations in nucleotide sequences encoding one or more proteins selected from the group consisting of capsid (C), pre-membrane (prM), envelope (E), non-structural protein 1 (NS1), non-structural protein 3 (NS3), and non-structural protein 5 (NS5), wherein the flavivirus genome includes yellow fever virus sequences in which sequences encoding pre-membrane and envelope proteins are replaced with sequences encoding pre-membrane and envelope proteins of a tick-borne encephalitis virus or a Langat virus, and sequences encoding the signal sequence between the capsid and pre-membrane proteins of the flavivirus genome include a hybrid of sequences encoding yellow fever virus and tick-borne encephalitis or Langat virus capsid/pre-membrane signal sequences, or a variant thereof. In various examples, the sequences encoding the capsid/pre-membrane signal sequence of the flavivirus genome include yellow fever virus sequences in the 5' region and tick-borne encephalitis or Langat virus sequences in the 3' region.

Further, the invention includes replication-deficient pseudoinfectious flaviviruses including a flavivirus genome including one or more deletions or mutations in nucleotide sequences encoding one or more proteins selected from the group consisting of capsid (C), pre-membrane (prM), envelope (E), non-structural protein 1 (NS1), non-structural protein 3 (NS3), and non-structural protein 5 (NS5), wherein the flavivirus genome includes West Nile virus sequences in which sequences encoding pre-membrane and envelope proteins are replaced with sequences encoding pre-membrane and envelope proteins of a tick-borne encephalitis or a Langat virus, and the sequences encoding the signal sequence between the capsid and pre-membrane proteins of the flavivirus genome include sequences encoding a tick-borne encephalitis or a Langat virus capsid/pre-membrane signal sequence, or a variant thereof.

In addition, the invention includes replication-deficient pseudoinfectious flaviviruses including a flavivirus genome including one or more deletions or mutations in nucleotide sequences encoding one or more proteins selected from the group consisting of capsid (C), pre-membrane (prM), envelope (E), non-structural protein 1 (NS1), non-structural protein 3 (NS3), and non-structural protein 5 (NS5), wherein any capsid (C) and non-structural (NS) proteins in the flavivirus genome are from Langat virus and any pre-membrane (prM) and envelope (E) proteins are from a tick-borne encephalitis virus.

By "replication-deficient pseudoinfectious flavivirus" or "PIV" is meant a flavivirus that is replication-deficient due to a deletion or mutation in the flavivirus genome. The deletion or mutation can be, for example, a deletion of a large sequence, such as most of the capsid protein, as described herein (with the cyclization sequence remaining; see below). In other examples, sequences encoding different proteins (e.g., prM, E, NS1, NS3, and/or NS5; see below) or combinations of proteins (e.g., prM-E or C-prM-E) are deleted. This type of deletion may be advantageous if the PIV is to be used a vector to deliver a heterologous immunogen, as the deletion can permit insertion of sequences that may be, for example, at least up to the size of the deleted sequence. In other examples, the mutation can be, for example, a point mutation, provided that it results in replication deficiency, as discussed above. Because of the deletion or mutation, the genome does not encode all proteins necessary to produce a full flavivirus particle. The missing sequences can be provided in trans by a complementing cell line that is engineered to express the missing sequence (e.g., by use of a replicon; s-PIV; see below), or by co-expression of two replication-deficient genomes in the same cell, where the two replication-deficient genomes, when considered together, encode all proteins necessary for production (d-PIV system; see below).

Upon introduction into cells that do not express complementing proteins, the genomes replicate and, in some instances, generate "virus-like particles," which are released from the cells and are able to leave the cells and be immunogenic, but cannot infect other cells and lead to the generation of further particles. For example, in the case of a PIV including a deletion in capsid protein encoding sequences, after infection of cells that do not express capsid, VLPs including prM-E proteins are released from the cells. Because of the lack of capsid protein, the VLPs lack capsid and a nucleic acid genome. In the case of the d-PIV approach, production of further PIVs is possible in cells that are infected with two PIVs that complement each other with respect to the production of all required proteins (see below).

The invention provides several advantages. For example, the PIV vectors and PIVs of the invention are highly attenuated and highly efficacious after one-to-two doses, providing durable immunity. Further, unlike inactivated vaccines, PIVs mimic whole virus infection, which can result in increased efficacy due to the induction of robust B- and T-cell responses, higher durability of immunity, and decreased dose requirements. In addition, similar to whole viruses, PIV vaccines target antigen-presenting cells, such as dendritic cells, stimulate toll-like receptors (TLRs), and induce balanced Th1/Th2 immunity. PIV constructs have also been shown to grow to high titers in substrate cells, with little or no CPE, allowing for high-yield manufacture, optionally employing multiple harvests and/or expansion of infected substrate cells. Further, the PIV vectors of the invention provide an option for developing vaccines against non-flavivirus pathogens for which no vaccines are currently available.

Other features and advantages of the invention will be apparent from the following detailed description, the drawings, and the claims.

BRIEF DESCRIPTION OF THE DRAWINGS

FIG. 1 is a schematic illustration of single component PIV (s-PIV) technology.

FIG. 2 is a schematic illustration of two-component PIV (d-PIV) technology.

FIG. 3 is a schematic illustration of a general experimental design for testing immunogenicity and efficacy of PIVs in mice.

FIG. 4 is a graph comparing the humoral immune response induced by PIV-WN (RV-WN) with that of YF/WN LAV (CV-WN) in mice.

FIG. 5 is a series of graphs showing the results of challenging hamsters immunized with PIV-YF (RV-YF), YF17D, PIV-WN (RV-WN), and YF/WN LAV (CVWN) with hamster-adapted Asibi (PIV-YF and YF17D vaccinees) and wild type WN-NY99 (PIV-WN and YF/WN LAV vaccinees).

FIG. 6 is a table showing YF/TBE and YF/LGT virus titers and plaque morphology obtained with the indicated chimeric flaviviruses.

FIG. 7 is a table showing WN/TBE PIV titers and examples of immunofluorescence of cells containing the indicated PIVs.

FIG. 8 is a set of graphs showing the replication kinetics of YF/TBE LAV and PIV-WN/TBE in Vero and BHK cell lines (CV-Hypr=YF/Hypr LAV; CV-LGT=YF/LGT LAV; RV-WN/TBEV=PIV-WN/TBEV).

FIG. 9 is a series of graphs showing survival of mice inoculated IC with PIV-TBE and YF/TBE LAV constructs in a neurovirulence test (3.5 week old ICR mice; RV-WN/Hypr=PIV-WN/TBE(Hypr); CV-Hypr+YF/TBE(Hypr) LAV; CV-LGT=YF/LGT LAV).

FIG. 10 is a graph showing survival of mice inoculated IP with PIV-WN/TBE(Hypr) (RV-WN/Hypr), YF/TBE(Hypr) LAV (CV-Hypr), and YF/LGT LAV (CV-LGT) constructs and YF17D in a neuroinvasiveness test (3.5 week old ICR mice).

FIG. 11 is a series of graphs illustrating morbidity in mice measured by dynamics of body weight loss after TBE virus challenge, for groups immunized with S-PIV-TBE candidates (upper left panel), YF/TBE and YF/LGT chimeric viruses (upper right panel), and controls (YF 17D, human killed TBE vaccine, and mock; bottom panel).

FIG. 12 is a schematic representation of PIV constructs expressing rabies virus G protein, as well as illustration of packaging of the constructs to make pseudoinfectious virus and immunization.

FIG. 13 is a schematic representation of insertion designs resulting in viable/expressing constructs (exemplified by rabies G).

FIG. 14 is series of images showing immunofluorescence analysis and graphs showing growth curves of cells transfected with the indicated PIV-WN constructs (ΔC-Rabies G, ΔPrM-E-Rabies G, and ΔC-PrM-E-Rabies G).

FIG. 15 is a series of images showing immunofluorescence analysis of RabG expressed on the plasma membranes of Vero cells transfected with the indicated PIV constructs (ΔC-Rabies G, ΔPrM-E-Rabies G, and ΔC-PrM-E-Rabies G).

FIG. 16 is a schematic illustration of a PIV-WN-rabies G construct and a series of images showing that this construct spreads in helper cells, but not in naïve cells.

FIG. 17 is a series of graphs showing stability of the rabies G protein gene in PIV-WN vectors.

FIG. 18 is a set of images showing a comparison of spread of single-component vs. two-component PIV-WN-rabies G variants in Vero cells.

FIG. 19 is a set of immunofluorescence images showing expression of full-length RSV F protein (strain A2) by the ΔprM-E component of d-PIV-WN in helper cells after transfection.

DETAILED DESCRIPTION OF THE INVENTION

The invention provides replication-defective or deficient pseudoinfectious virus (PIV) vectors including flavivirus sequences, which can be used in methods for inducing immunity against heterologous pathogen, cancer, and allergy-related immunogens inserted into the vectors as well as, optionally, the vectors themselves. The invention also includes compositions including combinations of PIVs and/or PIV vectors, as described herein, and methods of using such compositions to induce immune responses against inserted immunogen sequences and/or sequences of the PIVs themselves. Further, the invention includes particular PIVs and live, attenuated chimeric flaviviruses including tick-borne encephalitis virus sequences, and related vectors, compositions, and methods of use. The PIV vectors, PIVs, live attenuated chimeric flaviviruses, compositions, and methods of the invention are described further below.

PIV Vectors and PIVs

The PIV vectors and PIVs of the invention can be based on the single- or two-component PIVs described above (also see WO 2007/098267 and WO 2008/137163). Thus, for example, in the case of single component PIVs, the PIV vectors and PIVs can include a genome including a large deletion in capsid protein encoding sequences and be produced in a complementing cell line that produces capsid protein in trans (single component; FIG. 1 and FIG. 12). According to this approach, most of the capsid-encoding region is deleted, which prevents the PIV genome from producing infectious progeny in normal cell lines (i.e., cell lines not expressing capsid sequences) and vaccinated subjects. The capsid deletion typically does not disrupt RNA sequences required for genome cyclization (i.e., the sequence encoding amino acids in the region of positions 1-26), and/or the prM sequence required for maturation of prM to M. In specific examples, the deleted sequences correspond to those encoding amino acids 26-100, 26-93, 31-100, or 31-93 of the C protein.

Single component PIV vectors and PIVs can be propagated in cell lines that express either C or a C-prM-E cassette, where they replicate to high levels. Exemplary cell lines that can be used for expression of single component PIV vectors and PIVs include BHK-21 (e.g., ATCC CCL-10), Vero (e.g., ATCC CCL-81), C7/10, and other cells of vertebrate or mosquito origin. The C or C-prM-E cassette can be expressed in such cells by use of a viral vector-derived replicon, such as an alphavirus replicon (e.g., a replicon based on Venezuelan Equine Encephalitis virus (VEEV), Sindbis virus, Semliki Forest virus (SFV), Eastern Equine Encephalitis virus (EEEV), Western Equine Encephalitis virus (WEEV), or Ross River virus). To decrease the possibility of productive recombination between the PIV vectors/PIVs and complementing sequences, the sequences in the replicons (encoding C, prM, and/or E) can include nucleotide mutations. For example, sequences encoding a complementing C protein can include an unnatural cyclization sequence. The mutations can result from codon optimization, which can provide an additional benefit with respect to PIV yield. Further, in the case of complementing cells expressing C protein sequences (and not a C-prM-E cassette), it may be beneficial to include an anchoring sequence at the carboxy terminus of the C protein including, for example, about 20 amino acids of prM (see, e.g., WO 2007/098267).

The PIV vectors and PIVs of the invention can also be based on the two-component genome technology described above. This technology employs two partial genome constructs, each of which is deficient in expression of at least one protein required for productive replication (capsid or prM/E) but, when present in the same cell, result in the production of all components necessary to make a PIV. Thus, in one example of the two-component genome technology, the first component includes a large deletion of C, as described above in reference to single component PIVs, and the second component includes a deletion of prM and E (FIG. 2 and FIG. 12). In another example, the first component includes a deletion of C, prM, and E, and the second component includes a deletion of NS1 (FIG. 12). Both components can include cis-acting promoter elements required for RNA replication and a complete set of non-structural proteins, which form the replicative enzyme complex. Thus, both defective genomes can include a 5'-untranslated region and at least about 60 nucleotides (Element 1) of the following, natural protein-coding sequence, which comprises an amino-terminal fragment of the capsid protein. This sequence can be followed by a protease cleavage sequence such as, for example, a ubiquitine or foot-and-mouth disease virus (FAMDV)-specific 2A protease sequence, which can be fused with either capsid or envelope (prM-E) coding sequences. Further, artificial, codon optimized sequences can be used to exclude the possibility of recombination between the two defective viral genomes, which could lead to formation of replication-competent viruses (see, e.g., WO 2008/137163). Use of the two-component genome approach does not require the development of cell lines expressing complementing genomes, such as the cells transformed with replicons, as discussed above in reference to the single component PIV approach. Exemplary cell lines that can be used in the two-component genome approach include Vero (e.g., ATCC CCL-81), BHK-21 (e.g., ATCC CCL-10), C7/10, and other cells of vertebrate or mosquito origin.

Additional examples of d-PIV approaches that can be used in the invention are based on use of complementing genomes including deletions in NS3 or NS5 sequences. A deletion in, e.g., NS1, NS3, or NS5 proteins can be used as long as several hundred amino acids in the ORF, removing the entire chosen protein sequence, or as short as 1 amino acid inactivating protein enzymatic activity (e.g., NS5 RNA polymerase activity, NS3 helicase activity, etc.). Alternatively, point amino acid changes (as few as 1 amino acid mutation, or optionally more mutations) can be introduced into any NS protein, inactivating enzymatic activity. In addition, several ANS deletions can be combined in one helper molecule. The same heterologous gene, i.e., expressed by the first d-PIV component, can be expressed in place or in combination with the NS deletion(s) in the second component, increasing the amount of expressed immunogen. Notably, the insertion capacity of the helper will increase proportionally to the size of NS deletion(s). Alternatively, a different foreign immunogen(s) can be inserted in place of deletion(s) of the helper to produce multivalent vaccines.

Further, additional approaches that can be used in making PIV vectors and PIVs for use in the present invention are described, for example, in WO 99/28487, WO 03/046189, WO 2004/108936, US 2004/0265338, US 2007/0249032, and U.S. Pat. No. 7,332,322.

The PIV vectors and PIVs of the invention can be comprised of sequences from a single flavivirus type (e.g., tick-borne encephalitis (TBE, e.g., strain Hypr), Langat (LGT), yellow fever (e.g., YF17D), West Nile, Japanese encephalitis, dengue (serotype 1-4), St. Louis encephalitis, Kunjin, Rocio encephalitis, Ilheus, Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, and Apoi viruses), or can comprise sequences from two or more different flaviviruses. Sequences of some strains of these viruses are readily available from generally accessible sequence databases; sequences of other strains can be easily determined by methods well known in the art. In the case of PIV vectors and PIVs including sequences of more than one flavivirus, the sequences can be those of a chimeric flavivirus, as described above (also see, e.g., U.S. Pat. No. 6,962,708; U.S. Pat. No. 6,696,281; and U.S. Pat. No. 6,184,024). In certain examples, the chimeras include pre-membrane and envelope sequences from one flavivirus (such as a flavivirus to which immunity may be desired), and capsid and non-structural sequences from a second, different flavivirus. In one specific example, the second flavivirus is a yellow fever virus, such as the vaccine strain YF17D. Other examples include the YF/TBE, YF/LGT, WN/TBE, and WN/LGT chimeras described below. Another example is an LGT/TBE chimera based on LGT virus backbone containing TBE virus prM-E proteins. A PIV vaccine based on this genetic background would have an advantage, because LGT replicates very efficiently in vitro and is highly attenuated and immunogenic for humans. Thus, a chimeric LGT/TBE PIV vaccine is expected to provide a robust specific immune response in humans against TBE, particularly due to inclusion of TBE prM-E genes.

Vectors of the invention can be based on PIV constructs or live, attenuated chimeric flaviviruses as described herein (in particular, YF/TBE, YF/LGT, WN/TBE, and WN/LGT; see below). Use of PIV constructs as vectors provides particular advantages in certain circumstances, because these constructs by necessity include large deletions, which render the constructs more amenable to accommodation of insertions that are at least up to the size of the deleted sequences, without there being a loss in replication efficiency. Thus, PIV vectors in general can comprise very small insertions (e.g., in the range 6-10, 11-20, 21-100, 101-500, or more amino acid residues combined with the ΔC deletion or other deletions), as well as relatively large insertions or insertions of intermediate size (e.g., in the range 501-1000, 1001-1700, 1701-3000, or 3001-4000 or more residues). In contrast, in certain examples, it may be advantageous to express relatively short sequences in live attenuated viruses, particularly if the insertions are made in the absence of a corresponding deletion. Additional information concerning insertion sites that can be used in the invention is provided below. In addition, as discussed further below, expression of non-flavivirus immunogens in PIVs and chimeric flaviviruses of the invention can result in dual vaccines that elicit protective immunity against both a flavivirus vector virus pathogen and a target heterologous immunogen (e.g., a pathogen (such as a bacterial, viral, parasite, or fungal pathogen), cancer, or allergy-related immunogen).

As discussed above, the PIV vectors and PIVs of the invention can comprise sequences of chimeric flaviviruses, for example, chimeric flaviviruses including pre-membrane and envelope sequences of a first flavivirus (e.g., a flavivirus to which immunity is sought), and capsid and non-structural sequences of a second, different flavivirus, such as a yellow fever virus (e.g., YF17D; see above and also U.S. Pat. No. 6,962,708; U.S. Pat. No. 6,696,281; and U.S. Pat. No. 6,184,024). Further, chimeric flaviviruses of the invention, used as a source for constructing PIVs, or as vaccines/vaccine vectors per se, can optionally include one or more specific attenuating mutations (e.g., E protein mutations, prM protein mutations, deletions in the C protein, and/or deletions in the 3'UTR), such as any of those described in WO 2006/116182. For example, the C protein or 3'UTR deletions can be directly applied to YF/TBE or YF/LGT chimeras. Similar deletions can be designed and introduced in other chimeric LAV candidates such as based on LGT/TBE, WN/TBE, and WN/LGT genomes. With respect to E protein mutations, attenuating mutations similar to those described for YF/WN chimera in WO 2006/116182 can be designed, e.g., based on the knowledge of crystal structure of the E protein (Rey et al., Nature 375(6529):291-298, 1995), and employed. Further, additional examples of attenuating E protein mutations described for TBE virus and other flaviviruses are provided in Table 9. These can be similarly introduced into chimeric vaccine candidates.

The invention also provides new, particular chimeric flaviviruses, which can be used as a basis for the design of PIV vectors and PIVs, as live attenuated chimeric flavivirus vectors, and as vaccines against the source(s) of the pre-membrane and envelope components of the chimeras. These chimeras include tick-borne encephalitis (TBE) virus or related prM-E sequences. Thus, the chimeras can include prM-E sequences from, for example, the Hypr strain of TBE or Langat (LGT) virus. Capsid and non-structural proteins of the chimeras can include those from yellow fever virus (e.g., YF17D) or West Nile virus (e.g., NY99).

A central feature of these exemplary YF/TBE, YF/LGT, WN/TBE, and WN/LGT chimeras is the signal sequence between the capsid and prM proteins. As is shown in the Examples, below, we have found that, in the case of YF-based PIV chimeras, it is advantageous to use a signal sequence comprising yellow fever and TBE sequences (see below). In one example, the signal sequence includes yellow fever sequences in the amino terminal region (e.g., SHDVLTVQ-FLIL) and TBE sequences in the carboxy terminal region (e.g., GMLGMTIA), resulting in the sequence SHDVLTVQ-FLILGMLGMTIA. We have also found that, in the case of WN-based PIV chimeras, it is advantageous to use a signal sequence comprising TBE sequences (e.g., GGTDWM-SWLLVIGMLGMTIA). The invention thus includes YF/TBE, YF/LGT, WN/TBE, and WN/LGT chimeras, both PIVs and LAVs, which include the above-noted signal sequences, or variants thereof having, e.g., 1-8, 2-7, 3-6, or 4-5 amino acid substitutions, deletions, or insertions, which do not substantially interfere with processing at the signal sequence. In various examples, the substitutions are "conservative substitutions," which are characterized by replacement of one amino acid residue with another, biologically similar residue. Examples of conservative substitutions include the substitution of one hydrophobic residue such as isoleucine, valine, leucine, or methionine for another, or the substitution of one polar residue for another, such as between arginine and lysine, between glutamic and aspartic acids, or between glutamine and asparagine and the like. Additional information concerning these chimeras is provided below, in the Examples.

Insertion Sites

Sequences encoding immunogens can be inserted at one or more different sites within the vectors of the invention. Relatively short peptides can be delivered on the surface of PIV or LAV glycoproteins (e.g., prM, E, and/or NS1 proteins) and/or in the context of other proteins (to induce predominantly B-cell and T-cell responses, respectively). Other inserts, including larger portions of foreign proteins, as well as complete proteins, can be expressed intergenically, at the N- and C-termini of the polyprotein, or bicistronically (e.g., within the ORF under an IRES or in the 3'UTR under an IRES; see, e.g., WO 02/102828, WO 2008/036146, WO 2008/094674, WO 2008/100464, WO 2008/115314, and below for further details). In PIV constructs, there is an additional option of inserting a foreign amino acid sequence directly in place of introduced deletion(s). Insertions can be made in, for example, ΔC, ΔprM-E, ΔC-prM-E, ΔNS1, ΔNS3, and ΔNS5. Thus, in one example, in the case of s-PIVs and the ΔC component of d-PIVs, immunogen-encoding sequences can be inserted in place of deleted capsid sequences. Immunogen-encoding sequences can also, optionally, be inserted in place of deleted prM-E sequences in the ΔprM-E component of d-PIVs. In another example, the sequences are inserted in place of or combined with deleted sequences in ΔC-prM-E constructs. Examples of such insertions are provided in the Examples section, below.

In the case of making insertions into PIV deletions, the insertions can be made with a few (e.g., 1, 2, 3, 4, or 5) additional vector-specific residues at the N- and/or C-termini of the foreign immunogen, if the sequence is simply fused in-frame (e.g., ~20 first a.a. and a few last residues of the C protein if the sequence replaces the ΔC deletion), or without, if the foreign immunogen is flanked by appropriate elements well known in the field (e.g., viral protease cleavage sites; cellular protease cleavage sites, such as signalase, furin, etc.; autoprotease; termination codon; and/or IRES elements).

If a protein is expressed outside of the continuous viral open reading frame (ORF), e.g., if vector and non-vector sequences are separated by an internal ribosome entry site (IRES), cytoplasmic expression of the product can be achieved or the product can be directed towards the secretory pathway by using appropriate signal/anchor segments, as desired. If the protein is expressed within the vector ORF, important considerations include cleavage of the foreign protein from the nascent polyprotein sequence, and maintaining correct topology of the foreign protein and all viral proteins (to ensure vector viability) relative to the ER membrane, e.g., translocation of secreted proteins into the ER lumen, or keeping cytoplasmic proteins or membrane-associated proteins in the cytoplasm/in association with the ER membrane.

In more detail, the above-described approaches to making insertions can employ the use of, for instance, appropriate vector-derived, insert-derived, or unrelated signal and anchor sequencess included at the N and C termini of glycoprotein inserts. Standard autoproteases, such as FMDV 2A autoprotease (~20 amino acids) or ubiquitin (gene ~500 nt), or flanking viral NS2B/NS3 protease cleavage sites can be used to direct cleavage of an expressed product from a growing polypeptide chain, to release a foreign protein from a vector polyprotein, and to ensure viability of the construct. Optionally, growth of the polyprotein chain can be terminated by using a termination codon, e.g., following a foreign gene insert, and synthesis of the remaining proteins in the constructs can be re-initiated by incorporation of an IRES element, e.g., the encephalomyocarditis virus (EMCV) IRES commonly used in the field of RNA virus vectors. Viable recombinants can be recovered from helper cells (or regular cells for d-PIV versions). Optionally, backbone PIV sequences can be rearranged, e.g., if the latter results in more efficient expression of a foreign gene. For example, a gene rearrangement has been applied to TBE virus, in which the prM-E genes were moved to the 3' end of the genome under the control of an IRES (Orlinger et al., J. Virol. 80:12197-12208, 2006). Translocation of prM-E or any other genes can be applied to PIV flavivirus vaccine candidates and expression vectors, according to the invention.

Additional details concerning different insertion sites that can be used in the invention are as follows (also see WO 02/102828, WO 2008/036146, WO 2008/094674, WO 2008/100464, WO 2008/115314, as noted above). Peptide sequences can be inserted within the envelope protein, which is the principle target for neutralizing antibodies. The sequences can be inserted into the envelope in, for example, positions corresponding to amino acid positions 59, 207, 231, 277, 287, 340, and/or 436 of the Japanese encephalitis virus envelope protein (see, e.g., WO 2008/115314 and WO 02/102828). To identify the corresponding loci in different flaviviruses, the flavivirus sequences are aligned with that of Japanese encephalitis virus. As there may not be an exact match, it should be understood that, in non-JE viruses, the site of insertion may vary by, for example, 1, 2, 3, 4, or 5 amino acids, in either direction. Further, given the identification of such sites as being permissive in JE, they can also vary in JE by, for example, 1, 2, 3, 4, or 5 amino acids, in either direction. Additional permissive sites can be identified using methods such as transposon mutagenesis (see, e.g., WO 02/102828 and WO 2008/036146). The insertions can be made at the indicated amino acids by insertion just C-terminal to the indicated amino acids (i.e., between amino acids 51-52, 207-208, 231-232, 277-278, 287-288, 340-341, and 436-437), or in place of short deletions (e.g., deletions of 1, 2, 3, 4, 5, 6, 7, or 8 amino acids) beginning at the indicated amino acids (or within 1-5 positions thereof, in either direction).

In addition to the envelope protein, insertions can be made into other virus proteins including, for example, the membrane/pre-membrane protein and NS1 (see, e.g., WO 2008/

036146). For example, insertions can be made into a sequence preceding the capsid/pre-membrane cleavage site (at, e.g., −4, −2, or −1) or within the first 50 amino acids of the pre-membrane protein (e.g., at position 26), and/or between amino acids 236 and 237 of NS1 (or in regions surrounding the indicated sequences, as described above). In other examples, insertions can be made intergenically. For example, an insertion can be made between E and NS1 proteins and/or between NS2B and NS3 proteins (see, e.g., WO 2008/100464). In one example of an intergenic insertion, the inserted sequence can be fused with the C-terminus of the E protein of the vector, after the C-terminal signal/anchor sequence of the E protein, and the insertion can include a C-terminal anchor/signal sequence, which is fused with vector NS1 sequences. In another example of an intergenic insertion, the inserted sequences, with flanking protease cleavage sites (e.g., YF17D cleavage sites), can be inserted into a unique restriction site introduced at the NS2B/NS3 junction (WO 2008/100464).

In other examples, a sequence can be inserted in the context of an internal ribosome entry site (IRES, e.g., an IRES derived from encephalomyocarditis virus; EMCV), as noted above, such as inserted in the 3'-untranslated region (WO 2008/094674). In one example of such a vector, employing, for example, yellow fever virus sequences, an IRES-immunogen cassette can be inserted into a multiple cloning site engineered into the 3'-untranslated region of the vector, e.g., in a deletion (e.g., a 136 nucleotide deletion in the case of a yellow fever virus-based example) after the polyprotein stop codon (WO 2008/094674).

Details concerning the insertion of rabies virus G protein and full-length respiratory syncytial virus (RSV) F protein into s-PIV and d-PIV vectors of the invention are provided below in Example 3. The information provided in Example 3 can be applied in the context of other vectors and immunogens described herein.

Immunogens

PIVs (s-PIVs and d-PIVs) based on flavivirus sequences and live, attenuated chimeric flaviviruses (e.g., YF/TBE, YF/LGT, WN/TBE, and WN/LGT), as described above, can be used in the invention to deliver foreign (e.g., non-flavivirus) pathogen (e.g., viral, bacterial, fungal, and parasitic pathogens), cancer, and allergy-related immunogens. As discussed further below, in certain examples, it may be advantageous to target several pathogens occupying the same ecological niche, in a particular geographical region. Specific, non-limiting examples of such immunogens are provided as follows.

In addition to TBE virus, ticks are known to transmit another major disease, Lyme disease. Thus, in a first example, PIVs of the invention, such as PIVs including TBE/LGT sequences, as well as chimeric flaviviruses including TBE sequences (e.g., YF/TBE, YF/LGT, WN/TBE, LGT/TBE, and WN/LGT; in all instances where "TBE" is indicated, this includes the option of using the Hypr strain), can be used as vectors to deliver protective immunogens of the causative agent of Lyme disease (tick-borne spirochete *Borrelia burgdorferi*). This combination, targeting both infectious agents (TBE and *B. burgdorferi*) is advantageous, because TBE and Lyme disease are both tick-borne diseases. The PIV approaches can be applied to chimeras (e.g., YF/TBE, YF/LGT, to WN/TBE, or WN/LGT), according to the invention, as well as to non-chimeric TBE and LGT viruses. An exemplary immunogen from *B. burgdorferi* that can be used in the invention is OspA (Gipson et al., Vaccine 21:3875-3884, 2003). Optionally, to increase safety and/or immunogenicity, OspA can be mutated to reduce chances of autoimmune responses and/or to eliminate sites for unwanted post-translational modification in vertebrate animal cells, such as N-linked glycosylation, which may affect immunogenicity of the expression product. Mutations that decrease autoimmunity can include, e.g., those described by Willett et al., Proc. Natl. Acad. Sci. U.S.A. 101:1303-1308, 2004. In one example, FTK-OspA, a putative cross-reactive T cell epitope, Bb $OSA_{165-173}$ (YVLEGTLTA) is altered to resemble the corresponding peptide sequence of *Borrelia afzelli* (FTLEGKVAN). In FTK-OspA, the corresponding sequence is FTLEGKLTA.

The sequence of OspA is as follows:

```
  1  mkkyllgigl ilaliackqn vssldeknsv svdlpgemkv
     lvskeknkdg kydliatvdk 61  lelkgtsdkn ngsgvlegvk adkskvklti sddlgqttle
     vfkedgktlv skkvtskdks 121  steekfnekg evsekiitra dgtrleytgi ksdgsgkake
     vlkgyvlegt ltaekttlvv 181  kegtvtlskn isksgevsve lndtdssaat kktaawnsgt
     stltitvnsk ktkdlvftke 241  ntitvqqyds ngtklegsav eitkldeikn alk
```

The full-length sequence and/or immunogenic fragments of the full-length sequence can be used in the present invention. Exemplary fragments can include one or more of domains 1 (amino acids 34-41), 2 (amino acids 65-75), 3 (amino acids 190-220), and 4 (amino acids 250-270) (Jiang et al., Clin. Diag. Lab. Immun. 1(4):406-412, 1994). Thus, for example, a peptide comprising any one (or more) of the following sequences (which include sequence variations that can be included in the sequence listed above, in any combination) can be delivered: LPGE/GM/IK/T/GVL; GTSDKN/S/DNGSGV/T; N/H/EIS/P/L/A/SK/NSGEV/IS/TV/AE/ALN/DDT/SD/NS/TS/TA/Q/RATKKTA/GA/K/TWN/DS/AG/N/KT; SN/AGTK/NLEGS/N/K/TAVEIT/KK/TLD/KEI/LKN.

In addition to *B. burgdorferi* immunogens, tick saliva proteins, such as 64TRP, Isac, and Salp20, can be expressed, e.g., to generate a vaccine candidate of trivalent-specificity (TBE+Lyme disease+ticks). Alternatively, tick saliva proteins can be expressed instead of *B. burgdorferi* immunogens in TBE sequence-containing vectors. In to addition, there are many other candidate tick saliva proteins that can be used for tick vector vaccine development according to the invention (Francischetti et al., Insect Biochem. Mol. Biol. 35:1142-1161, 2005). One or more of these immunogens can be expressed in s-PIV-TBE. However, d-PIV-TBE may also be selected, because of its large insertion capacity. In addition to PIV-TBE, other PIV vaccines can be used as vectors, e.g., to protect from Lyme disease and another flavivirus disease, such as West Nile virus. Expression of these immunogens can be evaluated in cell culture, and immunogenicity/protection examined in available animal models (e.g., as described in Gipson et al., Vaccine 21:3875-3884, 2003; Labuda et al., Pathog. 2(e27):0251-0259, 2006). Immunogens of other pathogens can be similarly expressed, in addition to Lyme disease and tick immunogens, with the purpose of making multivalent vaccine candidates. Exemplary tick saliva immunogens that can be used in the invention include the following:

```
64TRP (AF469170)
MKAFFVLSLL STAALTNAAR AGRLGSDLDT FGRVHGNLYA GIERAGPRGY PGLTASIGGE

VGARLGGRAG VGVSSYGYGY PSWGYPYGGY GGYGGYGGYG GYDQGFGSAY GGYPGYYGYY

YPSGYGGGYG GSYGGSYGGS YTYPNVRASA GAAA

Isac (AF270496)
MRTAFTCALL AISFLGSPCS SSEDGLEQDT IVETTTQNLY ERHYRNHSGL CGAQYRNSSH

AEAVYNCTLN HLPPVVNATW EGIRHRINKT IPQFVKLICN FTVAMPQEFY LVYMGSDGNS

DFEEDKESTG TDEDSNTGSS AAAKVTEALI IEAEENCTAH ITGWTTETPT TLEPTTESQF EAIP

Salp20 (EU008559)
MRTALTCALL AISFLGSPCS SSEGGLEKDS RVETTTQNLY ERYYRKHPGL CGAQYRNSSH

AEAVYNCTLS LLPLSVNTTW EGIRHRINKT IPEFVNLICN FTVAMPDQFY LVYMGSNGNS

YSEEDEDGKT GSSAAVQVTE QLIIQAEENC TAHITGWTTE APTTLEPTTE TQFEAIS
```

Additional details concerning the TBE-related PIVs and LAVs are provided in Example 2, below.

The invention further provides PIV and LAV-vectored vaccines against other non-flavivirus pathogens, including vaccines having dual action, eliciting protective immunity against both flavivirus (as specified by the vector envelope proteins) and non-flavivirus pathogens (as specified by expressed immunologic determinant(s)). These are similar to the example of PIV-TBE-Lyme disease-tick vector vaccines described above. As mentioned above, such dual-action vaccines can be developed against a broad range of pathogens by expression of immunogens from, for example, viral, bacterial, fungal, and parasitic pathogens, and immunogens associated with cancer and allergy. As specific non-limiting examples, we describe herein the design and biological properties of PIV vectored-rabies and -respiratory syncytial virus (RSV) vaccine candidates constructed by expression of rabies virus G protein or full-length RSV F protein in place of or in combination with various deletions in one- and two-component PIV vectors (see Example 3, below).

As is demonstrated in the Examples, below, s-PIV constructs may be advantageously used to stably deliver relatively short foreign immunogens (similar to Lyme disease agent OspA protein and tick saliva proteins), because insertions are combined with a relatively short ΔC deletion. Two-component PIV vectors may be advantageously used to stably express relatively large immunogens, such as rabies G protein and RSV F, as the insertions in such vectors are combined with, for example, large ΔprM-E, ΔC-prM-E, and/or ΔNS1 deletions. Some of the d-PIV components can be manufactured and used as vaccines individually, for instance, the PIV-RSV F construct described below containing a ΔC-prM-E deletion. In this case, the vaccine induces an immune response (e.g., neutralizing antibodies) predominantly against the expressed protein, but not against the flavivirus vector virus pathogen. In other examples of the invention, dual immunity is obtained by having immunity induced both to vector and insert components. Additionally, because of the large insertion capacity of PIV vectors, and the option of using two-component genomes, PIV vectors offer the opportunity to target several non-flavivirus pathogens simultaneously, e.g., by expressing foreign immunogens from two different non-flavivirus pathogens in the two components of a d-PIV.

In addition to the RSV F protein, rabies G protein, Lyme disease protective immunogens, and tick saliva proteins, as examples of foreign immunogens described above, other foreign immunogens can be expressed to target respective diseases including, for example, influenza virus type A and B immunogens. In these examples, a to few short epitopes and/or whole genes of viral particle proteins can be used, such as the M2, HA, and NA genes of influenza A, and/or the NB or BM2 genes of influenza B. Shorter fragments of M2, NB, and BM2, corresponding for instance to M2e, the extracellular fragment of M2, can also be used. In addition, fragments of the HA gene, including epitopes identified as HA0 (23 amino acids in length, corresponding to the cleavage site in HA) can be used. Specific examples of influenza-related sequences that can be used in the invention include PAKLLKERGFF-GAIAGFLE (HA0), PAKLLKERGFFGAIAGFLEGSGC (HA0), NNATFNYTNVNPISHIRGS (NBe), MSLLTEVET-PIRNEWGCRCNDSSD (M2e), MSLLTEVETPTRNEWE-CRCSDSSD (M2e), MSLLTEVETLTRNGWGCRCSDSSD (M2e), EVETPTRN (M2e), SLLTEVET-PIRNEWGCRCNDSSD (M2e), and SLLTEVET-PIRNEWGCR (M2e). Additional M2e sequences that can be used in the invention include sequences from the extracellular domain of BM2 protein of influenza B (consensus MLEPFQ, e.g., LEPFQILSISGC), and the M2e peptide from the H5N1 avian flu (MSLLTEVETLTRNGWGCRCSDSSD).

Other examples of pathogen immunogens that can be delivered in the vectors of the invention include codon-optimized SIV or HIV gag (55 kDa), gp120, gp160, Sly mac239-rev/tat/nef genes or analogs from HIV, and other HIV immunogens; immunogens from HPV viruses, such as HPV16, HPV18, etc., e.g., the capsid protein L1 which self-assembles into HPV-like particles, the capsid protein L2 or its immunodominant portions (e.g., amino acids 1-200, 1-88, or 17-36), the E6 and E7 proteins which are involved in transforming and immortalizing mammalian cells fused together and appropriately mutated (fusion of the two genes creates a fusion protein, referred to as E6E7Rb⁻, that is about 10-fold less capable of transforming fibroblasts, and mutations of the E7 component at 2 residues renders the resulting fusion protein mutant incapable of inducing transformation (Boursnell et al., Vaccine 14:1485-1494, 1996). Other immunogens include protective immunogens from HCV, CMV, HSV2, viruses, malaria parasite, *Mycobacterium tuberculosis* causing tuberculosis, *C. difficile*, and other nosocomial infections, that are known in the art, as well as fungal pathogens, cancer immunogens, and proteins associated with allergy that can be used as vaccine targets.

Foreign immunogen inserts of the invention can be modified in various ways. For instance, codon optimization is used to increase the level of expression and eliminate long repeats in nucleotide sequences to increase insert stability in the RNA genome of PIV vectors. Immunogenicity can be increased by chimerization of proteins with immunostimulatory moieties well known in the art, such as TLR agonists, stimulatory cytokines, components of complement, heat-shock proteins, etc. (e.g., reviewed in "Immunopotentiators in Modern Vaccines," Schijns and O'Hagan Eds., 2006, Elsevier Academic Press: Amsterdam, Boston).

With respect to construction of dual vaccines against rabies and other flavivirus diseases, other combinations, such as TBE+rabies, YF+rabies, etc., can be of interest both for human and veterinary use in corresponding geographical regions, and thus can be similarly generated. Possible designs of expression constructs are not limited to those described herein. For example deletions and insertions can be modified, genetic elements can be rearranged, or other genetic elements (e.g. non-flavivirus, non-rabies signals for secretion, intracellular transport determinants, inclusion of or fusion with immunostimulatory moieties such as cytokines, TLR agonists such as flagellin, multimerization components such as leucine zipper, and peptides that increase the period of protein circulation in the blood) can be used to facilitate antigen presentation and increase immunogenicity. Further, such designs can be applied to s-PIV and d-PIV vaccine candidates based on vector genomes of other flaviviruses, and expressing immunogens of other pathogens, e.g., including but not limited to pathogens described in elsewhere herein.

Other examples of PIV and LAV vectors of the invention including combination vaccines such as DEN+Chikungunya virus (CHIKV) and YF+CHIKV. CHIKV, an alphavirus, is endemic in Africa, South East Asia, Indian subcontinent and the Islands, and the Pacific Islands and shares ecological/geographical niches with YF and DEN1-4. It causes serious disease primarily associated with severe pain (arthritis, other symptoms similar to DEN) and long-lasting sequelae in the majority of patients (Simon et al., Med. Clin. North Am. 92:1323-1343, 2008; Seneviratne et al., J. Travel Med. 14:320-325, 2007). Other examples of PIV and LAV vectors of the invention include YF+Ebola or DEN+Ebola, which co-circulate in Africa.

Immunogens for the above-noted non-flavivirus pathogens, sequences of which are well known in the art, may include glycoprotein B or a pp 65/IEI fusion protein of CMV (Reap et al., Vaccine 25(42):7441-7449, 2007; and references therein), several TB proteins (reviewed in Skeiky et al., Nat. Rev. Microbiol. 4(6):469-476, 2006), malaria parasite antigens such as RTS, S (a pre-erythrocytic circumsporozoite protein, CSP) and others (e.g., reviewed in Li et al., Vaccine 25(14):2567-2574, 2007), CHIKV envelope proteins E1 and E2 (or the C-E2-E1, E2-E1 cassettes), HCV structural proteins C-E1-E2 forming VLPs (Ezelle et al., J. Virol. 76(23): 12325-12334, 2002) or other proteins to induce T-cell responses, Ebola virus glycoprotein GP (Yang et al., Virology 377(2):255-264, 2008).

In addition to the immunogens described above, the vectors described herein may include one or more immunogen(s) derived from or that direct an immune response against one or more viruses (e.g., viral target antigen(s)) including, for example, a dsDNA virus (e.g., adenovirus, herpesvirus, epstein-barr virus, herpes simplex type 1, herpes simplex type 2, human herpes virus simplex type 8, human cytomegalovirus, varicella-zoster virus, poxvirus); ssDNA virus (e.g., parvovirus, papillomavirus (e.g., E1, E2, E3, E4, E5, E6, E7, E8, BPV1, BPV2, BPV3, BPV4, BPV5, and BPV6 (In Papillomavirus and Human Cancer, edited by H. Pfister (CRC Press, Inc. 1990)); Lancaster et al., Cancer Metast. Rev. pp. 6653-6664, 1987; Pfister et al., Adv. Cancer Res. 48:113-147, 1987)); dsRNA viruses (e.g., reovirus); (+)ssRNA viruses (e.g., picornavirus, coxsackie virus, hepatitis A virus, poliovirus, togavirus, rubella virus, flavivirus, hepatitis C virus, yellow fever virus, dengue virus, west Nile virus); (−)ssRNA viruses (e.g., orthomyxovirus, influenza virus, rhabdovirus, paramyxovirus, measles virus, mumps virus, parainfluenza virus, rhabdovirus, rabies virus); ssRNA-RT viruses (e.g., retrovirus, human immunodeficiency virus (HIV)); and dsDNA-RT viruses (e.g. hepadnavirus, hepatitis B). Immunogens may also be derived from other viruses not listed above but available to those of skill in the art.

With respect to HIV, immunogens may be selected from any HIV isolate. As is to well-known in the art, HIV isolates are now classified into discrete genetic subtypes. HIV-1 is known to comprise at least ten subtypes (A, B, C, D, E, F, G, H, J, and K). HIV-2 is known to include at least five subtypes (A, B, C, D, and E). Subtype B has been associated with the HIV epidemic in homosexual men and intravenous drug users worldwide. Most HIV-1 immunogens, laboratory adapted isolates, reagents and mapped epitopes belong to subtype B. In sub-Saharan Africa, India, and China, areas where the incidence of new HIV infections is high, HIV-1 subtype B accounts for only a small minority of infections, and subtype HIV-1 C appears to be the most common infecting subtype. Thus, in certain embodiments, it may be desirable to select immunogens from HIV-1 subtypes B and/or C. It may be desirable to include immunogens from multiple HIV subtypes (e.g., HIV-1 subtypes B and C, HIV-2 subtypes A and B, or a combination of HIV-1 and HIV-2 subtypes) in a single immunological composition. Suitable HIV immunogens include ENV, GAG, POL, NEF, as well as variants, derivatives, and fusion proteins thereof, for example.

Immunogens may also be derived from or direct an immune response against one or more bacterial species (spp.) (e.g., bacterial target antigen(s)) including, for example, *Bacillus* spp. (e.g., *Bacillus anthracis*), *Bordetella* spp. (e.g., *Bordetella pertussis*), *Borrelia* spp. (e.g., *Borrelia burgdorferi*), *Brucella* spp. (e.g., *Brucella abortus, Brucella canis, Brucella melitensis, Brucella suis*), *Campylobacter* spp. (e.g., *Campylobacter jejuni*), *Chlamydia* spp. (e.g., *Chlamydia pneumoniae, Chlamydia psittaci, Chlamydia trachomatis*), *Clostridium* spp. (e.g., *Clostridium botulinum, Clostridium difficile, Clostridium perfringens, Clostridium tetani*), *Corynebacterium* spp. (e.g., *Corynebacterium diptheriae*), *Enterococcus* spp. (e.g., *Enterococcus faecalis, enterococcus faecum*), *Escherichia* spp. (e.g., *Escherichia coli*), *Francisella* spp. (e.g., *Francisella tularensis*), *Haemophilus* spp. (e.g., *Haemophilus influenza*), *Helicobacter* spp. (e.g., *Helicobacter pylori*), *Legionella* spp. (e.g., *Legionella pneumophila*), *Leptospira* spp. (e.g., *Leptospira interrogans*), *Listeria* spp. (e.g., *Listeria monocytogenes*), *Mycobacterium* spp. (e.g., *Mycobacterium leprae, Mycobacterium tuberculosis*), *Mycoplasma* spp. (e.g., *Mycoplasma pneumoniae*), *Neisseria* spp. (e.g., *Neisseria gonorrhea, Neisseria meningitidis*), *Pseudomonas* spp. (e.g., *Pseudomonas aeruginosa*), *Rickettsia* spp. (e.g., *Rickettsia rickettsii*), *Salmonella* spp. (e.g., *Salmonella typhi, Salmonella typhinurium*), *Shigella* spp. (e.g., *Shigella sonnei*), *Staphylococcus* spp. (e.g., *Staphylococcus aureus, Staphylococcus epidermidis, Staphylococcus saprophyticus*, coagulase negative *staphylococcus* (e.g., U.S. Pat. No. 7,473,762)), *Streptococcus* spp. (e.g., *Streptococcus agalactiae, Streptococcus pneumoniae, Streptococcus pyrogenes*), *Treponema* spp. (e.g., *Treponema pallidum*), *Vibrio* spp. (e.g., *Vibrio cholerae*), and *Yersinia* spp. (*Yersinia pestis*). Immunogens may also be derived from or direct the immune response against other bacterial species not listed above but available to those of skill in the art.

Immunogens may also be derived from or direct an immune response against one or more parasitic organisms (spp.) (e.g., parasitic target antigen(s)) including, for example, *Ancylostoma* spp. (e.g., *A. duodenale*), *Anisakis* spp., *Ascaris lumbricoides*, *Balantidium coli*, *Cestoda* spp., *Cimicidae* spp., *Clonorchis sinensis*, *Dicrocoelium dendriticum*, *Dicrocoelium hospes*, *Diphyllobothrium latum*, *Dracunculus* spp., *Echinococcus* spp. (e.g., *E. granulosus*, *E. multilocularis*), *Entamoeba histolytica*, *Enterobius vermicularis*, *Fasciola* spp. (e.g., *F. hepatica*, *F. magna*, *F. gigantica*, *F. jacksoni*), *Fasciolopsis buski*, *Giardia* spp. (*Giardia lamblia*), *Gnathostoma* spp., *Hymenolepis* spp. (e.g., *H. nana*, *H. diminuta*), *Leishmania* spp., *Loa loa*, *Metorchis* spp. (*M. conjunctus*, *M. albidus*), *Necator americanus*, *Oestroidea* spp. (e.g., botfly), *Onchocercidae* spp., *Opisthorchis* spp. (e.g., *O. viverrini*, *O. felineus*, *O. guayaquilensis*, and *O. noverca*), *Plasmodium* spp. (e.g., *P. falciparum*), *Protofasciola robusta*, *Parafasciolopsis fasciomorphae*, *Paragonimus westermani*, *Schistosoma* spp. (e.g., *S. mansoni*, *S. japonicum*, *S. mekongi*, *S. haematobium*), *Spirometra erinaceieuropaei*, *Strongyloides stercoralis*, *Taenia* spp. (e.g., *T. saginata*, *T. solium*), *Toxocara* spp. (e.g., *T. canis*, *T. cati*), *Toxoplasma* spp. (e.g., *T. gondii*), *Trichobilharzia regenti*, *Trichinella spiralis*, *Trichuris trichiura*, *Trombiculidae* spp., *Trypanosoma* spp., *Tunga penetrans*, and/or *Wuchereria bancrofti*. Immunogens may also be derived from or direct the immune response against other parasitic organisms not listed above but available to those of skill in the art.

Immunogens may be derived from or direct the immune response against tumor target antigens (e.g., tumor target antigens). The term tumor target antigen (TA) may include both tumor-associated antigens (TAAs) and tumor-specific antigens (TSAs), where a cancerous cell is the source of the antigen. A TA may be an antigen that is expressed on the surface of a tumor cell in higher amounts than is observed on normal cells or an antigen that is expressed on normal cells during fetal development. A TSA is typically an antigen that is unique to tumor cells and is not expressed on normal cells. TAs are typically classified into five categories according to their expression pattern, function, or genetic origin: cancer-testis (CT) antigens (i.e., MAGE, NY-ESO-1); melanocyte differentiation antigens (e.g., Melan A/MART-1, tyrosinase, gp100); mutational antigens (e.g., MUM-1, p53, CDK-4); overexpressed 'self' antigens (e.g., HER-2/neu, p53); and viral antigens (e.g., HPV, EBV). Suitable TAs include, for example, gp100 (Cox et al., Science 264:716-719, 1994), MART-1/Melan A (Kawakami et al., J. Exp. Med., 180:347-352, 1994), gp75 (TRP-1) (Wang et al., J. Exp. Med., 186: 1131-1140, 1996), tyrosinase (Wolfe) et al., Eur. J. Immunol., 24:759-764, 1994), NY-ESO-1 (WO 98/14464; WO 99/18206), melanoma proteoglycan (Hellstrom et al., J. Immunol., 130:1467-1472, 1983), MAGE family antigens (e.g., MAGE-1, 2, 3, 4, 6, and 12; Van der Bruggen et al., Science 254:1643-1647, 1991; U.S. Pat. No. 6,235,525), BAGE family antigens (Boel et al., Immunity 2:167-175, 1995), GAGE family antigens (e.g., GAGE-1,2; Van den Eynde et al., J. Exp. Med. 182:689-698, 1995; U.S. Pat. No. 6,013,765), RAGE family antigens (e.g., RAGE-1; Gaugler et al., Immunogenetics 44:323-330, 1996; U.S. Pat. No. 5,939,526), N-acetylglucosaminyltransferase-V (Guilloux et al., J. Exp. Med. 183:1173-1183, 1996), p15 (Robbins et al., J. Immunol. 154:5944-5950, 1995), β-catenin (Robbins et al., J. Exp. Med., 183:1185-1192, 1996), MUM-1 (Coulie et al., Proc. Natl. Acad. Sci. U.S.A. 92:7976-7980, 1995), cyclin dependent kinase-4 (CDK4) (Wolfel et al., Science 269: 1281-1284, 1995), p21-ras (Fossum et al., Int. J. Cancer 56:40-45, 1994), BCR-abl (Bocchia et al., Blood 85:2680-2684, 1995), p53 (Theobald et al., Proc. Natl. Acad. Sci. U.S.A. 92:11993-11997, 1995), p185 HER2/neu (erb-B1; Fisk et al., J. Exp. Med., 181:2109-2117, 1995), epidermal growth factor receptor (EGFR) (Harris et al., Breast Cancer Res. Treat, 29:1-2, 1994), carcinoembryonic antigens (CEA) (Kwong et al., J. Natl. Cancer Inst., 85:982-990, 1995) U.S. Pat. Nos. 5,756,103; 5,274,087; 5,571,710; 6,071,716; 5,698, 530; 6,045,802; EP 263933; EP 346710; and EP 784483; carcinoma-associated mutated mucins (e.g., MUC-1 gene products; Jerome et al., J. Immunol., 151:1654-1662, 1993); EBNA gene products of EBV (e.g., EBNA-1; Rickinson et al., Cancer Surveys 13:53-80, 1992); E7, E6 proteins of human papillomavirus (Ressing et al., J. Immunol. 154:5934-5943, 1995); prostate specific antigen (PSA; Xue et al., The Prostate 30:73-78, 1997); prostate specific membrane antigen (PSMA; Israeli et al., Cancer Res. 54:1807-1811, 1994); idiotypic epitopes or antigens, for example, immunoglobulin idiotypes or T cell receptor idiotypes (Chen et al., J. Immunol. 153:4775-4787, 1994); KSA (U.S. Pat. No. 5,348,887), kinesin 2 (Dietz, et al., Biochem. Biophys. Res. Commun. 275(3): 731-738, 2000), HIP-55, TGFβ-1 anti-apoptotic factor (Toomey et al., Br. J. Biomed. Sci. 58(3):177-183, 2001), tumor protein D52 (Bryne et al., Genomics 35:523-532, 1996), $H_1FT$, NY-BR-1 (WO 01/47959), NY-BR-62, NY-BR-75, NY-BR-85, NY-BR-87, and NY-BR-96 (Scanlan, M. Serologic and Bioinformatic Approaches to the Identification of Human Tumor Antigens, in Cancer Vaccines 2000, Cancer Research Institute, New York, N.Y.), and/or pancreatic cancer antigens (e.g., SEQ ID NOs: 1-288 of U.S. Pat. No. 7,473, 531). Immunogens may also be derived from or direct the immune response against include TAs not listed above but available to one of skill in the art.

In addition to the specific immunogen sequences listed above, the invention also includes the use of analogs of the sequences. Such analogs include sequences that are, for example, at least 80%, 90%, 95%, or 99% identical to the reference sequences, or fragments thereof. The analogs also include fragments of the reference sequences that include, for example, one or more immunogenic epitopes of the sequences. Further, the analogs include truncations or expansions of the sequences (e.g., insertion of additional/repeat immunodominant/helper epitopes) by, e.g., 1, 2, 3, 4, 5, 6, 7, 8, 9, 10, 11-20, etc., amino acids on either or both ends. Truncation may remove immunologically unimportant or interfering sequences, e.g., within known structural/immunologic domains, or between domains; or whole undesired domains can be deleted; such modifications can be in the ranges 21-30, 31-50, 51-100, 101-400, etc. amino acids. The ranges also include, e.g., 20-400, 30-100, and 50-100 amino acids.

Cocktails

The invention also includes compositions including mixtures of two or more PIVs and/or PIV vectors, as described herein. As discussed above, use of such mixtures or cocktails may be particularly advantageous when induction of immunity to more than one immunogen and/or pathogen is desired. This may be useful, for example, in vaccination against different flaviviruses that may be endemic to the region in which the vaccine recipient resides. This may also be useful in the context of administration of multiple immunogens against the same target.

Non-limiting examples of PIV cocktails included in the invention are those including PIV-JE+PIV-DEN, and PIV-YF+PIV-DEN. In both of these examples, the PIVs for either or both components can be single or dual component PIVs, as described above. In addition, in the case of the PIV-DEN, the PIV can include sequences of just one dengue serotype selected from the group consisting of dengue serotypes 1-4, or the cocktail can include PIVs expressing sequences from two, three, or all four of the serotypes. Further, the TBE/*Borrelia burgdorferi*/tick saliva protein (e.g., 64TRP, Isac, Salp20) vaccines described herein can be based on including the different immunogens within a single PIV or live attenuated flavivirus, or can be based on mixtures of PIVs (or LAVs), which each include one or more of the immunogens. The cocktails of the invention can be formulated as such or can be mixed just prior to administration.

Use, Formulation, and Administration

The invention includes the PIV vectors, PIVs, LAV vectors, and LAVs, as well as corresponding nucleic acid molecules, pharmaceutical or vaccine compositions, and methods of their use and preparation. The PIV vectors, PIVs, LAV vectors, and LAVs of the invention can be used, for example, in vaccination methods to induce an immune response to TBE or other flavivirus, and/or another expressed immunogen, as described herein. These methods can be prophylactic, in which case they are carried out on subjects (e.g., human subjects or other mammalian subjects) not having, but at risk of developing infection or disease caused by TBE or another flavivirus and/or a pathogen from which the other expressed immunogen is derived. The methods can also be therapeutic, in which they are carried out on subjects already having an infection by one or more of the relevant pathogens. Further, the viruses and vectors can be used individually or in combination with one another or other vaccines. The subjects treated according to the methods of the invention include humans, as well as non-human mammals (e.g., livestock, such as, cattle, pigs, horses, sheep, and goats, and domestic animals, including dogs and cats).

Formulation of the PIV vectors, PIVs, LAV vectors, and LAVs of the invention can be carried out using methods that are standard in the art. Numerous pharmaceutically acceptable solutions for use in vaccine preparation are well known and can readily be adapted for use in the present invention by those of skill in this art (see, e.g., *Remington's Pharmaceutical Sciences* (18th edition), ed. A. Gennaro, 1990, Mack Publishing Co., Easton, Pa.). In two specific examples, the PIV vectors, PIVs, LAV vectors, and LAVs are formulated in Minimum Essential Medium Earle's Salt (MEME) containing 7.5% lactose and 2.5% human serum albumin or MEME containing 10% sorbitol. However, the PIV vectors, PIVs, LAV vectors, and LAVs can simply be diluted in a physiologically acceptable solution, such as sterile saline or sterile buffered saline.

The PIV vectors, PIVs, LAV vectors, and LAVs of the invention can be administered using methods that are well known in the art, and appropriate amounts of the viruses and vectors to be administered can readily be determined by those of skill in the art. What is determined to be an appropriate amount of virus to administer can be determined by consideration of factors such as, e.g., the size and general health of the subject to whom the virus is to be administered. For example, in the case of live, attenuated viruses of the invention, the viruses can be formulated as sterile aqueous solutions containing between $10^2$ and $10^8$, e.g., $10^3$ to $10^7$, infectious units (e.g., plaque-forming units or tissue culture infectious doses) in a dose volume of 0.1 to 1.0 ml. PIVs can be administered at similar doses and in similar volumes; PIV titers however are usually measured in, e.g., focus-forming units determined by immunostaining of foci, as these defective constructs tend not to form virus-like plaques. Doses can range between $10^2$ and $10^8$ FFU and administered in volumes of 0.1 to 1.0 ml.

All viruses and vectors of the invention can be administered by, for example, intradermal, subcutaneous, intramuscular, intraperitoneal, or oral routes. In specific examples, dendritic cells are targeted by intradermal or transcutaneous administration, by use of, for example, microneedles or microabrasion devices. Further, the vaccines of the invention can be administered in a single dose or, optionally, administration can involve the use of a priming dose followed by a booster dose that is administered, e.g., 2-6 months later, as determined to be appropriate by those of skill in the art. Optionally, PIV vaccines can be administered via DNA or RNA immunization using methods known to those skilled in the art (Chang et al., Nat. Biotechnol. 26:571-577, 2008; Kofler et al., Proc. Natl. Acad. Sci. U.S.A. 101:1951-1956, 2004).

Optionally, adjuvants that are known to those skilled in the art can be used in the administration of the viruses and vectors of the invention. Adjuvants that can be used to enhance the immunogenicity of the viruses include, for example, liposomal formulations, synthetic adjuvants, such as (e.g., QS21), muramyl dipeptide, monophosphoryl lipid A, polyphosphazine, CpG oligonucleotides, or other molecules that appear to work by activating Toll-like Receptor (TLR) molecules on the surface of cells or on nuclear membranes within cells. Although these adjuvants are typically used to enhance immune responses to inactivated vaccines, they can also be used with live or replication-defective vaccines. Both agonists of TLRs or antagonists may be useful in the case of live or replication-defective vaccines. The vaccine candidates can be designed to express TLR agonists. In the case of a virus delivered via a mucosal route, for example, orally, mucosal adjuvants such as the heat-labile toxin of *E. coli* (LT) or mutant derivations of LT can be used as adjuvants. In addition, genes encoding cytokines that have adjuvant activities can be inserted into the vaccine candidates. Thus, genes encoding desired cytokines, such as GM-CSF, IL-2, IL-12, IL-13, IL-5, etc., can be inserted together with foreign immunogen genes to produce a vaccine that results in enhanced immune responses, or to modulate immunity directed more specifically towards cellular, humoral, or mucosal responses (e.g., reviewed in "Immunopotentiators in Modern Vaccines", Schijns and O'Hagan Eds., 2006, Elsevier Academic Press: Amsterdam, Boston, etc.). Optionally, a patch containing a layer of an appropriate toxin-derived adjuvant, can be t0 applied over the injection site. Toxin promotes local inflammation attracting lymphocytes, which leads to a more robust immune response.

EXAMPLES

Additional details concerning the invention are provided in the Examples, below. In the Examples, experiments are described in which PIVs based on WN, JE, and YF viruses (see, e.g., WO 2007/098267 and WO 2008/137163) were tested. Firstly, we demonstrated that the constructs are significantly more attenuated in a sensitive suckling mouse neurovirulence model (zero mortality at all tested doses) as compared to available LAV controls (YF17D, YF/JE LAV, and YF/WN LAV). We demonstrated for the first time that d-PIV constructs were avirulent in this model and thus that two-component PIVs do not undergo uncontrolled (unlimited) spread in vivo and cannot cause clinical signs. Secondly, we performed comparisons of the immunogenicity and efficacy of the PIVs and the LAVs, and demonstrated that PIV vaccines can induce immune response comparable to LAVs and be equally efficacious (e.g., as observed for PIV-WN and YF/WN LAV pair of vaccines). In one pair examined, YF17D LAV was significantly more immunogenic than PIV-YF. Thus, production of VLPs can vary between different, similarly designed PIV constructs. Specifically, we propose that PIV-YF does not generate a large amount of YF VLPs compared to PIV-WN (WN VLPs), and that increased production of VLPs can be achieved by genetic modifications at the C/prM junction in suboptimal PIV constructs. Specifically, the C/prM junction is an important location in the flavivirus polyprotein orchestrating the formation of viral envelope and synthesis of viral proteins (Yamshchikov and Compans, Virology 192:38-51, 1993; Amberg and Rice, J. Virol. 73:8083-8094, 1999; Stocks and Lobigs, J. Virol. 72:2141-2149, 1998). We propose that secretion of VLPs in PIV infected cells (in contrast to production of viral particles in whole viruses) can be increased by uncoupling of the viral protease and signalase cleavages at the junction, or use of a strong heterologous signal peptide (tPA, etc.) in place of the signal for prM, or by mutagenesis of the signal for prM. The efficiency of signalase cleavage at the C/prM junction of flaviviruses is low (Stocks and Lobigs, J. Virol. 72:2141-2149, 1998), e.g., as predicted by SignalP 3.0 on-line program. It is expected that more efficient cleavage efficiency can be achieved by analysis of specific amino acid substitutions near the cleavage site with SignalP 3.0 (e.g., as described in application WO 2008/100464), followed by incorporation of chosen mutation(s) into PIV genomes, recovery of PIV progeny and measuring VLP secretion. Non-flavivirus signals are inserted by methods standard in the art. Uncoupling between the viral protease and signalase cleavages can be achieved by ablating the viral cleavage site by any non-conservative mutation (e.g., RRS in YF17D C to RRA or GRS or RSS, etc.), or deletion of the entire site or some of its 3 residues. If necessary, formation of free N-terminus of the signal of foreign protein can be achieved by using such elements as autoprotease, or termination codon followed by an IRES. Alternatively, the native AUG initiation codon of C can be ablated (in constructs where C protein sequence is unnecessary, e.g., ΔC PIV) and AUG placed in front of foreign gene. Optimization of vector signal can be performed by random mutagenesis, e.g., by insertion of synthetic randomized sequence followed by identification of viable PIV variants with increased VLP secretion.

We also discovered that PIV constructs were substantially more immunogenic in hamsters when administered by the IP route, as compared to the subcutaneous route. We concluded that this was most likely due to better targeting of antigen presenting cells in lymphoid tissues, which are abundant in the abdomen, but not abundant in tissues underlying the skin. Based on these observations, we concluded that efficient targeting of PIVs to dendritic cells, abundant in the skin, can be achieved by cutaneous inoculation, e.g., via skin microabrasion or intradermal injection using microneedles (Dean et al., Hum Vaccin. 1:106-111, 2005).

Further, we have carried out experiments to show the feasibility of administering mixtures, or cocktails, of different PIVs, such as those described herein (e.g., JE+DEN and YF+DEN). In order to administer cocktails, it is important to verify that there is no interference between co-administered components, and that a balanced immune response is induced. Several PIV mixtures were used to immunize rodents and immune responses were compared to PIV constructs administered individually. No interference was observed in mixtures, and thus cocktail PIV vaccines are feasible. Such formulations may be of particular significance in geographical regions where different flaviviruses co-circulate. This could be also used to simultaneously administer several PIV-based vaccines against non-flavivirus pathogens.

Further, we have demonstrated that no neutralizing antibody response is induced against packaging envelope after at least two doses of PIV (and thus antibodies are elicited against VLPs secreted from infected cells). This was demonstrated using the helper (ΔprM-E) component of a d-PIV (see in FIG. 2) packaged individually, or by measuring neutralizing antibodies to heterologous packaging envelopes (e.g., to the WN envelope used to package PIV-JE in helper cells providing WN-specific C-prM-E proteins in trans). The latter observations support sequential use of different PIV vaccines manufactured in a universal helper packaging cells line, and sequential use of different recombinant PIV-vectored vaccines in the same individual, as discussed above. In addition, we confirmed previous observations that PIV constructs can be stably propagated to high yields in vitro, and that no recombination restoring whole virus occurs after prolonged passaging in substrate cells (Mason et al., Virology 351:432-443, 2006; Shustov et al., J. Virol. 21:11737-11748, 2007).

These and other aspects of the invention are further described in the Examples, below.

Example 1

Pseudoinfectious Virus Platform Development Studies

Attenuation in Suckling Mouse Neurovirulence (NV) Model

Materials used in the studies described below are described in Table 1 and the references cited therein. These include s-PIV-WN (based on wt WN virus strain NY99 sequences), s-PIV-JE, s-PIV-WN/JE (based on wt WN virus backbone and prM-E genes from wt JE virus Nakayama strain), s-PIV-YF/WN (YF17D backbone and prM-E genes from WN virus), and s-PIV-YF (based on YF17D sequences). Additional materials include d-PIV-YF (YF d-PIV, grown in regular BHK cells (Shustov et al., J. Virol. 21:11737-11748, 2007), and two-component d-PIV-WN (grown in regular Vero cells; Suzuki et al., J. Virol. 82:6942-6951, 2008).

Attenuation of these PIV prototypes was compared to LAVs YF17D, a chimeric YF/JE virus, and a chimeric YF/WN virus in suckling mouse NV test (IC inoculation) using highly susceptible 5-day old ICR mice (the chimeric viruses include yellow fever capsid and non-structural sequences, and JE or WN prM-E sequences). None of the animals that received Ply constructs showed clinical signs or died, while mortality was observed in animals inoculated with LAVs (Table 2). The YF17D virus is neurovirulent for mice of all ages, while the chimeric vaccines are not neurovirulent for adult mice, but can cause dose-dependent mortality in more sensitive suckling mice (Guirakhoo et al., Virology 257:363-372, 1999; Arroyo et al., J. Virol. 78:12497-12507, 2004). Accordingly, 90%-100% of suckling mice that received doses as low as 1 PFU of YF17D died. YF/JE and YF/WN LAVs caused partial mortality at much higher doses (>2 $\log_{10}$ PFU and 3 $\log_{10}$ PFU, respectively), with longer average survival time (AST) of animals that died, as expected. Thus, PIV constructs are completely avirulent in this sensitive model (at least 20,000-200,000 times less neurovirulent than the licensed YF17D vaccine).

The YF d-PIV and WN d-PIV caused no mortality or clinical signs. Thus, the two-component PIV variants that theoretically could spread within brain tissue from cells co-infected by both of their components did not cause disease. Moreover, we tried to detect the d-PIVs in the brains of additional animals in this experiment, sacrificed on day 6 post-inoculation by titration, and detected none (brain tissues from 10 and 11 mice that received 4 $\log_{10}$ FFU of YF d-PIV and WN d-PIV, respectively, were homogenized and used for titration). Thus, the d-PIVs did not cause spreading infection characteristic of whole virus. YF/JE LAV has been shown to replicate in the brain of adult ICR mice inoculated by the IC route with a peak titer of ~6 $\log_{10}$ PFU/g on day 6, albeit without clinical signs (Guirakhoo et al., Virology 257:363-372, 1999). Co-infection of cells with components of a d-PIV is clearly a less efficient process than infection with whole virus. The data show that d-PIV replication in vivo is quickly brought under control by innate immune responses (and adaptive responses in older animals).

Immunogenicity/Efficacy in Mice and Hamsters

Immunogenicity/efficacy of the PIV prototypes described above was compared to that of chimeric LAV counterparts and YF17D in mice and Syrian hamsters. The general experiment design is illustrated in FIG. 3 (mice, IP immunization). Experiments in hamsters were performed similarly (plus-minus a few days, SC or IP inoculation with doses indicated below). 3.5-week old ICR mice (for s-PIV-WN and -YF, YF/WN LAV, and YF17D groups) or C57/BL6 mice (for s-PIV-JE and YF/JE LAV groups) were immunized IP with graded doses of PIV constructs (4-6 $\log_{10}$ FFU/dose) or chimeric LAV and YF17D LAV controls (4 $\log_{10}$ PFU). Select P1V-WN, -JE and -YF groups were boosted on day 21 with 5 $\log_{10}$ FFU of corresponding constructs (Table 3). Neutralizing antibody responses were determined in animal sera by standard $PRNT_{50}$ against YF/WN or /JE LAVs, or YF17D viruses. PIV-WN induced very high WN-specific neutralizing antibody responses in all groups, with or without boost, as evidenced by $PRNT_{50}$ titers determined in pools of sera from immunized animals on days 20 and 34, which was comparable to that in the YF/WN LAV control group. Accordingly, animals immunized with both PIV-WN and YF/WN LAV were protected from lethal challenge on day 35 with wt WN virus (IP, 270 $LD_{50}$), but not mock-immunized animals (Table 3). When WN neutralizing antibodies were measured in sera from individual mice, high uniformity of immune responses was observed (FIG. 4). Thus, single-round PIV vaccines can be as immunogenic and efficacious as corresponding LAVs. PIV-JE was also highly immunogenic (black mice), while immunogenicity of PIV-YF was significantly lower compared to the YF17D control (ICR mice). Yet, dose-dependent protection of PIV-YF immunized animals (but not mock-immunized animals) was observed following a severe lethal IC challenge with wt YF strain Asibi virus (500 $LD_{50}$) (Table 3), which is in agreement with the knowledge that neutralizing antibody titers as low 1:10 are protective against flavivirus infections.

The YF17D control virus was highly immunogenic (e.g., $PRNT_{50}$ titer 1:1,280 on day 34), and thus it is able to infect cells and replicate efficiently in vivo, and its envelope is a strong immunogen. Therefore, it is unlikely that low immunogenicity of PIV-YF was due to its inability to infect cells or replicate efficiently in infected cells in vivo. We believe that the low immunogenicity of PIV-YF (e.g., compared to PIV-WN) was most likely due to a low-level production of YF-specific VLPs in PIV-YF infected cells (while VLP secretion is high in PIV-WN infected cells). As discussed above, we propose that immunogenicity of PIV-YF can be significantly increased, e.g., by appropriate modifications at the C/prM junction, e.g., by uncoupling the two protease cleavages that occur at this junction (viral protease and signalase cleavages), and/or by using a strong heterologous signal [e.g., rabies virus G protein signal, or eukaryotic tissue plasminogen activator (tPA) signal (Malin et al., Microbes and Infection, 2:1677-1685, 2000), etc.] in place of the YF signal for prM.

A similar experiment was performed in ~4.5-week old Syrian hamsters, to compare immunogenicity of PIV constructs to LAV controls in this model. Animals were immunized SC with graded doses of the test articles (Table 4). PIV-WN was highly immunogenic, e.g., WN-specific $PRNT_{50}$ titers on day 38 (pre-challenge) were 1:320, 1:640, and 1:1280 in groups that received 5, 6, and 6 (prime)+5 (boost) $\log_{10}$ FFU doses, respectively. This was somewhat lower compared to YF/WN LAV 4 $\log_o$ PFU control (≥1:2560). PIV-JE and -YF induced detectable specific neutralizing antibody responses, albeit with lower titers compared to YF/JE LAV and YF17D controls. All animals immunized with PIV-WN and YF/WN were solidly protected from lethal challenge with wt WN virus as evidenced by the absence of mortality and morbidity (e.g., loss of body weight after challenge), as well as absence or a significant reduction of postchallenge WN virus viremia. Mock-immunized animals were not protected (Table 4). PIV-JE and -WN protected animals from respective challenge in dose-dependent fashion. Protective efficacy in this experiment is additionally illustrated in FIG. 5. For example, high post-challenge YF virus (hamster adapted Asibi strain) viremia was observed in mock immunized animals, peaking on day 3 at a titer of >8 $\log_{10}$ PFU/ml (upper left panel); all of the animals lost weight, and 1 out of 4 died (upper right panel). In contrast, viremia was significantly reduced or absent in hamsters immunized with PIV-YF (two doses; despite relatively low neutralizing titers) or YF17D; none of these animals lost weight. Similarly, animals immunized with PIV-WN or YF/WN LAV were significantly or completely protected in terms of post-challenge WN virus viremia and body weigh loss/mortality, in contrast to mock controls (compare in bottom panels). Thus, high immunogenicity/efficacy of PIV was demonstrated in a second animal model.

In another hamster experiment, animals were immunized with PIV constructs by the IP route, with two doses. Table 5 compares neutralizing immune responses (specific for each vaccine) determined in pooled sera of hamsters in the above-described experiment (SC inoculation) to those after IP immunization, for PIV-WN, -YF/WN, -WN/JE, and -YF after the first dose (days 20-21) and second dose (days 34-38). A clear effect of the immunization route was observed both after the $1^{st}$ and $2^{nd}$ doses. For instance, for PIV-WN after $1^{st}$ dose, SC immunization resulted in WN-specific PRNT50 titer of 1:40, while IP inoculation resulted in much higher titer 1:320 (and after the $2^{nd}$ dose, titers were similar). A more pronounced effect was observed for other constructs after both the $1^{st}$ and $2^{nd}$ doses. Interestingly, PIV-YF/WN was very highly immunogenic by IP route (titer 1:320 after $1^{st}$ IP dose vs. 1:20 by SC, and 1:1,280 after $2^{nd}$ dose vs. 1:160 by SC). Similarly, immunogenicity of PIV-JE was significantly increased (e.g., JE-specific titer of 1:640 after two IP poses). Thus, better targeting of lymphoid cells, specifically antigen-presenting cells (which are more abundant in the abdomen as opposed to tissues under the skin), is an important consideration for use of PIV vaccines. In humans, efficient targeting of dendritic cells of the skin, increasing the magnitude of immune response, can be achieved by intradermal delivery, which we thus propose for a route for PIV immunization of humans.

In the above-described experiments, we also determined whether a neutralizing antibody response was induced against packaging envelopes (as opposed to response to VLPs encoded by PIV constructs and secreted by infected cells). No WN-specific neutralizing antibodies were detected by $PRNT_{50}$ in animals immunized with 5 $\log_{in}$ FFU of the second component of WN d-PIV, containing the ΔC-prM-E deletion and thus not encoding VLPs, but packaged into the WN envelope in BHK-CprME(WN) helper cells, and no YF-specific neutralizing activity was found in sera from animals immunized with 4 $\log_{10}$ FFU of the second component of YF d-PIV packaged in YF envelope. No YF-specific neutralizing response was induced by two doses of PIV-YF/WN packaged into YF envelope, and similarly, no WN-specific response was induced by two doses of PIV-JE packaged into WN envelope. The absence of neutralizing response against packaging envelopes permits manufacturing different PIV vaccines in one (universal) manufacturing helper cell line, or immunization of one individual with different recombinant vaccines based on the same vector, according to the present invention.

PIV Cocktails

Because PIVs undergo a single (optionally several, but limited) round(s) of replication in vivo, we considered that mixtures of different PIV vaccines can be administered without interference between individual constructs in the mixture (cocktail). To elucidate whether PIV vaccines can be used in cocktail formulations, immune responses in mice and hamsters to several PIV constructs given as mixtures were compared to the same constructs given individually. Similar results were obtained in both animal models. Results of mouse experiments are shown in Table 6. Similar anti-JE neutralizing antibody titers were observed in pools of sera from animals that were given one or two doses of either PIV-JE+PIV-WN mixture or PIV-JE alone (1:20 vs. 1:80 and 1:640 vs. 1:160, for one and two doses, respectively). Similarly, WN-specific titers against PIV-JE+PIV-WN mixture and PIV-WN alone were similar (1:320 vs. 1:640 and 1:5,120 vs. 1:5,120 for one and 2 doses, respectively). No or little cross-specific response was induced by either PIV-JE or -WN. The result was also confirmed by measuring $PRNT_{50}$ titers in sera from individual animals. Thus, it is clear that PIV vaccines can be efficiently administered as cocktails, inducing immunity against two or more flavivirus pathogens. In addition, as discussed above, various cocktails can be made between non-flavivirus PIV vaccines, or between any of flavivirus and non-flavivirus PIV vaccines.

In Vitro Studies

Different PIV prototypes were serially passaged up to 10 times in helper BHK cells, for s-PIVs, or in regular Vero cells, for d-PIVs. Samples harvested after each passage were titrated in Vero cells by immunostaining. Constructs grew to high titers, and no recombination restoring whole virus was observed. For instance, PIV-WN consistently grew to titers 7-8 $\log_{10}$ FFU/ml in BHK-CprME(WN) helper cells (containing a VEE replicon expressing the WN virus C-prM-E proteins), and WN d-PIV grew to titers exceeding 8 $\log_{10}$ FFU/ml in Vero cells, without recombination.

Example 2

PIV-TBE

PIV-TBE vaccine candidates can be assembled based entirely on sequences from wt TBE virus or the closely serologically related Langat (LGT) virus (naturally attenuated virus, e.g., wt strain TP-21 or its empirically attenuated variant, strain E5), or based on chimeric sequences containing the backbone (capsid and non-structural sequences) from YF 17D or other flaviviruses, such as WN virus, and the prM-E envelope protein genes from TBE, LGT, or other serologically related flaviviruses from the TBE serocomplex. YF/TBE LAV candidates are constructed based on the backbone from YF 17D and the prM-E genes from TBE or related viruses (e.g., the E5 strain of LGT), similar to other chimeric LAV vaccines.

Construction of PIV-TBE and YF/TBE LAV vaccine prototypes was performed by cloning of appropriate genetic elements into plasmids for PIV-WN (Mason et al., Virology 351:432-443, 2006; Suzuki et al., J. Virol. 82:6942-6951, 2008), or plasmids for chimeric LAVs (e.g., pBSA-AR1, a single-plasmid version of infectious clone of YF/JE LAV; WO 2008/036146), respectively, using standard methods in the art of reverse genetics. The prM-E sequences of TBE virus strain Hypr (GenBank accession number U39292) and LGT strain E5 (GenBank accession number AF253420) were first computer codon-optimized to conform to the preferential codon usage in the human genome, and to eliminate nucleotide sequence repeats longer than 8 nt to ensure high genetic stability of inserts (if determined to be necessary, further shortening of nt sequence repeats can be performed). The genes were chemically synthesized and cloned into plasmids for PIV-WN and YF/JE LAV, in place of corresponding prM-E genes. Resulting plasmids were in vitro transcribed and appropriate cells (Vero for chimeric viruses, and helper BHK cells for PIV) were transfected with RNA transcripts to generate virus/PIV samples.

YF/TBE LAV Constructs

In YF/TBE constructs containing either the TBE Hypr (plasmids p42, p45, and p59) or LGT E5 (plasmid P43) prM-E genes, two different types of the C/prM junction were first examined (see in FIG. 6; C/prM junctions only are shown in Sequence Appendix 1, and complete 5'-terminal sequences covering the 5'UTR-C-prM-E-beginning of NS1 region are shown in Sequence Appendix 2). The p42-derived YF17D/Hypr chimera contained a hybrid YF17D/Hypr signal peptide for the prM protein, while the p45-derived YF17D/Hypr chimera contained a hybrid YF17D/WN signal peptide for prM (Sequence Appendix 1). The former chimeric virus produced very high titers at both P0 (immediately after transfection) and P1 (the next passage in Vero cells), up to 7.9 $\log_{10}$ PFU/ml, which were 0.5 $\log_{10}$ times higher, compared to the latter virus; in addition it formed significantly larger plaques in Vero cells (FIG. 6). Thus, use of TBE-specific residues in the signal peptide for prM conferred a significant growth advantage over the signal containing WN-specific residues. The p43-derived YF17D/LGT chimera had the same prM signal as the p42-derived virus; it also produced very high titers at P0 and P1 passages (up to 8.1 $\log_{10}$ PFU/ml) and formed large plaques. A derivative of the p42-derived virus was also produced from plasmid p59, which contained a strong attenuating mutation characterized previously in the context of a YF/WN LAV vaccine virus, specifically, a 3-a.a. deletion in the YF17D-specific C protein (PSR, residues 40-42 in the beginning of α-Helix 1; WO 2006/116182). As expected, the p59 virus grew to lower titers (5.6 and 6.5 $\log_{10}$ PFU/ml at P0 and P1, respectively), and formed small plaques (determined in a separate titration experiment and thus not shown in FIG. 6), compared to the parent p42-derived chimera. These initial observations of growth properties of YF/TBE LAV prototypes, and correlation of replication in vitro with plaque morphologies, have been confirmed in growth curve experiments (FIG. 8).

PIV-TBE Constructs

PIV-WN/TBE variants were constructed, and packaged PIV samples were derived from plasmids p39 and p40 (FIG. 7; Sequence Appendix 1 for C/prM junction sequences, and Sequence Appendix 3 for complete 5'UTR-ΔC-prM-E-beginning of NS1 sequences). These contained complete Hypr or WN prM signals, respectively. Both PIVs were successfully recovered and propagated in BHK-CprME(WN) or BHK-C (WN) helper cells (Mason et al., Virology 351:432-443, 2006; Widman et al., Vaccine 26:2762-2771, 2008). The P0 and P1 sample titers of the p39 variant were 0.2-1.0 $\log_{10}$ times, higher than p40 variant. In addition, Vero cells infected with p39 variant were stained brighter in immunofluorescence assay using a polyclonal TBE-specific antibody, compared to p40, indicative of more efficient replication (FIG. 7). The higher rate of replication of the p39 candidate than p40 candidate was confirmed in a growth curve experiment (FIG. 8). In the latter experiment, both candidates appeared to grow better in the BHK-C(WN) helper cells compared to BHK-CprME(WN), with the p39 variant reaching titer of ~7 $\log_{10}$ PFU/ml on day 5 (note that peak titers have not been reached). The discovery of the effect of prM signal on replication rates of both PIV and chimeric LAV vaccine candidates, and head-to-head comparison of different signals to generate the most efficiently replicating and immunogenic (see above) construct, are a distinguishing feature of our approach. As discussed above, the invention also includes the use of other flavivirus signals, including with appropriate mutations, the uncoupling the viral protease and signalase cleavages at the C/prM junction, e.g., by mutating or deleting the viral protease cleavage site at the C-terminus of C preceding the prM signal, the use of strong non-flavivirus signals (e.g., tPA signal, etc.) in place of prM signal, as well as optimization of sequences downstream from the signalase cleavage site.

Other PIV-TBE variants based entirely on wt TBE (Hypr strain) and LGT virus (TP21 wild type strain or attenuated E5 strain), and chimeric YF 17D backbone/prM-E (TBE or LGT) sequences are also included in the invention. Helper cells providing appropriate C, C-prM-E, etc., proteins (e.g., TBE-specific) for trans-complementation can be constructed by means of stable DNA transfection or through the use of an appropriate vector, e.g., an alphavirus replicon, such as based on VEE strain TC-83, with antibiotic selection of replicon-containing cells. Vero and BHK21 cells can be used in practice of the invention. The former are an approved substrate for human vaccine manufacture; any other cell line acceptable for human and/or veterinary vaccine manufacturing can be also used. In addition to s-PIV constructs, d-PIV constructs can also be assembled. To additionally ascertain safety for vaccinees and the environment, appropriate modifications can be employed, including the use of degenerate codons and complementary mutations in the 5' and 3' CS elements, to minimize chances of recombination that theoretically could result in viable virus. Following construction, all vaccine candidates can be evaluated in vitro for manufacturability/stability, and in vivo for attenuation and immunogenicity/efficacy, in available pre-clinical animal models, such as those used in development and quality control of TBE and YF vaccines.

Neurovirulence and Neuroinvasiveness in Mice of PIV-TBE and YF/TBE LAV Constructs Young adult ICR mice (~3.5 week-old), were inoculated with graded doses of PIV-TBE and YF/TBE LAV candidates by the IC route to measure neurovirulence, or IP route to measure neuroinvasiveness (and later immunogenicity/efficacy). Animals that received 5 $\log_{10}$ FFU of PIV-Hypr (p39 and p40) variants by both routes survived and showed no signs of sickness, similar to mock-inoculated animals (Table 7), and thus PIV-TBE vaccines are completely avirulent. Mice inoculated IC with YF 17D control (1-3 $\log_{10}$ PFU) showed dose-dependent mortality, while all animals inoculated IP (5 $\log_{10}$ PFU) survived, in accord with the knowledge that YF 17D virus is not neuroinvasive. All animals that received graded IC doses (2-4 $\log_{10}$ PFU) of YF/TBE LAV prototypes p42, p45, p43, and p59 died (moribund animals were humanely euthanized). These variants appear to be less attenuated than YF 17D, e.g., as evidenced by complete mortality and shorter AST at the 2 $\log_{10}$ PFU dose, the lowest dose tested for YF/TBE LAV candidates. The non-neurovirulent phenotype of PIV-TBE, virulent phenotype of YF/TBE LAV and intermediate-virulence phenotype of YF 17D are also illustrated in FIG. 9, showing survival curves of mice after IC inoculation. It should be noted that the p43 (LGT prM-E genes) and p59 (the dC2 deletion variant of YF/Hypr LAV) were less neurovirulent than p42 and p45 YF/Hypr LAV constructs as evidenced by larger AST values for corresponding doses (Table 7). In addition, p43 and p59 candidates were non-neuroinvasive, while p42 and p45 caused partial mortality after IP inoculation (5 $\log_{10}$ PFU/dose) (Table 7; FIG. 10). It should be noted however that all the YF/TBE LAV constructs were significantly attenuated as compared to wt TBE viruses, e.g., compared to wt TBE Hypr virus, which is uniformly highly virulent for mice, both at very low IC ($LD_{50}$~0.1 PFU) and IP ($LD_{50} \le 10$ PFU) doses (Wallner et al., J. Gen. Virol. 77:1035-1042, 1996; Mandl et al., J. Virol. 72:2132-2140, 1998; Mandl et al., J. Gen. Virol. 78:1049-1057, 1997

Immunogenicity/Efficacy of PIV-TBE and YF/TBE LAV Constructs in Mice

TBE-specific neutralizing antibody responses in mice immunized IP with one or two doses of the PIV-TBE or YF/TBE LAV variants described above, or a human formalin-inactivated TBE vaccine control (1:30 of human dose) are being measured. Animals have been challenged with a high IP dose (500 PFU) of wt Hypr TBE virus; morbidity (e.g., weight loss), and mortality after challenge are monitored.

Immunogenicity/Efficacy of PIV-TBE and YF/TBE LAV Constructs in Mice

TBE-specific neutralizing antibody responses in mice immunized IP with one or two doses of the PIV-TBE or YF/TBE LAV variants described above (from experiment in Table 7), or a human formalin-inactivated TBE vaccine control (1:20 of human dose; one or two doses), or YF 17D and mock controls, were measured on day 20 by $PRNT_{50}$ against wt TBE Hypr virus (Table 8; second dose of indicated test articles was given on day 14). [Titers were determined in individual sera, or pooled sera from two animals in most cases, or pooled sera from 4 animals for the YF17D and Mock negative controls]. Titers in individual test samples as well as GMTs for each group are provided in Table 8. Titers in test samples were similar within each group, e.g., in groups immunized with PIVs, indicating high uniformity of immune response in animals. As expected, no TBE-specific neutralizing antibodies were detected in negative control groups (YF 17D and Mock; GMTs <1:10); accordingly, animals in these groups were not protected from challenge on day 21 post-immunization with a high IP dose (500 PFU) of wt Hypr TBE virus. Mortalities from partial observation (on day 9 post-challenge; observation being continued) are provided in Table 8, and dynamics of average post-challenge body weights indicative of morbidity are shown in FIG. 11. Neutralizing antibodies were detected in killed vaccine controls, which were particularly high after two doses (GMT 1:1,496); animals in the 2-dose group were completely protected in that there was no mortality or body weight loss (but not animals in the 1-dose group). Animals that received both one and two doses of PIV-Hypr p39 had very high antibody titers (GMTs 1:665 and 1:10,584) and were solidly protected, demonstrating that robust protective immunity can be induced by s-PIV-TBE, defective vaccine. The two animals that survived immunization with YF/Hypr p42 chimera (see in Table 7) also had high antibody titers (GMT 1:6,085) and were protected (Table 8; FIG. 11). Interestingly, PIV-Hypr p40 and YF/Hypr p45 were poorly immunogenic (GMTs 1:15 and 1:153 for one and two doses, and 1:68, respectively). As discussed above, these contained WN-specific sequences in the signal for prM, while the highly immunogenic PIV-Hypr p39 and YF/Hypr p42 constructs contained TBE-specific signal sequences. In agreement with discussion above, this result demonstrates the importance of choosing the right prM signal, e.g., the TBE-specific signal, to achieve high-level replication/VLP secretion, which in this experiment in vivo resulted in drastically different immune responses. Immunogenicity of YF/LGT p43 and YF/Hypr dC2 p59 chimeras was relatively low which could be expected, because of the use of a heterologous envelope (LGT, different from challenge TBE virus) and high attenuating effect of the dC2 deletion, respectively.

Example 3

Foreign Gene Expression

In the examples of recombinant PIV constructs described below, genes of interest were codon optimized (e.g., for efficient expression in a target vaccination host) and to eliminate long nt sequence repeats to increase insert stability (≥8 nt long; additional shortening of repeats can be performed if necessary), and then chemically synthesized. The genes were cloned into PIV-WN vector plasmids using standard methods of molecular biology well known in the art, and packaged PIVs were recovered following in vitro transcription and transfection of appropriate helper (for s-PIVs) or regular (for d-PIVs) cells.

Expression of Rabies Virus G Protein in WN s-PIV and d-PIV

Rabies virus, Rhabdoviridae family, is a significant human and veterinary pathogen. Despite the availability of several (killed) vaccines, improved vaccines are still needed for both veterinary and human use (e.g. as an inexpensive pre-exposure prophylactic vaccines). Rabies virus glycoprotein G mediates entry of the virus into cells and is the main immunogen. It has been expressed in other vectors with the purpose of developing veterinary vaccines (e.g., Pastoret and Brochier, Epidemio. Infect. 116:235-240, 1996; Li et al., Virology 356:147-154, 2006).

Full length rabies virus G protein (original Pasteur virus isolate, GenBank accession number NC_001542) was codon-optimized, chemically synthesized, and inserted adjacent to the ΔC, ΔprM-E and ΔC-prM-E deletions in PIV-WN vectors (FIG. 12). The sequences of constructs are provided in Sequence Appendix 4. General designs of the constructs are illustrated in FIG. 13. The entire G protein containing its own signal peptide was inserted in-frame downstream from the WN C protein either with the ΔC deletion (ΔC and ΔC-prM-E constricts) or without (ΔprM-E) and a few residues from the prM signal. Foot and mouth disease virus (FMDV) 2A autoprotease was placed downstream from the transmembrane C-terminal anchor of G to provide cleavage of C-terminus of G from the viral polyprotein during translation. The FMDV 2A element is followed by WN-specific signal for prM and prM-E-NS1-5 genes in the ΔC construct, or signal for NS1 and NS1-5 genes in ΔprM-E and ΔC-prM-E constructs.

Packaged WN(ΔC)-rabiesG, WN(ΔprME)-rabiesG, and WN(ΔCprME)-rabiesG PIVs were produced by transfection of helper BHK cells complementing the PIV vector deletion [containing a Venezuelan equine encephalitis virus (strain TC-83) replicon expressing WN virus structural proteins for trans-complementation]. Efficient replication and expression of rabies G protein was demonstrated for the three constructs by transfection/infection of BHK-C(WN) and/or BHK-C-prM-E(WN) helper cells, as well as regular BHK cells, by immunostaining and immunofluorescence assay (IFA) using anti-Rabies G monoclonal antibody (RabG-Mab) (FIG. 14). Titers were determined in Vero cells by immunostaining with the Mab or an anti-WN virus polyclonal antibody. Growth curves of the constructs in BHK-CprME(WN) cells after transfection with in vitro RNA transcripts are shown in FIG. 14, bottom panels. The PIVs grew efficiently to titers ~6 to >7 $\log_{10}$ FFU/ml. Importantly, nearly identical titers were detected by both RabG-Mab and WN-antibody staining, which was the first evidence of genetic stability of the insert. In PIV-infected Vero cells, which were fixed but not permeabilized, strong membrane staining was observed by RabG-Mab staining, demonstrating that the product was efficiently delivered to the cell surface (FIG. 15). The latter is known to be the main prerequisite for high immunogenicity of expressed G. Individual packaged PIVs can spread following infection of helper BHK cells, but cannot spread in regular cells as illustrated for WN(ΔC)-rabiesG PIV in FIG. 16. The fact that there is no spread in naïve BHK cells demonstrates that the recombinant RNA genomes cannot be non-specifically packaged into membrane vesicles containing the G protein, if produced by PIV infected cells. An identical result was obtained with the G protein of another rhabdovirus, Vesicular stomatitis virus (VSV), contrary to previous observations of non-specific packaging of Semliki Forest virus (SFV) replicon expressing VSV G protein (Rolls et al., Cell 79:497-506, 1994). The latter is a desired safety feature. [Alternatively, some non-specific packaging could result in a limited spread of PIV in vivo, potentially enhancing anti-rabies immune response. The latter could be also a beneficial feature, given that such PIV is demonstrated to be safe]. The stability of the rabies G insert in the three PIVs was demonstrated by serial passages in helper BHK-CprME(WN) cells at high or low MOI (0.1 or 0.001 FFU/cell). At each passage, cell supernatants were harvested and titrated in regular cells (e.g., Vero cells) using immunostaining with an anti-WN polyclonal antibody to determine total PIV titer, or anti-rabies G monoclonal antibody to determine titer of particles containing the G gene (illustrated for MOI 0.1 in FIG. 17; similar results were obtained at MOI 0.001). The WN(ΔC)-rabiesG PIV was stable for 5 passages, while the titer of insert-containing PIV started declining at passage 6, indicative of insert instability. This could be expected, because in this construct, large G gene insert (~1500 nt) is combined with a small ΔC deletion (~200 nt), significantly increasing the overall size of the recombinant RNA genome. In contrast, in WN(ΔprME)-rabiesG, and WN(ΔCprME)-rabiesG PIVs, the insert is combined with a much larger deletion (~2000 nt). Therefore, these constructs stably maintained the insert for all 10 passages examined (FIG. 17). Further, it can be seen in FIG. 17 that at some passages, titers as high as 8 $\log_{10}$ FFU/ml, or higher, were attained for all three PIVs, additionally demonstrating that PIVs can be easily propagated to high yields.

Following inoculation in vivo individually, the WN(ΔC)-rabiesG s-PIV is expected to induce strong neutralizing antibody immune responses against both rabies and WN viruses, as well as T-cell responses. The WN(ΔprME)-rabiesG and WN(ΔCprME)-rabiesG PIVs will induce humoral immune response only against rabies because they do not encode the WN prM-E genes. WN(ΔC)-rabiesG s-PIV construct can be also co-inoculated with WN(ΔprME)-rabiesG construct in a d-PIV formulation (see in FIG. 12), increasing the dose of expressed G protein, and with enhanced immunity against both pathogens due to limited spread. As an example of spread, titration results in Vero cells of a s-PIV sample, WN(ΔprME)-rabiesG, and a d-PIV sample, WN(ΔprME)-rabiesG+WN(ΔC) PIV (the latter did not encode rabies G protein), are shown in FIG. 18. Infection of naïve Vero cells with s-PIV gave only individual cells stainable with RabG-Mab (or small clusters formed due to division of cells). In contrast, large foci were observed following infection with the d-PIV sample (FIG. 18, right panel) that were products of coinfection with the two PIV types.

The WN(ΔCprME)-rabiesG construct can be also used in a d-PIV formulation, if it is co-inoculated with a helper genome providing C-prM-E in trans (see in FIG. 12). For example it can be a WN virus genome containing a deletion of one of the NS proteins, e.g., NS1, NS3, or NS5, which are known to be trans-complementable (Khromykh et al., J. Virol. 73:10272-10280, 1999; Khromykh et al., J. Virol. 74:3253-3263, 2000). We have constructed a WN-ΔNS1 genome (sequence provided in Sequence Appendix 4) and obtained evidence of co-infection with WN(ΔprME)-rabiesG or WN(ΔCprME)-rabiesG constructs, and spread in vitro, by immunostaining. In the case of such d-PIVs, rabies G protein can be also inserted and expressed in helper genome, e.g., WN-ΔNS1 genome, to increase the amount of expressed rabies G protein resulting in an increased anti-rabies immune response. As with any dPIV versions, one immunogen can be from one pathogen (e.g., rabies G) and the other from a second pathogen, resulting in three antigenic specificities of vaccine. As discussed above, ΔNS1 deletions can be replaced with or used in combination with ΔNS3 and/or ΔNS5 deletions/mutations, in other examples.

Expression of RSV F Protein in WN s-PIV and d-PIV

Respiratory syncytial virus (RSV), member of Paramyxoviridae family, is the leading cause of severe respiratory tract disease in young children worldwide (Collins and Crowe, Respiratory Syncytial Virus and Metapneumovirus, In: Knipe et al. Eds., Fields Virology, 5$^{th}$ ed., Philadelphia: Wolters Kluwer/Lippincott Williams and Wilkins, 2007:1601-1646). Fusion protein F of the virus is a lead viral antigen for developing a safe and effective vaccine. To avoid post-vaccination exacerbation of RSV infection observed previously with a formalin-inactivated vaccine candidate, a balanced Th1/Th2 response to F is required which can be achieved by better TLR stimulation, a prerequisite for induction of high-affinity antibodies (Delgado et al., Nat. Med. 15:34-41, 2009), which should be achievable through delivering F in a robust virus-based vector. We have previously demonstrated the capacity of yellow fever virus-based chimeric LAV vectors to induce a strong, balanced Th1/Th2 response in vivo against an influenza antigen (WO 2008/036146). In the present invention, both yellow fever virus-based chimeric LAVs and PIV vectors are used for delivering RSV F to induce optimal immune response profile. Other LAVs and PIV vectors described herein can also be used for this purpose.

Full-length RSV F protein of A2 strain of the virus (GenBank accession number P03420) was codon optimized as described above, synthesized, and cloned into plasmids for PIV-WN s-PIV and d-PIV, using the insertion schemes shown in FIGS. 12 and 13 for rabies G protein, by applying standard methods of molecular biology. Exact sequences of the insertions and surrounding genetic elements are provided in Sequence Appendix 5. In vitro RNA transcripts of resulting WN(ΔC)-RSV F, WN(ΔprME)-RSV F, and WN(ΔCprME)-RSV F PIV constructs were used to transfect helper BHK-CprME(WN) cells. Efficient replication and expression of RSV F protein was first demonstrated by immunostaining of transfected cells with an anti-RSV F Mab, as illustrated for the WN(ΔprME)-RSV F construct in FIG. 19. The presence of packaged PIVs in the supernatants from transfected cells (titer as high as 7 log10 FFU/ml) was determined by titration in Vero cells with immunostaining. Additionally, similar constructs can be used that contain a modified full length F protein gene. Specifically, the N-terminal native signal peptide of F is replaced in modified F protein with the one from rabies virus G protein. The modification is intended to elucidate whether the use of a heterologous signal can increase the rate of F protein synthesis and/or replication of PIVs.

TABLE 1

PIV prototype constructs used in platform development studies

| Construct | Genetic composition | Packaged in |
|---|---|---|
| PIV-WN | wt NY99 WN virus | WN envelope; BHK-CprME(WN) or BHK-C(WN) helper cells (Mason et al., Virology 2006, 351: 432-43; Widman et al., Vaccine 2008, 26: 2762-71) |
| PIV-YF/WN | Envelope (VLP): wt WN NY99 Backbone: YF 17D | YF 17D envelope; BHK-CprME(YF) helper cells (Widman et al., Adv Virus Res. 2008, 72: 77-126) |
| PIV-WN/JE | Envelope (VLP): wt JE Nakayama Backbone: wt WN NY99 | JE or WN envelope; BHK-C(WN) or BHK-CprME(WN) helper cells (Ishikawa et al., Vaccine 2008, 26: 2772-8) |
| PIV-YF | YF 17D | YF 17D envelope; BHK-CprME(YF) or BHK-C(YF) helper cells (Mason et al., Virology 2006, 351: 432-43) |

TABLE 2

Safety: Suckling mouse neurovirulence[1]

| Construct | Doses (log$_{10}$) | Mortality (%) | AST (days)[2] |
|---|---|---|---|
| PIV-YF | 1-4 | 0/10 (0%) | na |
| PIV-WN | 2-5 | 0/10 (0%) | na |
| PIV-WN/JE | 1-4 | 0/11 (0%) | na |

TABLE 2-continued

Safety: Suckling mouse neurovirulence[1]

| Construct | Doses ($\log_{10}$) | Mortality (%) | AST (days)[2] |
|---|---|---|---|
| PIV-YF/WN | 1-4 | 0/10-11 (0%) | na |
| WN d-PIV | 1-4 | 0/10-11 (0%) | na |
| YF d-PIV | 1-4 | 0/10 (0%) | na |
| YF17D | 2 | 10/10 (100%) | 7.6 |
|  | 1 | 10/10 (100%) | 9.3 |
|  | 0 | 9/10 (90%) | 9.9 |
|  | −1 | 3/10 (30%) | 9.6 |
| YF/JE | 4 | 9/11 (82%) | 9.7 |
|  | 3 | 7/10 (70%) | 12.3 |
|  | 2 | 3/11 (27%) | 12 |
|  | 1 | 0/11 (0%) | na |
| YF/WN | 3 | 2/11 (18%) | 12.5 |
|  | 0-2 | 0/10-11 (0%) | na |

[1]Single dose, IC inoculation, ICR 5-day old mice, graded log doses administered.
[2]AST for mice that died; na, not applicable.

TABLE 3

PIV highly immunosenic and efficacious in mice[1]

| Group | Dose | PRNT Day 20 | PRNT Day 34 | Post-challenge mortality (%) |
|---|---|---|---|---|
| PIV-WN | $10^5$ | 640 | 1280 | 0/8 (0%) |
| | $10^6$ | 1280 | 2560 | 1/8 (12.5%) |
| | $10^6 + 10^5$ | 2560 | 2560 | 0/6 (0%) |
| YF/WN control | $10^4$ | 1280 | 2560 | 1/8 (12.5%) |
| PIV-WN/JE | $10^4$ | 10 | 20 | N/D |
| | $10^5$ | 20 | 20 | N/D |
| | $10^5 + 10^5$ | 20 | 160 | N/D |
| YF/JE control | $10^4$ | 160 | 320 | N/D |
| PIV-YF | $10^4$ | <10 | <10 | 8/8 (100%) |
| | $10^5$ | <10 | <10 | 5/7 (71%) |
| | $10^5 + 10^5$ | 10 | 10 | 2/5 (40%) |
| YF17D control | $10^4$ | 640 | 1280 | 0/7 (0%) |
| Mock control | | | | |
| WN challenge | Diluent | N/D | 0 | 7/7 (100%) |
| YF challenge | Diluent | N/D | 0 | 8/8 (100%) |

[1]IP immunization (d 0 prime, and d 21 boost in select groups); challenge on d 35: wt WN NY99, 3 $log_{10}$ PFU IP, 270 LD50; wt YF Asibi, 3 $log_{10}$ PFU IC, 500 LD50; N/D, not determined.

TABLE 4

PIV are immunogenic in hamsters and protect against challenge[1]

| Group | Dose(s) | PRNT Day 38 | POST-CHALLENGE Mortality | Morbidity | Peak viremia (log) |
|---|---|---|---|---|---|
| PIV-WN | $10^5$ | 320 | 0/5 (0%) | 0/5 (0%) | 2.3 |
| | $10^6$ | 640 | 0/5 (0%) | 0/5 (0%) | 1.8 |
| | $10^6 + 10^5$ | 1280 | 0/5 (0%) | 0/5 (0%) | <1.3 |
| YF/WN control | $10^4$ | ≥2560 | 0/5 (0%) | 0/5 (0%) | <1.3 |
| PIV-WN/JE | $10^4$ | 20 | 2/5 (40%) | 2/5 (40%) | 2.2 |
| | $10^5 + 10^5$ | 40 | 0/5 (0%) | 0/5 (0%) | <1.3 |
| YF/JE control | $10^4$ | 2560 | 0/5 (0%) | 0/5 (0%) | 1.3 |
| PIV-YF | $10^4$ | <10 | 1/3 (33%) | 3/3 (100%) | 8.3 |
| | $10^5$ | <10 | 1/5 (20%) | 4/5 (80%) | 8.3 |
| | $10^5 + 10^5$ | 20 | 0/4 (0%) | 0/4 (0%) | 2.5 |
| YF17D control | $10^4$ | ≥2560 | 0/4 (0%) | 0/4 (0%) | <1.3 |
| Mock control | | | | | |
| WN challenge | Diluent | <10 | 3/4 (75%) | 4/4 (100%) | 4.0 |
| YF challenge | Diluent | <10 | 1/4 (25%) | 4/4 (100%) | 8.4 |
| JE challenge | Diluent | <10 | 2/5 (40%) | 2/5 (40%) | 3.0 |

[1]Syrian hamsters, SC inoculation (d 0, and d 21 in select groups); challenge (d 39): wt WN NY385/99 6 $log_{10}$ PFU IP, wt JE Nakayama 5.8 $log_{10}$ PFU IC, or hamster-adapted YF Asibi 7 $log_{10}$ PFU IP (McArthur et al., J. Virol. 77: 1462-1468, 2003; McArthur et al., Virus Res. 110: 65-71, 2005).

TABLE 5

Immunization of hamsters with PIV: comparison of SC and IP routes

| Inoculums | PRNT Day 20-21 SC | PRNT Day 20-21 IP | Boost ($log_{10}$) | PRNT Day 34-38 SC | PRNT Day 34-38 IP |
|---|---|---|---|---|---|
| PIV-WN | 40 | 320 | 5 | 1280 | 1280 |
| PIV-YF/WN | 10 | 320 | 5 | 160 | 1280 |
| PIV-WN/JE | 10 | 80 | 5 | 40 | 640 |
| PIV-YF | <10 | 10 | 5 | 20 | 80 |

TABLE 6

Immune responses to PIV cocktails (mice)[1]

| Group | Dose | PRNT Day 20 Anti-JE | PRNT Day 20 Anti-WN | PRNT Day 34 Anti-JE | PRNT Day 34 Anti-WN |
|---|---|---|---|---|---|
| PIV-WN/JE + RV-WN | $10^5 + 10^5$ | 20 | 320 | 640 | 5120 |
| PIV-WN/JE alone | $10^5$ | 80 | <10 | 160 | 20 |
| PIV-WN alone | $10^5$ | <10 | 640 | <10 | 5120 |
| Mock | — | <10 | <10 | <10 | <10 |

[1]C57/BL6 mice, IP inoculations on days 0 and 21; pooled serum PRNT liters.

TABLE 7

Neurovirulence (IC inoculation) and neuroinvasiveness (IP inoculation) of PIV-TBE and YF/TBE vaccine constructs in adult ICR mice

| Construct | Neurovirulence (IC route) | | | Neuroinvasiveness (IP route) | | |
|---|---|---|---|---|---|---|
| | Dose(s) ($\log_{10}$) | Mortality (%) | AST, days[1] | Dose(s) ($\log_{10}$) | Mortality (%) | AST, days[1] |
| PIV-Hypr p39 | 5 | 0/7 (0%) | na | 5 | 0/16 (0%) | na |
| PIV-Hypr p40 | 5 | 0/6 (0%) | na | 5 | 0/16 (0%) | na |
| YF/Hypr p42 | 4 | 8/8 (100%) | 6.3 | 5 | 6/8 (75%) | 13.3 |
| | 3 | 8/8 (100%) | 6.4 | | | |
| | 2 | 8/8 (100%) | 7.4 | | | |
| YF/LGT p43 | 4 | 8/8 (100%) | 7.9 | 5 | 0/8 (0%) | na |
| | 3 | 8/8 (100%) | 7.6 | | | |
| | 2 | 8/8 (100%) | 8.4 | | | |
| YF/Hypr p45 | 4 | 8/8 (100%) | 6.1 | 5 | 5/8 (62.5%) | 11.2 |
| | 3 | 8/8 (100%) | 6.6 | | | |
| | 2 | 8/8 (100%) | 6.8 | | | |
| YF/Hypr dC2 p59 | 4 | 8/8 (100%) | 6.6 | 5 | 0/8 (0%) | na |
| | 3 | 8/8 (100%) | 7.4 | | | |
| | 2 | 8/8 (100%) | 8.1 | | | |
| YF 17D | 3 | 8/8 (100%) | 9 | 5 | 0/8 (0%) | na |
| | 2 | 7/8 (87.5%) | 9.6 | | | |
| | 1 | 4/8 (50%) | 10 | | | |
| Mock (diluent) | none | 0/8 (0%) | na | none | 0/8 (0%) | na |

[1] AST for mice that died.

TABLE 8

Neutralizing antibody titers ($PRNT_{50}$) in mice immunized IP (determined against wt TBE virus Hypr), and protection from challenge (postchallenge observation, day 9)

| Immunogen | Dose(s), $\log_{10}$ | $PRNT_{50}$ titer, individ. samples[1] | $PRNT_{50}$ GMT | Postchallenge mortality (%) on day 9[2] |
|---|---|---|---|---|
| PIV-Hypr p39, 1 dose | 5 | 1746 (2) | 665 | 0/8 (0%) |
| | | 1187 (2) | | |
| | | 164 (2) | | |
| | | 574 (2) | | |
| PIV-Hypr p39, 2 doses | 5 + 5 | 16229 (2) | 10,584 | 0/8 (0%) |
| | | 12928 (2) | | |
| | | 12927 (2) | | |
| | | 4627 (2) | | |
| PIV-Hypr p40, 1 dose | 5 | <10 (2) | 15 | 6/8 (75%) |
| | | <10 (2) | | |
| | | 18 (2) | | |
| | | 33 (2) | | |
| PIV-Hypr p40, 2 doses | 5 + 5 | 169 (2) | 153 | 1/8 (12.5%) |
| | | 638 (2) | | |
| | | 26 (2) | | |
| | | 192 (2) | | |
| YF/Hypr p42 | 5 | 9210 (1) | 6,085 | 0/2 (0%) |
| | | 4020 (1) | | |
| YF/LGT p43 | 5 | 123 (2) | 64 | 1/8 (12.5%) |
| | | 32 (2) | | |
| | | 96 (2) | | |
| | | 45 (2) | | |
| YF/Hypr p45 | 5 | 292 (2) | 68 | 0/3 (0%) |
| | | 16 (1) | | |
| YF/Hypr dC2 p59 | 5 | 194 (2) | 68 | 0/8 (0%) |
| | | 93 (2) | | |
| | | 45 (2) | | |
| | | 26 (2) | | |
| Killed human TBE vaccine, 1 dose (at 1/20 of human dose) | 1/20 | 19 (2) | 12 | 1/8 (12.5%) |
| | | <10 (2) | | |
| | | 13 (2) | | |
| | | <10 (2) | | |
| Killed human TBE vaccine, 2 doses (each at 1/20 of human dose) | 1/20 + 1/20 | 3435 (2) | 1,496 | 0/6 (0%) |
| | | 1267 (2) | | |
| | | 770 (2) | | |
| YF 17D control | 5 | <10 (4) | <10 | 5/8 (62.5%) |
| | | 11 (4) | | |

TABLE 8-continued

Neutralizing antibody titers (PRNT$_{50}$) in mice immunized IP (determined against wt TBE virus Hypr), and protection from challenge (postchallenge observation, day 9)

| Immunogen | Dose(s), log$_{10}$ | PRNT$_{50}$ titer, individ. samples[1] | PRNT$_{50}$ GMT | Postchallenge mortality (%) on day 9[2] |
|---|---|---|---|---|
| Mock | none | <10 (4) <br> <10 (4) | <10 | 4/8 (50%) |

[1]Numbers in parenthesis correspond to number of mice in each pooled serum sample tested.
[2]Mortalities on day 9 are shown.

TABLE 9

Examples of published attenuating E protein mutations that can be used for attenuation of chimeric TBE LAV candidates

| Residue | Domain | Comments | Attenuation in | Reference |
|---|---|---|---|---|
| N52R | II | DI-DII hinge, possibly involved in hinge motion required for fusion activation | JE, YF | Hasegawa et al, 1992, Schlesinger et al, 1996 |
| E84K | II | conserved, E in TBE, K/R in others, attenuated by passage in *Ixodes ricinus* ticks, DII contains flavivirus cross reactive epitopes | TBE | Labuda et al, 1994 |
| E85K | II | conserved, E in TBE, K/R in others, attenuation obtained as plaque variants in Vero cells, DII contains flavivirus cross reactive epitopes | JE | Wu et al, 1997 |
| H104K | II | within highly conserved fusion peptide (aa 98-113), H in TBE, G in others | TBE | Rey et al, 1995 |
| L107F | II | within highly conserved fusion peptide (aa 98-113), L in all flaviviruses, F in attenuated JE | TBE, JE, WN | Rey et al, 1995, Arroyo et al, 1999, 2004 |
| T123K | II | DI-DII hinge, T in TBE, A in KFD | TBE | Holzmann et al, 1997 |
| K126E | II | DI-DII hinge, K in TBE, E in D-2 | DEN2 | Bray, 98 |
| K136E | II | DI-DII hinge, K in TBE and JE, E in D-2 | JE | |
| N154L(Y) | I | glycosylation site, packed with conserved H 104, involved in fusion. | DEN2, DEN4, YF | Guirakhoo et al, 1993, Pletnev et al, 1993, Kawano et al, 1993, Jennings et al, 1994 |
| K171E | I | external edge of DI, involved in fusion | TBE | Mandl, 1989, Holzmann, 1997 |
| I173T | | external edge of DI, involved in fusion | YF | Chambers and Nickells 2001 |
| D181Y | | DI-DII hinge | TBE | Holzmann et al, 1997 |
| K204R | | Lining Hydrophobic pocket, involve in fusion | DEN1, DEN3 | Guirakhoo et al, 2004 |
| P272S | II | highly conserved, junction of one the of 2 alpha helices | JE | Cecilia et al, 1991 |
| G308N | III | cell attachment, DKT in TBE, EGS in KFD, T-X in others, change to N produced glycosylation site in LI and reduced virulence N-X-T/S glycosylation motif | LI | Jiang et al, 1993, Gao et al, 1994 |
| S310K | III | putative cell attachment, change from E to G in JE reduced virulence | JE | Jiang et al, 1993, Gao et al, 1994 Wu et al, 1997 |
| K311E | III | highly conserved, putative cell attachment | TBE, YF | Rey et al, 1995, Jennings, 1994 |
| T333L | III | putative cell attachment | YF, LGT | Raynman et al, 1998 |
| G334K | III | putative cell attachment | YF | Chambers and Nickells, 2001 |
| S335K | III | putative cell attachment | JE | Wu et al, 1997 |
| K336D | III | putative cell attachment | JE | Cecilia and Gould, 1991 |
| P337D | III | putative cell attachment | JE | Cecilia and Gould, 1991 |
| G368R | III | putative cell attachment | TBE, JE | Holzman et al 1997, Hasegawa et al 1992 |
| Y384H | III | change to H attenuated TBE, putative cell attachment, −3 position to deleted RGD in TBE | TBE | Holzmann et al, 1990 |
| V385R | III | conserved, −2 position to deleted RGD in TBE, putative cell attachment | D2 | Hiramatsu et al, 1996, Lobigs, 1990 |
| G386R | III | highly conserved, −1 position to deleted RGD in TBE, putative cell attachment | D2, MVE | Hiramatsu, 1996, Lobigs et al, 1990 |
| E387R | III | conserved, +2 position to deleted RGD in TBE, putative cell attachment | D2, MVE | Hiramatsu, 1996, Lobigs et al, 1990 |
| F403K | none | highly conserved, C-terminal region not included in crystal structure sE | D-2, D-4 | Kawano et al, 1993, Bray et al, 1998 |
| H438Y | None | highly conserved, C-terminal region not included in crystal structure sE | LGT | Campbell and Pletnev 2000 |

TABLE 9-continued

Examples of published attenuating E protein mutations that can be used for attenuation of chimeric TBE LAV candidates

| Residue | Domain | Comments | Attenuation in | Reference |
|---------|--------|----------|----------------|-----------|
| H496R | none | highly conserved, C-terminal region not included in crystal structure sE | TBE | Gritsun et al, 2001 |

References: Hasegawa et al., Virology 191(1): 158-165; Schlesinger et al., J. Gen. Virol. 1996, 77 (Pt 6): 1277-1285, 1996; Labuda et al., Virus Res. 31(3): 305-315, 1994; Wu et al., Virus Res. 51(2): 173-181, 1997; Holzmann et al., J. Gen. Virol. 78 (Pt 1): 31-37, 1997; Bray et al., J. Virol. 72(2): 1647-1651, 1998; Guirakhoo et al., Virology 194(1): 219-223, 1993; Pletnev et al., J. Virol. 67(8): 4956-4963, 1993; Kawano et al., J. Virol. 67(11): 6567-6575, 1993; Jennings et al., J. Infect. Dis. 169(3): 512-518, 1994; Mandl et al., J. Virol. 63(2): 564-571, 1989; Chambers et al., J. Virol. 75(22): 10912-10922, 2001; Cecilia et al., Virology 181(1): 70-77, 1991; Jiang et al., J. Gen. Virol. 74 (Pt 5): 931-935, 1993; Gao et al., J. Gen. Virol. 75 (Pt 3): 609-614, 1994; Holzmann et al., J. Virol. 64(10): 5156-5159, 1990; Hiramatsu et al., Virology 224(2): 437-445, 1996; Lobigs et al., Virology 176(2): 587-595, 1990; Campbell et al., Virology 269(1): 225-237, 2000; Gritsun et al., J. Gen. Virol. 82(Pt 7): 1667-1675, 2001.

SEQUENCE APPENDIX 1

CV-TBEV Hypr or CV-LGT E5 with YFV/TBEV chimeric signal (p42, p59, and p43 constructs)

```
                    YF17D partial signal
                    ----------------------------------------
                                                    TBEV partial signal
                                                    -------------------------
                                                                    Hypr or LGT E5
    C protein YF17D                                                 protein prM
    --------------                                                  -------------
      R   K   R   R   S   H   D   V   L   T   V   Q   F   L   I   L   G   M   L   G   M   T   I   A   A   T   V   R
401 A GGAAACGCCG TTCCCATGAT GTTCTGACTG TGCAATTCCT AATTTTGGGC ATGCTGGGCA TGACAATCGC AGCTACGGTT CGC
    T CCTTTGCGGC AAGGGTACTA CAAGACTGAC ACGTTAAGGA TTAAAACCCG TACGACCCGT ACTGTTAGCG TCGATGCCAA GCG
```

CV-TBEV Hypr with YFV/WNV chimeric signal (p45)

```
    C protein YF17D                                 WNV partial signal
    --------------                                  -------------------------
                                                                    Hypr prM
                    YF 17D partial signal                           protein
                    ----------------------------------------        -------------
      R   K   R   R   S   H   D   V   L   T   V   Q   F   L   I   L   G   M   L   A   C   V   G   A   A   T   V   R
401 A GGAAACGCCG TTCCCATGAT GTTCTGACTG TGCAATTCCT AATTTTGGGC ATGCTGGCTT GTGTCGGAGC AGCTACCGTG CGA
    T CCTTTGCGGC AAGGGTACTA CAAGACTGAC ACGTTAAGGA TTAAAACCCG TACGACCGAA CACAGCCTCG TCGATGGCAC GCT
```

RV-WNV/TBEV Hypr with TBEV signal (p39)

```
                    TBEV signal
                    --------------------------------------------------------------------
                                                                    Hypr prM
    WNV C protein                                                   protein
    -------------                                                   -------------
      Q   K   K   R   G   G   T   D   W   M   S   W   L   L   V   I   G   M   L   G   M   T   I   A   A   T   V   R
201 CAAAAGAAA CGGGGGGGAA CAGACTGGAT GAGCTGGCTG CTCGTAATCG GCATGCTGGG CATGACAATC GCAGCTACGG TTCGC
    GTTTTCTTT GCCCCCCCTT GTCTGACCTA CTCGACCGAC GAGCATTAGC CGTACGACCC GTACTGTTAG CGTCGATGCC AAGCG
```

RV-WNV/TBEV Hypr with WNV signal (p40)

```
                    WNV signal
                    ------------------------------------------------------------
                                                                    Hypr
    WNV C protein                                                   prM protein
    -------------                                                   -------------
      Q   K   K   R   G   G   K   T   G   I   A   V   M   I   G   M   L   A   C   V   G   A   A   T   V   R
201 CAAAAGAAA CGCGGGGGAA AGACAGGCAT AGCTGTGATG ATAGGCATGC TGGCTTGTGT CGGAGCAGCT ACCGTGCGA
    GTTTTCTTT GCGCCCCCTT TCTGTCCGTA TCGACACTAC TATCCGTACG ACCGAACACA GCCTCGTCGA TGGCACGCT
```

SEQUENCE APPENDIX 2

CV-TBEV Hypr with YFV/TBEV chimeric signal (p42)

```
                                            5' UTR
      ------------------------------------------------------------------------------------
   1  AGTAAATCCT GTGTGCTAAT TGAGGTGCAT TGGTCTGCAA ATCGAGTTGC TAGGCAATAA ACACATTTGG ATTAATTTTA
      TCATTTAGGA CACACGATTA ACTCCACGTA ACCAGACGTT TAGCTCAACG ATCCGTTATT TGTGTAAACC TAATTAAAAT
             5' UTR
      --------------------
      ATCGTTCGTT GAGCGATTAG
      TAGCAAGCAA CTCGCTAATC

5' UTR
      ------------------                                       C protein
                                            ---------------------------------------------------------------------
                         M   S   R   K   A   Q   G   K   T   L   G   V   N   M   V   R   R   G   V   R
 101  CAGAGAACTG ACCAGAACAT GTCTGGTCGT AAAGCTCAGG GAAAAACCCT GGGCGTCAAT ATGGTACGAC GAGGAGTTCG
      GTCTCTTGAC TGGTCTTGTA CAGACCAGCA TTTCGAGTCC CTTTTTGGGA CCCGCAGTTA TACCATGCTG CTCCTCAAGC
             C protein
      ---------------------
       S   L   S   N   K   I   K •
      CTCCTTGTCA AACAAAATAA
      GAGGAACAGT TTGTTTTATT C protein
      ------------------------------------------------------------------------------------
      •  Q   K   T   K   Q   I   G   N   R   P   G   P   S   R   G   V   Q   G   F   I   F   F   F   L   F   N
 201  AACAAAAAAC AAAACAAATT GGAAACAGAC CTGGACCTTC AAGAGGTGTT CAAGGATTTA TCTTTTTCTT TTTGTTCAAC
      TTGTTTTTTG TTTTGTTTAA CCTTTGTCTG GACCTGGAAG TTCTCCACAA GTTCCTAAAT AGAAAAAGAA AAACAAGTTG
             C protein
      ---------------------
       I   L   T   G   K   K   I •
      ATTTTGACTG GAAAAAAGAT
      TAAAACTGAC CTTTTTTCTA C protein
      ------------------------------------------------------------------------------------
      •  T   A   H   L   K   R   L   W   K   M   L   D   P   R   Q   G   L   A   V   L   R   K   V   K   R   V   V
 301  CACAGCCCAC CTAAAGAGGT TGTGGAAAAT GCTGGACCCA AGACAAGGCT TGGCTGTTCT AAGGAAAGTC AAGAGAGTGG
      GTGTCGGGTG GATTTCTCCA ACACCTTTTA CGACCTGGGT TCTGTTCCGA ACCGACAAGA TTCCTTTCAG TTCTCTCACC
             C protein
      ---------------------
       A   S   L   M   R   G
      TGGCCAGTTT GATGAGAGGA
      ACCGGTCAAA CTACTCTCCT YF17D partial signal
                                  ----------------------------------------
                                                                                THEV partial signal
                                                                          ---------------------------
             C protein
      ----------------------
       L   S   S   R   K   R   R   S   H   D   V   L   T   V   Q   F   L   I   L   G   M   L   G   M   T   I   A
 401  TTGTCCTCAA GGAAACGCCG TTCCCATGAT GTTCTGACTG TGCAATTCCT AATTTTGGGC ATGCTGGGCA TGACAATCGC
      AACAGGAGTT CCTTTGCGGC AAGGGTACTA CAAGACTGAC ACGTTAAGGA TTAAAACCCG TACGACCCGT ACTGTTAGCG
             prM protein
      ----------------------
       A   T   V   R   K   E   R •
      AGCTACGGTT CGCAAGGAAA
      TCGATGCCAA GCGTTCCTTT prM protein
      ------------------------------------------------------------------------------------
      •  D   G   S   T   V   I   R   A   E   G   K   D   A   A   T   Q   V   R   V   E   N   G   T   C   V   I
 501  GAGACGGCAG TACGGTCATA CGCGCGGAAG GTAAGGATGC CGCTACCCAA GTGAGAGTGG AAAATGGTAC CTGCGTCATT
      CTCTGCCGTC ATGCCAGTAT GCGCGCCTTC CATTCCTACG GCGATGGGTT CACTCTCACC TTTTACCATG GACGCAGTAA
             prM protein
      ---------------------
       L   A   T   D   M   G   S •
      CTGGCCACCG ACATGGGCTC
      GACCGGTGGC TGTACCCGAG
```

SEQUENCE APPENDIX 2-continued

```
                                       prM protein
      ------------------------------------------------------------------------------------
      • W  C  D   D  S  L  S   Y  E  C   V  T  I   D  Q  G  E   E  P  V   D  V  D   C  F  C  R
  601 TTGGTGTGAT GATAGCCTTT CTTATGAGTG CGTAACCATA GATCAAGGTG AGGAACCTGT TGACGTTGAT TGCTTCTGCC
      AACCACACTA CTATCGGAAA GAATACTCAC GCATTGGTAT CTAGTTCCAC TCCTTGGACA ACTGCAACTA ACGAAGACGG
             prM protein
      ---------------------
         N  V  D   G  V  Y
      GAAACGTGGA TGGGGTGTAT
      CTTTGCACCT ACCCCACATA prM protein
      ------------------------------------------------------------------------------------
        L  E  Y  G   R  C  G   K  Q  E   G  S  R  T   R  R  S   V  L  I   P  S  H  A   Q  G  E
  701 CTCGAATATG GACGGTGTGG TAAACAAGAA GGAAGCAGAA CCAGACGCTC AGTGCTTATA CCCTCCCACG CTCAAGGAGA
      GAGCTTATAC CTGCCACACC ATTTGTTCTT CCTTCGTCTT GGTCTGCGAG TCACGAATAT GGGAGGGTGC GAGTTCCTCT
            prM protein
      ---------------------
         L  T  G   R  G  H  K •
      GCTGACCGGA CGGGGACATA
      CGACTGGCCT GCCCCTGTAT prM protein
      ------------------------------------------------------------------------------------
      • W  L  E   G  D  S   L  R  T  H   L  T  R   V  E  G   W  V  W  K   N  R  L   L  A  L
  801 AATGGTTGGA GGGCGACTCA CTCCGAACAC ATTTGACCCG CGTCGAGGGC TGGGTCTGGA AAAATCGGCT GTTGGCCCTC
      TTACCAACCT CCCGCTGAGT GAGGCTTGTG TAAACTGGGC GCAGCTCCCG ACCCAGACCT TTTTAGCCGA CAACCGGGAG
              prM protein
      ---------------------
         A  M  V  T   V  V  W •
      GCTATGGTGA CAGTCGTTTG
      CGATACCACT GTCAGCAAAC Hypr E
                                                                                     Protein
                                                                                     ----------
                                       prM protein
      ------------------------------------------------------------------------------------
      • L  T  L   E  S  V  V   T  R  V   A  V  L   V  V  L  L   C  L  A   P  V  Y   A  S  R  C
  901 GCTCACGCTG GAGTCTGTGG TTACTCGCGT GGCAGTGCTG GTGGTGCTCC TCTGTCTTGC CCCTGTCTAC GCGTCCAGGT
      CGAGTGCGAC CTCAGACACC AATGAGCGCA CCGTCACGAC CACCACGAGG AGACAGAACG GGACAGATG CGCAGGTCCA
           Hypr E protein
      ---------------------
         T  H  L   E  N  R
      GTACTCATTT GGAAAACAGA
      CATGAGTAAA CCTTTTGTCT Hypr E protein
      ------------------------------------------------------------------------------------
         D  F  V  T   G  T  Q   G  T  T   R  V  T  L   V  L  E   L  G  G   C  V  T  I   T  A  E
 1001 GATTTTGTCA CCGGCACCCA GGGGACGACT CGGGTAACCC TGGTGCTTGA ACTGGGTGGT TGCGTTACTA TTACCGCTGA
      CTAAAACAGT GGCCGTGGGT CCCCTGCTGA GCCCATTGGG ACCACGAACT TGACCCACCA ACGCAATGAT AATGGCGACT
            Hypr E protein
      ---------------------
         G  K  P   S  M  D  V •
      GGGCAAACCC TCTATGGATG
      CCCGTTTGGG AGATACCTAC Hypr E protein
      ------------------------------------------------------------------------------------
      • W  L  D   A  I  Y   Q  E  N  P   A  Q  T   R  E  Y   C  L  H  A   K  L  S   D  T  K
 1101 TGTGGCTGGA TGCAATCTAT CAGGAGAATC CCGCACAAAC CAGGGAATAT TGCCTTCACG CAAAGCTGTC CGATACAAAG
      ACACCGACCT ACGTTAGATA GTCCTCTTAG GGCGTGTTTG GTCCCTTATA ACGGAAGTGC GTTTCGACAG GCTATGTTTC
           Hypr E protein
      ---------------------
         V  A  A  R   C  P  T •
      GTCGCGGCTA GGTGCCCAAC
      CAGCGCCGAT CCACGGGTTG Hypr E protein
      ------------------------------------------------------------------------------------
      • M  G  P   A  T  L  A   E  E  H   Q  G  G   T  V  C  K   R  D  Q   S  D  R   G  W  G  N
 1201 AATGGGACCG GCCACCCTGG CGGAGGAACA TCAGGGAGGT ACAGTGTGCA AACGGGACCA GAGTGATAGA GGCTGGGGTA
      TTACCCTGGC CGGTGGGACC GCCTCCTTGT AGTCCCTCCA TGTCACACGT TTGCCCTGGT CTCACTATCT CCGACCCCAT
            Hypr E protein
      ---------------------
         H  C  G   L  F  G
      ATCACTGCGG CCTGTTCGGC
      TAGTGACGCC GGACAAGCCG
```

SEQUENCE APPENDIX 2-continued

```
                                            Hypr E protein
         -----------------------------------------------------------------------------------
          K  G  S  I  V  A  C   V  K  A   A  C  E   A  K  K   A  T  G   H  V  Y  D   A  N  K
    1301 AAAGGAAGTA TTGTCGCTTG CGTCAAGGCA GCCTGTGAGG CCAAAAAGAA GGCTACTGGG CACGTCTATG ACGCCAACAA
         TTTCCTTCAT AACAGCGAAC GCAGTTCCGT CGGACACTCC GGTTTTTCTT CCGATGACCC GTGCAGATAC TGCGGTTGTT
             Hypr E protein
         ---------------------
          I   V  Y   T  V  K  V•
         GATCGTTTAT ACAGTGAAAG
         CTAGCAAATA TGTCACTTTC Hypr E protein
         -----------------------------------------------------------------------------------
          •  E  P  H   T  G  D   Y  V  A  A   N  E  T   H  S  G   R  K  T  A   S  F  T   V  S  S
    1401 TGGAACCACA CACAGGGGAT TACGTGGCGG CCAACGAGAC TCATTCCGGT CGCAAAACGG CCAGCTTCAC CGTGTCATCC
         ACCTTGGTGT GTGTCCCCTA ATGCACCGCC GGTTGCTCTG AGTAAGGCCA GCGTTTTGCC GGTCGAAGTG GCACAGTAGG
             Hypr E protein
         ---------------------
          E  K  T   I   L  T  M•
         GAAAAGACCA TCCTCACTAT
         CTTTTCTGGT AGGAGTGATA Hypr E protein
         -----------------------------------------------------------------------------------
          •G  E  Y    G  D  V  S   L  L  C   R  V  A   S  G  V  D   L  A  Q   T  V  I   L  E  L  D
    1501 GGGGGAGTAT GGCGACGTTT CTCTGCTCTG CCGGGTGGCT AGCGGAGTCG ACCTGGCCCA GACAGTCATC CTGGAACTGG
         CCCCCTCATA CCGCTGCAAA GAGACGAGAC GGCCCACCGA TCGCCTCAGC TGGACCGGGT CTGTCAGTAG GACCTTGACC
             Hypr E protein
         ---------------------
          K  T  V    E  H  L
         ATAAAACAGT TGAGCATCTG
         TATTTTGTCA ACTCGTAGAC Hypr E protein
         -----------------------------------------------------------------------------------
          P  T  A  W   Q  V  H   R  D  W   F  N  D  L   A  L  P   W  K  H   E  G  A  R   N  W  N
    1601 CCTACCGCTT GGCAGGTGCA CAGGGATTGG TTTAACGACC TTGCCCTGCC ATGGAAACAT GAAGGAGCGA GAAACTGGAA
         GGATGGCGAA CCGTCCACGT GTCCCTAACC AAATTGCTGG AACGGGACGG TACCTTTGTA CTTCCTCGCT CTTTGACCTT
             Hypr E protein
         ---------------------
          N  A  E   R  L  V  E•
         TAATGCAGAG CGACTCGTAG
         ATTACGTCTC GCTGAGCATC Hypr E protein
         -----------------------------------------------------------------------------------
          •  F  G  A    P  H  A   V  K  M  D   V  Y  N   L  G  D   Q  T  G  V   L  L  K   A  L  A
    1701 AATTCGGTGC CCCTCATGCC GTGAAGATGG ACGTCTACAA TCTGGGTGAT CAGACCGGCG TTCTCCTTAA AGCTCTCGCT
         TTAAGCCACG GGGAGTACGG CACTTCTACC TGCAGATGTT AGACCCACTA GTCTGGCCGC AAGAGGAATT TCGAGAGCGA
             Hypr E protein
         ---------------------
          G  V  P   V   A  H  I•
         GGCGTACCAG TTGCCCACAT
         CCGCATGGTC AACGGGTGTA Hypr E protein
         -----------------------------------------------------------------------------------
          •E  G  T    K  Y  H  L   K  S  G   H  V  T   C  E  V  G   L  E  K   L  K  M   K  G  L  T
    1801 CGAAGGAACG AAGTACCACC TGAAGTCAGG CCATGTAACT TGCGAGGTGG GCCTGGAGAA GTTGAAAATG AAAGGTCTTA
         GCTTCCTTGC TTCATGGTGG ACTTCAGTCC GGTACATTGA ACGCTCCACC CGGACCTCTT CAACTTTTAC TTTCCAGAAT
             Hypr E protein
         ---------------------
          Y  T  M   C  D  K
         CGTACACAAT GTGTGACAAG
         GCATGTGTTA CACACTGTTC Hypr E protein
         -----------------------------------------------------------------------------------
          T  K  F  T   W  K  R   A  P  T   D  S  G  H   D  T  V   V  M  E   V  T  F  S   G  T  K
    1901 ACCAAGTTCA CATGGAAGAG GGCCCCCACA GATAGCGGCC ACGATACTGT GGTGATGGAG GTGACCTTTT CTGGAACAAA
         TGGTTCAAGT GTACCTTCTC CCGGGGGTGT CTATCGCCGG TGCTATGACA CCACTACCTC CACTGGAAAA GACCTTGTTT
             Hypr E protein
         ---------------------
          P  C  R   I  P  V  R•
         ACCCTGCAGA ATACCCGTGC
         TGGGACGTCT TATGGGCACG
```

SEQUENCE APPENDIX 2-continued

Hypr E protein
```
         A   V   A   H   G   S   P   D   V   N   V   A   M   L   I   T   P   N   P   T   I   E   N   N   G   G
2001 GGGCTGTAGC TCACGGATCT CCCGATGTCA ATGTTGCTAT GCTGATTACA CCTAACCCTA CCATCGAGAA TAACGGTGGT
     CCCGACATCG AGTGCCTAGA GGGCTACAGT TACAACGATA CGACTAATGT GGATTGGGAT GGTAGCTCTT ATTGCCACCA
```
Hypr E protein
```
      G   F   I   E   M   Q   L•
     GGTTTTATTG AGATGCAGCT
     CCAAAATAAC TCTACGTCGA
```

Hypr E protein
```
     •P   P   G   D   N   I   I   Y   V   G   E   L   S   Y   Q   W   F   Q   K   G   S   S   I   G   R   V   F
2101 TCCGCCAGGC GATAACATCA TCTACGTGGG CGAACTCTCT TACCAGTGGT TTCAGAAAGG GAGTTCAATT GGGCGGGTCT
     AGGCGGTCCG CTATTGTAGT AGATGCACCC GCTTGAGAGA ATGGTCACCA AAGTCTTTCC CTCAAGTTAA CCCGCCCAGA
```
Hypr E protein
```
      Q   K   T   K   K   G
     TCCAAAAAAC GAAGAAGGGA
     AGGTTTTTTG CTTCTTCCCT
```

Hypr E protein
```
      I   E   R   L   T   V   I   G   E   H   A   W   D   F   G   S   A   G   G   F   L   S   S   I   G   K   A
2201 ATCGAACGAT TGACGGTTAT CGGCGAGCAC GCATGGGATT TTGGTTCCGC AGGGGGATTC CTGTCTTCTA TTGGTAAGGC
     TAGCTTGCTA ACTGCCAATA GCCGCTCGTG CGTACCCTAA AACCAAGGCG TCCCCCTAAG GACAGAAGAT AACCATTCCG
```
Hypr E protein
```
      L   H   T   V   L   G   G•
     ACTGCATACC GTGCTGGGGG
     TGACGTATGG CACGACCCCC
```

Hypr E protein
```
     •A   F   N   S   I   F   G   G   V   G   F   L   P   K   L   L   G   V   A   L   A   W   L   G   L
2301 GCGCATTCAA TTCTATTTTC GGGGGCGTGG GGTTCCTGCC TAAACTCCTG CTGGGAGTAG CCCTGGCCTG GTTGGGACTG
     CGCGTAAGTT AAGATAAAAG CCCCCGCACC CCAAGGACGG ATTTGAGGAC GACCCTCATC GGGACCGGAC CAACCCTGAC
```
Hypr E protein
```
      N   M   R   N   P   T   M•
     AATATGCGGA ATCCGACGAT
     TTATACGCCT TAGGCTGCTA
```

Hypr E protein                                                                         NS1 gene
                                                                                       of YF17D
```
     •S   M   S   F   L   L   A   G   V   L   V   L   A   M   T   L   G   V   G   A   D   Q   G   C   A   I   N
2401 GTCCATGTCA TTCCTCTTGG CCGGCGTGCT TGTACTGGCC ATGACACTGG GCGTTGGCGC CGATCAAGGA TGCGCCATCA
     CAGGTACAGT AAGGAGAACC GGCCGCACGA ACATGACCGG TACTGTGACC CGCAACCGCG GCTAGTTCCT ACGCGGTAGT
```
NS1 gene of YF17D
```
      F   G   K   R   E   L
     ACTTTGGCAA GAGAGAGCTC
     TGAAACCGTT CTCTCTCGAG
```

---

CV-TBEV Hypr with YFV/WNV chimeric signal (p45)

5' UTR
```
   1 AGTAAATCCT GTGTGCTAAT TGAGGTGCAT TGGTCTGCAA ATCGAGTTGC TAGGCAATAA ACACATTTGG ATTAATTTTA
     TCATTTAGGA CACACGATTA ACTCCACGTA ACCAGACGTT TAGCTCAACG ATCCGTTATT TGTGTAAACC TAATTAAAT
```
5' UTR
```
     ATCGTTCGTT GAGCGATTAG
     TAGCAAGCAA CTCGCTAATC
```

5' UTR
                                                                C protein YF17D
```
                            M   S   G   R   K   A   Q   G   K   T   L   G   V   N   M   V   R   R   G   V   R
 101 CAGAGAACTG ACCAGAACAT GTCTGGTCGT AAAGCTCAGG GAAAAACCCT GGGCGTCAAT ATGGTACGAC GAGGAGTTCG
     GTCTCTTGAC TGGTCTTGTA CAGACCAGCA TTTCGAGTCC CTTTTTGGGA CCCGCAGTTA TACCATGCTG CTCCTCAAGC
```
C protein YF17D
```
      S   L   S   N   K   I   K•
     CTCCTTGTCA AACAAAATAA
```

SEQUENCE APPENDIX 2-continued

```
GAGGAACAGT TTGTTTTATT
```

C protein YF17D
    ------------------------------------------------------------------------------------------
    • Q   K   T   K   Q   I   G   N   R   P   G   P   S   R   G   V   Q   G   F   I   F   F   F   L   F   N
201 AACAAAAAC AAAACAAATT GGAAACAGAC CTGGACCTTC AAGAGGTGTT CAAGGATTTA TCTTTTTCTT TTTGTTCAAC
    TTGTTTTTG TTTTGTTTAA CCTTTGTCTG GACCTGGAAG TTCTCCACAA GTTCCTAAAT AGAAAAAGAA AACAAGTTG
        C protein YF17D
    ---------------------
    I   L   T   G   K   K   I•
    ATTTTGACTG GAAAAAAGAT
    TAAAACTGAC CTTTTTTCTA C protein YF17D
    ------------------------------------------------------------------------------------------
    • T   A   H   L   K   R   L   W   K   M   L   D   P   R   Q   G   L   A   V   L   R   K   V   K   R   V   V
301 CACAGCCCAC CTAAAGAGGT TGTGGAAAAT GCTGGACCCA AGACAAGGCT TGGCTGTTCT AAGGAAAGTC AAGAGAGTGG
    GTGTCGGGTG GATTTCTCCA ACACCTTTTA CGACCTGGGT TCTGTTCCGA ACCGACAAGA TTCCTTTCAG TTCTCTCACC
        C protein YF17D
    --------------------
    A   S   L   M   R   G
    TGGCCAGTTT GATGAGAGGA
    ACCGGTCAAA CTACTCTCCT C protein YF17D                                           WNV partial signal
    -----------------------                                       --------------------------
                                    YF 17D partial signal
                                   ------------------------------------------
    L   S   S   R   K   R   R   S   H   D   V   L   T   V   Q   F   L   I   L   G   M   L   A   C   V   G   A
401 TTGTCCTCAA GGAAACGCCG TTCCCATGAT GTTCTGACTG TGCAATTCCT AATTTTGGGC ATGCTGGCTT GTGTCGGAGC
    AACAGGAGTT CCTTTGCGGC AAGGGTACTA CAAGACTGAC ACGTTAAGGA TTAAAACCCG TACGACCGAA CACAGCCTCG
        Hypr prM protein
    ---------------------
    A   T   V   R   K   E   R•
    AGCTACCGTG CGAAAAGAAC
    TCGATGGCAC GCTTTTCTTG Hypr prM protein
    ------------------------------------------------------------------------------------------
    • D   G   S   T   V   I   R   A   E   G   K   D   A   A   T   Q   V   R   V   E   N   G   T   C   V   I
501 GCGACGGAAG CACCGTGATA AGGGCTGAGG GTAAGGATGC GGCTACGCAG GTGAGAGTAG AGAATGGCAC TTGCGTAATA
    CGCTGCCTTC GTGGCACTAT TCCCGACTCC CATTCCTACG CCGATGCGTC CACTCTCATC TCTTACCGTG AACGCATTAT
        Hypr prM protein
    ---------------------
    L   A   T   D   M   G   S•
    CTCGCGACTG ATATGGGATC
    GAGCGCTGAC TATACCCTAG Hypr prM protein
    ------------------------------------------------------------------------------------------
    • W   C   D   D   S   L   S   Y   E   C   V   T   I   D   Q   G   E   E   P   V   D   V   D   C   F   C   R
601 CTGGTGTGAC GATAGCCTCA GTTATGAATG CGTAACAATA GACCAGGGCG AAGAACCTGT GGACGTTGAC TGTTTCTGTA
    GACCACACTG CTATCGGAGT CAATACTTAC GCATTGTTAT CTGGTCCCGC TTCTTGGACA CCTGCAACTG ACAAAGACAT
        Hypr prM protein
    ---------------------
    N   V   D   G   V   Y
    GAAATGTGGA TGGCGTTTAT
    CTTTACACCT ACCGCAAATA Hypr prM protein
    ------------------------------------------------------------------------------------------
    L   E   Y   G   R   C   G   K   Q   E   G   S   R   T   R   R   S   V   L   I   P   S   H   A   Q   G   E
701 CTGGAGTACG GCCGCTGTGG AAAACAGGAG GGCTCACGAA CTCGAAGATC TGTGCTGATT CCAAGTCACG CGCAAGGAGA
    GACCTCATGC CGGCGACACC TTTTGTCCTC CCGAGTGCTT GAGCTTCTAG ACACGACTAA GGTTCAGTGC GCGTTCCTCT
        Hypr prM protein
    ---------------------
    L   T   G   R   G   H   K•
    GTTGACCGGT AGAGGCCACA
    CAACTGGCCA TCTCCGGTGT Hypr prM protein
    ------------------------------------------------------------------------------------------
    • W   L   E   G   D   S   L   R   T   H   L   T   R   V   E   G   W   V   W   K   N   R   L   L   A   L
801 AGTGGCTTGA AGGGGACTCA TTGAGGACCC ACCTGACTAG GGTGGAGGGT TGGGTTTGGA AGAATCGGTT GCTCGCGCTC
    TCACCGAACT TCCCCTGAGT AACTCCTGGG TGGACTGATC CCACCTCCCA ACCCAAACCT TCTTAGCCAA CGAGCGCGAG
        Hypr prM protein
    ---------------------
    A   M   V   T   V   V   W•
    GCTATGGTCA CCGTCGTGTG
    CGATACCAGT GGCAGCACAC SEQUENCE APPENDIX 2-continued

```
                                       Hypr prM protein
-------------------------------------------------------------------------------
                                                                      Hypr E
                                                                      Protein
                                                                      ----------
       • L  T  L    E  S  V  V    T  R  V    A  V  L    V  V  L  L    C  L  A    P  V  Y    A  S  R  C
 901  GCTGACACTG  GAGAGTGTCG  TGACTCGGGT  TGCTGTGTTG  GTTGTCCTCC  TCTGTTTGGC  CCCAGTGTAC  GCGTCCAGGT
      CGACTGTGAC  CTCTCACAGC  ACTGAGCCCA  ACGACACAAC  CAACAGGAGG  AGACAAACCG  GGGTCACATG  CGCAGGTCCA
          Hypr E protein
      --------------------
         T  H  L    E  N  R
      GTACTCATTT  GGAAAACAGA
      CATGAGTAAA  CCTTTTGTCT Hypr E protein
-------------------------------------------------------------------------------
         D  F  V  T    G  T  Q    G  T  T    R  V  T  L    V  L  E    L  G  G    C  V  T  I    T  A  E
1001  GATTTTGTCA  CCGGCACCCA  GGGGACGACT  CGGGTAACCC  TGGTGCTTGA  ACTGGGTGGT  TGCGTTACTA  TTACCGCTGA
      CTAAAACAGT  GGCCGTGGGT  CCCCTGCTGA  GCCCATTGGG  ACCACGAACT  TGACCCACCA  ACGCAATGAT  AATGGCGACT
          Hypr E protein
      --------------------
         G  K  P    S  M  D  V•
      GGGCAAACCC  TCTATGGATG
      CCCGTTTGGG  AGATACCTAC Hypr E protein
-------------------------------------------------------------------------------
       • W  L  D    A  I  Y    Q  E  N  P    A  Q  T    R  E  Y    C  L  H  A    K  L  S    D  T  K
1101  TGTGGCTGGA  TGCAATCTAT  CAGGAGAATC  CCGCACAAAC  CAGGGAATAT  TGCCTTCACG  CAAAGCTGTC  CGATACAAAG
      ACACCGACCT  ACGTTAGATA  GTCCTCTTAG  GGCGTGTTTG  GTCCCTTATA  ACGGAAGTGC  GTTTCGACAG  GCTATGTTTC
          Hypr E protein
      --------------------
         V  A  A  R    C  P  T•
      GTCGCGGCTA  GGTGCCCAAC
      CAGCGCCGAT  CCACGGGTTG Hypr E protein
-------------------------------------------------------------------------------
       • M  G  P    A  T  L    A  E  E  H    Q  G  G    T  V  C  K    R  D  Q    S  D  R    G  W  G  N
1201  AATGGGACCG  GCCACCCTGG  CGGAGGAACA  TCAGGGAGGT  ACAGTGTGCA  AACGGGACCA  GAGTGATAGA  GGCTGGGGTA
      TTACCCTGGC  CGGTGGGACC  GCCTCCTTGT  AGTCCCTCCA  TGTCACACGT  TTGCCCTGGT  CTCACTATCT  CCGACCCCAT
          Hypr E protein
      --------------------
         H  C  G    L  F  G
      ATCACTGCGG  CCTGTTCGGC
      TAGTGACGCC  GGACAAGCCG Hypr E protein
-------------------------------------------------------------------------------
         K  G  S  I    V  A  C    V  K  A    A  C  E  A    K  K  K    A  T  G    H  V  Y  D    A  N  K
1301  AAAGGAAGTA  TTGTCGCTTG  CGTCAAGGCA  GCCTGTGAGG  CCAAAAAGAA  GGCTACTGGG  CACGTCTATG  ACGCCAACAA
      TTTCCTTCAT  AACAGCGAAC  GCAGTTCCGT  CGGACACTCC  GGTTTTTCTT  CCGATGACCC  GTGCAGATAC  TGCGGTTGTT
          Hypr E protein
      --------------------
         I  V  Y    T  V  K  V•
      GATCGTTTAT  ACAGTGAAAG
      CTAGCAAATA  TGTCACTTTC Hypr E protein
-------------------------------------------------------------------------------
       • E  P  H    T  G  D    Y  V  A  A    N  E  T    H  S  G    R  K  T  A    S  T  V    S  S
1401  TGGAACCACA  CACAGGGGAT  TACGTGGCGG  CCAACGAGAC  TCATTCCGGT  CGCAAAACGG  CCAGCTTCAC  CGTGTCATCC
      ACCTTGGTGT  GTGTCCCCTA  ATGCACCGCC  GGTTGCTCTG  AGTAAGGCCA  GCGTTTTGCC  GGTCGAAGTG  GCACAGTAGG
          Hypr E protein
      --------------------
         E  K  T    I  L  T  M•
      GAAAAGACCA  TCCTCACTAT
      CTTTTCTGGT  AGGAGTGATA Hypr E protein
-------------------------------------------------------------------------------
       • G  E  Y    G  D  V  S    L  L  C    R  V  A    S  G  V  D    L  A  Q    T  V  I    L  E  L  D
1501  GGGGGAGTAT  GGCGACGTTT  CTCTGCTCTG  CCGGGTGGCT  AGCGGAGTCG  ACCTGGCCCA  GACAGTCATC  CTGGAACTGG
      CCCCCTCATA  CCGCTGCAAA  GAGACGAGAC  GGCCCACCGA  TCGCCTCAGC  TGGACCGGGT  CTGTCAGTAG  GACCTTGACC
          Hypr E protein
      --------------------
         K  T  V    E  H  L
      ATAAAACAGT  TGAGCATCTG
      TATTTTGTCA  ACTCGTAGAC
```

SEQUENCE APPENDIX 2-continued

```
                                       Hypr E protein
     ------------------------------------------------------------------------------------
       P   T   A   W   Q   V   H   R   D   W   F   N   D   L   A   L   P   W   K   H   E   G   A   R   N   W   N
1601 CCTACCGCTT GGCAGGTGCA CAGGGATTGG TTTAACGACC TTGCCCTGCC ATGGAAACAT GAAGGAGCGA GAAACTGGAA
     GGATGGCGAA CCGTCCACGT GTCCCTAACC AAATTGCTGG AACGGGACGG TACCTTTGTA CTTCCTCGCT CTTTGACCTT
         Hypr E protein
         --------------------
       N   A   E   R   L   V   E•
     TAATGCAGAG CGACTCGTAG
     ATTACGTCTC GCTGAGCATC Hypr E protein
     ------------------------------------------------------------------------------------
     •  F   G   A   P   H   A   V   K   M   D   V   Y   N   L   G   D   Q   T   G   V   L   L   K   A   L   A
1701 AATTCGGTGC CCCTCATGCC GTGAAGATGG ACGTCTACAA TCTGGGTGAT CAGACCGGCG TTCTCCTTAA AGCTCTCGCT
     TTAAGCCACG GGGAGTACGG CACTTCTACC TGCAGATGTT AGACCCACTA GTCTGGCCGC AAGAGGAATT TCGAGAGCGA
         Hypr E protein
         --------------------
       G   V   P   V   A   H   I•
     GGCGTACCAG TTGCCCACAT
     CCGCATGGTC AACGGGTGTA Hypr E protein
     ------------------------------------------------------------------------------------
     •E   G   T   K   Y   H   L   K   S   G   H   V   T   C   E   V   G   L   E   K   L   K   M   K   G   L   T
1801 CGAAGGAACG AAGTACCACC TGAAGTCAGG CCATGTAACT TGCGAGGTGG GCCTGGAGAA GTTGAAAATG AAAGGTCTTA
     GCTTCCTTGC TTCATGGTGG ACTTCAGTCC GGTACATTGA ACGCTCCACC CGGACCTCTT CAACTTTTAC TTTCCAGAAT
         Hypr E protein
         --------------------
       Y   T   M   C   D   K
     CGTACACAAT GTGTGACAAG
     GCATGTGTTA CACACTGTTC Hypr E protein
     ------------------------------------------------------------------------------------
       T   K   F   T   W   K   R   A   P   T   D   S   G   H   D   T   V   V   M   E   V   T   F   S   G   T   K
1901 ACCAAGTTCA CATGGAAGAG GGCCCCCACA GATAGCGGCC ACGATACTGT GGTGATGGAG GTGACCTTTT CTGGAACAAA
     TGGTTCAAGT GTACCTTCTC CCGGGGGTGT CTATCGCCGG TGCTATGACA CCACTACCTC CACTGGAAAA GACCTTGTTT
         Hypr E protein
         --------------------
       P   C   R   I   P   V   R•
     ACCCTGCAGA ATACCCGTGC
     TGGGACGTCT TATGGGCACG Hypr E protein
     ------------------------------------------------------------------------------------
     •  A   V   A   H   G   S   P   D   V   N   V   A   M   L   I   T   P   N   P   T   I   E   N   N   G   G
2001 GGGCTGTAGC TCACGGATCT CCCGATGTCA ATGTTGCTAT GCTGATTACA CCTAACCCTA CCATCGAGAA TAACGGTGGT
     CCCGACATCG AGTGCCTAGA GGGCTACAGT TACAACGATA CGACTAATGT GGATTGGGAT GGTAGCTCTT ATTGCCACCA
         Hypr E protein
         --------------------
       G   F   I   E   M   Q   L•
     GGTTTTATTG AGATGCAGCT
     CCAAAATAAC TCTACGTCGA Hypr E protein
     ------------------------------------------------------------------------------------
     •P   P   G   D   N   I   I   Y   V   G   E   L   S   Y   Q   W   F   Q   K   G   S   S   I   G   R   V   F
2101 TCCGCCAGGC GATAACATCA TCTACGTGGG CGAACTCTCT TACCAGTGGT TTCAGAAAGG GAGTTCAATT GGGCGGGTCT
     AGGCGGTCCG CTATTGTAGT AGATGCACCC GCTTGAGAGA ATGGTCACCA AAGTCTTTCC CTCAAGTTAA CCCGCCCAGA
         Hypr E protein
         --------------------
       Q   K   T   K   K   G
     TCCAAAAAAC GAAGAAGGGA
     AGGTTTTTTG CTTCTTCCCT Hypr E protein
     ------------------------------------------------------------------------------------
       I   E   R   L   T   V   I   G   E   H   A   W   D   F   G   S   A   G   G   F   L   S   S   I   G   K   A
2201 ATCGAACGAT TGACGGTTAT CGGCGAGCAC GCATGGGATT TTGGTTCCGC AGGGGGATTC CTGTCTTCTA TTGGTAAGGC
     TAGCTTGCTA ATGCCAATA GCCGCTCGTG CGTACCCTAA AACCAAGGCG TCCCCCTAAG GACAGAAGAT AACCATTCCG
         Hypr E protein
         --------------------
       L   H   T   V   L   G   G•
     ACTGCATACC GTGCTGGGGG
     TGACGTATGG CACGACCCCC
```

SEQUENCE APPENDIX 2-continued

Hypr E protein

```
         • A  F  N   S  I  F   G  G  V   G  F  L   P  K  L   L  G  V   A  L  A   W  L  G  L
2301 GCGCATTCAA TTCTATTTTC GGGGGCGTGG GGTTCCTGCC TAAACTCCTG CTGGGAGTAG CCCTGCCTG GTTGGGACTG
     CGCGTAAGTT AAGATAAAAG CCCCCGCACC CCAAGGACGG ATTTGAGGAC GACCCTCATC GGGACCGGAC CAACCCTGAC
         Hypr E protein
         ---------------------
         N  M  R  N   P  T  M•
     AATATGCGGA ATCCGACGAT
     TTATACGCCT TAGGCTGCTA
```

Hypr E protein

```
                                                                                NS1 gene of YF17D
                                                                                ---------------------
         • S  M  S   F  L  L  A   G  V  L   V  L  A   M  T  L  G   V  G  A   D  Q  G   C  A  I  N
2401 GTCCATGTCA TTCCTCTTGG CCGGCGTGCT TGTACTGGCC ATGACACTGG GCGTTGGCGC CGATCAAGGA TGCGCCATCA
     CAGGTACAGT AAGGAGAACC GGCCGCACGA ACATGACCGG TACTGTGACC CGCAACCGCG GCTAGTTCCT ACGCGGTAGT
         NS1 gene of YF17D
         ---------------------
         F  G  K   R  E  L
     ACTTTGGCAA GAGAGAGCTC
     TGAAACCGTT CTCTCTCGAG
```

CV-LGTV E5 with YFV/TBEV chimeric signal (p43)

5' UTR

```
   1 AGTAAATCCT GTGTGCTAAT TGAGGTGCAT TGGTCTGCAA ATCGAGTTGC TAGGCAATAA ACACATTTGG ATTAATTTTA
     TCATTTAGGA CACACGATTA ACTCCACGTA ACCAGACGTT TAGCTCAACG ATCCGTTATT TGTGTAAACC TAATTAAAAT
         5' UTR
         -------------------
     ATCGTTCGTT GAGCGATTAG
     TAGCAAGCAA CTCGCTAATC
```

5' UTR

```
                                                                                 C protein YF17D
                                                                        ---------------------------------
                          M  S   G  R  K   A  Q  G   K  T  L   G  V  N   M  V  R  R   G  V  R
 101 CAGAGAACTG ACCAGAACAT GTCTGGTCGT AAAGCTCAGG GAAAAACCCT GGGCGTCAAT ATGGTACGAC GAGGAGTTCG
     GTCTCTTGAC TGGTCTTGTA CAGACCAGCA TTTCGAGTCC CTTTTTGGGA CCCGCAGTTA TACCATGCTG CTCCTCAAGC
         C protein YF17D
         ---------------------
         S  L  S   N  K  I  K•
     CTCCTTGTCA AACAAAATAA
     GAGGAACAGT TTGTTTTATT
```

C protein YF17D

```
         • Q  K  T   K  Q  I   G  N  R   P  G  P  S   R  G  V   Q  G  F  I   F  F  F   L  F  N
 201 AACAAAAAAC AAAACAAATT GGAAACAGAC CTGGACCTTC AAGAGGTGTT CAAGGATTTA TCTTTTTCTT TTTGTTCAAC
     TTGTTTTTTG TTTTGTTTAA CCTTTGTCTG GACCTGGAAG TTCTCCACAA GTTCCTAAAT AGAAAAAGAA AAACAAGTTG
         C protein YF17D
         ---------------------
         I  L  T  G   K  K  I•
     ATTTTGACTG GAAAAAGAT
     TAAAACTGAC CTTTTTCTA
```

C protein YF17D

```
         • T  A  H   L  K  R  L   W  K  M   L  D  P   R  Q  G   L  A  V   L  R  K  V   K  R  V  V
 301 CACAGCCCAC CTAAAGAGGT TGTGGAAAAT GCTGGACCCA AGACAAGGCT TGGCTGTTCT AAGGAAAGTC AAGAGAGTGG
     GTGTCGGGTG GATTTCTCCA ACACCTTTTA CGACCTGGGT TCTGTTCCGA ACCGACAAGA TTCCTTTCAG TTCTCTCACC
         C protein YF17D
         ---------------------
         A  S  L   M  R  G
     TGGCCAGTTT GATGAGAGGA
     ACCGGTCAAA CTACTCTCCT
```

SEQUENCE APPENDIX 2-continued

```
    C protein YF17D                                     TBEV partial signal
    ───────────────────                                 ────────────────────────
                              YF 17D partial signal
                              ─────────────────────────────────────────
      L   S   S   R   K   R   R    S   H   D   V   L   T   V    Q   F   L    I   L   G    M   L   G   M   T   I   A
401 TTGTCCTCAA GGAAACGCCG TTCCCATGAT GTTCTGACTG TGCAATTCCT AATTTTGGGC ATGCTGGGGA TGACGATCGC
    AACAGGAGTT CCTTTGCGGC AAGGGTACTA CAAGACTGAC ACGTTAAGGA TTAAAACCCG TACGACCGAA ACTGCTAGCG
    prM protein Langat E5
    ─────────────────────
      A   T   V   R   R   E   R•
    AGCTACTGTG CGAAGGGAGA
    TCGATGGCAC GCTTCCCTCT prM protein Langet E5
                              ──────────────────────────────────────────────────────────
    •D   G   S    M   V   I    R   A   E   G    R   D   A    A   T   Q    V   R   V   E    N   G   T    C   V   I
501 GAGACGGCTC TATGGTGATC AGAGCCGAAG GTAGGGACGC TGCGACCCAG GTGAGGGTCG AAAATGGCAC CTGTGTTATT
    CTCTGCCGAG ATACCACTAG TCTCGGCTTC CATCCCTGCG ACGCTGGGTC CACTCCCAGC TTTTACCGTG GACACAATAA
    prM protein Langet E5
    ─────────────────────
      L   A   T   D    M   G   S•
    CTGGCGACCG ACATGGGCTC
    GACCGCTGGC TGTACCCGAG prM protein Langet E5
                              ──────────────────────────────────────────────────────────────
    •W   C   D    D   S   L   A    Y   E   C    V   T   I    D   Q   G   E      P   V    D   V   D    C   F   C   R
601 CTGGTGTGAT GATTCTCTGG CTTATGAATG TGTTACTATT GATCAGGGTG AAGAGCCTGT GGACGTGGAC TGTTTCTGTA
    GACCACACTA CTAAGAGCC GAATACTTAC ACAATGATAA CTAGTCCCAC TTCTCGGACA CCTGCACCTG ACAAAGACAT
    prM protein Langat E5
    ─────────────────────
      G   V   E    K   V   T
    GAGGCGTCGA GAAAGTGACC
    CTCCGCAGCT CTTTCACTGG prM protein Langat E5
                              ───────────────────────────────────────────────────────────────────
      L   E   Y   G    R   C   G    R   R   E    G   S   R   S    R   R   S    V   L   I    P   S   H   A    Q   R   D
701 CTGGAATATG GACGATGTGG CCGGCGAGAA GGCTCCAGGA GTCGGAGATC CGTGTTGATC CCTTCACATG CGCAGCGCGA
    GACCTTATAC CTGCTACACC GGCCGCTCTT CCGAGGTCCT CAGCCTCTAG GCACAACTAG GGAAGTGTAC GCGTCGCGCT
    prM protein Langat E5
    ─────────────────────
      L   T   G    R   G   H   Q
    TCTGACAGGG AGGGGTCACC
    AGACTGTCCC TCCCCAGTGG prM protein Langat E5
                              ───────────────────────────────────────────────────────────
    •   W   L   E    G   E   A    V   K   A   H    L   T   R    V   E   G    W   V   W    K   N   K   L    F   T   L
801 AGTGGCTCGA AGGCGAAGCA GTCAAGGCCC ATCTGACTCG CGTTGAAGGC TGGGTGTGGA AAAACAAACT CTTTACCCTT
    TCACCGAGCT TCCGCTTCGT CAGTTCCGGG TAGACTGAGC GCAACTTCCG ACCCACACCT TTTTGTTTGA GAAATGGGAA
    prM protein Langat E5
    ─────────────────────
      S   L   V   M    V   A   W
    AGCCTGGTGA TGGTCGCGTG
    TCGGACCACT ACCAGCGCAC prM protein Langat E5
                              ─────────────────────────────────────────────────────────────
                                                                                                        E
                                                                                                     protein
                                                                                                     Langat
                                                                                                        E5
                                                                                                     ────────
    •L   M   V    D   G   L   L    P   R   I    L   I   V    V   V   A   L    A   L   A    P   A   Y    A   S   R   C
901 GCTGATGGTA GACGGACTCC TTCCCCCGCAT TCTCATTGTT GTGGTGGCTC TCGCGCTCGC CCCTGCATAC GCGTCCAGGT
    CGACTACCAT CTGCCTGAGG AAGGGGCGTA AGAGTAACAA CACCACCGAG AGCGCGAGCG GGGACGTATG CGCAGGTCCA
        E protein Langat E5
        ─────────────────────
          T   H   L    E   N   R
        GTACGCACCT CGAAAATCGA
        CATGCGTGGA GCTTTTAGCT
```

SEQUENCE APPENDIX 2-continued

E protein Langat E5
```
         D   F   V   T       G   V   Q       G   T   T       R   L   T   L       V   L   E       L   G   G       C   V   T   V       T   A   D
1001 GATTTCGTCA CAGGCGTCCA AGGTACTACC CGGCTCACCC TCGTGCTGGA GCTGGGAGGC TGTGTCACTG TTACAGCCGA
     CTAAAGCAGT GTCCGCAGGT TCCATGATGG GCCGAGTGGG AGCACGACCT CGACCCTCCG ACACAGTGAC AATGTCGGCT
```
E protein Langat E5
```
     G   K   P       S   L   D   V
     CGGAAAACCT AGTCTGGATG
     GCCTTTTGGA TCAGACCTAC
```

E protein Langat E5
```
     •   W   L   D       S   I   Y       Q   E   S   P       A   Q   T       R   E   Y       C   L   H   A       K   L   T       G   T   K
1101 TGTGGCTGGA CTCCATCTAT CAGGAGAGCC CGGCACAGAC CAGGGAGTAC TGCCTCCACG CTAAGCTGAC TGGGACAAAG
     ACACCGACCT GAGGTAGATA GTCCTCTCGG GCCGTGTCTG GTCCCTCATG ACGGAGGTGC GATTCGACTG ACCCTGTTTC
```
E protein Langat E5
```
     V   A   A   R       C   P   T
     GTAGCCGCAA GATGTCCCAC
     CATCGGCGTT CTACAGGGTG
```

E protein Langat E5
```
     •M  G   P       A   T   L   P       E   E   H       Q   S   G       T   V   C   K       R   D   Q       S   D   R       G   W   G   N
1201 AATGGGGCCT GCCACCTTGC CCGAGGAACA CCAATCCGGT ACGGTATGCA AGCGAGATCA GTCTGATCGC GGATGGGGGA
     TTACCCCGGA CGGTGGAACG GGCTCCTTGT GGTTAGGCCA TGCCATACGT TCGCTCTAGT CAGACTAGCG CCTACCCCCT
```
E protein Langat E5
```
       H   C   G       L   F   G
     ATCATTGCGG CCTCTTCGGT
     TAGTAACGCC GGAGAAGCCA
```

E protein Langat E5
```
     K   G   S   I       V   T   C       V   K   V       T   C   E   D       K   K   K       A   T   G       H   V   Y   D       V   N   K
1301 AAAGGCAGCA TTGTCACTTG CGTGAAGGTG ACATGCGAGG ACAAGAAGAA GGCCACAGGT CATGTATATG ATGTGAACAA
     TTTCCGTCGT AACAGTGAAC GCACTTCCAC TGTACGCTCC TGTTCTTCTT CCGGTGTCCA GTACATATAC TACACTTGTT
```
E protein Langat E5
```
     I   T   Y       T   I   K   V
     AATCACATAT ACCATTAAGG
     TTAGTGTATA TGGTAATTCC
```

E protein Langat E5
```
     •   E   P   H       T   G   E       F   V   A   A       N   E   T       H   S   G       R   K   S   A       S   F   T       V   S   S
1401 TAGAACCACA TACAGGGGAA TTCGTGGCAG CAAACGAGAC TCATAGCGGA CGAAAGTCCG CCTCCTTCAC CGTCTCCTCC
     ATCTTGGTGT ATGTCCCCTT AAGCACCGTC GTTTGCTCTG AGTATCGCCT GCTTTCAGGC GGAGGAAGTG GCAGAGGAGG
```
E protein Langat E5
```
     E   K   T   I       L   T   L
     GAGAAAACAA TCCTGACCCT
     CTCTTTTGTT AGGACTGGGA
```

E protein Langat E5
```
     •G  D   Y       G   D   V   S       L   L   C       R   V   A       S   G   V   D       L   A   Q       T   V   V       L   A   L   D
1501 CGGAGACTAC GGCGACGTAT CTTTGCTGTG CAGGGTGGCC AGCGGCGTGG ACCTTGCTCA GACAGTCGTG TTGGCCCTGG
     GCCTCTGATG CCGCTGCATA GAAACGACAC GTCCCACCGG TCGCCGCACC TGGAACGAGT CTGTCAGCAC AACCGGGACC
```
E protein Langat E5
```
       K   T   H       E   H   L
     ACAAGACACA TGAGCACTTG
     TGTTCTGTGT ACTCGTGAAC
```

E protein Langat E5
```
     P   T   A   W       Q   V   H       R   D   W       F   N   D   L       A   L   P       W   K   H       D   G   A   E       A   W   N
1601 CCAACAGCCT GGCAGGTGCA CAGGGACTGG TTTAACGACC TGGCGCTCCC GTGGAAACAT GACGGCGCTG AAGCATGGAA
     GGTTGTCGGA CCGTCCACGT GTCCCTGACC AAATTGCTGG ACCGCGAGGG CACCTTTGTA CTGCCGCGAC TTCGTACCTT
```
E protein Langat E5
```
     E   A   G       R   L   V   E
     TGAGGCAGGG AGACTGGTGG
     ACTCCGTCCC TCTGACCACC
```

SEQUENCE APPENDIX 2-continued

```
                                      E protein Langat E5
     ---------------------------------------------------------------------------------
      • F  G  T   P  H  A   V  K  M   D  V  F   N  L  G   D  Q  T   G  V  L   L  K  S   L  A
1701 AATTTGGAAC CCCACACGCC GTAAAGATGG ACGTTTTCAA TCTTGGTGAC CAGACAGGGG TGCTCCTGAA ATCACTGGCG
     TTAAACCTTG GGGTGTGCGG CATTTCTACC TGCAAAAGTT AGAACCACTG GTCTGTCCCC ACGAGGACTT TAGTGACCGC
      E protein Langat E5
     ---------------------
        G  V   P  V  A   S  I •
     GGCGTGCCTG TAGCCAGCAT
     CCGCACGGAC ATCGGTCGTA E protein Langat E5
     ---------------------------------------------------------------------------------
      • E  G  T   K  Y  H   L  K  S   G  H  V   T  C  E   V  G  L   E  K  L   K  M  K   G  L  T
1801 CGAGGGCACA AAGTATCACC TGAAGTCTGG GCATGTAACC TGCGAAGTGG GCCTGGAAAA GCTGAAGATG AAAGGACTTA
     GCTCCCGTGT TTCATAGTGG ACTTCAGACC CGTACATTGG ACGCTTCACC CGGACCTTTT CGACTTCTAC TTTCCTGAAT
      E protein Langat E5
     ---------------------
       Y  T   V  C  D   K
     CGTACACTGT TTGTGATAAG
     GCATGTGACA AACACTATTC E protein Langat E5
     ---------------------------------------------------------------------------------
        T  K  F   T  W  K   R  A  P   T  D  S   G  H  D   T  V  M   E  V  G   F  S  G   T  R
1901 ACCAAGTTTA CATGGAAGCG AGCCCCAACG GATTCCGGCC ATGATACCGT CGTGATGGAG GTTGGTTTCT CCGGCACCAG
     TGGTTCAAAT GTACCTTCGC TCGGGGTTGC CTAAGGCCGG TACTATGGCA GCACTACCTC CAACCAAAGA GGCCGTGGTC
      E protein Langat E5
     ---------------------
       P  C  R   I  P  V   R •
     ACCATGTAGA ATACCAGTGA
     TGGTACATCT TATGGTCACT E protein Langat E5
     ---------------------------------------------------------------------------------
      • A  V  A   H  G  V   P  E  V   N  V  A   M  L  I   T  P  N   P  T  M   E  N  N   G  G
2001 GAGCTGTCGC CCACGGTGTA CCCGAGGTAA ACGTGGCCAT GCTGATTACA CCGAATCCCA CTATGGAGAA CAATGGCGGA
     CTCGACAGCG GGTGCCACAT GGGCTCCATT TGCACCGGTA CGACTAATGT GGCTTAGGGT GATACCTCTT GTTACCGCCT
      E protein Langat E5
     ---------------------
        G  F   I  E  M   Q  L •
     GGGTTCATCG AAATGCAGCT
     CCCAAGTAGC TTTACGTCGA E protein Langat E5
     ---------------------------------------------------------------------------------
      • P  P  G   D  N  I   I  Y  V   G  D  L   D  H  Q   W  F  Q   K  G  S   S  I  G   R  V  L
2101 GCCGCCTGGA GACAACATCA TTTATGTCGG CGACCTCGAT CATCAATGGT TCCAGAAAGG GTCTTCCATC GGCCGCGTCC
     CGGCGGACCT CTGTTGTAGT AAATACAGCC GCTGGAGCTA GTAGTTACCA AGGTCTTTCC CAGAAGGTAG CCGGCGCAGG
      E protein Langat E5
     ---------------------
        Q  K   T  R  K   G
     TTCAGAAGAC ACGAAAAGGC
     AAGTCTTCTG TGCTTTTCCG E protein Langat E5
     ---------------------------------------------------------------------------------
        I  E  R  L   T  V  L   G  E  H   A  W  D   F  G  S   V  G  G   V  M  T   S  I  G   R  A
2201 ATTGAAAGAC TTACAGTCCT GGGCGAACAT GCCTGGGACT TCGGGTCAGT GGCGGGGTA ATGACAAGCA TAGGCAGAGC
     TAACTTTCTG AATGTCAGGA CCCGCTTGTA CGGACCCTGA AGCCCAGTCA CCGCCCCAT TACTGTTCGT ATCCGTCTCG
      E protein Langat E5
     ---------------------
        M  H  T   V  L  G   G •
     TATGCACACC GTTCTCGGTG
     ATACGTGTGG CAAGAGCCAC E protein Langat E5
     ---------------------------------------------------------------------------------
      • A  F  N   T  L  L   G  G  V   G  F  L   P  K  I   L  L  G   V  A  M   A  W  L   G  L
2301 GGGCATTTAA TACTCTGTTG GGTGGCGTGG GTTTTCTTCC GAAAATCCTG CTCGGTGTCG CAATGGCCTG GCTTGGACTG
     CCCGTAAATT ATGAGACAAC CCACCGCACC CAAAAGAAGG CTTTTAGGAC GAGCCACAGC GTTACCGGAC CGAACCTGAC
      E protein Langat E5
     ---------------------
        N  M   R  N  P   T  L •
     AATATGCGCA ATCCTACACT
     TTATACGCGT TAGGATGTGA
```

SEQUENCE APPENDIX 2-continued

```
                 E protein Langat E5
     ------------------------------------------------------------------------
                                                                     NS1 gene
                                                                     of YF17D
                                                                     --------------------
        • S   M   G   F   L   L   S   G   G   L   V   L   A   M   T   L   G   V   G   A   D   Q   G   C   A   I   N
     2401 GAGTATGGGG TTTCTTCTGT CAGGAGGCCT GGTCCTGGCA ATGACTCTGG GAGTGGGCGC CGATCAAGGA TGCGCCATCA
          CTCATACCCC AAAGAAGACA GTCCTCCGGA CCAGGACCGT TACTGAGACC CTCACCCGCG GCTAGTTCCT ACGCGGTAGT
              NS1 gene of YF17D
              --------------------
            F   G   K   R   E   L
          ACTTTGGCAA GAGAGAGCTC
          TGAAACCGTT CTCTCTCGAG
```

```
                 CV-TBEV Hypr with YFV/TBEV chimeric signal and dC2 deletion in C protein (p59)

5' UTR
                 -----------------------------------------------------------------------------
     1 AGTAAATCCT GTGTGCTAAT TGAGGTGCAT TGGTCTGCAA ATCGAGTTGC TAGGCAATAA ACACATTTGG ATTAATTTTA
       TCATTTAGGA CACACGATTA ACTCCACGTA ACCAGACGTT TAGCTCAACG ATCCGTTATT TGTGTAAACC TAATTAAAAT
           5' UTR
           --------------------
       ATCGTTCGTT GAGCGATTAG
       TAGCAAGCAA CTCGCTAATC

5' UTR
           ------------------
                                                                   C protein
                         ------------------------------------------------------------------------
                M   S   G   R   K   A   Q   G   K   T   L   G   V   N   M   V   R   R   G   V   R
     101 CAGAGAACTG ACCAGAACAT GTCTGGTCGT AAAGCTCAGG GAAAAACCCT GGGCGTCAAT ATGGTACGAC GAGGAGTTCG
         GTCTCTTGAC TGGTCTTGTA CAGACCAGCA TTTCGAGTCC CTTTTTGGGA CCCGCAGTTA TACCATGCTG CTCCTCAAGC
              C protein
              ---------------------
            S   L   S   N   K   I   K•
          CTCCTTGTCA AACAAAATAA
          GAGGAACAGT TTGTTTTATT
```

```
                                         dC2 deletion (PSR)
                                               -
                                           C protein
                 -----------------------------------------------------------------------------
        • Q   K   T   K   Q   I   G   N   R   P   G   G   V   Q   G   F   I   F   F   F   L   F   N   I   L   T
     201 AACAAAAAAC AAAACAAATT GGAAACAGAC CTGGAGGTGT TCAAGGATTT ATCTTTTTCT TTTTGTTCAA CATTTTGACT
         TTGTTTTTTG TTTTGTTTAA CCTTTGTCTG GACCTCCACA AGTTCCTAAA TAGAAAAAGA AAAACAAGTT GTAAAACTGA
              C protein
              ---------------------
            G   K   K   I   T   A   H•
          GGAAAAAAGA TCACAGCCCA
          CCTTTTTTCT AGTGTCGGGT
```

```
                                           C protein
                 -----------------------------------------------------------------------------
        • L   K   R   L   W   K   M   L   D   P   R   Q   G   L   A   V   L   R   K   V   K   R   V   V   A   S   L
     301 CCTAAAGAGG TTGTGGAAAA TGCTGGACCC AAGACAAGGC TTGGCTGTTC TAAGGAAAGT CAAGAGAGTG GTGGCCAGTT
         GGATTTCTCC AACACCTTTT ACGACCTGGG TTCTGTTCCG AACCGACAAG ATTCCTTTCA GTTCTCTCAC CACCGGTCAA
              C protein
              ---------------------
            M   R   G   L   S   S
          TGATGAGAGG ATTGTCCTCA
          ACTACTCTCC TAACAGGAGT
```

```
                 YF17D partial signal
                 ----------------------------------------
                                                              TBEV partial signal
                                                              -------------------------
                                                                                    Hypr prM
           C protein                                                                protein
           -------------                                                            ---------
            R   K   R   R   S   H   D   V   L   T   V   Q   F   L   I   L   G   M   L   G   M   T   I   A   A   T   V
     401 AGGAAACGCC GTTCCCATGA TGTTCTGACT GTGCAATTCC TAATTTTGGG CATGCTGGGC ATGACAATCG CAGCTACGGT
         TCCTTTGCGG CAAGGGTACT ACAAGACTGA CACGTTAAGG ATTAAAACCC GTACGACCCG TACTGTTAGC GTCGATGCCA
              Hypr prM protein
              ---------------------
            R   K   E   R   D   G   S•
          TCGCAAGGAA AGAGACGGCA
          AGCGTTCCTT TCTCTGCCGT
```

SEQUENCE APPENDIX 2-continued

```
                                        Hypr prM protein
    -------------------------------------------------------------------------------
     •  T   V   I   R   A   E   G   K   D   A   A   T   Q   V   R   V   E   N   G   T   C   V   I   L   A   T
501  GTACGGTCAT ACGCGCGGAA GGTAAGGATG CCGCTACCCA AGTGAGAGTG GAAAATGGTA CCTGCGTCAT TCTGGCCACC
     CATGCCAGTA TGCGCGCCTT CCATTCCTAC GGCGATGGGT TCACTCTCAC CTTTTACCAT GGACGCAGTA AGACCGGTGG
         Hypr prM protein
         ---------------------
       D   M   G   S   W   C   D•
     GACATGGGCT CTTGGTGTGA
     CTGTACCCGA GAACCACACT Hypr prM protein
    -------------------------------------------------------------------------------
     •  D   S   L   S   Y   E   C   V   T   I   D   Q   G   E   E   P   V   D   V   D   C   F   C   R   N   V   D
601  TGATAGCCTT TCTTATGAGT GCGTAACCAT AGATCAAGGT GAGGAACCTG TTGACGTTGA TTGCTTCTGC CGAAACGTGG
     ACTATCGGAA AGAATACTCA CGCATTGGTA TCTAGTTCCA CTCCTTGGAC AACTGCAACT AACGAAGACG GCTTTGCACC
         Hypr prM protein
         ---------------------
         G   V   Y   L   E   Y
     ATGGGGTGTA TCTCGAATAT
     TACCCCACAT AGAGCTTATA Hypr prM protein
    -------------------------------------------------------------------------------
        G   R   C   G   K   Q   E   G   S   R   T   R   R   S   V   L   I   P   S   H   A   Q   G   E   L   T   G
701  GGACGGTGTG GTAAACAAGA AGGAAGCAGA ACCAGACGCT CAGTGCTTAT ACCCTCCCAC GCTCAAGGAG AGCTGACCGG
     CCTGCCACAC CATTTGTTCT TCCTTCGTCT TGGTCTGCGA GTCACGAATA TGGGAGGGTG CGAGTTCCTC TCGACTGGCC
         Hypr prM protein
         ---------------------
       R   G   H   K   W   L   E•
     ACGGGGACAT AAATGGTTGG
     TGCCCCTGTA TTTACCAACC Hypr prM protein
    -------------------------------------------------------------------------------
     •  G   D   S   L   R   T   H   L   T   R   V   E   G   W   V   W   K   N   R   L   L   A   L   A   M   V
801  AGGGCGACTC ACTCCGAACA CATTTGACCC GCGTCGAGGG CTGGGTCTGG AAAAATCGGC TGTTGGCCCT CGCTATGGTG
     TCCCGCTGAG TGAGGCTTGT GTAAACTGGG CGCAGCTCCC GACCCAGACC TTTTTAGCCG ACAACCGGGA GCGATACCAC
         Hypr prM protein
         ---------------------
       T   V   V   W   L   T   L•
     ACAGTCGTTT GGCTCACGCT
     TGTCAGCAAA CCGAGTGCGA
                                                                                        Hypr E
                                                                                        protein
                                                                                        ------------------
                               Hypr prM protein
    -------------------------------------------------------------------------------
     •  E   S   V   V   T   R   V   A   V   L   V   V   L   L   C   L   A   P   V   Y   A   S   R   C   T   H   L
901  GGAGTCTGTG GTTACTCGCG TGGCAGTGCT GGTGGTGCTC CTCTGTCTTG CCCCTGTCTA CGCGTCCAGG TGTACTCATT
     CCTCAGACAC CAATGAGCGC ACCGTCACGA CCACCACGAG GAGACAGAAC GGGGACAGAT GCGCAGGTCC ACATGAGTAA
         Hypr E protein
         ---------------------
         E   N   R   D   F   V
     TGGAAAACAG AGATTTTGTC
     ACCTTTTGTC TCTAAAACAG Hypr E protein
    -------------------------------------------------------------------------------
        T   G   T   Q   G   T   T   R   V   T   L   V   L   E   L   G   G   C   V   T   I   T   A   E   G   K   P
1001 ACCGGCACCC AGGGGACGAC TCGGGTAACC CTGGTGCTTG AACTGGGTGG TTGCGTTACT ATTACCGCTG AGGGCAAACC
     TGGCCGTGGG TCCCCTGCTG AGCCCATTGG GACCACGAAC TTGACCCACC AACGCAATGA TAATGGCGAC TCCCGTTTGG
         Hypr E protein
         ---------------------
         S   M   D   V   W   L   D•
     CTCTATGGAT GTGTGGCTGG
     GAGATACCTA CACACCGACC Hypr E protein
    -------------------------------------------------------------------------------
     •  A   I   Y   Q   E   N   P   A   Q   T   R   E   Y   C   L   H   A   K   L   S   D   T   K   V   A   A
1101 ATGCAATCTA TCAGGAGAAT CCCGCACAAA CCAGGGAATA TTGCCTTCAC GCAAAGCTGT CCGATACAAA GGTCGCGGCT
     TACGTTAGAT AGTCCTCTTA GGGCGTGTTT GGTCCCTTAT AACGGAAGTG CGTTTCGACA GGCTATGTTT CCAGCGCCGA
         Hypr E protein
         ---------------------
       R   C   P   T   M   G   P•
     AGGTGCCCAA CAATGGGACC
     TCCACGGGTT GTTACCCTGG
```

SEQUENCE APPENDIX 2-continued

```
                                  Hypr E protein
     -----------------------------------------------------------------------------
      • A  T  L     A  E  E  H     Q  G  G     T  V  C     K  R  D  Q     S  D  R     G  W  G     N  H  C  G
1201 GGCCACCCTG GCGGAGGAAC ATCAGGGAGG TACAGTGTGC AAACGGGACC AGAGTGATAG AGGCTGGGGT AATCACTGCG
     CCGGTGGGAC CGCCTCCTTG TAGTCCCTCC ATGTCACACG TTTGCCCTGG TCTCACTATC TCCGACCCCA TTAGTGACGC
         Hypr E protein
         ---------------------
        L  F  G     K  G  S
     GCCTGTTCGG CAAAGGAAGT
     CGGACAAGCC GTTTCCTTCA Hypr E protein
     -----------------------------------------------------------------------------
        I  V  A  C     V  K  A     A  C  E     A  K  K  K     A  T  G     H  V  Y     D  A  N  K     I  V  Y
1301 ATTGTCGCTT GCGTCAAGGC AGCCTGTGAG GCCAAAAAGA AGGCTACTGG GCACGTCTAT GACGCCAACA AGATCGTTTA
     TAACAGCGAA CGCAGTTCCG TCGGACACTC CGGTTTTTCT TCCGATGACC CGTGCAGATA CTGCGGTTGT TCTAGCAAAT
         Hypr E protein
         ---------------------
        T  V  K     V  E  P  H•
     TACAGTGAAA GTGGAACCAC
     ATGTCACTTT CACCTTGGTG Hypr E protein
     -----------------------------------------------------------------------------
      • T  G  D     Y  V  A     A  N  E  T     H  S  G     R  K  T     A  S  F  T     V  S  S     E  K  T
1401 ACACAGGGGA TTACGTGGCG GCCAACGAGA CTCATTCCGG TCGCAAAACG GCCAGCTTCA CCGTGTCATC CGAAAAGACC
     TGTGTCCCCT AATGCACCGC CGGTTGCTCT GAGTAAGGCC AGCGTTTTGC CGGTCGAAGT GGCACAGTAG GCTTTTCTGG
         Hypr E protein
         ---------------------
        I  L  T  M     G  E  Y•
     ATCCTCACTA TGGGGGAGTA
     TAGGAGTGAT ACCCCCTCAT Hypr E protein
     -----------------------------------------------------------------------------
      • G  D  V     S  L  L  C     R  V  A     S  G  V     D  L  A  Q     T  V  I     L  E  L     D  K  T  V
1501 TGGCGACGTT TCTCTGCTCT GCCGGGTGGC TAGCGGAGTC GACCTGGCCC AGACAGTCAT CCTGGAACTG GATAAAACAG
     ACCGCTGCAA AGAGACGAGA CGGCCCACCG ATCGCCTCAG CTGGACCGGG TCTGTCAGTA GGACCTTGAC CTATTTTGTC
         Hypr E protein
         ---------------------
        E  H  L     P  T  A
     TTGAGCATCT GCCTACCGCT
     AACTCGTAGA CGGATGGCGA Hypr E protein
     -----------------------------------------------------------------------------
        W  Q  V  H     R  D  W     F  N  D     L  A  L  P     W  K  H     E  G  A     R  N  W  N     N  A  E
1601 TGGCAGGTGC ACAGGGATTG GTTTAACGAC CTTGCCCTGC CATGGAAACA TGAAGGAGCG AGAAACTGGA ATAATGCAGA
     ACCGTCCACG TGTCCCTAAC CAAATTGCTG GAACGGGACG GTACCTTTGT ACTTCCTCGC TCTTTGACCT TATTACGTCT
         Hypr E protein
         ---------------------
        R  L  V     E  F  G  A•
     GCGACTCGTA GAATTCGGTG
     CGCTGAGCAT CTTAAGCCAC Hypr E protein
     -----------------------------------------------------------------------------
      • P  H  A     V  K  M     D  V  Y  N     L  G  D     Q  T  G     V  L  L  K     A  L  A     G  V  P
1701 CCCCTCATGC CGTGAAGATG GACGTCTACA ATCTGGGTGA TCAGACCGGC GTTCTCCTTA AAGCTCTCGC TGGCGTACCA
     GGGGAGTACG GCACTTCTAC CTGCAGATGT TAGACCCACT AGTCTGGCCG CAAGAGGAAT TTCGAGAGCG ACCGCATGGT
         Hypr E protein
         ---------------------
        V  A  H  I     E  G  T•
     GTTGCCCACA TCGAAGGAAC
     CAACGGGTGT AGCTTCCTTG Hypr E protein
     -----------------------------------------------------------------------------
      • K  Y  H     L  K  S  G     H  V  T     C  E  V     G  L  E  K     L  K  M     K  G  L     T  Y  T  M
1801 GAAGTACCAC CTGAAGTCAG GCCATGTAAC TTGCGAGGTG GGCCTGGAGA AGTTGAAAAT GAAAGGTCTT ACGTACACAA
     CTTCATGGTG GACTTCAGTC CGGTACATTG AACGCTCCAC CCGGACCTCT TCAACTTTTA CTTTCCAGAA TGCATGTGTT
         Hypr E protein
         ---------------------
        C  D  K     T  K  F
     TGTGTGACAA GACCAAGTTC
     ACACACTGTT CTGGTTCAAG
```

SEQUENCE APPENDIX 2-continued

```
                                         Hypr E protein
     ------------------------------------------------------------------------------------------
        T   W   K   R    A   P   T   D   S   G    H   D   T   V   V   M   E    V   T   F    S   G   T   K    P   C   R
   1901 ACATGGAAGA GGGCCCCCAC AGATAGCGGC CACGATACTG TGGTGATGGA GGTGACCTTT TCTGGAACAA AACCCTGCAG
        TGTACCTTCT CCCGGGGGTG TCTATCGCCG GTGCTATGAC ACCACTACCT CCACTGGAAA AGACCTTGTT TTGGGACGTC
            Hypr E protein
        ---------------------
          I   P   V   R   A   V   A•
        AATACCCGTG CGGGCTGTAG
        TTATGGGCAC GCCCGACATC Hypr E protein
     ------------------------------------------------------------------------------------------
        •H   G   S    P   D   V    N   V   A   M    L   I   T    P   N   P    T   I   E   N    N   G   G    G   F   I
   2001 CTCACGGATC TCCCGATGTC AATGTTGCTA TGCTGATTAC ACCTAACCCT ACCATCGAGA ATAACGGTGG TGGTTTTATT
        GAGTGCCTAG AGGGCTACAG TTACAACGAT ACGACTAATG TGGATTGGGA TGGTAGCTCT TATTGCCACC ACCAAAATAA
            Hypr E protein
        ---------------------
          E   M   Q   L    P   P   G•
        GAGATGCAGC TTCCGCCAGG
        CTCTACGTCG AAGGCGGTCC Hypr E protein
     ------------------------------------------------------------------------------------------
        •D   N   I    I   Y   V   G    E   L   S    Y   Q   W    F   Q   K   G    S   S   I    G   R   V    F   Q   K   T
   2101 CGATAACATC ATCTACGTGG GCGAACTCTC TTACCAGTGG TTTCAGAAAG GGAGTTCAAT TGGGCGGGTC TTCCAAAAAA
        GCTATTGTAG TAGATGCACC CGCTTGAGAG AATGGTCACC AAAGTCTTTC CCTCAAGTTA ACCCGCCCAG AAGGTTTTTT
            Hypr E protein
        ---------------------
          K   K   G    I   E   R
        CGAAGAAGGG AATCGAACGA
        GCTTCTTCCC TTAGCTTGCT Hypr E protein
     ------------------------------------------------------------------------------------------
        L   T   V   I    G   E   H    A   W   D    F   G   S    A   G   G    F   L   S   S    I   G   K   A    L   H   T
   2201 TTGACGGTTA TCGGCGAGCA CGCATGGGAT TTTGGTTCCG CAGGGGGATT CCTGTCTTCT ATTGGTAAGG CACTGCATAC
        AACTGCCAAT AGCCGCTCGT GCGTACCCTA AAACCAAGGC GTCCCCCTAA GGACAGAAGA TAACCATTCC GTGACGTATG
            Hypr E protein
        ---------------------
          V   L   G    G   A   F   N•
        CGTGCTGGGG GGCGCATTCA
        GCACGACCCC CCGCGTAAGT Hypr E protein
     ------------------------------------------------------------------------------------------
        •S   I   F    G   G   V    G   F   L   P    K   L   L    L   G   V    A   L   A   W    L   G   L    N   M   R
   2301 ATTCTATTTT CGGGGGCGTG GGGTTCCTGC CTAAACTCCT GCTGGGAGTA GCCCTGGCCT GGTTGGGACT GAATATGCGG
        TAAGATAAAA GCCCCCGCAC CCCAAGGACG GATTTGAGGA CGACCCTCAT CGGGACCGGA CCAACCCTGA CTTATACGCC
            Hypr E protein
        ---------------------
          N   P   T    M   S   M   S•
        AATCCGACGA TGTCCATGTC
        TTAGGCTGCT ACAGGTACAG Hypr E protein
        ----------------------------------------------------------
                                                                            NS1 gene
                                                                            of YF17D
                                                                      -------------------------
        •F   L   L    A   G   V   L    V   L   A   M   T   L    G   V   G   A    D   Q   G    C   A   I    N   F   G   K
   2401 ATTCCTCTTG GCCGGCGTGC TTGTACTGGC CATGACACTG GGCGTTGGCG CCGATCAAGG ATGCGCCATC AACTTTGGCA
        TAAGGAGAAC CGGCCGCACG AACATGACCG GTACTGTGAC CCGCAACCGC GGCTAGTTCC TACGCGGTAG TTGAAACCGT
        NS1 gene of YF17D
        ------------
          R   E   L
        AGAGAGAGCT C
        TCTCTCTCGA G
```

SEQUENCE APPENDIX 3

PIV-WN/TBEV Hypr with TBEV signal (p39)

```
                                          5' UTR
     ----------------------------------------------------------------------------------
  1  AGTAGTTCGC CTGTGTGAGC TGACAAACTT AGTAGTGTTT GTGAGGATTA ACAACAATTA ACACAGTGCG AGCTGTTTCT
     TCATCAAGCG ACACACTCG ACTGTTTGAA TCATCACAAA CACTCCTAAT TGTTGTTAAT TGTGTCACGC TCGACAAAGA
                     deleted C
                     ----

5' UTR
     -----------------
                 M  S •
     TAGCACGAAG ATCTCGATGT
     ATCGTGCTTC TAGAGCTACA

WNV deleted C protein
     -------------------------------------------------------------------------------------
     •  K   K   P   G   G   P   G   K   S   R   A   V   Y   L   L   K   R   G   M   P   R   V   L   S   L   I
 101 CTAAGAAACC AGGAGGGCCC GGCAAGAGCC GGGCTGTCTA TTTGCTAAAA CGCGGAATGC CCCGCGTGTT GTCCTTGATT
     GATTCTTTGG TCCTCCCGGG CCGTTCTCGG CCCGACAGAT AAACGATTTT GCGCCTTACG GGCGCACAA CAGGAACTAA
     WNV deleted C protein
     --------------------
       G   L   K   R   S   S   K •
     GGACTTAAGC GGAGCTCCAA
     CCTGAATTCG CCTCGAGGTT TBEV signal
                 ----------------------------------------------------------------------
       deleted C                                                              prM Hypr
     --------------                                                           --------
     •  Q   K   K   R   G   G   T   D   W   M   S   W   L   V   I   G   M   L   G   M   T   I   A   A   T   V
 201 ACAAAAGAAA CGGGGGGGAA CAGACTGGAT GAGCTGGCTG CTCGTAATCG GCATGCTGGG CATGACAATC GCAGCTACGG
     TGTTTTCTTT GCCCCCCCTT GTCTGACCTA CTCGACCGAC GAGCATTAGC CGTACGACCC GTACTGTTAG CGTCGATGCC
         prM Hypr
     --------------------
       R   K   E   R   D   G
     TTCGCAAGGA AAGAGACGGC
     AAGCGTTCCT TTCTCTGCCG prM Hypr
     -------------------------------------------------------------------------------------
       S   T   V   I   R   A   E   G   K   D   A   A   T   Q   V   R   V   E   N   G   T   C   V   I   L   A   T
 301 AGTACGGTCA TACGCGCGGA AGGTAAGGAT GCCGCTACCC AAGTGAGAGT GGAAAATGGT ACCTGCGTCA TTCTGGCCAC
     TCATGCCAGT ATGCGCGCCT TCCATTCCTA CGGCGATGGG TTCACTCTCA CCTTTTACCA TGGACGCAGT AAGACCGGTG
         prM Hypr
     --------------------
       D   M   G   S   W   C   D •
     CGACATGGGC TCTTGGTGTG
     GCTGTACCCG AGAACCACAC prM Hypr
     -------------------------------------------------------------------------------------
     •  D   S   L   S   Y   E   C   V   T   I   D   Q   G   E   E   P   V   D   V   D   C   F   C   R   N   V
 401 ATGATAGCCT TTCTTATGAG TGCGTAACCA TAGATCAAGG TGAGGAACCT GTTGACGTTG ATTGCTTCTG CCGAAACGTG
     TACTATCGGA AAGAATACTC ACGCATTGGT ATCTAGTTCC ACTCCTTGGA CAACTGCAAC TAACGAAGAC GGCTTTGCAC
         prM Hypr
     --------------------
       D   G   V   Y   L   E   Y •
     GATGGGGTGT ATCTCGAATA
     CTACCCCACA TAGAGCTTAT prM Hypr
     -------------------------------------------------------------------------------------
     •  G   R   C   G   K   Q   E   G   S   R   T   R   R   S   V   L   I   P   S   H   A   Q   G   E   L   T   G
 501 TGGACGGTGT GGTAAACAAG AAGGAAGCAG AACCAGACGC TCAGTGCTTA TACCCTCCCA CGCTCAAGGA GAGCTGACCG
     ACCTGCCACA CCATTTGTTC TTCCTTCGTC TTGGTCTGCG AGTCACGAAT ATGGGAGGGT GCGAGTTCCT CTCGACTGGC
         prM Hypr
     --------------------
       R   G   H   K   W   L
     GACGGGACA TAAATGGTTG
     CTGCCCTGT ATTTACCAAC prM Hypr
     -------------------------------------------------------------------------------------
       E   G   D   S   L   R   T   H   L   T   R   V   E   G   W   V   W   K   N   R   L   L   A   L   A   M   V
 601 GAGGGCGACT CACTCCGAAC ACATTTGACC CGCGTCGAGG GCTGGGTCTG GAAAAATCGG CTGTTGGCCC TCGCTATGGT
     CTCCCGCTGA GTGAGGCTTG TGTAAACTGG GCGCAGCTCC CGACCCAGAC CTTTTTAGCC GACAACCGGG AGCGATACCA
         prM Hypr
     --------------------
       T   V   V   W   L   T   L •
     GACAGTCGTT TGGCTCACGC
```

```
                                                            SEQUENCE APPENDIX 3-continued CTGTCAGCAA ACCGAGTGCG
                                                                                              E Hypr
                                                                                              -----------------
                                           prM Hypr
           ----------------------------------------------------------------------------
           • E S V   V T R   V A V L   V V L   L C L   A P V Y   A S R   C T H
     701 TGGAGTCTGT GGTTACTCGC GTGGCAGTGC TGGTGGTGCT CCTCTGTCTT GCCCCTGTCT ACGCGTCCAG TGTACTCAT
         ACCTCAGACA CCAATGAGCG CACCGTCACG ACCACCACGA GGAGACAGAA CGGGGACAGA TGCGCAGGTC ACATGAGTA
                   E Hypr
                   ----------------------
          L E N R   D F V •
         TTGGAAAACA GAGATTTTGT
         AACCTTTTGT CTCTAAAACA E Hypr
           ----------------------------------------------------------------------------
           • T G T   Q G T T   R V T   L V L   E L G G   C V T   I T A   E G K P
     801 CACCGGCACC CAGGGGACGA CTCGGGTAAC CCTGGTGCTT GAACTGGGTG GTTGCGTTAC TATTACCGCT GAGGGCAAAC
         GTGGCCGTGG GTCCCCTGCT GAGCCCATTG GGACCACGAA CTTGACCCAC CAACGCAATG ATAATGGCGA CTCCCGTTTG
                   E Hypr
                   ----------------------
            S M D   V W L
         CCTCTATGGA TGTGTGGCTG
         GGAGATACCT ACACACCGAC E Hypr
           ----------------------------------------------------------------------------
           D A I Y   Q E N   P A Q   T R E Y   C L H   A K L   S D T K   V A A
     901 GATGCAATCT ATCAGGAGAA TCCCGCACAA ACCAGGGAAT ATTGCCTTCA CGCAAAGCTG TCCGATACAA AGGTCGCGGC
         CTACGTTAGA TAGTCCTCTT AGGGCGTGTT TGGTCCCTTA TAACGGAAGT GCGTTTCGAC AGGCTATGTT TCCAGCGCCG
                   E Hypr
                   ----------------------
           R C P   T M G P •
         TAGGTGCCCA ACAATGGGAC
         ATCCACGGGT TGTTACCCTG E Hypr
           ----------------------------------------------------------------------------
           • A T L   A E E   H Q G G   T V C   K R D   Q S D R   G W G   N H C
    1001 CGGCCACCCT GGCGGAGGAA CATCAGGGAG GTACAGTGTG CAAACGGGAC CAGAGTGATA GAGGCTGGGG TAATCACTGC
         GCCGGTGGGA CCGCCTCCTT GTAGTCCCTC CATGTCACAC GTTTGCCCTG GTCTCACTAT CTCCGACCCC ATTAGTGACG
                   E Hypr
                   ----------------------
           G L F   G K G S •
         GGCCTGTTCG GCAAAGGAAG
         CCGGACAAGC CGTTTCCTTC E Hypr
           ----------------------------------------------------------------------------
           • I V A   C V K A   A C E   A K K   K A T G   H V Y   D A N   K I V Y
    1101 TATTGTCGCT TGCGTCAAGG CAGCCTGTGA GGCCAAAAAG AAGGCTACTG GCACGTCTA TGACGCCAAC AAGATCGTTT
         ATAACAGCGA ACGCAGTTCC GTCGGACACT CCGGTTTTTC TTCCGATGAC CGTGCAGAT ACTGCGGTTG TTCTAGCAAA
                   E Hypr
                   ----------------------
            T V K   V E P
         ATACAGTGAA AGTGGAACCA
         TATGTCACTT TCACCTTGGT E Hypr
           ----------------------------------------------------------------------------
           H T G D   Y V A   A N E   T H S G   R K T   A S F   T V S S   E K T
    1201 CACACAGGGG ATTACGTGGC GGCCAACGAG ACTCATTCCG GTCGCAAAAC GGCCAGCTTC ACCGTGTCAT CCGAAAAGAC
         GTGTGTCCCC TAATGCACCG CCGGTTGCTC TGAGTAAGGC CAGCGTTTTG CCGGTCGAAG TGGCACAGTA GGCTTTTCTG
                   E Hypr
                   ----------------------
            I L T   M G E Y •
         CATCCTCACT ATGGGGGAGT
         GTAGGAGTGA TACCCCCTCA E Hypr
           ----------------------------------------------------------------------------
           • G D V   S L L   C R V A   S G V   D L A   Q T V I   L E L   D K T
    1301 ATGGCGACGT TTCTCTGCTC TGCCGGGTGG CTAGCGGAGT CGACCTGGCC CAGACAGTCA TCCTGGAACT GGATAAAACA
         TACCGCTGCA AAGAGACGAG ACGGCCCACC GATCGCCTCA GCTGGACCGG GTCTGTCAGT AGGACCTTGA CCTATTTTGT
                   E Hypr
                   ----------------------
           V E H L   P T A •
         GTTGAGCATC TGCCTACCGC
         CAACTCGTAG ACGGATGGCG
```

SEQUENCE APPENDIX 3-continued

```
                                           E Hypr
     -------------------------------------------------------------------------------
       •W  Q   V  H R D W   F N D   L A L   P W K H   E G A   R N W   N N A E
1401  TTGGCAGGTG CACAGGGATT GGTTTAACGA CCTTGCCCTG CCATGAAAC ATGAAGGAGC GAGAAACTGG AATAATGCAG
      AACCGTCCAC GTGTCCCTAA CCAAATTGCT GGAACGGGAC GGTACCTTTG TACTTCCTCG CTCTTTGACC TTATTACGTC
           E Hypr
      --------------------
        R  L V   E F G
      AGCGACTCGT AGAATTCGGT
      TCGCTGAGCA TCTTAAGCCA E Hypr
     -------------------------------------------------------------------------------
        A   P  H A   V K M   D V Y   N L G D   Q T G   V L L   K A L A   G V P
1501  GCCCCTCATG CCGTGAAGAT GGACGTCTAC AATCTGGGTG ATCAGACCGG CGTTCTCCTT AAAGCTCTCG CTGGCGTACC
      CGGGGAGTAC GGCACTTCTA CCTGCAGATG TTAGACCCAC TAGTCTGGCC GCAAGAGGAA TTTCGAGAGC GACCGCATGG
             E Hypr
      --------------------
         V  A H   I E G T•
      AGTTGCCCAC ATCGAAGGAA
      TCAACGGGTG TAGCTTCCTT E Hypr
     -------------------------------------------------------------------------------
       • K   Y  H   L K S   G H V T   C E V   G L E   K L K M   K G L   T Y T
1601  CGAAGTACCA CCTGAAGTCA GGCCATGTAA CTTGCGAGGT GGGCCTGGAG AAGTTGAAAA TGAAAGGTCT TACGTACACA
      GCTTCATGGT GGACTTCAGT CCGGTACATT GAACGCTCCA CCCGGACCTC TTCAACTTTT ACTTTCCAGA ATGCATGTGT
            E Hypr
      --------------------
        M  C  D  K   T K F•
      ATGTGTGACA AGACCAAGTT
      TACACACTGT TCTGGTTCAA E Hypr
     -------------------------------------------------------------------------------
       •T  W  K   R A P T   D S G   H D T   V V M E   V T F   S G T   K P C R
1701  CACATGGAAG AGGGCCCCCA CAGATAGCGG CCACGATACT GTGGTGATGG AGGTGACCTT TTCTGGAACA AAACCCTGCA
      GTGTACCTTC TCCCGGGGGT GTCTATCGCC GGTGCTATGA CACCACTACC TCCACTGGAA AAGACCTTGT TTTGGGACGT
            E Hypr
      --------------------
         I  P V   R A V
      GAATACCCGT GCGGGCTGTA
      GAATACCCGT GCGGGCTGTA E Hypr
     -------------------------------------------------------------------------------
        A   H  G  S   P D V   N V A   M L I T   P N P   T I E   N N G   G F I
1801  GCTCACGGAT CTCCCGATGT CAATGTTGCT ATGCTGATTA CACCTAACCC TACCATCGAG AATAACGGTG GTGGTTTTAT
      CGAGTGCCTA GAGGGCTACA GTTACAACGA TACGACTAAT GTGGATTGGG ATGGTAGCTC TTATTGCCAC CACCAAAATA
            E Hypr
      --------------------
         E  M Q   L P P G•
      TGAGATGCAG CTTCCGCCAG
      ACTCTACGTC GAAGGCGGTC E Hypr
     -------------------------------------------------------------------------------
       • D   N  I   I Y V   G E L S   Y Q W   F Q K   G S S   I G R V   F Q K
1901  GCGATAACAT CATCTACGTG GGCGAACTCT CTTACCAGTG GTTTCAGAAA GGGAGTTCAA TTGGGCGGGT CTTCCAAAAA
      CGCTATTGTA GTAGATGCAC CCGCTTGAGA GAATGGTCAC CAAAGTCTTT CCCTCAAGTT AACCCGCCCA GAAGGTTTTT
            E Hypr
      --------------------
        T  K K G   I E R•
      ACGAAGAAGG GAATCGAACG
      TGCTTCTTCC CTTAGCTTGC E Hypr
     -------------------------------------------------------------------------------
       •L  T  V   I G E H   A W D   F G S   A G G F   L S S   I G K   A L H T
2001  ATTGACGGTT ATCGGCGAGC ACGCATGGGA TTTTGGTTCC GCAGGGGGAT CCTGTCTTCC TATTGGTAAG GCACTGCATA
      TAACTGCCAA TAGCCGCTCG TGCGTACCCT AAAACCAAGG CGTCCCCCTA GGACAGAAGA TAACCATTC CGTGACGTAT
            E Hypr
      --------------------
         V  L G   G A F
      CCGTGCTGGG GGGCGCATTC
      GGCACGACCC CCCGCGTAAG
```

SEQUENCE APPENDIX 3-continued

```
                                           E Hypr
       -------------------------------------------------------------------------------
         N   S   I   F   G   G   V   G   F   L   P   K   L   L   L   G   V   A   L   A   W   L   G   L   N   M   R
  2101 AATTCTATTT TCGGGGGCGT GGGGTTCCTG CCTAAACTCC TGCTGGGAGT AGCCCTGGCC TGGTTGGGAC TGAATATGCG
       TTAAGATAAA AGCCCCCGCA CCCCAAGGAC GGATTTGAGG ACGACCCTCA TCGGGACCGG ACCAACCCTG ACTTATACGC
              E Hypr
       --------------------
         N   P   T   M   S   M   S  •
       GAATCCGACG ATGTCCATGT
       CTTAGGCTGC TACAGGTACA E Hypr
       ----------------------------------------------------------
                                                                                      WNV NS1 protein
                                                                             ------------------------------
        •  F   L   L   A   G   V   L   V   L   A   M   T   L   G   V   G   A   D   T   G   C   A   I   D   I   S
  2201 CATTCCTCTT GGCCGGCGTG CTTGTACTGG CCATGACACT GGGCGTTGGC GCCGACACTG GGTGTGCCAT AGACATCAGC
       GTAAGGAGAA CCGGCCGCAC GAACATGACC GGTACTGTGA CCCGCAACCG CGGCTGTGAC CCACACGGTA TCTGTAGTCG
       WNV NS1
       protein
       ------
         R   Q
       CGGCAA
       GCCGTT
```

```
                               PIV-WN/TBEV Hypr with WNV signal (p40)

5' UTR
       -------------------------------------------------------------------------------
     1 AGTAGTTCGC CTGTGTGAGC TGACAAACTT AGTAGTGTTT GTGAGGATTA ACAACAATTA ACACAGTGCG AGCTGTTTCT
       TCATCAAGCG GACACACTCG ACTGTTTGAA TCATCACAAA CACTCCTAAT TGTTGTTAAT TGTGTCACGC TCGACAAAGA
                     deleted C
                     ----
              5' UTR
       ------------------
                          M   S  •
       TAGCACGAAG ATCTCGATGT
       ATCGTGCTTC TAGAGCTACA WNV deleted C
       -----------------------------------------------------------------------------------
        •  K   K   P   G   G   P   G   K   S   R   A   V   Y   L   L   K   R   G   M   P   R   V   L   S   L   I
   101 CTAAGAAACC AGGAGGGCCC GGCAAGAGCC GGGCTGTCTA TTTGCTAAAA CGCGGAATGC CCCGCGTGTT GTCCTTGATT
       GATTCTTTGG TCCTCCCGGG CCGTTCTCGG CCCGACAGAT AAACGATTTT GCGCCTTACG GGGCGCACAA CAGGAACTAA
              WNV deleted C
       ---------------------
         G   L   K   R   S   S   K  •
       GGACTTAAGC GGAGCTCCAA
       CCTGAATTCG CCTCGAGGTT WNV signal
                           ------------------------------------------------------------
            WNV deleted C                                                      prM Hypr
            --------------                                                     ---------------
        •  Q   K   K   R   G   G   K   T   G   I   A   V   M   I   G   M   L   A   C   V   G   A   A   T   V   R   K
   201 GCAAAAGAAA CGCGGGGGAA AGACAGGCAT AGCTGTGATG ATAGGCATGC TGGCTTGTGT CGGAGCAGCT ACCGTGCGAA
       CGTTTTCTTT GCGCCCCCTT TCTGTCCGTA TCGACACTAC TATCCGTACG ACCGAACACA GCCTCGTCGA TGGCACGCTT
              prM Hypr
       ---------------------
         E   R   D   G   S   T
       AAGAACGCGA CGGAAGCACC
       TTCTTGCGCT GCCTTCGTGG prM Hypr
       ---------------------------------------------------------------------------------
         V   I   R   A   E   G   K   D   A   A   T   Q   V   R   V   E   N   G   T   C   V   I   L   A   T   D   M
   301 GTGATAAGGG CTGAGGGTAA GGATGCGGCT ACGCAGGTGA GAGTAGAGAA TGGCACTTGC GTAATACTCG CGACTGATAT
       CACTATTCCC GACTCCCATT CCTACGCCGA TGCGTCCACT CTCATCTCTT ACCGTGAACG CATTATGAGC GCTGACTATA
              prM Hypr
       ---------------------
         G   S   W   C   D   D   S  •
       GGGATCCTGG TGTGACGATA
       CCCTAGGACC ACACTGCTAT
```

SEQUENCE APPENDIX 3-continued

```
                                                   prM Hypr
     ----------------------------------------------------------------------------
      • L   S   Y   E   C   V     T   I   D   Q   G   E   E     P   V   D     V   D   C     F   R   N   V   D   G
 401 GCCTCAGTTA TGAATGCGTA ACAATAGACC AGGGCGAAGA ACCTGTGGAC GTTGACTGTT TCTGTAGAAA TGTGGATGGC
     CGGAGTCAAT ACTTACGCAT TGTTATCTGG TCCCGCTTCT TGGACACCTG CAACTGACAA AGACATCTTT ACACCTACCG
           prM Hypr
     ---------------------
       V   Y   L   E   Y   G   R •
     GTTTATCTGG AGTACGGCCG
     CAAATAGACC TCATGCCGGC prM Hypr
     ----------------------------------------------------------------------------
      • C   G   K     Q   E   G   S     R   T   R   R   S   V     L   I   P   S     H   A   Q     G   E   L     T   G   R   G
 501 CTGTGGAAAA CAGGAGGGCT CACGAACTCG AAGATCTGTG CTGATTCCAA GTCACGCGCA AGGAGAGTTG ACCGGTAGAG
     GACACCTTTT GTCCTCCCGA GTGCTTGAGC TTCTAGACAC GACTAAGGTT CAGTGCGCGT TCCTCTCAAC TGGCCATCTC
           prM Hypr
     ---------------------
       H   K   W     L   E   G
     GCCACAAGTG GCTTGAAGGG
     CGGTGTTCAC CGAACTTCCC prM Hypr
     ----------------------------------------------------------------------------
       D   S   L   R     T   H   L     T   R   V     E   G   W   V     W   K   N     R   L   L     A   L   A   M     V   T   V
 601 GACTCATTGA GGACCCACCT GACTAGGGTG GAGGGTTGGG TTTGGAAGAA TCGGTTGCTC GCGCTCGCTA TGGTCACCGT
     CTGAGTAACT CCTGGGTGGA CTGATCCCAC CTCCCAACCC AAACCTTCTT AGCCAACGAG CGCGAGCGAT ACCAGTGGCA
           prM Hypr
     ---------------------
       V   W   L     T   L   E   S •
     CGTGTGGCTG ACACTGGAGA
     GCACACCGAC TGTGACCTCT E Hypr
                                                                    -------------------------
                                                   prM Hypr
     ----------------------------------------------------------------------
      • V   V   T     R   V   A     V   L   V   V     L   L   C     L   A   P     V   Y   A   S     R   C   T     H   L   E
 701 GTGTCGTGAC TCGGGTTGCT GTGTTGGTTG TCCTCCTCTG TTTGGCCCCA GTGTACGCGT CCAGGTGTAC TCATTTGGAA
     CACAGCACTG AGCCCAACGA CACAACCAAC AGGAGGAGAC AAACCGGGGT CACATGCGCA GGTCCACATG AGTAAACCTT
            E Hypr
     ---------------------
       N   R   D   F     V   T   G •
     AACAGAGATT TTGTCACCGG
     TTGTCTCTAA AACAGTGGCC E Hypr
     ----------------------------------------------------------------------------
      • T   Q   G     T   T   R   V     T   L   V     L   E   L     G   G   C   V     T   I   T     A   E   G     K   P   S   M
 801 CACCCAGGGG ACGACTCGGG TAACCCTGGT GCTTGAACTG GGTGGTTGCG TTACTATTAC CGCTGAGGGC AAACCCTCTA
     GTGGGTCCCC TGCTGAGCCC ATTGGGACCA CGAACTTGAC CCACCAACGC AATGATAATG GCGACTCCCG TTTGGGAGAT
            E Hypr
     ---------------------
       D   V   W     L   D   A
     TGGATGTGTG GCTGGATGCA
     ACCTACACAC CGACCTACGT E Hypr
     ----------------------------------------------------------------------------
       I   Y   Q     E   N   P   A     Q   T   R     E   Y   C   L     H   A   K     L   S   D     T   K   V     A   A   R   C
 901 ATCTATCAGG AGAATCCCGC ACAAACCAGG GAATATTGCC TTCACGCAAA GCTGTCCGAT ACAAAGGTCG CGGCTAGGTG
     TAGATAGTCC TCTTAGGGCG TGTTTGGTCC CTTATAACGG AAGTGCGTTT CGACAGGCTA TGTTTCCAGC GCCGATCCAC
            E Hypr
     ---------------------
       P   T   M     G   P   A   T •
     CCCAACAATG GGACCGGCCA
     GGGTTGTTAC CCTGGCCGGT E Hypr
     ----------------------------------------------------------------------------
      • L   A   E     E   H   Q     G   G   T   V     C   K   R     D   Q   S     D   R   G   W     G   N   H     C   G   L
1001 CCCTGGCGGA GGAACATCAG GGAGGTACAG TGTGCAAACG GGACCAGAGT GATAGAGGCT GGGGTAATCA CTGCGGCCTG
     GGGACCGCCT CCTTGTAGTC CCTCCATGTC ACACGTTTGC CCTGGTCTCA CTATCTCCGA CCCCATTAGT GACGCCGGAC
            E Hypr
     ---------------------
       F   G   K   G     S   I   V •
     TTCGGCAAAG GAAGTATTGT
     AAGCCGTTTC CTTCATAACA
```

SEQUENCE APPENDIX 3-continued

```
                                                    E Hypr
     ---------------------------------------------------------------------------------
      • A   C   V     K   A   A   C     E   A   K     K   K   A     T   G   H     V   Y   D     A   N   K   I     V   Y   T   V
1101 CGCTTGCGTC AAGGCAGCCT GTGAGGCCAA AAAGAAGGCT ACTGGGCACG TCTATGACGC CAACAAGATC GTTTATACAG
     GCGAACGCAG TTCCGTCGGA CACTCCGGTT TTTCTTCCGA TGACCCGTGC AGATACTGCG GTTGTTCTAG CAAATATGTC
              E Hypr
     ---------------------
       K   V   E     P   H   T
     TGAAAGTGGA ACCACACACA
     ACTTTCACCT TGGTGTGTGT E Hypr
     ---------------------------------------------------------------------------------
       G   D   Y   V     A   A   N     E   T   H     S   G   R   K     T   A   S     F   T   V     S   S   E   K     T   I   L
1201 GGGGATTACG TGGCGGCCAA CGAGACTCAT TCCGGTCGCA AAACGGCCAG CTTCACCGTG TCATCCGAAA AGACCATCCT
     CCCCTAATGC ACCGCCGGTT GCTCTGAGTA AGGCCAGCGT TTTGCCGGTC GAAGTGGCAC AGTAGGCTTT TCTGGTAGGA
              E Hypr
     ---------------------
       T   M   G     E   Y   G   D •
     CACTATGGGG GAGTATGGCG
     GTGATACCCC CTCATACCGC E Hypr
     ---------------------------------------------------------------------------------
      • V   S   L     L   C   R     V   A   S   G     V   D   L     A   Q   T     V   I   L   E     L   D   K     T   V   E
1301 ACGTTTCTCT GCTCTGCCGG GTGGCTAGCG GAGTCGACCT GGCCCAGACA GTCATCCTGG AACTGGATAA AACAGTTGAG
     TGCAAAGAGA CGAGACGGCC CACCGATCGC CTCAGCTGGA CCGGGTCTGT CAGTAGGACC TTGACCTATT TTGTCAACTC
              E Hypr
     ---------------------
       H   L   P     T   A   W   Q •
     CATCTGCCTA CCGCTTGGCA
     GTAGACGGAT GGCGAACCGT E Hypr
     ---------------------------------------------------------------------------------
      • V   H   R     D   W   F   N     D   L   A     L   P   W     K   H   E   G     A   R   N     W   N   N     A   E   R   L
1401 GGTGCACAGG GATTGGTTTA ACGACCTTGC CCTGCCATGG AAACATGAAG GAGCGAGAAA CTGGAATAAT GCAGAGCGAC
     CCACGTGTCC CTAACCAAAT TGCTGGAACG GGACGGTACC TTTGTACTTC CTCGCTCTTT GACCTTATTA CGTCTCGCTG
              E Hypr
     ---------------------
       V   E   F     G   A   P
     TCGTAGAATT CGGTGCCCCT
     AGCATCTTAA GCCACGGGGA E Hypr
     ---------------------------------------------------------------------------------
       H   A   V   K     M   D   V     Y   N   L     G   D   Q   T     G   V   L     L   K   A     L   A   G   V     P   V   A
1501 CATGCCGTGA AGATGGACGT CTACAATCTG GGTGATCAGA CCGGCGTTCT CCTTAAAGCT CTCGCTGGCG TACCAGTTGC
     GTACGGCACT TCTACCTGCA GATGTTAGAC CCACTAGTCT GGCCGCAAGA GGAATTTCGA GAGCGACCGC ATGGTCAACG
              E Hypr
     ---------------------
       H   I   E     G   T   K   Y •
     CCACATCGAA GGAACGAAGT
     GGTGTAGCTT CCTTGCTTCA E Hypr
     ---------------------------------------------------------------------------------
      • H   L   K     S   G   H     V   T   C   E     V   G   L     E   K   L     K   M   K   G     L   T   Y     T   M   C
1601 ACCACCTGAA GTCAGGCCAT GTAACTTGCG AGGTGGGCCT GGAGAAGTTG AAAATGAAAG GTCTTACGTA CACAATGTGT
     TGGTGGACTT CAGTCCGGTA CATTGAACGC TCCACCCGGA CCTCTTCAAC TTTTACTTTC CAGAATGCAT GTGTTACACA
              E Hypr
     ---------------------
       D   K   T   K     F   T   W •
     GACAAGACCA AGTTCACATG
     CTGTTCTGGT TCAAGTGTAC E Hypr
     ---------------------------------------------------------------------------------
      • K   R   A     P   T   D   S     G   H   D     T   V   V     M   E   V   T     F   S   G     T   K   P     C   R   I   P
1701 GAAGAGGGCC CCCACAGATA GCGGCCACGA TACTGTGGTG ATGGAGGTGA CCTTTTCTGG AACAAAACCC TGCAGAATAC
     CTTCTCCCGG GGGTGTCTAT CGCCGGTGCT ATGACACCAC TACCTCCACT GGAAAAGACC TTGTTTTGGG ACGTCTTATG
              E Hypr
     ---------------------
       V   R   A     V   A   H
     CCGTGCGGGC TGTAGCTCAC
     GGCACGCCCG ACATCGAGTG
```

SEQUENCE APPENDIX 3-continued

```
                                    E Hypr
       -----------------------------------------------------------------------------------
        G   S   P   D   V   N   V   A   M   L   I   T   P   N   P   T   I   E   N   N   G   G   G   F   I   E   M
 1801  GGATCTCCCG ATGTCAATGT TGCTATGCTG ATTACACCTA ACCCTACCAT CGAGAATAAC GGTGGTGGTT TTATTGAGAT
       CCTAGAGGGC TACAGTTACA ACGATACGAC TAATGTGGAT TGGGATGGTA GCTCTTATTG CCACCACCAA AATAACTCTA
            E Hypr
       ---------------------
        Q   L   P   P   G   D   N •
       GCAGCTTCCG CCAGGCGATA
       CGTCGAAGGC GGTCCGCTAT E Hypr
       -----------------------------------------------------------------------------------
        •  I   I   Y   V   G   E   L   S   Y   Q   W   F   Q   K   G   S   I   G   R   V   F   Q   K   T   K
 1901  ACATCATCTA CGTGGGCGAA CTCTCTTACC AGTGGTTTCA GAAAGGGAGT TCAATTGGGC GGGTCTTCCA AAAAACGAAG
       TGTAGTAGAT GCACCCGCTT GAGAGAATGG TCACCAAAGT CTTTCCCTCA AGTTAACCCG CCCAGAAGGT TTTTTGCTTC
            E Hypr
       ---------------------
        K   G   I   E   R   L   T •
       AAGGGAATCG AACGATTGAC
       TTCCCTTAGC TTGCTAACTG E Hypr
       -----------------------------------------------------------------------------------
        •V  I   G   E   H   A   W   D   F   G   S   A   G   G   F   L   S   S   I   G   K   A   L   H   T   V   L
 2001  CGTTATCGGC GAGCACGCAT GGGATTTTGG TTCCGCAGGG GGATTCCTGT CTTCTATTGG TAAGGCACTG CATACCGTGC
       CCAATAGCCG CTCGTGCGTA CCCTAAAACC AAGGCGTCCC CCTAAGGACA GAAGATAACC ATTCCGTGAC GTATGGCACG
            E Hypr
       ---------------------
        G   G   A   F   N   S
       TGGGGGGCGC ATTCAATTCT
       ACCCCCCGCG TAAGTTAAGA E Hypr
       -----------------------------------------------------------------------------------
        I   F   G   G   V   G   F   L   P   K   L   L   L   G   V   A   L   A   W   L   G   L   N   M   R   N   P
 2101  ATTTTCGGGG GCGTGGGGTT CCTGCCTAAA CTCCTGCTGG GAGTAGCCCT GGCCTGGTTG GGACTGAATA TGCGGAATCC
       TAAAAGCCCC CGCACCCCAA GGACGGATTT GAGGACGACC CTCATCGGGA CCGGACCAAC CCTGACTTAT ACGCCTTAGG
            E Hypr
       ---------------------
        T   M   S   M   S   F   L •
       GACGATGTCC ATGTCATTCC
       CTGCTACAGG TACAGTAAGG E Hypr
       ------------------------------------------------------
                                                                        WNV NS1 protein
                                                              ---------------------------------------
        •  L   A   G   V   L   V   L   A   M   T   L   G   V   G   A   D   T   G   C   A   I   D   I   S   R   Q
 2201  TCTTGGCCGG CGTGCTTGTA CTGGCCATGA CACTGGGCGT TGGCGCCGAC ACTGGGTGTG CCATAGACAT CAGCCGGCAA
       AGAACCGGCC GCACGAACAT GACCGGTACT GTGACCCGCA ACCGCGGCTG TGACCCACAC GGTATCTGTA GTCGGCCGTT
```

SEQUENCE APPENDIX 4.

WN PIV constructs expressing rabies virus G protein.

WN (ΔCprME)-Rabies PIV sequence (partial)

```
                                    5' UTR
       -----------------------------------------------------------------------------------
    1  AGTAGTTCGC CTGTGTGAGC TGACAAACTT AGTAGTGTTT GTGAGGATTA ACAACAATTA ACACAGTGCG AGCTGTTTCT
       TCATCAAGCG GACACACTCG ACTGTTTGAA TCATCACAAA CACTCCTAAT TGTTGTTAAT TGTGTCACGC TCGACAAAGA
            N-terminus of C
            ----
         5' UTR
       ----------------
                    M   S •
                    ----
       TAGCACGAAG ATCTCGATGT
       ATCGTGCTTC TAGAGCTACA
```

SEQUENCE APPENDIX 4.-continued

WN PIV constructs expressing rabies virus G protein.

```
                                  N-terminus of C
    -----------------------------------------------------------------------------
     • K   K   P    G   G   P    G   K   S    R   A   V    Y   L   L    K   R   G    M   P   R    V   L   S    L   I
    -----------------------------------------------------------------------------
101  CTAAGAAACC  AGGAGGGCCC  GGCAAGAGCC  GGGCTGTCTA  TTTGCTAAAA  CGCGGAATGC  CCCGCGTGTT  GTCCTTGATT
     GATTCTTTGG  TCCTCCCGGG  CCGTTCTCGG  CCCGACAGAT  AAACGATTTT  GCGCCTTACG  GGCGCACAA   CAGGAACTAA
        N-terminus of C
     ---------------------
       G   L   K   Q    K   K   R •
     ---------------------
     GGACTTAAGC  AAAAGAAGCG
     CCTGAATTCG  TTTTCTTCGC N-terminus of C                                     Rabies-G signal
     --                                       -----------------------------------------------------------
              partial C signal
            -----------------------------
     • G   G   K    T   G   I    A   V   I    V   P   Q    A   L   L    F   V   P    L   L   V    F   P   L    C   F   G
     -----------------------------------------------------------------------------
201  AGGGGGCAAG  ACTGGTATAG  CTGTGATCGT  TCCTCAGGCT  CTTTTGTTTG  TACCCTTGCT  GGTATTTCCC  CTTTGCTTTG
     TCCCCCGTTC  TGACCATATC  GACACTAGCA  AGGAGTCCGA  GAAAACAAAC  ATGGGAACGA  CCATAAAGGG  GAAACGAAAC
        Rabies-G protein
     ---------------------
       K   F   P    I   Y   T
     ---------------------
     GTAAATTTCC  TATCTATACC
     CATTTAAAGG  ATAGATATGG Rabies-G protein
    -----------------------------------------------------------------------------
       I   P   D    K   L   G    P   W   S    P   I   D    I   H   H    L   S   C    P   N   L    V   V   E    D   E
    -----------------------------------------------------------------------------
301  ATCCCTGATA  AGCTCGGGCC  TTGGAGTCCC  ATTGATATTC  ACCATTTGAG  CTGCCCAAAC  AACCTCGTCG  TTGAGGATGA
     TAGGGACTAT  TCGAGCCCGG  AACCTCAGGG  TAACTATAAG  TGGTAAACTC  GACGGGTTTG  TTGGAGCAGC  AACTCCTACT
        Rabies-G protein
     ---------------------
       G   C   T    N   L   S   G •
     ---------------------
     AGGGTGCACT  AATCTTTCTG
     TCCCACGTGA  TTAGAAAGAC Rabies-G protein
    -----------------------------------------------------------------------------
     • F   S   Y    M   E   L    K   V   G    Y   I   S    A   I   K    M   N   G    F   T   C    T   G   V    V   T
    -----------------------------------------------------------------------------
401  GATTTTCCTA  CATGGAGTTG  AAAGTGGGCT  ATATTTCAGC  CATTAAGATG  AACGGCTTTA  CTTGTACAGG  AGTCGTGACC
     CTAAAAGGAT  GTACCTCAAC  TTTCACCCGA  TATAAAGTCG  GTAATTCTAC  TTGCCGAAAT  GAACATGTCC  TCAGCACTGG
        Rabies-G protein
     ---------------------
       E   A   E   T   Y   T   N •
     ---------------------
     GAAGCCGAGA  CATATACAAA
     CTTCGGCTCT  GTATATGTTT Rabies-G protein
    -----------------------------------------------------------------------------
     • F   V   G    Y   V   T    T   T   F    K   R   K    H   F   R    P   T   P    D   A   C    R   A   A    Y   N   W
    -----------------------------------------------------------------------------
501  TTTCGTGGGA  TACGTCACCA  CCACCTTCAA  GAGAAAACAC  TTCCGCCCAA  CGCCTGACGC  TTGTCGGGCC  GCTTACAACT
     AAAGCACCCT  ATGCAGTGGT  GGTGGAAGTT  CTCTTTTGTG  AAGGCGGGTT  GCGGACTGCG  AACAGCCCGG  CGAATGTTGA
        Rabies-G protein
     ---------------------
       K   M   A    G   D   P
     ---------------------
     GGAAGATGGC  AGGAGATCCT
     CCTTCTACCG  TCCTCTAGGA Rabies-G protein
    -----------------------------------------------------------------------------
       R   Y   E    E   S   L    H   N   P    Y   P   D    Y   H   W    L   R   T    V   K   T    T   K   E    S   L   V
    -----------------------------------------------------------------------------
601  CGATATGAAG  AATCTCTGCA  CAACCCGTAT  CCTGATTACC  ATTGGCTGCG  GACAGTCAAG  ACTACCAAGG  AGAGTCTGGT
     GCTATACTTC  TTAGAGACGT  GTTGGGCATA  GGACTAATGG  TAACCGACGC  CTGTCAGTTC  TGATGGTTCC  TCTCAGACCA
        Rabies-G protein
     ---------------------
       I   I   S    P   S   V   A •
     ---------------------
     CATTATATCA  CCAAGCGTGG
```

SEQUENCE APPENDIX 4.-continued

WN PIV constructs expressing rabies virus G protein.

```
    GTAATATAGT GGTTCGCACC
                                    Rabies-G protein
    ------------------------------------------------------------------
    • D   L   D   P   Y   D   R   S   L   H   S   R   V   F   P   G   N   C   S   G   V   A   V   S   S
    ------------------------------------------------------------------
701 CCGATCTTGA TCCTTATGAT AGATCCCTGC ACAGTAGGGT TTTCCTGGC GGGAATTGTA GCGGTGTTGC AGTATCAAGT
    GGCTAGAACT AGGAATACTA TCTAGGGACG TGTCATCCCA AAAAGGACCG CCCTTAACAT CGCCACAACG TCATAGTTCA
        Rabies-G protein
    ---------------------
      T   Y   C   S   T   N   H •
    ---------------------
    ACCTACTGCT CCACTAACCA
    TGGATGACGA GGTGATTGGT Rabies-G protein
    ------------------------------------------------------------------
    • D   Y   T   I   W   M   P   E   N   P   R   L   G   M   S   C   D   I   F   T   N   S   R   G   K   R   A
    ------------------------------------------------------------------
801 CGACTACACT ATATGGATGC CTGAGAACCC TCGACTCGGT ATGAGTTGCG ACATTTTTAC GAACTCACGG GGCAAGCGGG
    GCTGATGTGA TATACCTACG GACTCTTGGG AGCTGAGCCA TACTCAACGC TGTAAAAATG CTTGAGTGCC CCGTTCGCCC
        Rabies-G protein
    ---------------------
      S   K   G   S   E   T
    ---------------------
    CATCTAAGGG GTCTGAAACA
    GTAGATTCCC CAGACTTTGT Rabies-G protein
    ------------------------------------------------------------------
      C   G   F   V   D   E   R   G   L   Y   K   S   L   K   G   A   C   K   L   K   L   C   G   V   L   G   L
    ------------------------------------------------------------------
901 TGCGGGTTTG TTGATGAGCG GGGGTTGTAT AAATCTCTTA AAGGCGCCTG TAAGCTGAAA CTCTGTGGCG TACTGGGGCT
    ACGCCCAAAC AACTACTCGC CCCCAACATA TTTAGAGAAT TTCCGCGGAC ATTCGACTTT GAGACACCGC ATGACCCCGA
        Rabies-G protein
    ---------------------
      R   L   M   D   G   T   W •
    ---------------------
    GCGCCTGATG GACGGCACAT
    CGCGGACTAC CTGCCGTGTA Rabies-G protein
    ------------------------------------------------------------------
    • V   A   M   Q   T   S   N   E   T   K   W   C   P   P   G   Q   L   V   N   L   H   D   F   R   S   D
    ------------------------------------------------------------------
1001 GGGTGGCTAT GCAGACAAGC AATGAAACAA AGTGGTGTCC CCCTGGTCAG CTGGTTAATC TGCACGACTT TAGGTCTGAC
     CCCACCGATA CGTCTGTTCG TTACTTTGTT TCACCACAGG GGGACCAGTC GACCAATTAG ACGTGCTGAA ATCCAGACTG
        Rabies-G protein
    ---------------------
      E   I   E   H   L   V   V •
    ---------------------
    GAAATCGAGC ACCTTGTGGT
    CTTTAGCTCG TGGAACACCA Rabies-G protein
    ------------------------------------------------------------------
    • E   E   L   V   K   K   R   E   E   C   L   D   A   L   E   S   I   M   T   T   K   S   V   S   F   R   R
    ------------------------------------------------------------------
1101 GGAGGAACTG GTGAAGAAAC GCGAAGAGTG CCTGGACGCA CTTGAGAGTA TTATGACCAC CAAATCCGTT TCCTTCAGAA
     CCTCCTTGAC CACTTCTTTG CGCTTCTCAC GGACCTGCGT GAACTCTCAT AATACTGGTG GTTTAGGCAA AGGAAGTCTT
        Rabies-G protein
    ---------------------
      L   S   H   L   R   K
    ---------------------
    GACTGAGCCA CCTGCGAAAG
    CTGACTCGGT GGACGCTTTC Rabies-G protein
    ------------------------------------------------------------------
      L   V   P   G   F   G   K   A   Y   T   I   F   N   K   T   L   M   E   A   D   A   H   Y   K   S   V   R
    ------------------------------------------------------------------
1201 CTGGTGCCAG GGTTCGGGAA GGCTTATACT ATTTTCAACA AGACTCTTAT GGAGGCGGAT GCCCATTATA AGTCAGTTAG
     GACCACGGTC CCAAGCCCTT CCGAATATGA TAAAAGTTGT TCTGAGAATA CCTCCGCCTA CGGGTAATAT TCAGTCAATC
        Rabies-G protein
    ---------------------
      T   W   N   E   I   I   P •
    ---------------------
    GACTTGGAAT GAGATAATTC
    CTGAACCTTA CTCTATTAAG
```

SEQUENCE APPENDIX 4.-continued

WN PIV constructs expressing rabies virus G protein.

```
                                      Rabies-G protein
     ----------------------------------------------------------------------------
      • S  K   G   C   L   R   V   G   G   R   C   H   P   H   V   N   G   V   F   F   N   G   I   I   L   G
     ----------------------------------------------------------------------------
1301 CCTCCAAAGG ATGTCTGAGA GTCGGTGGGA GATGCCACCC CCATGTCAAT GGGGTGTTCT TTAACGGAAT CATCCTGGGA
     GGAGGTTTCC TACAGACTCT CAGCCACCCT CTACGGTGGG GGTACAGTTA CCCCACAAGA AATTGCCTTA GTAGGACCCT
         Rabies-G protein
     --------------------
       P   D   G   N   V   L   I •
     --------------------
     CCTGACGGGA ACGTGCTGAT
     GGACTGCCCT TGCACGACTA Rabies-G protein
     ----------------------------------------------------------------------------
      • P  E   M   Q   S   S   L   L   Q   H   M   E   L   L   V   S   S   V   I   P   L   M   H   P   L   A
     ----------------------------------------------------------------------------
1401 TCCCGAGATG CAATCTTCCC TTCTGCAGCA ACACATGGAA CTCCTGGTGT CTTCAGTGAT ACCCCTGATG CACCCACTGG
     AGGGCTCTAC GTTAGAAGGG AAGACGTCGT TGTGTACCTT GAGGACCACA GAAGTCACTA TGGGGACTAC GTGGGTGACC
         Rabies-G protein
     --------------------
       D   P   S   T   V   F
     --------------------
     CCGACCCCAG CACTGTGTTC
     GGCTGGGGTC GTGACACAAG Rabies-G protein
     ----------------------------------------------------------------------------
        K  N   G   D   E   A   E   D   F   V   E   V   H   L   P   D   V   H   E   R   I   S   G   V   D   L   G
     ----------------------------------------------------------------------------
1501 AAAAATGGCG ATGAGGCCGA AGACTTTGTG GAAGTTCACC TGCCCGATGT ACACGAAAGG ATATCTGGAG TAGACCTGGG
     TTTTTACCGC TACTCCGGCT TCTGAAACAC CTTCAAGTGG ACGGGCTACA TGTGCTTTCC TATAGACCTC ATCTGGACCC
         Rabies-G protein
     --------------------
       L   P   N   W   G   K   Y •
     --------------------
     CCTTCCTAAT TGGGGTAAGT
     GGAAGGATTA ACCCCATTCA Rabies-G protein
     ----------------------------------------------------------------------------
      • V  L   L   S   A   G   A   L   T   A   L   M   L   I   I   F   L   M   T   C   W   R   R   V   N   R
     ----------------------------------------------------------------------------
1601 ACGTGCTCCT GAGTGCGGGT GCCTTGACCG CTTTGATGCT GATCATTTTT CTGATGACCT GCTGGCGGAG GGTGAATCGC
     TGCACGAGGA CTCACGCCCA CGGAACTGGC GAAACTACGA CTAGTAAAAA GACTACTGGA CGACCGCCTC CCACTTAGCG
         Rabies-G protein
     --------------------
       S   E   P   T   Q   H   N •
     --------------------
     TCCGAGCCGA CACAGCACAA
     AGGCTCGGCT GTGTCGTGTT Rabies-G protein
     ----------------------------------------------------------------------------
      • L  R   G   T   G   R   E   V   S   V   T   P   Q   S   G   K   I   I   S   S   W   E   S   Y   K   S   G
     ----------------------------------------------------------------------------
1701 TCTCAGAGGG ACAGGCCGGG AAGTAAGTGT GACTCCGCAA TCTGGCAAGA TTATTAGTAG TTGGGAGAGT TACAAGTCTG
     AGAGTCTCCC TGTCCGGCCC TTCATTCACA CTGAGGCGTT AGACCGTTCT AATAATCATC AACCCTCTCA ATGTTCAGAC
     Rabies-G protein
     ------------------          FMDV 2A
                                 ---
       G   E   T   G   L   N
     --------------------
     GAGGAGAGAC TGGGTTGAAT
     CTCCTCTCTG ACCCAACTTA
```

SEQUENCE APPENDIX 4.-continued

WN PIV constructs expressing rabies virus G protein.

```
                                              preNS1 signal
                                              ----------
              FMDV 2A                                         NS1 signal
     ------------------------------------    --------------------------
       F  D  L  L   K  L  A  G  D  V   E  S  N  P  G  P  A  R  D  R   S  I  A  L   T  F  L
     ----------------------------------------------------------------------------------------
1801 TTTGATCTGC TCAAACTTGC AGGCGATGTA GAATCAAATC CTGGACCCGC CCGGGACAGG TCCATAGCTC TCACGTTTCT
     AAACTAGACG AGTTTGAACG TCCGCTACAT CTTAGTTTAG GACCTGGGCG GGCCCTGTCC AGGTATCGAG AGTGCAAAGA
         NS1 signal
     --------------------
       A  V  G   G  V  L  L •
     --------------------
     CGCAGTTGGA GGAGTTCTGC
     GCGTCAACCT CCTCAAGACG NS1 signal
     ----------------------------
                                                              NS1
                                   ----------------------------------------------------------
     •  F  L  S   V  N  V  H  A  D  T   G  C  A  I  D  I   S  R  Q  E   L  R  C   G  S  G
     ----------------------------------------------------------------------------------------
1901 TCTTCCTCTC CGTGAACGTG CACGCTGACA CTGGGTGTGC CATAGACATC AGCCGGCAAG AGCTGAGATG TGGAAGTGGA
     AGAAGGAGAG GCACTTGCAC GTGCGACTGT GACCCACACG GTATCTGTAG TCGGCCGTTC TCGACTCTAC ACCTTCACCT
             NS1
     --------------------
        V  F  I  H   N  D  V •
     --------------------
     GTGTTCATAC ACAATGATGT
     CACAAGTATG TGTTACTACA
```

WN (ΔC)-Rabies G PIV sequence (partial).

```
                                              5'UTR
     ----------------------------------------------------------------------------------------
   1 AGTAGTTCGC CTGTGTGAGC TGACAAACTT AGTAGTGTTT GTGAGGATTA ACAACAATTA ACACAGTGCG AGCTGTTTCT
     TCATCAAGCG GACACACTCG ACTGTTTGAA TCATCACAAA CACTCCTAAT TGTTGTTAAT TGTGTCACGC TCGACAAAGA
             5'UTR
     -----------------
                           N-
                      terminus of C
                         ----
                         M  S •
                         ----
     TAGCACGAAG ATCTCGATGT
     ATCGTGCTTC TAGAGCTACA N-terminus of C
     ----------------------------------------------------------------------------------------
     •  K  K  P   G  G  P   G  K  S  R   A  V  N   M  L  K   R  G  M  P   R  V  L   S  L  I
     ----------------------------------------------------------------------------------------
 101 CTAAGAAACC AGGAGGGCCC GGCAAGAGCC GGGCTGTCAA TATGCTAAAA CGCGGAATGC CCCGCGTGTT GTCCTTGATT
     GATTCTTTGG TCCTCCCGGG CCGTTCTCGG CCCGACAGTT ATACGATTTT GCGCCTTACG GGGCGCACAA CAGGAACTAA
         N-terminus of C
     --------------------
        G  L  K  Q   K  K  R •
     --------------------
     GGACTTAAGC AAAAGAAGCG
     CCTGAATTCG TTTTCTTCGC N-terminus of C
     --
             partial C signal            RAbies-G signal
     --------------------------    ----------------------------
     •  G  G  K   T  G  I  A  V  I  V   P  Q  A   L  L  F  V   P  L  L   V  F  P   L  C  F  G
     ----------------------------------------------------------------------------------------
 201 AGGGGGCAAG ACTGGTATAG CTGTGATCGT TCCTCAGGCT CTTTTGTTTG TACCCTTGCT GGTATTTCCC CTTTGCTTTG
     TCCCCCGTTC TGACCATATC GACACTAGCA AGGAGTCCGA GAAAACAAAC ATGGGAACGA CCATAAAGGG GAAACAAAC
         Rabies-G protein
     ------------------
        K  F  P  I  Y  T
     --------------------
     GTAAATTTCC TATCTATACC
     CATTTAAAGG ATAGATATGG
```

SEQUENCE APPENDIX 4.-continued

WN PIV constructs expressing rabies virus G protein.

```
                                      Rabies-G protein
       I   P   D   K    L   G   P    W   S   P    I   D   I    H   L   S    C   P   N    L   V   V    E   D   E
   301 ATCCCTGATA AGCTCGGGCC TTGGAGTCCC ATTGATATTC ACCATTTGAG CTGCCCAAAC AACCTCGTCG TTGAGGATGA
       TAGGGACTAT TCGAGCCCGG AACCTCAGGG TAACTATAAG TGGTAAACTC GACGGGTTTG TTGGAGCAGC AACTCCTACT
            Rabies-G protein
         G   C   T    N   L   S    G •
       AGGGTGCACT AATCTTTCTG
       TCCCACGTGA TTAGAAAGAC Rabies-G protein
       •  F   S   Y    M   E   L    K   V   G   Y    I   S   A    I   K   M    N   G   F   T    C   T   G    V   V   T
   401 GATTTTCCTA CATGGAGTTG AAAGTGGGCT ATATTTCAGC CATTAAGATG AACGGCTTTA CTTGTACAGG AGTCGTGACC
       CTAAAAGGAT GTACCTCAAC TTTCACCCGA TATAAAGTCG GTAATTCTAC TTGCCGAAAT GAACATGTCC TCAGCACTGG
            Rabies-G protein
         E   A   E   T    Y   T   N •
       GAAGCCGAGA CATATACAAA
       CTTCGGCTCT GTATATGTTT Rabies-G protein
       •  F   V   G    Y   V   T   T    T   F   K    R   K   H    F   R   P    T   P   D    A   C   R    A   Y   N   W
   501 TTTCGTGGGA TACGTCACCA CCACCTTCAA GAGAAACAC TTCCGCCCAA CGCCTGACGC TTGTCGGGCC GCTTACAACT
       AAAGCACCCT ATGCAGTGGT GGTGGAAGTT CTCTTTTGTG AAGGCGGGTT GCGGACTGCG AACAGCCCGG CGAATGTTGA
            Rabies-G protein
         K   M   A    G   D   P
       GGAAGATGGC AGGAGATCCT
       CCTTCTACCG TCCTCTAGGA Rabies-G protein
          R   Y   E   E    S   L   H    N   P   Y    P   D   Y    H   W   L   R    T   V   K    T   T   K   E    S   L   V
   601 CGATATGAAG AATCTCTGCA CAACCCGTAT CCTGATTACC ATTGGCTGCG GACAGTCAAG ACTACCAAGG AGAGTCTGGT
       GCTATACTTC TTAGAGACGT GTTGGGCATA GGACTAATGG TAACCGACGC CTGTCAGTTC TGATGGTTCC TCTCAGACCA
            Rabies-G protein
         I   I   S    P   S   V   A •
       CATTATATCA CCAAGCGTGG
       GTAATATAGT GGTTCGCACC Rabies-G protein
       •  D   L   D    P   Y   D    R   S   L   H    S   R   V    F   P   G    G   N   C   S    G   V   A    V   S   S
   701 CCGATCTTGA TCCTTATGAT AGATCCCTGC ACAGTAGGGT TTTTCCTGGC GGGAATTGTA GCGGTGTTGC AGTATCAAGT
       GGCTAGAACT AGGAATACTA TCTAGGGACG TGTCATCCCA AAAAGGACCG CCCTTAACAT CGCCACAACG TCATAGTTCA
            Rabies-G protein
         T   Y   C    S   T   N   H •
       ACCTACTGCT CCACTAACCA
       TGGATGACGA GGTGATTGGT Rabies-G protein
       •  D   Y   T    I   W   M   P    E   N   P    R   L   G    M   S   C   D    I   F   T    N   S   R    G   K   R   A
   801 CGACTACACT ATATGGATGC CTGAGAACCC TCGACTCGGT ATGAGTTGCG ACATTTTTAC GAACTCACGG GGCAAGCGGG
       GCTGATGTGA TATACCTACG GACTCTTGGG AGCTGAGCCA TACTCAACGC TGTAAAAATG CTTGAGTGCC CCGTTCGCCC
            Rabies-G protein
         S   K   G    S   E   T
       CATCTAAGGG GTCTGAAACA
       GTAGATTCCC CAGACTTTGT
```

SEQUENCE APPENDIX 4.-continued

WN PIV constructs expressing rabies virus G protein.

```
                                          Rabies-G protein
     -------------------------------------------------------------------------------------
        C   G   F   V   D   E   R   G   L   Y   K   S   L   K   G   A   C   K   L   K   L   C   G   V   L   G   L
     -------------------------------------------------------------------------------------
 901 TGCGGGTTTG TTGATGAGCG GGGGTTGTAT AAATCTCTTA AAGGCGCCTG TAAGCTGAAA CTCTGTGGCG TACTGGGGCT
     ACGCCCAAAC AACTACTCGC CCCCAACATA TTTAGAGAAT TTCCGCGGAC ATTCGACTTT GAGACACCGC ATGACCCCGA
                                          Rabies-G protein
     ---------------------
        R   L   M   D   G   T   W •
     ---------------------
     GCGCCTGATG GACGGCACAT
     CGCGGACTAC CTGCCGTGTA Rabies-G protein
     -------------------------------------------------------------------------------------
      • V   A   M   Q   T   S   N   E   T   K   W   C   P   P   G   Q   L   V   N   L   H   D   F   R   S   D
     -------------------------------------------------------------------------------------
1001 GGGTGGCTAT GCAGACAAGC AATGAAACAA AGTGGTGTCC CCCTGGTCAG CTGGTTAATC TGCACGACTT TAGGTCTGAC
     CCCACCGATA CGTCTGTTCG TTACTTTGTT TCACCACAGG GGGACCAGTC GACCAATTAG ACGTGCTGAA ATCCAGACTG
                                          Rabies-G protein
     ---------------------
        E   I   E   H   L   V   V •
     ---------------------
     GAAATCGAGC ACCTTGTGGT
     CTTTAGCTCG TGGAACACCA Rabies-G protein
     -------------------------------------------------------------------------------------
      • E   E   L   V   K   K   R   E   E   C   L   D   A   L   E   S   T   M   T   T   K   S   V   S   F   R   R
     -------------------------------------------------------------------------------------
1101 GGAGGAACTG GTGAAGAAAC GCGAAGAGTG CCTGGACGCA CTTGAGAGTA TTATGACCAC CAAATCCGTT TCCTTCAGAA
     CCTCCTTGAC CACTTCTTTG CGCTTCTCAC GGACCTGCGT GAACTCTCAT AATACTGGTG GTTTAGGCAA AGGAAGTCTT
                                          Rabies-G protein
     ---------------------
        L   S   H   L   R   K
     ---------------------
     GACTGAGCCA CCTGCGAAAG
     CTGACTCGGT GGACGCTTTC Rabies-G protein
     -------------------------------------------------------------------------------------
        L   V   P   G   F   G   K   A   Y   T   I   F   N   K   T   L   M   E   A   D   A   H   Y   K   S   V   R
     -------------------------------------------------------------------------------------
1201 CTGGTGCCAG GGTTCGGGAA GGCTTATACT ATTTTCAACA AGACTCFTAT GGAGGCGGAT GCCCATTATA AGTCAGTTAG
     GACCACGGTC CCAAGCCCTT CCGAATATGA TAAAAGTTGT TCTGAGAATA CCTCCGCCTA CGGGTAATAT TCAGTCAATC
                                          Rabies-G protein
     ---------------------
        T   W   N   E   I   I   P •
     ---------------------
     GACTTGGAAT GAGATAATTC
     CTGAACCTTA CTCTATTAAG Rabies-G protein
     -------------------------------------------------------------------------------------
      • S   K   G   C   L   R   V   G   G   R   C   H   P   H   V   N   G   V   F   F   N   G   I   I   L   G
     -------------------------------------------------------------------------------------
1301 CCTCCAAAGG ATGTCTGAGA GTCGGTGGGA GATGCCACCC CCATGTCAAT GGGGTGTTCT TTAACGGAAT CATCCFGGGA
     GGAGGTTTCC TACAGACTCT CAGCCACCCT CTACGGTGGG GGTACAGTTA CCCCACAAGA AATTGCCTTA GTAGGACCCT
                                          Rabies-G protein
     ---------------------
        P   D   G   N   V   L   I •
     ---------------------
     CCTGACGGGA ACGTGCTGAT
     GGACTGCCCT TGCACGACTA Rabies-G protein
     -------------------------------------------------------------------------------------
      • P   E   M   Q   S   S   L   Q   Q   H   M   E   L   L   V   S   S   V   I   P   L   M   H   P   L   A
     -------------------------------------------------------------------------------------
1401 TCCCGAGATG CAATCTTCCC TTCTGCAGCA ACACATGGAA CTCCTGGTGT CTTCAGTGAT ACCCCTGATG CACCCACTGG
     AGGGCTCTAC GTTAGAAGGG AAGACGTCGT TGTGTACCTT GAGGACCACA GAAGTCACTA TGGGGACTAC GTGGGTGACC
                                          Rabies-G protein
     ---------------------
        D   P   S   T   V   F
     ---------------------
     CCGACCCCAG CACTGTGTTC
     GGCTGGGGTC GTGACACAAG
```

SEQUENCE APPENDIX 4.-continued

WN PIV constructs expressing rabies virus G protein.

```
                              Rabies-G protein
     -------------------------------------------------------------------------
       K   N   G   D   E   A   E   D   F   V   E   V   H   L   P   D   V   H   E   R   I   S   G   V   D   L   G
     -------------------------------------------------------------------------
1501 AAAAATGGCG ATGAGGCCGA AGACTTTGTG AAGTTCACC TGCCCGATGT ACACGAAAGG ATATCTGGAG TAGACCTGGG
     TTTTACCGC TACTCCGGCT TCTGAAACAC CTTCAAGTGG ACGGGCTACA TGTGCTTTCC TATAGACCTC ATCTGGACCC
         Rabies-G protein
         --------------------
       L   P   N   W   G   K   Y •
         --------------------
     CCTTCCTAAT TGGGGTAAGT
     GGAAGGATTA ACCCCATTCA Rabies-G protein
     -------------------------------------------------------------------------
     • V   L   L   S   A   G   A   L   T   A   L   M   L   I   I   F   L   M   T   C   W   R   R   V   N   R
     -------------------------------------------------------------------------
1601 ACGTGCTCCT GAGTGCGGGT GCCTTGACCG CTTTGATGCT GATCATTTTT CTGATGACCT GCTGGCGGAG GGTGAATCGC
     TGCACGAGGA CTCACGCCCA CGGAACTGGC GAAACTACGA CTAGTAAAAA GACTACTGGA CGACCGCCTC CCACTTAGCG
         Rabies-G protein
         --------------------
       S   E   P   T   Q   H   N •
         --------------------
     TCCGAGCCGA CACAGCACAA
     AGGCTCGGCT GTGTCGTGTT Rabies-G protein
     -------------------------------------------------------------------------
     • L   R   G   T   G   R   E   V   S   V   T   P   Q   S   G   K   I   I   S   S   W   E   S   Y   K   S   G
     -------------------------------------------------------------------------
1701 TCTCAGAGGG ACAGGCCGGG AAGTAAGTGT GACTCCGCAA CTGGCAAGA TTATTAGTAG TTGGGAGAGT TACAAGTCTG
     AGAGTCTCCC TGTCCGGCCC TTCATTCACA CTGAGGCGTT AGACCGTTCT AATAATCATC AACCCTCTCA ATGTTCAGAC
                        FMDV 2A
                        ---
     Rabies-G protein
     ------------------
       G   E   T   G   L   N
     ------------------
     GAGGAGAGAC TGGGTTGAAT
     CTCCTCTCTG ACCCAACTTA C/prM singal
                                                                            ---------------------------------------
                 FMDV 2A
     --------------------------------------------------------
       F   D   L   L   K   L   A   G   D   V   E   S   N   P   G   P   G   K   T   G   I   A   V   M   I   G
     --------------------------------------------------------
1801 TTTGATCTGC TCAAACTTGC AGGCGATGTA GAATCAAATC CTGGACCCGG AGGAAAGACC GGTATTGCAG TCATGATTGG
     AAACTAGACG AGTTTGAACG TCCGCTACAT CTTAGTTTAG GACCTGGGCC TCCTTTCTGG CCATAACGTC AGTACTAACC
         C/prM singal
         --------------------
       L   I   A   C   V   G   A •
         --------------------
     CCTGATCGCC TGCGTAGGAG
     GGACTAGCGG ACGCATCCTC C/prM signal
     --
                                               prM
     -------------------------------------------------------------------------
     • V   T   L   S   N   F   Q   G   K   V   M   M   T   V   N   A   T   D   V   T   D   V   I   T   I   P
     -------------------------------------------------------------------------
1901 CAGTTACCCT CTCTAACTTC CAAGGGAAGG TGATGATGAC GGTAAATGCT ACTGACGTCA CAGATGTCAT ACGATTCCA
     GTCAATGGGA GAGATTGAAG GTTCCCTTCC ACTACTACTG CCATTTACGA TGACTGCAGT GTCTACAGTA TGCTAAGGT
             prM
         --------------------
       T   A   A   G   K   N   L •
         --------------------
     ACAGCTGCTG GAAAGAACCT
     TGTCGACGAC CTTTCTTGGA
```

SEQUENCE APPENDIX 4.-continued

WN PIV constructs expressing rabies virus G protein.

```
                                                     prM
          ·C  I   V   R   A   M   D   V   G   Y   M   C   D   D   T   I   T   Y   E   C   P   V   L   S   A   G   N
2001 ATGCATTGTC AGAGCAATGG ATGTGGGATA CATGTGCGAT GATACTATCA CTTATGAATG CCCAGTGCTG TCGGCTGGTA
     TACGTAACAG TCTCGTTACC TACACCCTAT GTACACGCTA CTATGATAGT GAATACTTAC GGGTCACGAC AGCCGACCAT
             prM
         D   P   E   D   I   D
     ATGATCCAGA AGACATCGAC
     TACTAGGTCT TCTGTAGCTG prM
         C   W   C   T   K   S   A   V   Y   V   R   Y   G   R   C   T   K   T   R   H   S   R   R   S   R   R   S
2101 TGTTGGTGCA CAAAGTCAGC AGTCTACGTC AGGTATGGAA GATGCACCAA GACACGCCAC TCAAGACGCA GTCGGAGGTC
     ACAACCACGT GTTTCAGTCG TCAGATGCAG TCCATACCTT CTACGTGGTT CTGTGCGGTG AGTTCTGCGT CAGCCTCCAG
             prM
         L   T   V   Q   T   H   G ·
     ACTGACAGTG CAGACACACG
     TGACTGTCAC GTCTGTGTGC prM
         ·E  S   T   L   A   N   K   K   G   A   W   M   D   S   T   K   A   T   R   Y   L   V   K   T   E   S
2201 GAGAAAGCAC TCTAGCGAAC AAGAAGGGGG CTTGGATGGA CAGCACCAAG GCCACAAGGT ATTTGGTAAA AACAGAATCA
     CTCTTTCGTG AGATCGCTTG TTCTTCCCCC GAACCTACCT GTCGTGGTTC CGGTGTTCCA TAAACCATTT TTGTCTTAGT
             prM
         W   I   L   R   N   P   G ·
     TGGATCTTGA GGAACCCTGG
     ACCTAGAACT CCTTGGGACC prM
         ·Y  A   L   V   A   A   V   I   G   W   M   L   G   S   N   T   M   Q   R   V   V   F   V   V   L   L   L
2301 ATATGCCCTG GTGGCAGCCG TCATTGGTTG GATGCTTGGG AGCAACACCA TGCAGAGAGT TGTGTTTGTC GTGCTATTGC
     TATACGGGAC CACCGTCGGC AGTAACCAAC CTACGAACCC TCGTTGTGGT ACGTCTCTCA ACACAAACAG CACGATAACG
             prM
         L   V   A   P   A   Y
     TTTTGGTGGC CCCAGCTTAC
     AAAACCACCG GGGTCGAATG

E
     prM
     ---
         S   F   N   C   L   G   M   S   N   R   D   F   L   E   G   V   S   G   A   T   W   V   D   L   V   L   E
2401 AGCTTTAACT GCCTTGGAAT GAGCAACAGA GACTTCTTGG AAGGAGTGTC TGGAGCAACA TGGGTGGATT TGGTTCTCGA
     TCGAAATTGA CGGAACCTTA CTCGTTGTCT CTGAAGAACC TTCCTCACAG ACCTCGTTGT ACCCACCTAA ACCAAGAGCT
                 E
         G   D   S   C   V   T   I ·
     AGGCGACAGC TGCGTGACTA
     TCCGCTGTCG ACGCACTGAT

E
         ·M  S   K   D   K   P   T   I   D   V   K   M   M   N   M   E   A   A   N   L   A   E   V   R   S   Y
2501 TCATGTCTAA GGACAAGCCT ACCATCGATG TGAAGATGAT GAATATGGAG GCGGCCAACC TGGCAGAGGT CCGCAGTTAT
     AGTACAGATT CCTGTTCGGA TGGTAGCTAC ACTTCTACTA CTTATACCTC CGCCGGTTGG ACCGTCTCCA GGCGTCAATA
                 E
         C   Y   L   A   T   V   S ·
     TGCTATTTGG CTACCGTCAG
```

SEQUENCE APPENDIX 4.-continued

WN PIV constructs expressing rabies virus G protein.

```
      ACGATAAACC GATGGCAGTC
                                                        E
      -------------------------------------------------------------------------------
      • D   L   S   T   K   A   A   C   P   A   M   G   E   A   H   N   D   K   R   A   D   P   A   F   V   C   R
      -------------------------------------------------------------------------------
2601  CGATCTCTCC ACCAAAGCTG CGTGCCCGGC CATGGGAGAA GCTCACAATG ACAAACGTGC TGACCCAGCT TTTGTGTGCA
      GCTAGAGAGG TGGTTTCGAC GCACGGGCCG GTACCCTCTT CGAGTGTTAC TGTTTGCACG ACTGGGTCGA AAACACACGT
                      E
      ---------------------
          Q   G   V   V   D   R
      ---------------------
      GACAAGGAGT GGTGGACAGG
      CTGTTCCTCA CCACCTGTCC

E
      -------------------------------------------------------------------------------
          G   W   G   N   G   C   G   L   F   G   K   G   S   I   D   T   C   A   K   F   A   C   S   T   K   A   I
      -------------------------------------------------------------------------------
2701  GGCTGGGGCA ACGGCTGCGG ACTATTTGGC AAAGGAAGCA TTGACACATG CGCCAAATTT GCCTGCTCTA CCAAGGCAAT
      CCGACCCCGT TGCCGACGCC TGATAAACCG TTTCCTTCGT AACTGTGTAC GCGGTTTAAA CGGACGAGAT GGTTCCGTTA
                       E
      ---------------------
          G   R   T   I   L   K   E •
      ---------------------
      AGGAAGAACC ATTTTGAAAG
      TCCTTCTTGG TAAAACTTTC

E
      -------------------------------------------------------------------------------
      • N   I   K   Y   E   V   A   I   F   V   H   G   P   T   T   V   E   S   H   G   N   Y   S   T   Q   V
      -------------------------------------------------------------------------------
2801  AGAATATCAA GTACGAAGTG GCCATTTTTG TCCATGGACC AACTACTGTG GAGTCGCACG GAAACTACTC CACACAGGTT
      TCTTATAGTT CATGCTTCAC CGGTAAAAAC AGGTACCTGG TTGATGACAC CTCAGCGTGC CTTTGATGAG GTGTGTCCAA
                      E
      ---------------------
          G   A   T   Q   A   G   R
      ---------------------
      GGAGCCACTC AGGCAGGGAG
      CCTCGGTGAG TCCGTCCCTC

E
      -------------------------------------------------------------------------------
      • F   S   I   T   P   A   A   P   S   Y   T   L   K   L   G   E   Y   G   E   V   T   V   D   C   E   P   R
      -------------------------------------------------------------------------------
2901  ATTCAGCATC ACTCCTGCGG CGCCTTCATA CACACTAAAG CTTGGAGAAT ATGGAGAGGT GACAGTGGAC TGTGAACCAC
      TAAGTCGTAG TGAGGACGCC GCGGAAGTAT GTGTGATTTC GAACCTCTTA TACCTCTCCA CTGTCACCTG ACACTTGGTG
                       E
      ---------------------
          S   G   I   D   T   N
      ---------------------
      GGTCAGGGAT TGACACCAAT
      CCAGTCCCTA ACTGTGGTTA

E
      -------------------------------------------------------------------------------
          A   Y   Y   V   M   T   V   G   T   K   T   F   L   V   H   R   E   W   F   M   D   L   N   L   P   W   S
      -------------------------------------------------------------------------------
3001  GCATACTACG TGATGACTGT TGGAACAAAG ACGTTCTTGG TCCATCGTGA GTGGTTCATG GACCTCAACC TCCCTTGGAG
      CGTATGATGC ACTACTGACA ACCTTGTTTC TGCAAGAACC AGGTAGCACT CACCAAGTAC CTGGAGTTGG AGGGAACCTC
                      E
      ---------------------
          S   A   G   S   T   V   W •
      ---------------------
      CAGTGCTGGA AGTACTGTGT
      GTCACGACCT TCATGACACA

E
      -------------------------------------------------------------------------------
      • R   N   R   E   T   L   M   E   F   E   E   P   H   A   T   K   Q   S   V   I   A   L   G   S   Q   E
      -------------------------------------------------------------------------------
3101  GGAGGAACAG AGAGACGTTA ATGGAGTTTG AGGAACCACA CGCCACGAAG CAGTCTGTGA TAGCATTGGG CTCACAAGAG
      CCTCCTTGTC TCTCTGCAAT TACCTCAAAC TCCTTGGTGT GCGGTGCTTC GTCAGACACT ATCGTAACCC GAGTGTTCTC
                       E
      ---------------------
          G   A   L   H   Q   A   L •
      ---------------------
      GGAGCTCTGC ATCAAGCTTT
      CCTCGAGACG TAGTTCGAAA
```

SEQUENCE APPENDIX 4.-continued

WN PIV constructs expressing rabies virus G protein.

```
                                           E
       ---------------------------------------------------------------------
        • A   G   A   I   P   V   E   F   S   S   N   T   V   K   L   T   S   G   H   L   K   C   R   V   K   M   E
       ---------------------------------------------------------------------
3201   GGCTGGAGCC ATTCCTGTGG AATTTTCAAG CAACACTGTC AAGTTGACGT CGGGTCATTT GAAGTGTAGA GTGAAGATGG
       CCGACCTCGG TAAGGACACC TTAAAAGTTC GTTGTGACAG TTCAACTGCA GCCCAGTAAA CTTCACATCT CACTTCTACC
                             E
       ---------------------
          K   L   Q   L   K   G
       ---------------------
       AAAAATTGCA GTTGAAGGGA
       TTTTTAACGT CAACTTCCCT

E
       ---------------------------------------------------------------------
          T   T   Y   G   V   C   S   K   A   F   K   F   L   G   T   P   A   D   T   G   H   G   T   V   V   L   E
       ---------------------------------------------------------------------
3301   ACAACCTATG GCGTCTGTTC AAAGGCTTTC AAGTTTCTTG GGACTCCCGC AGACACAGGT CACGGCACTG TGGTGTTGGA
       TGTTGGATAC CGCAGACAAG TTTCCGAAAG TTCAAAGAAC CCTGAGGGCG TCTGTGTCCA GTGCCGTGAC ACCACAACCT
                             E
       ---------------------
          L   Q   Y   T   G   T   D •
       ---------------------
       ATTGCAGTAC ACTGGCACGG
       TAACGTCATG TGACCGTGCC

E
       ---------------------------------------------------------------------
        • G   P   C   K   V   P   I   S   S   V   A   S   L   N   D   L   T   P   V   G   R   L   V   T   V   N
       ---------------------------------------------------------------------
3401   ATGGACCTTG CAAAGTTCCT ATCTCGTCAG TGGCTTCATT GAACGACCTA ACGCCAGTGG GCAGATTGGT CACTGTCAAC
       TACCTGGAAC GTTTCAAGGA TAGAGCAGTC ACCGAAGTAA CTTGCTGGAT TGCGGTCACC CGTCTAACCA GTGACAGTTG
                             E
       ---------------------
          P   F   V   S   V   A   T •
       ---------------------
       CCTTTTGTTT CAGTGGCCAC
       GGAAAACAAA GTCACCGGTG

E
       ---------------------------------------------------------------------
        • A   N   A   K   V   L   I   E   L   E   P   P   F   G   D   S   Y   I   V   V   G   R   G   E   Q   Q   I
       ---------------------------------------------------------------------
3501   GGCCAACGCT AAGGTCCTGA TTGAATTGGA ACCACCCTTT GGAGACTCAT ACATAGTGGT GGGCAGAGGA GAACAACAGA
       CCGGTTGCGA TTCCAGGACT AACTTAACCT TGGTGGGAAA CCTCTGAGTA TGTATCACCA CCCGTCTCCT CTTGTTGTCT
                             E
       ---------------------
          N   H   H   W   H   K
       ---------------------
       TCAATCACCA CTGGCACAAG
       AGTTAGTGGT GACCGTGTTC

E
       ---------------------------------------------------------------------
          S   G   S   S   I   G   K   A   F   T   T   T   L   K   G   A   Q   R   L   A   A   L   G   D   T   A   W
       ---------------------------------------------------------------------
3601   TCTGGAAGCA GCATTGGCAA AGCCTTTACA ACCACCCTCA AAGGAGCGCA GAGACTAGCC GCTCTAGGAG ACACAGCTTG
       AGACCTTCGT CGTAACCGTT TCGGAAATGT TGGTGGGAGT TTCCTCGCGT CTCTGATCGG CGAGATCCTC TGTGTCGAAC
                             E
       ---------------------
          D   F   G   S   V   G   G •
       ---------------------
       GGACTTTGGA TCAGTTGGAG
       CCTGAAACCT AGTCAACCTC

E
       ---------------------------------------------------------------------
        • V   F   T   S   V   G   K   A   V   H   Q   V   F   G   G   A   F   R   S   L   F   G   G   M   S   W
       ---------------------------------------------------------------------
3701   GGGTGTTCAC CTCAGTTGGG AAGGCTGTCC ATCAAGTGTT CGGAGGAGCA TTCCGCTCAC TGTTCGGAGG CATGTCCTGG
       CCCACAAGTG GAGTCAACCC TTCCGACAGG TAGTTCACAA GCCTCCTCGT AAGGCGAGTG ACAAGCCTCC GTACAGGACC
                             E
       ---------------------
          I   T   Q   G   L   L   G •
       ---------------------
       ATAACGCAAG GATTGCTGGG
       TATTGCGTTC CTAACGACCC
```

SEQUENCE APPENDIX 4.-continued

WN PIV constructs expressing rabies virus G protein.

```
                                        E
       ------------------------------------------------------------------------------
     • A  L  L   L  W  M  G   I  N  A  R   D  R   S  I  A  L   T  F  L   A  V  G   V  L  L
       ------------------------------------------------------------------------------
3801 GGCTCTCCTG TTGTGGATGG GCATCAATGC TCGTGACAGG TCCATAGCTC TCACGTTTCT CGCAGTTGGA GGAGTTCTGC
     CCGAGAGGAC AACACCTACC CGTAGTTACG AGCACTGTCC AGGTATCGAG AGTGCAAAGA GCGTCAACCT CCTCAAGACG
                 E
       ---------------------
        F  L  S   V  N  V
       ---------------------
     TCTTCCTCTC CGTGAACGTG
     AGAAGGAGAG GCACTTGCAC

E
       ------
                                                                      NS1
                              ------------------------------------------------------------------
        H  A  D  T   G  C  A   I  D  I   S  R  Q  E   L  R  C   G  S  G   V  F  I  H   N  D  V
                              ------------------------------------------------------------------
3901 CACGCTGACA CTGGGTGTGC CATAGACATC AGCCGGCAAG AGCTGAGATG TGGAAGTGGA GTGTTCATAC ACAATGATGT
     GTGCGACTGT GACCCACACG GTATCTGTAG TCGGCCGTTC TCGACTCTAC ACCTTCACCT CACAAGTATG TGTTACTACA
                 NS1
       ---------------------
        E  A  W   M  D  R  Y •
       ---------------------
     GGAGGCTTGG ATGGACCGGT
     CCTCCGAACC TACCTGGCCA
```

WN (ΔprME)-Rabies G PIV sequence (partial)

```
                                             5' UTR
     ----------------------------------------------------------------------------------------
   1 AGTAGTTCGC CTGTGTGAGC TGACAAACTT AGTAGTGTTT GTGAGGATTA ACAACAATTA ACACAGTGCG AGCTGTTTCT
     TCATCAAGCG GACACACTCG ACTGTTTGAA TCATCACAAA CACTCCTAAT TGTTGTTAAT TGTGTCACGC TCGACAAAGA
                              C protein
                              ----
         5' UTR
       -----------------
                     M  S •
                     ----
     TAGCACGAAG ATCTCGATGT
     ATCGTGCTTC TAGAGCTACA C protein
       --------------------------------------------------------------------------------------
     • K  K  P   G  G  P   G  K  S  R   A  V  Y   L  L  K   R  G  M   P  R  V  L   S  L  I
       --------------------------------------------------------------------------------------
 101 CTAAGAAACC AGGAGGGCCC GGCAAGAGCC GGGCTGTCTA TTTGCTAAAA CGCGGAATGC CCCGCGTGTT GTCCTTGATT
     GATTCTTTGG TCCTCCCGGG CCGTTCTCGG CCCGACAGAT AAACGATTTT GCGCCTTACG GGGCGCACAA CAGGAACTAA
           C protein
       ---------------------
        G  L  K  R   A  M  L •
       ---------------------
     GGACTTAAGA GGGCTATGTT
     CCTGAATTCT CCCGATACAA C protein
       --------------------------------------------------------------------------------------
     • S  L  I   D  G  K  G   P  I  R   F  V  L   A  L  L  A   F  F  R   F  T  A   I  A  P  T
       --------------------------------------------------------------------------------------
 201 GAGCCTGATC GACGGCAAGG GGCCAATACG ATTTGTGTTG CTCTCTTGG CGTTCTTCAG GTTCACAGCA ATTGCTCCGA
     CTCGGACTAG CTGCCGTTCC CCGGTTATGC TAAACACAAC CGAGAGAACC GCAAGAAGTC CAAGTGTCGT TAACGAGGCT
           C protein
       ---------------------
        R  A  V   L  D  R
       ---------------------
     CCCGAGCAGT GCTGGATCGA
     GGGCTCGTCA CGACCTAGCT
```

SEQUENCE APPENDIX 4.-continued

WN PIV constructs expressing rabies virus G protein.

```
                                   C protein
        ------------------------------------------------------------------
          W   R   G   V   N   K   Q   T   A   M   K   H   L   L   S   F   K   K   E   L   G   T   L   T   S   A   I
        ------------------------------------------------------------------
    301 TGGAGAGGTG TGAACAAACA AACAGCGATG AAACACCTTC TGAGTTTCAA GAAGGAACTA GGGACCTTGA CCAGTGCTAT
        ACCTCTCCAC ACTTGTTTGT TTGTCGCTAC TTTGTGGAAG ACTCAAAGTT CTTCCTTGAT CCCTGGAACT GGTCACGATA
              C protein
        ---------------------
          N   R   R   S   S   K   Q •
        ---------------------
        CAATCGGCGG AGCTCAAAGC
        GTTAGCCGCC TCGAGTTTCG Rabies-G signal
                                                            ------------------------------------------------
         C protein         partial C signal
         protein
        ------------    ----------------------------
          • K   K   R   G   G   K   T   G   I   A   V   I   V   P   Q   A   L   L   F   V   P   L   L   V   F   P
        ------------------------------------------------------------------
    401 AAAAGAAGCG AGGGGGCAAG ACTGGTATAG CTGTGATCGT TCCTCAGGCT CTTTTGTTTG TACCCTTGCT GGTATTTCCC
        TTTTCTTCGC TCCCCCGTTC TGACCATATC GACACTAGCA AGGAGTCCGA GAAACAAAC ATGGGAACGA CCATAAAGGG
            Rabies-G
            signal
        -------------
                     RAbies-G
                     --------
          L   C   F   G   K   F   P •
        ---------------------
        CTTTGCTTTG GTAAATTTCC
        GAAACGAAAC CATTTAAAGG RAbies-G protein
        ------------------------------------------------------------------
          • I   Y   T   I   P   D   K   L   G   P   W   S   P   I   D   I   H   H   L   S   C   P   N   N   L   V   V
        ------------------------------------------------------------------
    501 TATCTATACC ATCCCTGATA AGCTCGGGCC TTGGAGTCCC ATTGATATTC ACCATTTGAG CTGCCCAAAC AACCTCGTCG
        ATAGATATGG TAGGGACTAT TCGAGCCCGG AACCTCAGGG TAACTATAAG TGGTAAACTC GACGGGTTTG TTGGAGCAGC
            RAbies-G protein
        ---------------------
          E   D   E   G   C   T
        ---------------------
        TTGAGGATGA AGGGTGCACT
        AACTCCTACT TCCCACGTGA Rabies-G protein
        ------------------------------------------------------------------
          N   L   S   G   F   S   Y   M   E   L   K   V   G   Y   I   S   A   I   K   M   N   G   F   T   C   T   G
        ------------------------------------------------------------------
    601 AATCTTTCTG GATTTTCCTA CATGGAGTTA AAAGTGGGCT ATATTTCAGC CATTAAGATG AACGGCTTTA CTTGTACAGG
        TTAGAAAGAC CTAAAGGAT GTACCTCAAC TTTCACCCGA TATAAAGTCG GTAATTCTAC TTGCCGAAAT GAACATGTCC
            RAbies-G protein
        ---------------------
          V   V   T   E   A   E   T •
        ---------------------
        AGTCGTGACC GAAGCCGAGA
        TCAGCACTGG CTTCGGCTCT Rabies-G protein
        ------------------------------------------------------------------
          • Y   T   N   F   V   G   Y   V   T   T   T   F   K   R   K   H   F   R   P   T   P   D   A   C   R   A
        ------------------------------------------------------------------
    701 CATATACAAA TTTCGTGGGA TACGTCACCA CCACCTTCAA GAGAAAACAC TTCCGCCCAA CGCCTGACGC TTGTCGGGCC
        GTATATGTTT AAAGCACCCT ATGCAGTGGT GGTGGAAGTT CTCTTTTGTG AAGGCGGGTT GCGGACTGCG AACAGCCCGG
            RAbies-G protein
        ---------------------
          A   Y   N   W   K   M   A •
        ---------------------
        GCTTACAACT GGAAGATGGC
        CGAATGTTGA CCTTCTACCG
```

SEQUENCE APPENDIX 4.-continued

WN PIV constructs expressing rabies virus G protein.

```
                                        Rabies-G protein
     •  G    D    P    R    Y    E    E    S    L    H    N    P    Y    P    D    Y    H    W    L    R    T    V    K    T    T    K    E 801  AGGAGATCCT CGATATGAAG AATCTCTGCA CAACCCGTAT CCTGATTACC ATTGGCTGCG GACAGTCAAG ACTACCAAGG
     TCCTCTAGGA GCTATACTTC TTAGAGACGT GTTGGGCATA GGACTAATGG TAACCGACGC CTGTCAGTTC TGATGGTTCC RAbies-G protein
        S    L    V    I    I    S

AGAGTCTGGT CATTATATCA
     TCTCAGACCA GTAATATAGT

Rabies-G protein
        P    S    V    A    D    L    D    P    Y    D    R    S    L    H    S    R    V    F    P    G    N    C    S    G    V    A 901  CCAAGCGTGG CCGATCTTGA TCCTTATGAT AGATCCCTGC ACAGTAGGGT TTTTCCTGGC GGGAATTGTA GCGGTGTTGC
     GGTTCGCACC GGCTAGAACT AGGAATACTA TCTAGGGACG TGTCATCCCA AAAAGGACCG CCCTTAACAT CGCCACAACG RAbies-G protein
        V    S    S    T    Y    C    S    •

AGTATCAAGT ACCTACTGCT
     TCATAGTTCA TGGATGACGA

Rabies-G protein
     •  T    N    H    D    Y    T    I    W    M    P    E    N    P    R    L    G    M    S    C    D    I    F    T    N    S    R 1001 CCACTAACCA CGACTACACT ATATGGATGC CTGAGAACCC TCGACTCGGT ATGAGTTGCA CATTTTTAC GAACTCACGG
     GGTGATTGGT GCTGATGTGA TATACCTACG GACTCTTGGG AGCTGAGCCA TACTCAACGC TGTAAAAATG CTTGAGTGCC RAbies-G protein
        G    K    R    A    S    K    G    •

GGCAAGCGGG CATCTAAGGG
     CCGTTCGCCC GTAGATTCCC

Rabies-G protein
     •  S    E    T    C    G    F    V    D    E    R    G    L    Y    K    S    L    K    G    A    C    K    L    K    L    C    G    V 1101 GTCTGAAACA TGCGGGTTTG TTGATGAGCG GGGGTTGTAT AAATCTCTTA AAGGCGCCTG TAAGCTGAAA CTCTGTGGCG
     CAGACTTTGT ACGCCCAAAC AACTACTCGC CCCCAACATA TTTAGAGAAT TTCCGCGGAC ATTCGACTTT GAGACACCGC RAbies-G protein
        L    G    L    R    L    M

TACTGGGGCT GCGCCTGATG
     ATGACCCCGA CGCGGACTAC

Rabies-G protein
        D    G    T    W    V    A    M    Q    T    S    N    E    T    K    W    C    P    P    G    Q    L    V    N    L    H    D    F 1201 GACGGCACAT GGGTGGCTAT GCAGACAAGC AATGAAACAA GTGGTGTCC CCCTGGTCAG CTGGTTAATC TGCACGACTT
     CTGCCGTGTA CCCACCGATA CGTCTGTTCG TTACTTTGTT TCACCACAGG GGGACCAGTC GACCAATTAG ACGTGCTGAA RAbies-G protein
        R    S    D    E    I    E    H    •

TAGGTCTGAC GAAATCGAGC
     ATCCAGACTG CTTTAGCTCG

Rabies-G protein
     •  L    V    V    E    E    L    V    K    K    R    E    E    C    L    D    A    L    E    S    I    M    T    T    K    S    V 1301 ACCTTGTGGT GGAGGAACTG GTGAAGAAAC GCGAAGAGTG CCTGGACGCA CTTGAGAGTA TTATGACCAC CAAATCCGTT
     TGGAACACCA CCTCCTTGAC CACTTCTTTG CGCTTCTCAC GGACCTGCGT GAACTCTCAT AATACTGGTG GTTTAGGCAA RAbies-G protein
        S    F    R    R    L    S    H    •

TCCTTCAGAA GACTGAGCCA
     AGGAAGTCTT CTGACTCGGT
```

SEQUENCE APPENDIX 4.-continued
WN PIV constructs expressing rabies virus G protein.

```
                                     Rabies-G protein
     • L   R   K   L   V   P   G   F   G   K   A   Y   T   I   F   N   K   T   L   M   E   A   D   A   H   Y   K
1401 CCTGCGAAAG CTGGTGCCAG GGTTCGGGAA GGCTTATACT ATTTTCAACA AGACTCTTAT GGAGGCGGAT GCCCATTATA
     GGACGCTTTC GACCACGGTC CCAAGCCCTT CCGAATATGA TAAAAGTTGT TCTGAGAATA CCTCCGCCTA CGGGTAATAT
         RAbies-G protein
        S   V   R   T   W   N
     AGTCAGTTAG GACTTGGAAT
     TCAGTCAATC CTGAACCTTA Rabies-G protein
       E   I   I   P   S   K   G   C   L   R   V   G   G   R   C   H   P   H   V   N   G   V   F   F   N   G   I
1501 GAGATAATTC CCTCCAAAGG ATGTCTGAGA GTCGGTGGGA GATGCCACCC CCATGTCAAT GGGGTGTTCT TTAACGGAAT
     CTCTATTAAG GGAGGTTTCC TACAGACTCT CAGCCACCCT CTACGGTGGG GGTACAGTTA CCCCACAAGA AATTGCCTTA
         RAbies-G protein
        I   L   G   P   D   G   N   •
     CATCCTGGGA CCTGACGGGA
     GTAGGACCCT GGACTGCCCT Rabies-G protein
     • V   L   I   P   E   M   Q   S   S   L   L   Q   Q   H   M   E   L   L   V   S   S   V   I   P   L   M
1601 ACGTGCTGAT TCCCGAGATG CAATCTTCCC TTCTGCAGCA ACACATGGAA CTCCTGGTGT CTTCAGTGAT ACCCCTGATG
     TGCACGACTA AGGGCTCTAC GTTAGAAGGG AAGACGTCGT TGTGTACCTT GAGGACCACA GAAGTCACTA TGGGGACTAC
         RAbies-G protein
         H   P   L   A   D   P   S   •
     CACCCACTGG CCGACCCCAG
     GTGGGTGACC GGCTGGGGTC Rabies-G protein
     • T   V   F   K   N   G   D   E   A   E   D   F   V   E   V   H   L   P   D   V   H   E   R   I   S   G   V
1701 CACTGTGTTC AAAAATGGCG ATGAGGCCGA AGACTTTGTG GAAGTTCACC TGCCCGATGT ACACGAAAGG ATATCTGGAG
     GTGACACAAG TTTTTACCGC TACTCCGGCT TCTGAAACAC CTTCAAGTGG ACGGGCTACA TGTGCTTTCC TATAGACCTC
         RAbies-G protein
         D   L   G   L   P   N
     TAGACCTGGG CCTTCCTAAT
     ATCTGGACCC GGAAGGATTA Rabies-G protein
       W   G   K   Y   V   L   L   S   A   G   A   L   T   A   L   M   L   I   I   F   L   M   T   C   W   R   R
1801 TGGGGTAAGT ACGTGCTCCT GAGTGCGGGT GCCTTGACCG CTTTGATGCT GATCATTTTT CTGATGACCT GCTGGCGGAG
     ACCCCATTCA TGCACGAGGA CTCACGCCCA CGGAACTGGC GAAACTACGA CTAGTAAAAA GACTACTGGA CGACCGCCTC
         RAbies-G protein
         V   N   R   S   E   P   T   •
     GGTGAATCGC TCCGAGCCGA
     CCACTTAGCG AGGCTCGGCT Rabies-G protein
     • Q   H   N   L   R   G   T   G   R   E   V   S   V   T   P   Q   S   G   K   I   I   S   S   W   E   S
1901 CACAGCACAA TCTCAGAGGG ACAGGCCGGG AAGTAAGTGT GACTCCGCAA TCTGGCAAGA TTATTAGTAG TTGGGAGAGT
     GTGTCGTGTT AGAGTCTCCC TGTCCGGCCC TTCATTCACA CTGAGGCGTT AGACCGTTCT AATAATCATC AACCCTCTCA
         RAbies-G protein
        Y   K   S   G   G   E   T   •
     TACAAGTCTG GAGGAGAGAC
     ATGTTCAGAC CTCCTCTCTG
```

SEQUENCE APPENDIX 4.-continued

WN PIV constructs expressing rabies virus G protein.

```
                           FMDV 2A                                                      NS1 signal
         ---------------------------------------------------------------              ---------------
     RAbies-G protein                                                 preNS1 signal
     -------                                                          -------------
     • G  L  N  F  D  L  L  K  L  A  G  D  V  E  S  N  P  G  P  A  R  D  R  S  I  A  L
     ---------------------------------------------------------------------------------------------
2001 TGGGTTGAAT TTTGATCTGC TCAAACTTGC AGGCGATGTA GAATCAAATC CTGGACCCGC CGGGACAGG TCCATAGCTC
     ACCCAACTTA AAACTAGACG AGTTTGAACG TCCGCTACAT CTTAGTTTAG GACCTGGGCG GCCCTGTCC AGGTATCGAG
           NS1 signal
     ---------------------
       T  F  L  A  V  G
     ---------------------
     TCACGTTTCT CGCAGTTGGA
     AGTGCAAAGA GCGTCAACCT NS1
                                                  --------------------------------------------------
                     NS1 signal
         ------------------------------------------
      G  V  L  L  F  L  S  V  N  V  H  A  D  T  G  C  A  I  D  I  S  R  Q  E  L  R  C
     ----------------------------------------------------------------------------------
2101 GGAGTTCTGC TCTTCCTCTC CGTGAACGTG CACGCTGACA CTGGGTGTGC CATAGACATC AGCCGGCAAG AGCTGAGATG
     CCTCAAGACG AGAAGGAGAG GCACTTGCAC GTGCGACTGT GACCCACACG GTATCTGTAG TCGGCCGTTC TCGACTCTAC
        NS1
     ---------------------
       G  S  G  V  F  I  H •
     ---------------------
     TGGAAGTGGA GTGTTCATAC
     ACCTTCACCT CACAAGTATG
```

PIV-WNV helper ΔNS1

```
                                                       5' UTR
     ---------------------------------------------------------------------------------------------
   1 AGTAGTTCGC CTGTGTGAGC TGACAAACTT AGTAGTGTTT GTGAGGATTA ACAACAATTA ACACAGTGCG AGCTGTTTCT
     TCATCAAGCG GACACACTCG ACTGTTTGAA TCATCACAAA CACTCCTAAT TGTTGTTAAT TGTGTCACGC TCGACAAAGA
                                          C
                                       ----
       5' UTR
     -----------------
                    M  S •
     TAGCACGAAG ATCTCGATGT
     ATCGTGCTTC TAGAGCTACA
```

```
                                                                       C
     ---------------------------------------------------------------------------------------------
     • K  K  P  G  G  P  G  K  S  R  A  V  N  M  L  K  R  G  M  P  R  V  L  S  L  I
 101 CTAAGAAACC AGGAGGGCCC GGCAAGAGCC GGGCTGTCAA TATGCTAAAA CGCGGAATGC CCCGCGTGTT GTCCTTGATT
     GATTCTTTGG TCCTCCCGGG CCGTTCTCGG CCCGACAGTT ATACGATTTT GCGCCTTACG GGGCGCACAA CAGGAACTAA
                                                                                C
       G  L  K  R  A  M  L •
     ---------------------
     GGACTTAAGA GGGCTATGTT
     CCTGAATTCT CCCGATACAA
```

```
                                                                       C
     ---------------------------------------------------------------------------------------------
     • S  L  I  D  G  K  G  P  I  R  F  V  L  A  L  L  A  F  F  R  F  T  A  I  A  P  T
 201 GAGCCTGATC GACGGCAAGG GGCCAATACG ATTTGTGTTG GCTCTCTTGG CGTTCTTCAG GTTCACAGCA ATTGCTCCGA
     CTCGGACTAG CTGCCGTTCC CCGGTTATGC TAAACACAAC CGAGAGAACC GCAAGAAGTC CAAGTGTCGT TAACGAGGCT
                                            C
     ---------------------
       R  A  V  L  D  R
     CCCGAGCAGT GCTGGATCGA
     GGGCTCGTCA CGACCTAGCT
```

```
                                                                       C
     ---------------------------------------------------------------------------------------------
      W  R  G  V  N  K  Q  T  A  M  K  H  L  L  S  F  K  K  E  L  G  T  L  T  S  A  I
 301 TGGAGAGGTG TGAACAAACA AACAGCGATG AAACACCTTC TGAGTTTCAA GAAGGAACTA GGGACCTTGA CCAGTGCTAT
     ACCTCTCCAC ACTTGTTTGT TTGTCGCTAC TTTGTGGAAG ACTCAAAGTT CTTCCTTGAT CCCTGGAACT GGTCACGATA
                                                       C
     ---------------------
       N  R  R  S  S  K  Q •
     CAATCGGCGG AGCTCAAAAC
     GTTAGCCGCC TCGAGTTTTG
```

SEQUENCE APPENDIX 4.-continued

WN PIV constructs expressing rabies virus G protein.

```
                             Signal peptide
         ------------------------------------------------------------
          C                                                                 prM
         ------------                                               ----------------
       • K   K   R   G   G   K   T   G   I   A   V   M   I   G   L   I   A   S   V   G   A   V   T   L   S   N
   401 AAAAGAAAAG AGGAGGAAAG ACCGGAATTG CAGTCATGAT TGGCCTGATC GCCAGCGTAG GAGCAGTTAC CCTCTCTAAC
       TTTTCTTTTC TCCTCCTTTC TGGCCTTAAC GTCAGTACTA ACCGGACTAG CGGTCGCATC CTCGTCAATG GGAGAGATTG
              prM
         ---------------------
         F   Q   G   K   V   M   M •
       TTCCAAGGGA AGGTGATGAT
       AAGGTTCCCT TCCACTACTA prM
         --------------------------------------------------------------------------
       • T   V   N   A   T   D   V   T   D   V   I   T   I   P   T   A   A   G   K   N   L   C   I   V   R   A   M
   501 GACGGTAAAT GCTACTGACG TCACAGATGT CATCACGATT CCAACAGCTG CTGGAAAGAA CCTATGCATT GTCAGAGCAA
       CTGCCATTTA CGATGACTGC AGTGTCTACA GTAGTGCTAA GGTTGTCGAC GACCTTTCTT GGATACGTAA CAGTCTCGTT
              prM
         ---------------------
          D   V   G   Y   M   C
       TGGATGTGGG ATACATGTGC
       ACCTACACCC TATGTACACG prM
         --------------------------------------------------------------------------
          D   D   T   I   T   Y   E   C   P   V   L   S   A   G   N   D   P   E   D   I   D   C   W   T   K   S
   601 GATGATACTA TCACTTATGA ATGCCCAGTC CTGTCGGCTG GTAATGATCC AGAAGACATC GACTGTTGGT GCACAAAGTC
       CTACTATGAT AGTGAATACT TACGGGTCAC GACAGCCGAC CATTACTAGG TCTTCTGTAG CTGACAACCA CGTGTTTCAG
              prM
         ---------------------
          A   V   Y   V   R   Y   G •
       AGCAGTCTAC GTCAGGTATG
       TCGTCAGATG CAGTCCATAC prM
         --------------------------------------------------------------------------
       • R   C   T   K   T   R   H   S   R   R   S   R   R   S   L   T   V   Q   T   H   G   E   S   T   L   A
   701 GAAGATGCAC CAAGACACGC CACTCAAGAC GCAGTCGGAG GTCACTGACA GTGCAGACAC ACGGAGAAAG CACTCTAGCG
       CTTCTACGTG GTTCTGTGCG GTGAGTTCTG CGTCAGCCTC CAGTGACTGT CACGTCTGTG TGCCTCTTTC GTGAGATCGC
              prM
         ---------------------
          N   K   K   G   A   W   M •
       AACAAGAAGG GGGCTTGGAT
       TTGTTCTTCC CCCGAACCTA prM
         --------------------------------------------------------------------------
       • D   S   T   K   A   T   R   Y   L   V   K   T   E   S   W   I   L   R   N   P   G   Y   A   L   V   A   A
   801 GGACAGCACC AAGGCCACAA GGTATTTGGT AAAAACAGAA TCATGGATCT TGAGGAACCC TGGATATGCC CTGGTGGCAG
       CCTGTCGTGG TTCCGGTGTT CCATAAACCA TTTTTGTCTT AGTACCTAGA ACTCCTTGGG ACCTATACGG GACCACCGTC
              prM
         ---------------------
          V   I   G   W   M   L
       CCGTCATTGG TTGGATGCTT
       GGCAGTAACC AACCTACGAA E
                                                                                                 ----------------
                                                   prM
         --------------------------------------------------------------------------
          G   S   N   T   M   Q   R   V   V   F   V   V   L   L   L   V   A   P   A   Y   S   F   N   C   L   G
   901 GGGAGCAACA CCATGCAGAG AGTTGTGTTT GTCGTGCTAT TGCTTTTGGT GGCCCCAGCT TACAGCTTTA ACTGCCTTGG
       CCCTCGTTGT GGTACGTCTC TCAACACAAA CAGCACGATA ACGAAAACCA CCGGGGTCGA ATGTCGAAAT TGACGGAACC
                   E
         ---------------------
          M   S   N   R   D   F   L •
       AATGAGCAAC AGAGACTTCT
       TTACTCGTTG TCTCTGAAGA
```

SEQUENCE APPENDIX 4.-continued
WN PIV constructs expressing rabies virus G protein.

```
                                                   E
       ----------------------------------------------------------------------------------
      • E G V   S G A   T W V D   L V L   E G D   S C V T   I M S   K D K
1001  TGGAAGGAGT GTCTGGAGCA ACATGGGTGG ATTTGGTTCT CGAAGGCGAC AGCTGCGTGA CTATCATGTC TAAGGACAAG
      ACCTTCCTCA CAGACCTCGT TGTACCCACC TAAACCAAGA GCTTCCGCTG TCGACGCACT GATAGTACAG ATTCCTGTTC
                     E
      ---------------------
       P  T  I  D   V  K  M •
      CCTACCATCG ATGTGAAGAT
      GGATGGTAGC TACACTTCTA

E
      ---------------------------------------------------------------------------------
     •M N M   E A A N   L A E   V R S   Y C Y L   A T V   S D L   S T K A
1101 GATGAATATG GAGGCGGCCA ACCTGGCAGA GGTCCGCAGT TATTGCTATT TGGCTACCGT CAGCGATCTC TCCACCAAAG
     CTACTTATAC CTCCGCCGGT TGGACCGTCT CCAGGCGTCA ATAACGATAA ACCGATGGCA GTCGCTAGAG AGGTGGTTTC
                    E
     ---------------------
      A  C  P   A  M  G
     CTGCGTGCCC GGCCATGGGA
     GACGCACGGG CCGGTACCCT

E
      ----------------------------------------------------------------------------------
       E A H N   D K R   A D P   A F V C   R Q G   V V D   R G W   G N G C
1201  GAAGCTCACA ATGACAAACG TGCTGACCCA GCTTTTGTGT GCAGACAAGG AGTGGTGGAC AGGGGCTGGG GCAACGGCTG
      CTTCGAGTGT TACTGTTTGC ACGACTGGGT CGAAAACACA CGTCTGTTCC TCACCACCTG TCCCCGACCC CGTTGCCGAC
                     E
      ---------------------
       G  L  F   G  K  G  S •
      CGGACTATTT GGCAAAGGAA
      GCCTGATAAA CCGTTTCCTT

E
      ----------------------------------------------------------------------------------
      • I D T   C A K   F A C S   T K A   I G R   T I L K   E N I   K Y E
1301  GCATTGACAC ATGCGCCAAA TTTGCCTGCT CTACCAAGGC AATAGGAAGA ACCATTTTGA AAGAGAATAT CAAGTACGAA
      CGTAACTGTG TACGCGGTTT AAACGGACGA GATGGTTCCG TTATCCTTCT TGGTAAAACT TTCTCTTATA GTTCATGCTT
                     E
      ---------------------
       V  A  I  F   V  H  G •
      GTGGCCATTT TTGTCCATGG
      CACCGGTAAA AACAGGTACC

E
      ----------------------------------------------------------------------------------
      •P T T   V E S H   G N Y   S T Q   V G A T   Q A G   R F S   I T P A
1401  ACCAACTACT GTGGAGTCGC ACGGAAACTA CTCCACACAG GTTGGAGCCA CTCAGGCAGG AGATTCAGC ATCACTCCTG
      TGGTTGATGA CACCTCAGCG TGCCTTTGAT GAGGTGTGTC CAACCTCGGT GAGTCCGTCC CTCTAAGTCG TAGTGAGGAC
                     E
      ---------------------
       A  P  S   Y  T  L
      CGGCGCCTTC ATACACACTA
      GCCGCGGAAG TATGTGTGAT

E
      ----------------------------------------------------------------------------------
       K L G E   Y G E   V T V   D C E P   R S G   I D T   N A Y Y   V M T
1501  AAGCTTGGAG AATATGGAGA GGTGACAGTG GACTGTGAAC CACGGTCAGG GATTGACACC AATGCATACT ACGTGATGAC
      TTCGAACCTC TTATACCTCT CCACTGTCAC CTGACACTTG GTGCCAGTCC CTAACTGTGG TTACGTATGA TGCACTACTG
                     E
      ---------------------
       V  G  T   K  T  F  L •
      TGTTGGAACA AAGACGTTCT
      ACAACCTTGT TTCTGCAAGA

E
      ----------------------------------------------------------------------------------
      • V H R   E W F   M D L N   L P W   S S A   G S T V   W R N   R E T
1601  TGGTCCATCG TGAGTGGTTC ATGGACCTCA ACCTCCCTTG GAGCAGTGCT GGAAGTACTG TGTGGAGGAA CAGAGAGACG
      ACCAGGTAGC ACTCACCAAG TACCTGGAGT TGGAGGGAAC CTCGTCACGA CCTTCATGAC ACACCTCCTT GTCTCTCTGC
                     E
      ---------------------
       L  M  E  F   E  E  P •
      TTAATGGAGT TTGAGGAACC
      AATTACCTCA AACTCCTTGG
```

SEQUENCE APPENDIX 4.-continued
WN PIV constructs expressing rabies virus G protein.

```
                                              E
     ---------------------------------------------------------------------------------
     •H A T   K Q S V   I A L   G S Q   E G A L   H Q A   L A G   A I P V
1701 ACACGCCACG AAGCAGTCTG TGATAGCATT GGGCTCACAA GAGGGAGCTC TGCATCAAGC TTTGGCTGGA GCCATTCCTG
     TGTGCGGTGC TTCGTCAGAC ACTATCGTAA CCCGAGTGTT CTCCCTCGAG ACGTAGTTCG AAACCGACCT CGGTAAGGAC
                E
     ---------------------
      E F S   S N T
     TGGAATTTTC AAGCAACACT
     ACCTTAAAAG TTCGTTGTGA

E
     ---------------------------------------------------------------------------------
     V K L T   S G H   L K C   R V K M   E K L   Q L K   G T T Y   G V C
1801 GTCAAGTTGA CGTCGGGTCA TTTGAAGTGT AGAGTGAAGA TGGAAAAATT GCAGTTGAAG GGAACAACCT ATGGCGTCTG
     CAGTTCAACT GCAGCCCAGT AAACTTCACA TCTCACTTCT ACCTTTTTAA CGTCAACTTC CCTTGTTGGA TACCGCAGAC
                E
     ---------------------
      S K A   F K F L •
     TTCAAAGGCT TTCAAGTTTC
     AAGTTTCCGA AAGTTCAAAG

E
     ---------------------------------------------------------------------------------
     •G T P   A D T   G H G T   V V L   E L Q   Y T G T   D G P   C K V
1901 TTGGGACTCC CGCAGACACA GGTCACGGCA CTGTGGTGTT GGAATTGCAG TACACTGGCA CGGATGGACC TTGCAAAGTT
     AACCCTGAGG GCGTCTGTGT CCAGTGCCGT GACACCACAA CCTTAACGTC ATGTGACCGT GCCTACCTGG AACGTTTCAA
                E
     ---------------------
      P I S S   V A S •
     CCTATCTCGT CAGTGGCTTC
     GGATAGAGCA GTCACCGAAG

E
     ---------------------------------------------------------------------------------
     •L N D   L T P V   G R L   V T V   N P F V   S V A   T A N   A K V L
2001 ATTGAACGAC CTAACGCCAG TGGGCAGATT GGTCACTGTC AACCCTTTTG TTTCAGTGGC CACGGCCAAC GCTAAGGTCC
     TAACTTGCTG GATTGCGGTC ACCCGTCTAA CCAGTGACAG TTGGGAAAAC AAAGTCACCG GTGCCGGTTG CGATTCCAGG
                E
     ---------------------
      I E L   E P P
     TGATTGAATT GGAACCACCC
     ACTAACTTAA CCTTGGTGGG

E
     ---------------------------------------------------------------------------------
      F G D S   Y I V   V G R   G E Q Q   I N H   H W H   K S G S   S I G
2101 TTTGGAGACT CATACATAGT GGTGGGCAGA GGAGAACAAC AGATCAATCA CCACTGGCAC AAGTCTGGAA GCAGCATTGG
     AAACCTCTGA GTATGTATCA CCACCCGTCT CCTCTTGTTG TCTAGTTAGT GGTGACCGTG TTCAGACCTT CGTCGTAACC
                E
     ---------------------
      K A F   T T T L •
     CAAAGCCTTT ACAACCACCC
     GTTTCGGAAA TGTTGGTGGG

E
     ---------------------------------------------------------------------------------
     •K G A   Q R L   A A L G   D T A   W D F   G S V G   G V F   T S V
2201 TCAAAGGAGC GCAGAGACTA GCCGCTCTAG GAGACACAGC TTGGGACTTT GGATCAGTTG GAGGGGTGTT CACCTCAGTT
     AGTTTCCTCG CGTCTCTGAT CGGCGAGATC CTCTGTGTCG AACCCTGAAA CCTAGTCAAC CTCCCCACAA GTGGAGTCAA
                E
     ---------------------
      G K A V   H Q V •
     GGGAAGGCTG TCCATCAAGT
     CCCTTCCGAC AGGTAGTTCA

E
     ---------------------------------------------------------------------------------
     •F G G   A F R S   L F G   G M S   W I T Q   G L L   G A L   L L W M
2301 GTTCGGAGGA GCATTCCGCT CACTGTTCGG AGGCATGTCC TGGATAACGC AAGGATTGCT GGGGCTCTC CTGTTGTGGA
     CAAGCCTCCT CGTAAGGCGA GTGACAAGCC TCCGTACAGG ACCTATTGCG TTCCTAACGA CCCCCGAGAG GACAACACCT
                E
     ---------------------
      G I N   A R D
     TGGGCATCAA TGCTCGTGAC
     ACCCGTAGTT ACGAGCACTG
```

SEQUENCE APPENDIX 4.-continued

WN PIV constructs expressing rabies virus G protein.

```
                                                                    deleted NS1
                                                                    -------------
             E
------------------------------------------------------------------------------
     R   S   I   A   L   T   F   L   A   V   G   G   V   L   L   F   L   S   V   N   V   H   A   D   T   G   I
2401 AGGTCCATAG CTCTCACGTT TCTCGCAGTT GGAGGAGTTC TGCTCTTCCT CTCCGTGAAC GTGCACGCTG ACACTGGGAT
     TCCAGGTATC GAGAGTGCAA AGAGCGTCAA CCTCCTCAAG ACGAGAAGGA GAGGCACTTG CACGTGCGAC TGTGACCCTA
         deleted NS1
         ---------------------
      H   R   G   P   A   T   R  •
     CCACCGTGGA CCTGCCACTC
     GGTGGCACCT GGACGGTGAG deleted NS1
     ----------------------------------------------------------------------------------------
     •  T   T   T   E   S   G   K   L   I   T   D   W   C   C   R   S   C   T   L   P   P   L   R   Y   Q   T
2501 GCACCACCAC AGAGAGCGGA AAGTTGATAA CAGATTGGTG CTGCAGGAGC TGCACCTTAC CACCACTGCG CTACCAAACT
     CGTGGTGGTG TCTCTCGCCT TTCAACTATT GTCTAACCAC GACGTCCTCG ACGTGGAATG GTGGTGACGC GATGGTTTGA
         deleted NS1
         ---------------------
      D   S   G   C   W   Y   G  •
     GACAGCGGCT GTTGGTATGG
     CTGTCGCCGA CAACCATACC deleted NS1
     ---------------------------------------------------------------------
                                                                                          NS2A
                                                                                   --------------------
     • M   E   I   R   P   Q   R   H   D   E   K   T   L   V   Q   S   Q   V   N   A   Y   N   A   D   M   I   D
2601 TATGGAGATC AGACCACAGA GACATGATGA AAAGACCCTC GTGCAGTCAC AAGTGAATGC TTATAATGCT GATATGATTG
     ATACCTCTAG TCTGGTGTCT CTGTACTACT TTTCTGGGAG CACGTCAGTG TTCACTTACG AATATTACGA CTATACTAAC
         NS2A
         ---------------------
      P   F   Q   L   G   L
     ACCCTTTTCA GTTGGGCCTT
     TGGGAAAAGT CAACCCGGAA
```

SEQUENCE APPENDIX 5

PIV-WNV(ΔprME)/RSV-F

```
                                                    5' UTR
     ---------------------------------------------------------------------------------------
   1 AGTAGTTCGC CTGTGTGAGC TGACAAACTT AGTAGTGTTT GTGAGGATTA ACAACAATTA ACACAGTGCG AGCTGTTTCT
     TCATCAAGCG GACACACTCG ACTGTTTGAA TCATCACAAA CACTCCTAAT TGTTGTTAAT TGTGTCACGC TCGACAAAGA
                   C protein
                   ----
         5' UTR
         -----------------
                       M   S  •
     TAGCACGAAG ATCTCGATGT
     ATCGTGCTTC TAGAGCTACA C protein
     ------------------------------------------------------------------------------------
     • K   K   P   G   G   P   G   K   S   R   A   V   Y   L   L   K   R   G   M   P   R   V   L   S   L   I
 101 CTAAGAAACC AGGAGGGCCC GGCAAGAGCC GGGCTGTCTA TTTGCTAAAA CGCGGAATGC CCCGCGTGTT GTCCTTGATT
     GATTCTTTGG TCCTCCCGGG CCGTTCTCGG CCCGACAGAT AAACGATTTT GCGCCTTACG GGGCGCACAA CAGGAACTAA
         C protein
         ---------------------
      G   L   K   R   A   M   L  •
     GGACTTAAGA GGGCTATGTT
     CCTGAATTCT CCCGATACAA C protein
     ------------------------------------------------------------------------------------
     • S   L   I   D   G   K   G   P   I   R   F   V   L   A   L   L   A   F   F   R   F   T   A   I   A   P   T
 201 GAGCCTGATC GACGGCAAGG GGCCAATACG ATTTGTGTTG CTCTCTTGG CGTTCTTCAG GTTCACAGCA ATTGCTCCGA
     CTCGGACTAG CTGCCGTTCC CCGGTTATGC TAAACACAAC CGAGAGAACC GCAAGAAGTC CAAGTGTCGT TAACGAGGCT
         C protein
         ---------------------
      R   A   V   L   D   R
     CCCGAGCAGT GCTGGATCGA
     GGGCTCGTCA CGACCTAGCT
```

SEQUENCE APPENDIX 5-continued

```
                            C protein
             ------------------------------------------------------------------------
              W  R  G  V   N  K  Q   T  A  M   K  H  L  L   S  F  K   K  E  L   G  T  L  T   S  A  I
         301 TGGAGAGGTG TGAACAAACA AACAGCGATG AAACACCTTC TGAGTTTCAA GAAGGAACTA GGGACCTTGA CCAGTGCTAT
             ACCTCTCCAC ACTTGTTTGT TTGTCGCTAC TTTGTGGAAG ACTCAAAGTT CTTCCTTGAT CCCTGGAACT GGTCACGATA
                             NS3 cleavage
                             ----
         C protein
         ----------------
              N  R  R   S  S  K  Q  •
             CAATCGGCGG AGCTCAAAGC
             GTTAGCCGCC TCGAGTTTCG F signal
             ------------------------------------------------------------------------
         NS3 cleavage
         ------------
              •  K  K  R   G  G  E   L  L  I  L   K  A  N   A  I  T   T  I  L  T   A  V  T   F  C  F
         401 AAAAGAAGCG AGGGGGCGAG TTGCTAATCC TCAAAGCAAA TGCAATTACC ACAATCCTCA CTGCAGTCAC ATTTTGTTTT
             TTTTCTTCGC TCCCCCGCTC AACGATTAGG AGTTTCGTTT ACGTTAATGG TGTTAGGAGT GACGTCAGTG TAAAACAAAA
                            F1
                            ---------------------
              A  S  G  Q   N  I  T  •
             GCTTCTGGTC AAACATCAC
             CGAAGACCAG TTTTGTAGTG F1
             ------------------------------------------------------------------------
              •  E  E  F   Y  Q  S  T   C  S  A   V  S  K   G  Y  L  S   A  L  R   T  G  W   Y  T  S  V
         501 TGAAGAATTT TATCAATCAA CATGCAGTGC AGTTAGCAAA GGCTATCTTA GTGCTCTGAG AACTGGTTGG TATACCAGTG
             ACTTCTTAAA ATAGTTAGTT GTACGTCACG TCAATCGTTT CCGATAGAAT CACGAGACTC TTGACCAACC ATATGGTCAC
                            F1
                            ---------------------
              I  T  I   E  L  S
             TTATAACTAT AGAATTAAGT
             AATATTGATA TCTTAATTCA F1
             ------------------------------------------------------------------------
              N  I  K  E   N  K  C   N  G  T   D  A  K  V   K  L  I   K  Q  E   L  D  K  Y   K  N  A
         601 AATATCAAGG AAAATAAGTG TAATGGAACA GATGCTAAGG TAAAATTGAT AAAACAAGAA TTAGATAAAT ATAAAAATGC
             TTATAGTTCC TTTTATTCAC ATTACCTTGT CTACGATTCC ATTTTAACTA TTTTGTTCTT AATCTATTTA TATTTTTACG
                            F1
                            ---------------------
              V  T  E   L  Q  L  L  •
             TGTAACAGAA TTGCAGTTGC
             ACATTGTCTT AACGTCAACG F1
             ------------------------------------------------------------------------
              •  M  Q  S   T  P  P   T  N  N  R   A  R  R   E  L  P   R  F  M  N   Y  T  L   N  N  A
         701 TCATGCAAAG CACACCACCA ACAAACAATC GAGCCAGAAG AGAACTACCA AGGTTTATGA ATTATACACT CAACAATGCC
             AGTACGTTTC GTGTGGTGGT TGTTTGTTAG CTCGGTCTTC TCTTGATGGT TCCAAATACT AATATGTGA GTTGTTACGG
                            F1
                            ---------------------
              K  K  T   N  V  T  L  •
             AAAAAAACCA ATGTAACATT
             TTTTTTTGGT TACATTGTAA F1
                            ------------------------
                                                  F2
             ------------------------------------------------------------------------
              •  S  K  K   R  K  R  R   F  L  G   F  L  L   G  V  G  S   A  I  A   S  G  V   A  V  S  K
         801 AAGCAAGAAA AGGAAAAGAA GATTTCTTGG TTTTTTGTTA GGTGTTGGAT CTGCAATCGC CAGTGGCGTT GCTGTATCTA
             TTCGTTCTTT TCCTTTTCTT CTAAAGAACC AAAAAACAAT CCACAACCTA GACGTTAGCG GTCACCGCAA CGACATAGAT
                            F2
                            ---------------------
              V  L  H   L  E  G
             AGGTCCTGCA CCTAGAAGGG
             TCCAGGACGT GGATCTTCCC
```

SEQUENCE APPENDIX 5-continued

```
                                                   F2
     ------------------------------------------------------------------------------------
        E   V   N   K   I   K   S   A   L   L   S   T   N   K   A   V   V   S   L   S   N   G   V   S   V   L   T
 901 GAAGTGAACA AGATCAAAAG TGCTCTACTA TCCACAAACA AGGCTGTAGT CAGCTTATCA AATGGAGTTA GTGTCTTAAC
     CTTCACTTGT TCTAGTTTTC ACGAGATGAT AGGTGTTTGT TCCGACATCA GTCGAATAGT TTACCTCAAT CACAGAATTG
                  F2
     ---------------------
         S   K   V   L   D   L   K •
     CAGCAAAGTG TTAGACCTCA
     GTCGTTTCAC AATCTGGAGT

F2
     ------------------------------------------------------------------------------------
      • N   Y   I   D   K   Q   L   L   P   I   V   N   K   Q   S   C   S   I   S   N   I   E   T   V   I   E
1001 AAAACTATAT AGATAAACAA TTGTTACCTA TTGTGAACAA GCAAAGCTGC AGCATATCAA ATATAGAAAC TGTGATAGAG
     TTTTGATATA TCTATTTGTT AACAATGGAT AACACTTGTT CGTTTCGACG TCGTATAGTT TATATCTTTG ACACTATCTC
                  F2
     ---------------------
        F   Q   Q   K   N   N   R •
     TTCCAACAAA AGAACAACAG
     AAGGTTGTTT TCTTGTTGTC

F2
     ------------------------------------------------------------------------------------
      • L   L   E   I   T   R   E   F   S   V   N   A   G   V   T   T   P   V   S   T   Y   M   L   T   N   S   E
1101 ACTACTAGAG ATTACCAGGG AATTTAGTGT TAATGCAGGT GTAACTACAC CTGTAAGCAC TTACATGTTA ACTAATAGTG
     TGATGATCTC TAATGGTCCC TTAAATCACA ATTACGTCCA CATTGATGTG GACATTCGTG AATGTACAAT TGATTATCAC
                  F2
     ---------------------
        L   L   S   L   I   N
     AATTATTGTC ATTAATCAAT
     TTAATAACAG TAATTAGTTA

F2
     ------------------------------------------------------------------------------------
        D   M   P   I   T   N   D   Q   K   K   L   M   S   N   N   V   Q   I   V   R   Q   Q   S   Y   S   I   M
1201 GATATGCCTA ACAAATGA TCAGAAAAAG TTAATGTCCA ACAATGTTCA AATAGTTAGA CAGCAAAGTT ACTCTATCAT
     CTATACGGAT ATTGTTTACT AGTCTTTTTC AATTACAGGT TGTTACAAGT TTATCAATCT GTCGTTTCAA TGAGATAGTA
                  F2
     ---------------------
        S   I   I   K   E   E   V •
     GTCCATAATA AAAGAGGAAG
     CAGGTATTAT TTTCTCCTTC

F2
     ------------------------------------------------------------------------------------
      • L   A   Y   V   V   Q   L   P   L   Y   G   V   I   D   T   P   C   W   K   L   H   T   S   P   L   C
1301 TCTTAGCATA TGTAGTACAA TTACCACTAT ATGGTGTTAT AGATACACCC TGTTGGAAAC TACACACATC CCCTCTATGT
     AGAATCGTAT ACATCATGTT AATGGTGATA TACCACAATA TCTATGTGGG ACAACCTTTG ATGTGTGTAG GGGAGATACA
                  F2
     ---------------------
        T   T   N   T   K   E   G •
     ACAACCAACA CAAAAGAAGG
     TGTTGGTTGT GTTTTCTTCC

F2
     ------------------------------------------------------------------------------------
      • S   N   I   C   L   T   R   T   D   R   G   W   Y   C   D   N   A   G   S   V   S   F   F   P   Q   A   E
1401 GTCCAACATC TGTTTAACAA GAACTGACAG AGGATGGTAC TGTGACAATG CAGGATCAGT ATCTTTCTTC CCACAAGCTG
     CAGGTTGTAG ACAAATTGTT CTTGACTGTC TCCTACCATG ACACTGTTAC GTCCTAGTCA TAGAAAGAAG GGTGTTCGAC
                  F2
     ---------------------
        T   C   K   V   Q   S
     AAACATGTAA AGTTCAATCA
     TTTGTACATT TCAAGTTAGT

F2
     ------------------------------------------------------------------------------------
        N   R   V   F   C   D   T   M   N   S   L   T   L   P   S   E   I   N   L   C   N   V   D   I   F   N   P
1501 AATCGAGTAT TTTGTGACAC AATGAACAGT TTAACATTAC AAGTGAAAT AAATCTCTGC AATGTTGACA TATTCAACCC
     TTAGCTCATA AAACACTGTG TTACTTGTCA AATTGTAATG GTTCACTTTA TTTAGAGACG TTACAACTGT ATAAGTTGGG
                  F2
     ---------------------
        K   Y   D   C   K   I   M •
     CAAATATGAT TGTAAAATTA
     GTTTATACTA ACATTTTAAT
```

```
                                             F2
       ------------------------------------------------------------------------------------
       • T  S  K   T  D  V   S  S  S   V  I  T   S  L  G   A  I  V   S  C  Y   G  K   T  K  C
  1601 TGACTTCAAA AACAGATGTA AGCAGCTCCG TTATCACATC TCTAGGAGCC ATTGTGTCAT GCTATGGCAA AACTAAATGT
       ACTGAAGTTT TTGTCTACAT TCGTCGAGGC AATAGTGTAG AGATCCTCGG TAACACAGTA CGATACCGTT TTGATTTACA
                   F2
       ---------------------
         T  A  S   N  K  N   R •
       ACAGCATCCA ATAAAAATCG
       TGTCGTAGGT TATTTTTAGC

F2
       ------------------------------------------------------------------------------------
       • G  I  I   K  T  F   S  N  G   C  D  Y   V  S  N   K  G  M   D  T  V   S  V   G  N  T  L
  1701 TGGAATCATA AAGACATTTT CTAACGGGTG CGATTATGTA TCAAATAAAG GGATGGACAC TGTGTCTGTA GGTAACACAT
       ACCTTAGTAT TTCTGTAAAA GATTGCCCAC GCTAATACAT AGTTTATTTC CCTACCTGTG ACACAGACAT CCATTGTGTA
                   F2
       ---------------------
         Y  Y  V   N  K  Q
       TATATTATGT AAATAAGCAA
       ATATAATACA TTTATTCGTT

F2
       ------------------------------------------------------------------------------------
         E  G  K   S  L  Y   V  K  G   E  P  I   I  N  F   Y  D  P   L  V   F  P  S   D  E  F   D
  1801 GAAGGTAAAA GTCTCTATGT AAAAGGTGAA CCAATAATAA ATTTCTATGA CCCATTAGTA TTCCCCTCTG ATGAATTTGA
       CTTCCATTTT CAGAGATACA TTTTCCACTT GGTTATTATT TAAAGATACT GGGTAATCAT AAGGGGAGAC TACTTAAACT
                   F2
       ---------------------
         A  S  I   S  Q  V   N •
       TGCATCAATA TCTCAAGTCA
       ACGTAGTTAT AGAGTTCAGT

F2
       ------------------------------------------------------------------------------------
       • E  K  I   N  Q  S   L  A  F   I  R  K   S  D  E   L  L  H   N  V  N   A  G   K  S  T
  1901 ACGAGAAGAT TAACCAGAGC CTAGCATTTA TTCGTAAATC CGATGAATTA TTACATAATG TAAATGCTGG TAAATCCACC
       TGCTCTTCTA ATTGGTCTCG GATCGTAAAT AAGCATTTAG GCTACTTAAT AATGTATTAC ATTTACGACC ATTTAGGTGG
           F2
       ------
                    TM Domain
                ----------------
         T  N  I   M   I  T  T •
       ACAAATATCA TGATAACTAC
       TGTTTATAGT ACTATTGATG TM Domain
       ------------------------------------------------------------
                                                          Cytoplasmic Tail
                                                    ---------------------------
       • I  I  I   V  I  I  V   I  L  L   S  L  I   A  V  G   L  L  Y   C  K  A   R  S  T  P
  2001 TATAATTATA GTGATTATAG TAATATTGTT ATCATTAATT GCTGTTGGAC TGCTCTTATA CTGTAAGGCC AGAAGCACAC
       ATATTAATAT CACTAATATC ATTATAACAA TAGTAATTAA CGACAACCTG ACGAGAATAT GACATTCCGG TCTTCGTGTG
          Cytoplasmic Tail
       ---------------------
         V  T  L   S  K  D
       CAGTCACACT AAGCAAAGAT
       GTCAGTGTGA TTCGTTTCTA FMDV 2A
                                                      -----------------------------------------------
       domain of WNV E (split)
             Cytoplasmic Tail
       ----------------------------------------
         Q  L  S   G  I  N  N   I  A  F   S  N  N   F  D  L  L   K  L  A   G  D  V   E  S  N   P
  2101 CAACTGAGTG GTATAAATAA TATTGCATTT AGTAACAATT TTGATCTGCT CAAACTTGCA GGCGATGTAG AATCAAATCC
       GTTGACTCAC CATATTTATT ATAACGTAAA TCATTGTTAA AACTAGACGA GTTTGAACGT CCGCTACATC TTAGTTTAGG
       FMDV 2A
       -------
                     Transmembrane
                     ----
                 pre E/NS1
                   signal
               ----------
         G  P  A   R  D  R  S •
       TGGACCCGCC CGGGACAGGT
       ACCTGGGCGG GCCCTGTCCA
```

SEQUENCE APPENDIX 5-continued

```
                                                                                  NS1
                                                                           -----------------
               Transmembrane domain of WNV E (split)
     ----------------------------------------------------------------------
     • I  A  L   T  F  L   A  V  G  G   V  L  L   F  L  S   V  N  V  H   A  D  T   G  C  A
2201 CCATAGCTCT CACGTTTCTC GCAGTTGGAG GAGTTCTGCT CTTCCTCTCC GTGAACGTGC ACGCTGACAC TGGGTGTGCC
     GGTATCGAGA GTGCAAAGAG CGTCAACCTC CTCAAGACGA GAAGGAGAGG CACTTGCACG TGCGACTGTG ACCCACACGG
            NS1
     -------------------
      I  D  I  S   R  Q
     ATAGACATCA GCCGGCAA
     TATCTGTAGT CGGCCGTT
```

PIV-WNV(ΔCprME)/RSV-F

```
                                          5' UTR
     -------------------------------------------------------------------------------------
   1 AGTAGTTCGC CTGTGTGAGC TGACAAACTT AGTAGTGTTT GTGAGGATTA ACAACAATTA ACACAGTGCG AGCTGTTTCT
     TCATCAAGCG GACACACTCG ACTGTTTGAA TCATCACAAA CACTCCTAAT TGTTGTTAAT TGTGTCACGC TCGACAAAGA
            deleted C protein
                      ----
           5' UTR
     -----------------
                       M  S •
     TAGCACGAAG ATCTCGATGT
     ATCGTGCTTC TAGAGCTACA deleted C protein
     -------------------------------------------------------------------------------------
     • K  K  P   G  G  P   G  K  S  R   A  V  N   M  L  K   R  G  M  P   R  V  L   S  L  I
 101 CTAAGAAACC AGGAGGGCCC GGCAAGAGCC GGGCTGTCAA TATGCTAAAA CGCGGAATGC CCCGCGTGTT GTCCTTGATT
     GATTCTTTGG TCCTCCCGGG CCGTTCTCGG CCCGACAGTT ATACGATTTT GCGCCTTACG GGGCGCACAA CAGGAACTAA
     deleted C
     protein
     ------
            NS3 cleavage
           --------------
       G  L  K  Q   K  K  R •
     GGACTTAAGC AAAAGAAGCG
     CCTGAATTCG TTTTCTTCGC F signal
      ------------------------------------------------------------------------
     NS3 cleavage                                                                 F1
     -                                                                       -----------
     •G  G  E   L  L  I  L   K  A  N   A  I  T   T  I  L  T   A  V  T   F  C  F   A  S  G  Q
 201 AGGGGGCGAG TTGCTAATCC TCAAAGCAAA TGCAATTACC ACAATCCTCA CTGCAGTCAC ATTTTGTTTT GCTTCTGGTC
     TCCCCCGCTC AACGATTAGG AGTTTCGTTT ACGTTAATGG TGTTAGGAGT GACGTCAGTG TAAAACAAAA CGAAGACCAG
               F1
     ---------------------
        N  I  T   E  E  F
     AAAACATCAC TGAAGAATTT
     TTTTGTAGTG ACTTCTTAAA F1
     -------------------------------------------------------------------------------------
      Y  Q  S  T   C  S  A   V  S  K   G  Y  L  S   A  L  R   T  G  W   Y  T  S  V   I  T  I
 301 TATCAATCAA CATGCAGTGC AGTTAGCAAA GGCTATCTTA GTGCTCTGAG AACTGGTTGG TATACCAGTG TTATAACTAT
     ATAGTTAGTT GTACGTCACG TCAATCGTTT CCGATAGAAT CACGAGACTC TTGACCAACC ATATGGTCAC AATATTGATA
               F1
     --------------------
       E  L  S   N  I  K  E •
     AGAATTAAGT AATATCAAGG
     TCTTAATTCA TTATAGTTCC F1
     -------------------------------------------------------------------------------------
     • N  K  C   N  G  T   D  A  K  V   K  L  I   K  Q  E   L  D  K  Y   K  N  A   V  T  E
 401 AAAATAAGTG TAATGGAACA GATGCTAAGG TAAAATTGAT AAAACAAGAA TTAGATAAAT ATAAAAATGC TGTAACAGAA
     TTTTATTCAC ATTACCTTGT CTACGATTCC ATTTTAACTA TTTTGTTCTT AATCTATTTA TATTTTTACG ACATTGTCTT
               F1
     --------------------
      L  Q  L  L   M  Q  S •
     TTGCAGTTGC TCATGCAAAG
     AACGTCAACG AGTACGTTTC

SEQUENCE APPENDIX 5-continued

```
                                       F1
         -------------------------------------------------------------------------------
      • T   P   P    T   N   N   R   A   R   R    E   L   P    R   F   M   N    Y   T   L    N   N   A    K   K   T   N
    501 CACACCACCA ACAAACAATC GAGCCAGAAG AGAACTACCA AGGTTTATGA ATTATACACT CAACAATGCC AAAAAAACCA
        GTGTGGTGGT TGTTTGTTAG CTCGGTCTTC TCTTGATGGT TCCAAATACT TAATATGTGA GTTGTTACGG TTTTTTTGGT
                   F1
         ----------------------
           V   T   L    S   K   K
         ATGTAACATT AAGCAAGAAA
         TACATTGTAA TTCGTTCTTT

F1
         -------------
                                                                           F2
         -------------------------------------------------------------------------------------
         R   K   R   R    F   L   G    F   L   L    G   V   G   S    A   I   A    S   G   V    A   V   S   K    V   L   H
    601 AGGAAAAGAA GATTTCTTGG TTTTTTGTTA GGTGTTGGAT CTGCAATCGC CAGTGGCGTT GCTGTATCTA AGGTCCTGCA
        TCCTTTTCTT CTAAAGAACC AAAAAACAAT CCACAACCTA GACGTTAGCG GTCACCGCAA CGACATAGAT TCCAGGACGT
                          F2
         ----------------------
           L   E   G    E   V   N   K •
         CCTAGAAGGG GAAGTGAACA
         GGATCTTCCC CTTCACTTGT

F2
         ----------------------------------------------------------------------------------
       • I   K   S    A   L   L    S   T   N   K    A   V   V    S   L   S    N   G   V   S    V   L   T    S   K   V
    701 AGATCAAAAG TGCTCTACTA TCCACAAACA AGGCTGTAGT CAGCTTATCA AATGGAGTTA GTGTCTTAAC CAGCAAAGTG
        TCTAGTTTTC ACGAGATGAT AGGTGTTTGT TCCGACATCA GTCGAATAGT TTACCTCAAT CACAGAATTG GTCGTTTCAC
                   F2
         ----------------------
           L   D   L   K   N   Y   I •
         TTAGACCTCA AAAACTATAT
         AATCTGGAGT TTTTGATATA

F2
         ----------------------------------------------------------------------------------
       • D   K   Q    L   L   P   I    V   N   K    Q   S   C    S   I   S   N    I   E   T    V   I   E    F   Q   Q   K
    801 AGATAAACAA TTGTTACCTA TTGTGAACAA GCAAAGCTGC AGCATATCAA ATATAGAAAC TGTGATAGAG TTCCAACAAA
        TCTATTTGTT AACAATGGAT AACACTTGTT CGTTTCGACG TCGTATAGTT TATATCTTTG ACACTATCTC AAGGTTGTTT
                   F2
         ----------------------
           N   N   R    L   L   E
         AGAACAACAG ACTACTAGAG
         TCTTGTTGTC TGATGATCTC

F2
         ----------------------------------------------------------------------------------
         I   T   R   E    F   S   V    N   A   G    V   T   T   P    V   S   T    Y   M   L    T   N   S   E    L   L   S
    901 ATTACCAGGG AATTTAGTGT TAATGCAGGT GTAACTACAC CTGTAAGCAC TTACATGTTA ACTAATAGTG AATTATTGTC
        TAATGGTCCC TTAAATCACA ATTACGTCCA CATTGATGTG GACATTCGTG AATGTACAAT TGATTATCAC TTAATAACAG
                   F2
         ----------------------
           L   I   N    D   M   P   I •
         ATTAATCAAT GATATGCCTA
         TAATTAGTTA CTATACGGAT

F2
         ----------------------------------------------------------------------------------
       • T   N   D    Q   K   K    L   M   S   N    N   V   Q    I   V   R    Q   Q   S   Y    S   I   M    S   I   I
   1001 TAACAAATGA TCAGAAAAAG TTAATGTCCA ACAATGTTCA AATAGTTAGA CAGCAAAGTT ACTCTATCAT GTCCATAATA
        ATTGTTTACT AGTCTTTTTC AATTACAGGT TGTTACAAGT TTATCAATCT GTCGTTTCAA TGAGATAGTA CAGGTATTAT
                   F2
         ----------------------
           K   E   E   V    L   A   Y •
         AAAGAGGAAG TCTTAGCATA
         TTTCTCCTTC AGAATCGTAT

F2
         ----------------------------------------------------------------------------------
       • V   V   Q    L   P   L   Y    G   V   I    D   T   P    C   W   K   L    H   T   S    P   L   C    T   T   N   T
                                            F2
         ----------------------
           K   E   G    S   N   I
   1101 TGTAGTACAA TTACCACTAT ATGGTGTTAT AGATACACCC TGTTGGAAAC TACACACATC CCCTCTATGT ACAACCAACA
        ACATCATGTT AATGGTGATA TACCACAATA TCTATGTGGG ACAACCTTTG ATGTGTGTAG GGGAGATACA TGTTGGTTGT
        CAAAAGAAGG GTCCAACATC
        GTTTTCTTCC CAGGTTGTAG
```

SEQUENCE APPENDIX 5-continued

```
                                            F2
     ---------------------------------------------------------------------------------
          C   L   T   R   T   D   R     G   W   Y     C   D   N   A     G   S   V     S   F   F     P   Q   A   E     T   C   K
1201 TGTTTAACAA GAACTGACAG AGGATGGTAC TGTGACAATG CAGGATCAGT ATCTTTCTTC CCACAAGCTG AAACATGTAA
     ACAAATTGTT CTTGACTGTC TCCTACCATG ACACTGTTAC GTCCTAGTCA TAGAAAGAAG GGTGTTCGAC TTTGTACATT
             F2
     ---------------------
          V   Q   S   N     R   V   F •
     AGTTCAATCA AATCGAGTAT
     TCAAGTTAGT TTAGCTCATA

F2
     ---------------------------------------------------------------------------------
        • C   D   T     M   N   S     L   T   L   P     S   E   I   N     L   C   N   V   D     I   F   N   P     K   Y   D
1301 TTTGTGACAC AATGAACAGT TTAACATTAC CAAGTGAAAT AAATCTCTGC AATGTTGACA TATTCAACCC CAAATATGAT
     AAACACTGTG TTACTTGTCA AATTGTAATG GTTCACTTTA TTTAGAGACG TTACAACTGT ATAAGTTGGG GTTTATACTA
             F2
     ---------------------
          C   K   I   M     T   S   K •
     TGTAAAATTA TGACTTCAAA
     ACATTTTAAT ACTGAAGTTT

F2
     ---------------------------------------------------------------------------------
        • T   D   V     S   S   S   V     I   T   S     L   G   A     I   V   S   C     Y   G   K     T   K   C     T   A   S   N
1401 AACAGATGTA AGCAGCTCCG TTATCACATC TCTAGGAGCC ATTGTGTCAT GCTATGGCAA AACTAAATGT ACAGCATCCA
     TTGTCTACAT TCGTCGAGGC AATAGTGTAG AGATCCTCGG TAACACAGTA CGATACCGTT TTGATTTACA TGTCGTAGGT
             F2
     ---------------------
         K   N   R     G   I   I
     ATAAAAATCG TGGAATCATA
     TATTTTTAGC ACCTTAGTAT

F2
     ---------------------------------------------------------------------------------
          K   T   F   S     N   G   C     D   Y   V     S   N   K   G     M   D   T     V   S   V     G   N   T   L     Y   Y   V
1501 AAGACATTTT CTAACGGGTG CGATTATGTA TCAAATAAAG GGATGGACAC TGTGTCTGTA GGTAACACAT ATATTATGT
     TTCTGTAAAA GATTGCCCAC GCTAATACAT AGTTTATTTC CCTACCTGTG ACACAGACAT CCATTGTGTA ATATAATACA
             F2
     ---------------------
          N   K   Q     E   G   K   S •
     AAATAAGCAA GAAGGTAAAA
     TTTATTCGTT CTTCCATTTT

F2
     ---------------------------------------------------------------------------------
        • L   Y   V     K   G   E     P   I   I   N     F   Y   D     P   L   V     F   P   S   D     E   F   D     A   S   I
1601 GTCTCTATGT AAAAGGTGAA CCAATAATAA ATTTCTATGA CCCATTAGTA TTCCCCTCTG ATGAATTTGA TGCATCAATA
     CAGAGATACA TTTTCCACTT GGTTATTATT TAAAGATACT GGGTAATCAT AAGGGGAGAC TACTTAAACT ACGTAGTTAT
             F2
     ---------------------
          S   Q   V   N     E   K   I •
     TCTCAAGTCA ACGAGAAGAT
     AGAGTTCAGT TGCTCTTCTA

F2
     ---------------------------------------------------------------------------------
                                                                                                                    TM Domain
                                                                                                                    -----
        • N   Q   S     L   A   F   I     R   K   S     D   E   L     L   H   N   V     N   A   G     K   S   T     T   N   I   M
1701 TAACCAGAGC CTAGCATTTA TTCGTAAATC CGATGAATTA TTACATAATG TAAATGCTGG TAAATCCACC ACAAATATCA
     ATTGGTCTCG GATCGTAAAT AAGCATTTAG GCTACTTAAT AATGTATTAC ATTTACGACC ATTTAGGTGG TGTTTATAGT
             TM Domain
     ---------------------
          I   T   T     I   I   I
     TGATAACTAC TATAATTATA
     ACTATTGATG ATATTAATAT TM Domain
     -------------------------------------------------
                                                       Cytoplasmic Tail
                                                       ----------------------------------------
          V   I   I   V     I   L   L     S   L   I     A   V   G   L     L   L   Y     C   K   A     R   S   T   P     V   T   L
1801 GTGATTATAG TAATATTGTT ATCATTAATT GCTGTTGGAC TGCTCTTATA CTGTAAGGCC AGAAGCACAC CAGTCACACT
     CACTAATATC ATTATAACAA TAGTAATTAA CGACAACCTG ACGAGAATAT GACATTCCGG TCTTCGTGTG GTCAGTGTGA
         Cytoplasmic Tail
     ---------------------
          S   K   D     Q   L   S   G •
     AAGCAAAGAT CAACTGAGTG
     TTCGTTTCTA GTTGACTCAC
```

SEQUENCE APPENDIX 5-continued

```
                                    FMDV 2A
                      ------------------------------------------------------------
          Cytoplasmic Tail                                              pre E/NS1 signal
     ----------------------------                                       ----
      • I N N   I A F   S N N F   D L L   K L A   G D V E   S N P   G P A
1901 GTATAAATAA TATTGCATTT AGTAACAATT TTGATCTGCT CAAACTTGCA GGCGATGTAG AATCAAATCC TGGACCCGCC
     CATATTTATT ATAACGTAAA TCATTGTTAA AACTAGACGA GTTTGAACGT CCGCTACATC TTAGTTTAGG ACCTGGGCGG
         membrane domain of WNV E (split)
         ---------------
     pre E/NS1
     signal
     ------
      R D R S   I A L •
     CGGGACAGGT CCATAGCTCT
     GCCCTGTCCA GGTATCGAGA Transmembrane domain of WNV E (split)
     ----------------------------------------------------------------
                                                                          NS1
                                                                    ----------------------------
     • T F L   A V G G   V L L   F L S   V N V H   A D T   G C A   I D I S
2001 CACGTTTCTC GCAGTTGGAG GAGTTCTGCT CTTCCTCTCC GTGAACGTGC ACGCTGACAC TGGGTGTGCC ATAGACATCA
     GTGCAAAGAG CGTCAACCTC CTCAAGACGA GAAGGAGAGG CACTTGCACG TGCGACTGTG ACCCACACGG TATCTGTAGT
              NS1
         ----------------
      R Q E   L R
     GCCGGCAAGA GCTGAGA
     CGGCCGTTCT CGACTCT
```

```
                                    PIV-WNV(ΔC)/RSV-F
     --------------------------------------------------------------------------------
   1 GATCCTAATA CGACTCACTA TAGAGTAGTT CGCCTGTGTG AGCTGACAAA CTTAGTAGTG TTTGTGAGGA TTAACAACAA
     CTAGGATTAT GCTGAGTGAT ATCTCATCAA GCGGACACAC TCGACTGTTT GAATCATCAC AAACACTCCT AATTGTTGTT
     TTAACACAGT GCGAGCTGTT
     AATTGTGTCA CGCTCGACAA

N-terminus of C
                                          ----------------------------------------------
                    M   S K K   P G G   P G K S   R A V   N M L   K R G M
 101 TCTTAGCACG AAGATCTCGA TGTCTAAGAA ACCAGGAGGG CCCGGCAAGA GCCGGGCTGT CAATATGCTA AAACGCGGAA
     AGAATCGTGC TTCTAGAGCT ACAGATTCTT TGGTCCTCCC GGGCCGTTCT CGGCCCGACA GTTATACGAT TTTGCGCCTT
          N-terminus of C
     ---------------------
       P R V   L S L
     TGCCCCGCGT GTTGTCCTTG
     ACGGGGCGCA CAACAGGAAC N-terminus of C                                         F signal
     ---------                       --------------------------------------------------------
              NS3 cleavage
              ----------------
        I G L K   Q K K   R G G   E L L I   L K A   N A I   T T I L   T A V
 201 ATTGGACTTA AGCAAAAGAA GCGAGGGGGC GAGTTGCTAA TCCTCAAAGC AAATGCAATT ACCACAATCC TCACTGCAGT
     TAACCTGAAT TCGTTTTCTT CGCTCCCCCG CTCAACGATT AGGAGTTTCG TTTACGTTAA TGGTGTTAGG AGTGACGTCA
            F signal
     --------------
                     F1
                     -------
       T F C   F A S G •
     CACATTTTGT TTTGCTTCTG
     GTGTAAAACA AAACGAAGAC F1
     --------------------------------------------------------------------------------------
     • Q N I   T E E   F Y Q S   T C S   A V S   K G Y L   S A L   R T G
 301 GTCAAAACAT CACTGAAGAA TTTTATCAAT CAACATGCAG TGCAGTTAGC AAAGGCTATC TTAGTGCTCT GAGAACTGGT
     CAGTTTTGTA GTGACTTCTT AAAATAGTTA GTTGTACGTC ACGTCAATCG TTTCCGATAG AATCACGAGA CTCTTGACCA
                   F1
         ---------------------
       W Y T S   V I T •
     TGGTATACCA GTGTTATAAC
     ACCATATGGT CACAATATTG
```

SEQUENCE APPENDIX 5-continued

```
                                        F1
       -----------------------------------------------------
     • I E L   S N I K   E N K   C N G   T D A K   V K L   I K Q   E L D K
401  TATAGAATTA AGTAATATCA AGGAAAATAA GTGTAATGGA ACAGATGCTA AGGTAAAATT GATAAAACAA GAATTAGATA
     ATATCTTAAT TCATTATAGT TCCTTTTATT CACATTACCT TGTCTACGAT TCCATTTTAA CTATTTTGTT CTTAATCTAT
                F1
     ---------------------
       Y K N   A V T
     AATATAAAAA TGCTGTAACA
     TTATATTTTT ACGACATTGT

F1
     ----------------------------------------------------------
       E L Q L   L M Q   S T P   P T N N   R A R   R E L   P R F   M N Y T
501  GAATTGCAGT TGCTCATGCA AGCACACCA CCAACAAACA ATCGAGCCAG AAGAGAACTA CCAAGGTTTA TGAATTATAC
     CTTAACGTCA ACGAGTACGT TCGTGTGGT GGTTGTTTGT TAGCTCGGTC TTCTCTTGAT GGTTCCAAAT ACTTAATATG
                F1
     ---------------------
       L N N   A K K T •
     ACTCAACAAT GCCAAAAAAA
     TGAGTTGTTA CGGTTTTTTT

F2
                                                    ---------------------------------------------
                    F1
     ----------------------------------------
     • N V T   L S K   K R K R   R F L   G F L   L G V G   S A I   A S G
601  CCAATGTAAC ATTAAGCAAG AAAAGGAAAA GAAGATTTCT TGGTTTTTTG TTAGGTGTTG GATCTGCAAT CGCCAGTGGC
     GGTTACATTG TAATTCGTTC TTTTCCTTTT CTTCTAAAGA ACCAAAAAAC AATCCACAAC CTAGACGTTA GCGGTCACCG
                F2
     ---------------------
       V A V S   K V L •
     GTTGCTGTAT CTAAGGTCCT
     CAACGACATA GATTCCAGGA

F2
     ---------------------------------------------------------
     • H L E   G E V N   K I K   S A L   L S T N   K A V   V S L   S N G V
701  GCACCTAGAA GGGGAAGTGA ACAAGATCAA AAGTGCTCTA CTATCCACAA ACAAGGCTGT AGTCAGCTTA TCAAATGGAG
     CGTGGATCTT CCCCTTCACT TGTTCTAGTT TTCACGAGAT GATAGGTGTT TGTTCCGACA TCAGTCGAAT AGTTTACCTC
                F2
     ---------------------
       S V L   T S K
     TTAGTGTCTT AACCAGCAAA
     AATCACAGAA TTGGTCGTTT

F2
     ----------------------------------------------------------
       V L D L   K N Y   I D K   Q L L P   I V N   K Q S   C S I S   N I E
801  GTGTTAGACC TCAAAAACTA TAGATAAA CAATTGTTAC CTATTGTGAA CAAGCAAAGC TGCAGCATAT CAAATATAGA
     CACAATCTGG AGTTTTTGAT ATATCTATTT GTTAACAATG GATAACACTT GTTCGTTTCG ACGTCGTATA GTTTATATCT
                F2
     ---------------------
       T V I   E F Q Q •
     AACTGTGATA GAGTTCCAAC
     TTGACACTAT CTCAAGGTTG

F2
     ----------------------------------------------------------
     • K N N   R L L   E I T R   E F S   V N A   G V T T   P V S   T Y M
901  AAAAGAACAA CAGACTACTA GAGATTACCA GGGAATTTAG TGTTAATGCA GGTGTAACTA CACCTGTAAG CACTTACATG
     TTTTCTTGTT GTCTGATGAT CTCTAATGGT CCCTTAAATC ACAATTACGT CCACATTGAT GTGGACATTC GTGAATGTAC
                F2
     ---------------------
       L T N S   E L L •
     TTAACTAATA GTGAATTATT
     AATTGATTAT CACTTAATAA

F2
     ----------------------------------------------------------
     • S L I   N D M P   I T N   D Q K   K L M S   N N V   Q I V   R Q Q S
1001 GTCATTAATC AATGATATGC CTATAACAAA TGATCAGAAA AAGTTAATGT CCAACAATGT TCAAATAGTT AGACAGCAAA
     CAGTAATTAG TTACTATACG GATATTGTTT ACTAGTCTTT TTCAATTACA GGTTGTTACA AGTTTATCAA TCTGTCGTTT
                F2
     ---------------------
       Y S I   M S I
     GTTACTCTAT CATGTCCATA
     CAATGAGATA GTACAGGTAT
```

SEQUENCE APPENDIX 5-continued

```
                                                              F2
      ------------------------------------------------------------------------------
         I   K   E   E   V   L   A   Y   V   V   Q   L   P   L   Y   G   V   I   D   T   P   C   W   K   L   H   T
    1101 ATAAAAGAGG AAGTCTTAGC ATATGTAGTA CAATTACCAC TATATGGTGT TATAGATACA CCCTGTTGGA AACTACACAC
         TATTTTCTCC TTCAGAATCG TATACATCAT GTTAATGGTG ATATACCACA ATATCTATGT GGGACAACCT TTGATGTGTG
                        F2
         ---------------------
           S   P   L   C   T   T   N   •
         ATCCCCTCTA TGTACAACCA
         TAGGGGAGAT ACATGTTGGT

F2
      ------------------------------------------------------------------------------
         •   T   K   E   G   S   N   I   C   L   T   R   T   D   R   G   W   Y   C   D   N   A   G   S   V   S   F
    1201 ACACAAAAGA AGGGTCCAAC ATCTGTTTAA CAAGAACTGA CAGAGGATGG TACTGTGACA ATGCAGGATC AGTATCTTTC
         TGTGTTTTCT TCCCAGGTTG TAGACAAATT GTTCTTGACT GTCTCCTACC ATGACACTGT TACGTCCTAG TCATAGAAAG
                        F2
         ---------------------
          F   P   Q   A   E   T   C   •
         TTCCCACAAG CTGAAACATG
         AAGGGTGTTC GACTTTGTAC

F2
      ------------------------------------------------------------------------------
        •K   V   Q   S   N   R   V   F   C   D   T   M   N   S   L   T   L   P   S   E   I   N   L   C   N   V   D
    1301 TAAAGTTCAA TCAAATCGAG TATTTTGTGA CACAATGAAC AGTTTAACAT TACCAAGTGA AATAAATCTC TGCAATGTTG
         ATTTCAAGTT AGTTTAGCTC ATAAAACACT GTGTTACTTG TCAAATTGTA ATGGTTCACT TTATTTAGAG ACGTTACAAC
         ---------------------
          I   F   N   P   K   Y
         ACATATTCAA CCCCAAATAT
         TGTATAAGTT GGGGTTTATA

F2
      ------------------------------------------------------------------------------
         D   C   K   I   M   T   S   K   T   D   V   S   S   S   V   I   T   S   L   G   A   I   V   S   C   Y   G
    1401 GATTGTAAAA TTATGACTTC AAAAACAGAT GTAAGCAGCT CCGTTATCAC ATCTCTAGGA GCCATTGTGT CATGCTATGG
         CTAACATTTT AATACTGAAG TTTTTGTCTA CATTCGTCGA GGCAATAGTG TAGAGATCCT CGGTAACACA GTACGATACC
                        F2
         ---------------------
           K   T   K   C   T   A   S   •
         CAAAACTAAA TGTACAGCAT
         GTTTTGATTT ACATGTCGTA

F2
      ------------------------------------------------------------------------------
         •  N   K   N   R   G   I   I   K   T   F   S   N   G   C   D   Y   V   S   N   K   G   M   D   T   V   S
    1501 CCAATAAAAA TCGTGGAATC ATAAAGACAT TTTCTAACGG GTGCGATTAT GTATCAAATA AAGGGATGGA CACTGTGTCT
         GGTTATTTTT AGCACCTTAG TATTTCTGTA AAAGATTGCC CACGCTAATA CATAGTTTAT TTCCCTACCT GTGACACAGA
                        F2
         ---------------------
           V   G   N   T   L   Y   Y   •
         GTAGGTAACA CATTATATTA
         CATCCATTGT GTAATATAAT

F2
      ------------------------------------------------------------------------------
         •V   N   K   Q   E   G   K   S   L   Y   V   K   G   E   P   I   I   N   F   Y   D   P   L   V   F   P   S
    1601 TGTAAATAAG CAAGAAGGTA AAAGTCTCTA TGTAAAAGGT GAACCAATAA TAAATTTCTA TGACCCATTA GTATTCCCCT
         ACATTTATTC GTTCTTCCAT TTTCAGAGAT ACATTTTCCA CTTGGTTATT ATTTAAAGAT ACTGGGTAAT CATAAGGGGA
                        F2
         ---------------------
           D   E   F   D   A   S
         CTGATGAATT TGATGCATCA
         GACTACTTAA ACTACGTAGT

F2
      ------------------------------------------------------------------------------
         I   S   Q   V   N   E   K   I   N   Q   S   L   A   F   I   R   K   S   D   E   L   L   H   N   V   N   A
    1701 ATATCTCAAG TCAACGAGAA GATTAACCAG AGCCTAGCAT TTATTCGTAA ATCCGATGAA TTATTACATA ATGTAAATGC
         TATAGAGTTC AGTTGCTCTT CTAATTGGTC TCGGATCGTA AATAAGCATT TAGGCTACTT AATAATGTAT TACATTTACG
                                   TM Domain
         ---------------------
          G   K   S   T   T   N   I   •
         TGGTAAATCC ACCACAAATA
         ACCATTTAGG TGGTGTTTAT
```

SEQUENCE APPENDIX 5-continued

```
         TM Domain
------------------------------------------------------------------------
                                                           Cytoplasmic Tail
                                                           ---------------
     • M   I   T     T   I   I     I   V   I   I     V   I   L     L   S   L     I   A   V     L   L   L     Y   C   K
1801 TCATGATAAC TACTATAATT ATAGTGATTA TAGTAATATT GTTATCATTA ATTGCTGTTG GACTGCTCTT ATACTGTAAG
     AGTACTATTG ATGATATTAA TATCACTAAT ATCATTATAA CAATAGTAAT TAACGACAAC CTGACGAGAA TATGACATTC
         Cytoplasmic Tail
         ---------------------
     A   R   S   T     P   V   T •
GCCAGAAGCA CACCAGTCAC
CGGTCTTCGT GTGGTCAGTG FMDV 2A
                                                             ----------------------------------
         Cytoplasmic Tail
     ----------------------------------------------------
     • L   S   K     D   Q   L   S     G   I   N   N     N   I   A     F   S   N   N     F   D   L     L   K   L     A   G   D   V
1901 ACTAAGCAAA GATCAACTGA GTGGTATAAA TAATATTGCA TTTAGTAACA ATTTTGATCT GCTCAAACTT GCAGGCGATG
     TGATTCGTTT CTAGTTGACT CACCATATTT ATTATAACGT AAATCATTGT TAAAACTAGA CGAGTTTGAA CGTCCGCTAC
             FMDV 2A
     ---------------------
       E   S   N     P   G   P
TAGAATCAAA TCCTGGACCC
ATCTTAGTTT AGGACCTGGG prM
                                                                         ----------------------------
         C/prM signal
     ----------------------------------------------------
       G   G   K   T     G   I   A     V   M   I     G   L   I   A     C   V   G     A   V   T     L   S   N     F   Q   G   K
2001 GGAGGAAAGA CCGGTATTGC AGTCATGATT GGCCTGATCG CCTGCGTAGG AGCAGTTACC CTCTCTAACT TCCAAGGGAA
     CCTCCTTTCT GGCCATAACG TCAGTACTAA CCGGACTAGC GGACGCATCC TCGTCAATGG AGAGATTGA AGGTTCCCTT
             prM
     ---------------------
       V   M   M     T   V   N   A •
GGTGATGATG ACGGTAAATG
CCACTACTAC TGCCATTTAC prM
                                        ----------------------------------------------------------------
     • T   D   V     T   D   V     I   T   I   P     T   A   A     G   K   N     L   C   I   V     R   A   M     D   V   G
2101 CTACTGACGT CACAGATGTC ATCACGATTC CAACAGCTGC TGGAAAGAAC CTATGCATTG TCAGAGCAAT GGATGTGGGA
     GATGACTGCA GTGTCTACAG TAGTGCTAAG GTTGTCGACG ACCTTTCTTG GATACGTAAC AGTCTCGTTA CCTACACCCT
             prM
     ---------------------
     Y   M   C   D     D   T   I •
TACATGTGCG ATGATACTAT
ATGTACACGC TACTATGATA prM
                                        ----------------------------------------------------------------
     • T   Y   E     C   P   V   L     S   A   G     N   D   P     E   D   I   D     C   W   C     T   K   S     A   V   Y   V
2201 CACTTATGAA TGCCCAGTGC TGTCGGCTGG TAATGATCCA GAAGACATCG ACTGTTGGTG CACAAAGTCA GCAGTCTACG
     GTGAATACTT ACGGGTCACG ACAGCCGACC ATTACTAGGT CTTCTGTAGC TGACAACCAC GTGTTTCAGT CGTCAGATGC
             prM
     ---------------------
       R   Y   G     R   C   T
TCAGGTATGG AAGATGCACC
AGTCCATACC TTCTACGTGG prM
                                        ----------------------------------------------------------------
       K   T   R   H     S   R   R     S   R   R     S   L   T   V     Q   T   H     G   E   S     T   L   A   N     K   K   G
2301 AAGACACGCC ACTCAAGACG CAGTCGGAGG TCACTGACAG TGCAGACACA CGGAGAAAGC ACTCTAGCGA ACAAGAAGGG
     TTCTGTGCGG TGAGTTCTGC GTCAGCCTCC AGTGACTGTC ACGTCTGTGT GCCTCTTTCG TGAGATCGCT TGTTCTTCCC
             prM
     ---------------------
       A   W   M     D   S   T   K •
GGCTTGGATG GACAGCACCA
CCGAACCTAC CTGTCGTGGT
```

SEQUENCE APPENDIX 5-continued

```
                                    prM
      --------------------------------------------------------------------------------
       • A  T  R   Y  L  V   K  T  E   S  W  I   L  R  N   P  G  Y   A  L  V   A  A  V   I  G
 2401 AGGCCACAAG GTATTTGGTA AAAACAGAAT CATGGATCTT GAGGAACCCT GGATATGCCC TGGTGGCAGC CGTCATTGGT
      TCCGGTGTTC CATAAACCAT TTTTGTCTTA GTACCTAGAA CTCCTTGGGA CCTATACGGG ACCACCGTCG GCAGTAACCA
                  prM
      ---------------------
       W  M  L   G  S  N  T •
      TGGATGCTTG GGAGCAACAC
      ACCTACGAAC CCTCGTTGTG prM
      --------------------------------------------------------------------------------
      • M  Q  R   V  V  F   V  V  L   L  L  V   A  P  A   Y  S  F   N  C  L   G  M  S   N  R
 2501 CATGCAGAGA GTTGTGTTTG TCGTGCTATT GCTTTTGGTG GCCCCAGCTT ACAGTTTAAC TGCCTTGGA ATGAGCAACA
      GTACGTCTCT CAACACAAAC AGCACGATAA CGAAAACCAC CGGGGTCGAA TGTCGAAATT GACGGAACCT TACTCGTTGT
                  prM
      ---------------------
        D  F  L   E  G  V
      GAGACTTCTT GGAAGGAGTG
      CTCTGAAGAA CCTTCCTCAC prM
      --------------------------------------------------------------------------------
                                                                                           E
                                                                                         ---
        S  G  A   T  W  V   D  L  V   L  E  G   D  S  C   V  T  I   M  S  K   D  K  P   T  I  D
 2601 TCTGGAGCAA CATGGGTGGA TTTGGTTCTC GAAGGCGACA GCTGCGTGAC TATCATGTCT AAGGACAAGC CTACCATCGA
      AGACCTCGTT GTACCCACCT AAACCAAGAG CTTCCGCTGT CGACGCACTG ATAGTACAGA TTCCTGTTCG GATGGTAGCT
                  E
      ---------------------
        V  K  M   M  N  M  E •
      TGTGAAGATG ATGAATATGG
      ACACTTCTAC TACTTATACC

E
      --------------------------------------------------------------------------------
      • A  A  N   L  A  E   V  R  S   Y  C  Y   L  A  T   V  S  D   L  S  T   K  A  A   C  P
 2701 AGGCGGCCAA CCTGGCAGAG GTCCGCAGTT ATTGCTATTT GGCTACCGTC AGCGATCTCT CCACCAAAGC TGCGTGCCCG
      TCCGCCGGTT GGACCGTCTC CAGGCGTCAA TAACGATAAA CCGATGGCAG TCGCTAGAGA GGTGGTTTCG ACGCACGGGC
                  E
      ---------------------
        A  M  G   E  A  H  N •
      GCCATGGGAG AAGCTCACAA
      CGGTACCCTC TTCGAGTGTT

E
      --------------------------------------------------------------------------------
      • D  K  R   A  D  P   A  F  V   C  R  Q   G  V  V   D  R  G   W  G  N   G  C  G   L  F  G
 2801 TGACAAACGT GCTGACCCAG CTTTTGTGTG CAGACAAGGA GTGGTGGACA GGGGCTGGGG CAACGGCTGC GGACTATTTG
      ACTGTTTGCA CGACTGGGTC GAAAACACAC GTCTGTTCCT CACCACCTGT CCCCGACCCC GTTGCCGACG CCTGATAAAC
                  E
      ---------------------
        K  G  S   I  D  T
      GCAAAGGAAG CATTGACACA
      CGTTTCCTTC GTAACTGTGT

E
      --------------------------------------------------------------------------------
         C  A  K   F  A  C  S   T  K  A   I  G  R   T  I  L   K  E  N   I  K  Y   E  V  A   I  F
 2901 TGCGCCAAAT TTGCCTGCTC TACCAAGGCA ATAGGAAGAA CCATTTTGAA AGAGAATATC AAGTACGAAG TGGCCATTTT
      ACGCGGTTTA AACGGACGAG ATGGTTCCGT TATCCTTCTT GGTAAAACTT TCTCTTATAG TTCATGCTTC ACCGGTAAAA
                  E
      ---------------------
        V  H  G   P  T  T  V •
      TGTCCATGGA CCAACTACTG
      ACAGGTACCT GGTTGATGAC

E
      --------------------------------------------------------------------------------
      • E  S  H   G  N  Y   S  T  Q   V  G  A   T  Q  A   G  R  F   S  I  T   P  A  A   P  S
 3001 TGGAGTCGCA CGGAAACTAC TCCACACAGG TTGGAGCCAC TCAGGCAGGG AGATTCAGCA TCACTCCTGC GGCGCCTTCA
      ACCTCAGCGT GCCTTTGATG AGGTGTGTCC AACCTCGGTG AGTCCGTCCC TCTAAGTCGT AGTGAGGACG CCGCGGAAGT
                  E
      ---------------------
        Y  T  L   K  L  G  E •
      TACACACTAA AGCTTGGAGA
      ATGTGTGATT TCGAACCTCT
```

```
                                                E
       --------------------------------------------------------------------------------
      •Y  G  E      V  T  V  D      C  E  P      R  S  G      I  D  T  N      A  Y  Y      V  M  T      V  G  T  K
3101 ATATGGAGAG GTGACAGTGG ACTGTGAACC ACGGTCAGGG ATTGACACCA ATGCATACTA CGTGATGACT GTTGGAACAA
     TATACCTCTC CACTGTCACC TGACACTTGG TGCCAGTCCC TAACTGTGGT TACGTATGAT GCACTACTGA CAACCTTGTT
                                                E
      ---------------------
         T  F  L     V  H  R
     AGACGTTCTT GGTCCATCGT
     TCTGCAAGAA CCAGGTAGCA

E
       --------------------------------------------------------------------------------
         E  W  F  M      D  L  N      L  P  W      S  S  A  G      S  T  V      W  R  N      R  E  T  L      M  E  F
3201 GAGTGGTTCA TGGACCTCAA CCTCCCTTGG AGCAGTGCTG GAAGTACTGT GTGGAGGAAC AGAGAGACGT TAATGGAGTT
     CTCACCAAGT ACCTGGAGTT GGAGGGAACC TCGTCACGAC CTTCATGACA CACCTCCTTG TCTCTCTGCA ATTACCTCAA
                                                E
      ---------------------
         E  E  P     H  A  T  K•
     TGAGGAACCA CACGCCACGA
     ACTCCTTGGT GTGCGGTGCT

E
       --------------------------------------------------------------------------------
      • Q  S  V      I  A  L      G  S  Q  E      G  A  L      H  Q  A      L  A  G  A      I  P  V      E  F  S
3301 AGCAGTCTGT GATAGCATTG GGCTCACAAG AGGGAGCTCT GCATCAAGCT TTGGCTGGAG CCATTCCTGT GGAATTTTCA
     TCGTCAGACA CTATCGTAAC CCGAGTGTTC TCCCTCGAGA CGTAGTTCGA AACCGACCTC GGTAAGGACA CCTTAAAAGT
                                                E
      ---------------------
        S  N  T  V      K  L  T•
     AGCAACACTG TCAAGTTGAC
     TCGTTGTGAC AGTTCAACTG

E
       --------------------------------------------------------------------------------
      •S  G  H     L  K  C  R      V  K  M      E  K  L      Q  L  K  G      T  T  Y      G  V  C      S  K  A  F
3401 GTCGGGTCAT TTGAAGTGTA GAGTGAAGAT GGAAAAATTG CAGTTGAAGG GAACAACCTA TGGCGTCTGT TCAAAGGCTT
     CAGCCCAGTA AACTTCACAT CTCACTTCTA CCTTTTTAAC GTCAACTTCC CTTGTTGGAT ACCGCAGACA AGTTTCCGAA
                                                E
      ---------------------
        K  F  L     G  T  P
     TCAAGTTTCT TGGGACTCCC
     AGTTCAAAGA ACCCTGAGGG

E
       --------------------------------------------------------------------------------
        A  D  T  G      H  G  T      V  V  L      E  L  Q  Y      T  G  T      D  G  P      C  K  V  P      I  S  S
3501 GCAGACACAG GTCACGGCAC TGTGGTGTTG GAATTGCAGT ACACTGGCAC GGATGGACCT TGCAAAGTTC CTATCTCGTC
     CGTCTGTGTC CAGTGCCGTG ACACCACAAC CTTAACGTCA TGTGACCGTG CCTACCTGGA ACGTTTCAAG GATAGAGCAG
                                                E
      ---------------------
        V  A  S     L  N  D  L•
     AGTGGCTTCA TTGAACGACC
     TCACCGAAGT AACTTGCTGG

E
       --------------------------------------------------------------------------------
      • T  P  V      G  R  L      V  T  V  N      P  F  V      S  V  A      T  A  N  A      K  V  L      I  E  L
3601 TAACGCCAGT GGGCAGATTG GTCACTGTCA ACCCTTTTGT TTCAGTGGCC ACGGCCAACG CTAAGGTCCT GATTGAATTG
     ATTGCGGTCA CCCGTCTAAC CAGTGACAGT TGGGAAAACA AAGTCACCGG TGCCGGTTGC GATTCCAGGA CTAACTTAAC
                                                E
      ---------------------
        E  P  P     F  G  D  S•
     GAACCACCCT TTGGAGACTC
     CTTGGTGGGA AACCTCTGAG

E
       --------------------------------------------------------------------------------
      •Y  I  V      V  G  R  G      E  Q  Q      I  N  H      H  W  H  K      S  G  S      S  I  G      K  A  F  T
3701 ATACATAGTG GTGGGCAGAG GAGAACAACA GATCAATCAC CACTGGCACA AGTCTGGAAG CAGCATTGGC AAAGCCTTTA
     TATGTATCAC CACCCGTCTC CTCTTGTTGT CTAGTTAGTG GTGACCGTGT TCAGACCTTC GTCGTAACCG TTTCGGAAAT
                                                E
      ---------------------
        T  T  L     K  G  A
     CAACCACCCT CAAAGGAGCG
     GTTGGTGGGA GTTTCCTCGC
```

SEQUENCE APPENDIX 5-continued

```
                                               E
       ------------------------------------------------------------------------------------
        Q   R   L   A    A   L   G    D   T   A   W   D   F   G    S   V   G   G   V   F    T   S   V   G   K   A   V
3801  CAGAGACTAG CCGCTCTAGG AGACACAGCT TGGGACTTTG GATCAGTTGG AGGGGTGTTC ACCTCAGTTG GGAAGGCTGT
      GTCTCTGATC GGCGAGATCC TCTGTGTCGA ACCCTGAAAC CTAGTCAACC TCCCCACAAG TGGAGTCAAC CCTTCCGACA
                 E
      ---------------------
        H   Q   V    F   G   G   A  •
      CCATCAAGTG TTCGGAGGAG
      GGTAGTTCAC AAGCCTCCTC

E
      ------------------------------------------------------------------------------------
       •  F   R   S    L   F   G    G   M   S   W    I   T   Q    G   L   L    G   A   L   L    L   W   M   G   I   N
3901  CATTCCGCTC ACTGTTCGGA GGCATGTCCT GGATAACGCA AGGATTGCTG GGGGCTCTCC TGTTGTGGAT GGGCATCAAT
      GTAAGGCGAG TGACAAGCCT CCGTACAGGA CCTATTGCGT TCCTAACGAC CCCCGAGAGG ACAACACCTA CCCGTAGTTA
                 E
      ---------------------
        A   R   D   R    S   I   A  •
      GCTCGTGACA GGTCCATAGC
      CGAGCACTGT CCAGGTATCG

NS1
                                                                                 -------------------------
                                     E
      ---------------------------------------------------------------------
       • L   T   F    L   A   V   G    G   V   L    L   F   L    S   V   N   V    H   A   D    T   G   C   A   I   D   I
4001  TCTCACGTTT CTCGCAGTTG GAGGAGTTCT GCTCTTCCTC TCCGTGAACG TGCACGCTGA CACTGGGTGT GCCATAGACA
      AGAGTGCAAA GAGCGTCAAC CTCCTCAAGA CGAGAAGGAG AGGCACTTGC ACGTGCGACT GTGACCCACA CGGTATCTGT
                 NS1
      ---------------------
        S   R   Q    E   L   R
      TCAGCCGGCA AGAGCTGAGA
      AGTCGGCCGT TCTCGACTCT
```

Other Embodiments

All publications, patent applications, and patents mentioned in this specification are incorporated herein by reference in their entirety as if each individual publication, patent application, or patent were specifically and individually indicated to be incorporated by reference.

Various modifications and variations of the described viruses, vectors, compositions, and methods of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the fields of medicine, pharmacology, or related fields are intended to be within the scope of the invention. Use of singular forms herein, such as "a" and "the," does not exclude indication of the corresponding plural form, unless the context indicates to the contrary. Similarly, use of plural terms does not exclude indication of a corresponding singular form. Other embodiments are within the scope of the following claims.

SEQUENCE LISTING

```
<160> NUMBER OF SEQ ID NOS: 78

<210> SEQ ID NO 1
<211> LENGTH: 12
<212> TYPE: PRT
<213> ORGANISM: Y

-continued

```
<210> SEQ ID NO 3
<211> LENGTH: 20
<212> TYPE: PRT
<213> ORGANISM: Artificial Sequence
<220> FEATURE:
<223> OTHER INFORMATION: Synthetic Construct

<400> SEQUENCE: 3

Ser His Asp Val Leu Thr Val Gln Phe Leu Ile Leu Gly Met Leu Gly
1               5                   10                  15

Met Thr Ile Ala
            20

<210> SEQ ID NO 4
<211> LENGTH: 20
<212> TYPE: PRT
<213> ORGANISM: Tick-borne Encephalitis Virus

<400> SEQUENCE: 4

Gly Gly Thr Asp Trp Met Ser Trp Leu Leu Val Ile Gly Met Leu Gly
1               5                   10                  15

Met Thr Ile Ala
            20

<210> SEQ ID NO 5
<211> LENGTH: 9
<212> TYPE: PRT
<213> ORGANISM: Borrelia burgdorferi

<400> SEQUENCE: 5

Tyr Val Leu Glu Gly Thr Leu Thr Ala
1               5

<210> SEQ ID NO 6
<211> LENGTH: 9
<212> TYPE: PRT
<213> ORGANISM: Borrelia afzelii

<400> SEQUENCE: 6

Phe Thr Leu Glu Gly Lys Val Ala Asn
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Phe Thr Leu Glu Gly Lys Leu Thr Ala
1               5

<210> SEQ ID NO 8
<211> LENGTH: 273
<212> TYPE: PRT
<213> ORGANISM: Borrelia burgdorferi

<400> SEQUENCE: 8

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
```

```
                    35                  40                  45
Asp Gly Lys Tyr Asp Leu Ile Ala Thr Val Asp Lys Leu Glu Leu Lys
         50                  55                  60
Gly Thr Ser Asp Lys Asn Asn Gly Ser Gly Val Leu Glu Gly Val Lys
 65                  70                  75                  80
Ala Asp Lys Ser Lys Val Lys Leu Thr Ile Ser Asp Asp Leu Gly Gln
                 85                  90                  95
Thr Thr Leu Glu Val Phe Lys Glu Asp Gly Lys Thr Leu Val Ser Lys
            100                 105                 110
Lys Val Thr Ser Lys Asp Lys Ser Ser Thr Glu Glu Lys Phe Asn Glu
        115                 120                 125
Lys Gly Glu Val Ser Glu Lys Ile Ile Thr Arg Ala Asp Gly Thr Arg
    130                 135                 140
Leu Glu Tyr Thr Gly Ile Lys Ser Asp Gly Ser Gly Lys Ala Lys Glu
145                 150                 155                 160
Val Leu Lys Gly Tyr Val Leu Glu Gly Thr Leu Thr Ala Glu Lys Thr
                165                 170                 175
Thr Leu Val Val Lys Glu Gly Thr Val Thr Leu Ser Lys Asn Ile Ser
            180                 185                 190
Lys Ser Gly Glu Val Ser Val Glu Leu Asn Asp Thr Asp Ser Ser Ala
        195                 200                 205
Ala Thr Lys Lys Thr Ala Ala Trp Asn Ser Gly Thr Ser Thr Leu Thr
    210                 215                 220
Ile Thr Val Asn Ser Lys Lys Thr Lys Asp Leu Val Phe Thr Lys Glu
225                 230                 235                 240
Asn Thr Ile Thr Val Gln Gln Tyr Asp Ser Asn Gly Thr Lys Leu Glu
                245                 250                 255
Gly Ser Ala Val Glu Ile Thr Lys Leu Asp Glu Ile Lys Asn Ala Leu
            260                 265                 270
Lys

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: X is Glu or Gly
<220> FEATURE:
<221> NAME/KEY: MISC_FEATURE
<222> LOCATION: (5)..(5)
<223> OTHER INFORMATION: X is Met or Ile
<220> FEATURE:
<221> NAME/KEY: MISC_FEATURE
<222> LOCATION: (6)..(6)
<223> OTHER INFORMATION: X is Lys, Thr or Gly

<400> SEQUENCE: 9

Leu Pro Gly Xaa Xaa Xaa Val Leu
 1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (6)..(6)
<223> OTHER INFORMATION: X is Asn, Ser, or Asp
<220> FEATURE:
<221> NAME/KEY: MISC_FEATURE
<222> LOCATION: (11)..(11)
<223> OTHER INFORMATION: X is Val, or Thr

<400> SEQUENCE: 10

Gly Thr Ser Asp Lys Xaa Asn Gly Ser Gly Xaa
1               5                   10

<210> SEQ ID NO 11
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Asn, His, or Glu
<220> FEATURE:
<221> NAME/KEY: MISC_FEATURE
<222> LOCATION: (3)..(3)
<223> OTHER INFORMATION: Xaa is Ser, Pro, Leu, Ala, or Ser
<220> FEATURE:
<221> NAME/KEY: MISC_FEATURE
<222> LOCATION: (4)..(4)
<223> OTHER INFORMATION: Xaa is Lys or Asn
<220> FEATURE:
<221> NAME/KEY: MISC_FEATURE
<222> LOCATION: (8)..(8)
<223> OTHER INFORMATION: Xaa is Val or Ile
<220> FEATURE:
<221> NAME/KEY: MISC_FEATURE
<222> LOCATION: (9)..(9)
<223> OTHER INFORMATION: Xaa is Ser or Thr
<220> FEATURE:
<221> NAME/KEY: MISC_FEATURE
<222> LOCATION: (10)..(10)
<223> OTHER INFORMATION: Xaa is Val or Ala
<220> FEATURE:
<221> NAME/KEY: MISC_FEATURE
<222> LOCATION: (11)..(11)
<223> OTHER INFORMATION: Xaa is Glu or Ala
<220> FEATURE:
<221> NAME/KEY: MISC_FEATURE
<222> LOCATION: (13)..(13)
<223> OTHER INFORMATION: Xaa is Asn or Asp
<220> FEATURE:
<221> NAME/KEY: MISC_FEATURE
<222> LOCATION: (15)..(15)
<223> OTHER INFORMATION: Xaa is Thr or Ser
<220> FEATURE:
<221> NAME/KEY: MISC_FEATURE
<222> LOCATION: (16)..(16)
<223> OTHER INFORMATION: Xaa is Asp or Asn
<220> FEATURE:
<221> NAME/KEY: MISC_FEATURE
<222> LOCATION: (17)..(17)
<223> OTHER INFORMATION: Xaa is Ser or Thr
<220> FEATURE:
<221> NAME/KEY: MISC_FEATURE
<222> LOCATION: (18)..(18)
<223> OTHER INFORMATION: Xaa is Ser or Thr
<220> FEATURE:
<221> NAME/KEY: MISC_FEATURE
<222> LOCATION: (19)..(19)
<223> OTHER INFORMATION: Xaa is Ala, Gln, or Arg
<220> FEATURE:
<221> NAME/KEY: MISC_FEATURE
<222> LOCATION: (25)..(25)
<223> OTHER INFORMATION: Xaa is Ala or Gly
<220> FEATURE:
<221> NAME/KEY: MISC_FEATURE
<222> LOCATION: (26)..(26)
```

```
<223> OTHER INFORMATION: Xaa is Ala, Lys, or Thr
<220> FEATURE:
<221> NAME/KEY: MISC_FEATURE
<222> LOCATION: (28)..(28)
<223> OTHER INFORMATION: Xaa is Asn or Asp
<220> FEATURE:
<221> NAME/KEY: MISC_FEATURE
<222> LOCATION: (29)..(29)
<223> OTHER INFORMATION: Xaa is Ser or Ala
<220> FEATURE:
<221> NAME/KEY: MISC_FEATURE
<222> LOCATION: (30)..(30)
<223> OTHER INFORMATION: Xaa is Gly, Asn, or Lys

<400> SEQUENCE: 11

Xaa Ile Xaa Xaa Ser Gly Glu Xaa Xaa Xaa Leu Xaa Asp Xaa Xaa
1               5                   10                  15

Xaa Xaa Xaa Ala Thr Lys Lys Thr Xaa Xaa Trp Xaa Xaa Xaa Thr
            20                  25                  30

<210> SEQ ID NO 12
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Asn or Ala
<220> FEATURE:
<221> NAME/KEY: MISC_FEATURE
<222> LOCATION: (5)..(5)
<223> OTHER INFORMATION: Xaa is Lys or Asn
<220> FEATURE:
<221> NAME/KEY: MISC_FEATURE
<222> LOCATION: (9)..(9)
<223> OTHER INFORMATION: Xaa is Ser, Asn, Lys, or Thr
<220> FEATURE:
<221> NAME/KEY: MISC_FEATURE
<222> LOCATION: (14)..(14)
<223> OTHER INFORMATION: Xaa is Thr or Lys
<220> FEATURE:
<221> NAME/KEY: MISC_FEATURE
<222> LOCATION: (15)..(15)
<223> OTHER INFORMATION: Xaa is Thr or Lys
<220> FEATURE:
<221> NAME/KEY: MISC_FEATURE
<222> LOCATION: (17)..(17)
<223> OTHER INFORMATION: Xaa is Asp or Lys
<220> FEATURE:
<221> NAME/KEY: MISC_FEATURE
<222> LOCATION: (19)..(19)
<223> OTHER INFORMATION: Xaa is Ile or Leu

<400> SEQUENCE: 12

Ser Xaa Gly Thr Xaa Leu Glu Gly Xaa Ala Val Glu Ile Xaa Xaa Leu
1               5                   10                  15

Xaa Glu Xaa Lys Asn
            20

<210> SEQ ID NO 13
<211> LENGTH: 154
<212> TYPE: PRT
<213> ORGANISM: Rhipicephalus appendiculatus

<400> SEQUENCE: 13

Met Lys Ala Phe Phe Val Leu Ser Leu Leu Ser Thr Ala Ala Leu Thr
1               5                   10                  15

Asn Ala Ala Arg Ala Gly Arg Leu Gly Ser Asp Leu Asp Thr Phe Gly
            20                  25                  30
```

```
Arg Val His Gly Asn Leu Tyr Ala Gly Ile Glu Arg Ala Gly Pro Arg
        35                  40                  45

Gly Tyr Pro Gly Leu Thr Ala Ser Ile Gly Gly Glu Val Gly Ala Arg
    50                  55                  60

Leu Gly Gly Arg Ala Gly Val Gly Val Ser Ser Tyr Gly Tyr Gly Tyr
65                  70                  75                  80

Pro Ser Trp Gly Tyr Pro Tyr Gly Gly Tyr Gly Gly Tyr Gly Gly Tyr
                85                  90                  95

Gly Gly Tyr Gly Gly Tyr Asp Gln Gly Phe Gly Ser Ala Tyr Gly Gly
            100                 105                 110

Tyr Pro Gly Tyr Tyr Gly Tyr Tyr Tyr Pro Ser Gly Tyr Gly Gly Gly
            115                 120                 125

Tyr Gly Gly Ser Tyr Gly Gly Ser Tyr Gly Gly Ser Tyr Thr Tyr Pro
        130                 135                 140

Asn Val Arg Ala Ser Ala Gly Ala Ala Ala
145                 150

<210> SEQ ID NO 14
<211> LENGTH: 184
<212> TYPE: PRT
<213> ORGANISM: Ixodes scapularis

<400> SEQUENCE: 14

Met Arg Thr Ala Phe Thr Cys Ala Leu Leu Ala Ile Ser Phe Leu Gly
1               5                   10                  15

Ser Pro Cys Ser Ser Ser Glu Asp Gly Leu Glu Gln Asp Thr Ile Val
            20                  25                  30

Glu Thr Thr Thr Gln Asn Leu Tyr Glu Arg His Tyr Arg Asn His Ser
        35                  40                  45

Gly Leu Cys Gly Ala Gln Tyr Arg Asn Ser Ser His Ala Glu Ala Val
    50                  55                  60

Tyr Asn Cys Thr Leu Asn His Leu Pro Pro Val Val Asn Ala Thr Trp
65                  70                  75                  80

Glu Gly Ile Arg His Arg Ile Asn Lys Thr Ile Pro Gln Phe Val Lys
                85                  90                  95

Leu Ile Cys Asn Phe Thr Val Ala Met Pro Gln Glu Phe Tyr Leu Val
            100                 105                 110

Tyr Met Gly Ser Asp Gly Asn Ser Asp Phe Glu Glu Asp Lys Glu Ser
        115                 120                 125

Thr Gly Thr Asp Glu Asp Ser Asn Thr Gly Ser Ser Ala Ala Ala Lys
    130                 135                 140

Val Thr Glu Ala Leu Ile Ile Glu Ala Glu Asn Cys Thr Ala His
145                 150                 155                 160

Ile Thr Gly Trp Thr Thr Glu Thr Pro Thr Thr Leu Glu Pro Thr Thr
                165                 170                 175

Glu Ser Gln Phe Glu Ala Ile Pro
            180

<210> SEQ ID NO 15
<211> LENGTH: 177
<212> TYPE: PRT
<213> ORGANISM: Ixodes scapularis

<400> SEQUENCE: 15

Met Arg Thr Ala Leu Thr Cys Ala Leu Leu Ala Ile Ser Phe Leu Gly
1               5                   10                  15
```

-continued

```
Ser Pro Cys Ser Ser Glu Gly Gly Leu Glu Lys Asp Ser Arg Val
             20                  25                  30

Glu Thr Thr Thr Gln Asn Leu Tyr Glu Arg Tyr Tyr Arg Lys His Pro
         35                  40                  45

Gly Leu Cys Gly Ala Gln Tyr Arg Asn Ser Ser His Ala Glu Ala Val
     50                  55                  60

Tyr Asn Cys Thr Leu Ser Leu Leu Pro Leu Ser Val Asn Thr Thr Trp
 65                  70                  75                  80

Glu Gly Ile Arg His Arg Ile Asn Lys Thr Ile Pro Glu Phe Val Asn
                 85                  90                  95

Leu Ile Cys Asn Phe Thr Val Ala Met Pro Asp Gln Phe Tyr Leu Val
            100                 105                 110

Tyr Met Gly Ser Asn Gly Asn Ser Tyr Ser Glu Glu Asp Glu Asp Gly
        115                 120                 125

Lys Thr Gly Ser Ser Ala Ala Val Gln Val Thr Glu Gln Leu Ile Ile
    130                 135                 140

Gln Ala Glu Glu Asn Cys Thr Ala His Ile Thr Gly Trp Thr Thr Glu
145                 150                 155                 160

Ala Pro Thr Thr Leu Glu Pro Thr Thr Glu Thr Gln Phe Glu Ala Ile
                165                 170                 175

Ser

<210> SEQ ID NO 16
<211> LENGTH: 19
<212> TYPE: PRT
<213> ORGANISM: Influenza A virus

<400> SEQUENCE: 16

Pro Ala Lys Leu Leu Lys Glu Arg Gly Phe Phe Gly Ala Ile Ala Gly
  1               5                  10                  15

Phe Leu Glu

<210> SEQ ID NO 17
<211> LENGTH: 23
<212> TYPE: PRT
<213> ORGANISM: Influenza A virus

<400> SEQUENCE: 17

Pro Ala Lys Leu Leu Lys Glu Arg Gly Phe Phe Gly Ala Ile Ala Gly
  1               5                  10                  15

Phe Leu Glu Gly Ser Gly Cys
            20

<210> SEQ ID NO 18
<211> LENGTH: 19
<212> TYPE: PRT
<213> ORGANISM: Influenza B virus

<400> SEQUENCE: 18

Asn Asn Ala Thr Phe Asn Tyr Thr Asn Val Asn Pro Ile Ser His Ile
  1               5                  10                  15

Arg Gly Ser

<210> SEQ ID NO 19
<211> LENGTH: 24
<212> TYPE: PRT
<213> ORGANISM: Influenza A virus
```

```
<400> SEQUENCE: 19

Met Ser Leu Leu Thr Glu Val Glu Thr Pro Ile Arg Asn Glu Trp Gly
1               5                   10                  15

Cys Arg Cys Asn Asp Ser Ser Asp
            20

<210> SEQ ID NO 20
<211> LENGTH: 24
<212> TYPE: PRT
<213> ORGANISM: Influenza A virus

<400> SEQUENCE: 20

Met Ser Leu Leu Thr Glu Val Glu Thr Pro Thr Arg Asn Glu Trp Glu
1               5                   10                  15

Cys Arg Cys Ser Asp Ser Ser Asp
            20

<210> SEQ ID NO 21
<211> LENGTH: 24
<212> TYPE: PRT
<213> ORGANISM: Influenza A virus

<400> SEQUENCE: 21

Met Ser Leu Leu Thr Glu Val Glu Thr Leu Thr Arg Asn Gly Trp Gly
1               5                   10                  15

Cys Arg Cys Ser Asp Ser Ser Asp
            20

<210> SEQ ID NO 22
<211> LENGTH: 8
<212> TYPE: PRT
<213> ORGANISM: Influenza A virus

<400> SEQUENCE: 22

Glu Val Glu Thr Pro Thr Arg Asn
1               5

<210> SEQ ID NO 23
<211> LENGTH: 23
<212> TYPE: PRT
<213> ORGANISM: Influenza A virus

<400> SEQUENCE: 23

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 24
<211> LENGTH: 17
<212> TYPE: PRT
<213> ORGANISM: Influenza A virus

<400> SEQUENCE: 24

Ser Leu Leu Thr Glu Val Glu Thr Pro Ile Arg Asn Glu Trp Gly Cys
1               5                   10                  15

Arg

<210> SEQ ID NO 25
<211> LENGTH: 6
<212> TYPE: PRT
<213> ORGANISM: Influenza B virus
```

<400> SEQUENCE: 25

Met Leu Glu Pro Phe Gln
1               5

<210> SEQ ID NO 26
<211> LENGTH: 12
<212> TYPE: PRT
<213> ORGANISM: Influenza B virus

<400> SEQUENCE: 26

Leu Glu Pro Phe Gln Ile Leu Ser Ile Ser Gly Cys
1               5                   10

<210> SEQ ID NO 27
<211> LENGTH: 24
<212> TYPE: PRT
<213> ORGANISM: Artificial Sequence
<220> FEATURE:
<223> OTHER INFORMATION: Avian Influenza A virus Subtype H5N1

<400> SEQUENCE: 27

Met Ser Leu Leu Thr Glu Val Glu Thr Leu Thr Arg Asn Gly Trp Gly
1               5                   10                  15

Cys Arg Cys Ser Asp Ser Ser Asp
            20

<210> SEQ ID NO 28
<211> LENGTH: 28
<212> TYPE: PRT
<213> ORGANISM: Artificial Sequence
<220> FEATURE:
<223> OTHER INFORMATION: Synthetic Construct

<400> SEQUENCE: 28

Arg Lys Arg Arg Ser His Asp Val Leu Thr Val Gln Phe Leu Ile Leu
1               5                   10                  15

Gly Met Leu Gly Met Thr Ile Ala Ala Thr Val Arg
            20                  25

<210> SEQ ID NO 29
<211> LENGTH: 84
<212> TYPE: DNA
<213> ORGANISM: Artificial Sequence
<220> FEATURE:
<223> OTHER INFORMATION: Synthetic Construct

<400> SEQUENCE: 29
aggaaacgcc gttcccatga tgttctgact gtgcaattcc taattttggg catgctgggc    60
atgacaatcg cagctacggt tcgc                                          84

<210> SEQ ID NO 30
<211> LENGTH: 84
<212> TYPE: DNA
<213> ORGANISM: Artificial Sequence
<220> FEATURE:
<223> OTHER INFORMATION: Synthetic Construct

<400> SEQUENCE: 30
tcctttgcgg caagggtact acaagactga cacgttaagg attaaaaccc gtacgacccg    60
tactgttagc gtcgatgcca agcg                                          84

<210> SEQ ID NO 31

```
<211> LENGTH: 28
<212> TYPE: PRT
<213> ORGANISM: Artificial Sequence
<220> FEATURE:
<223> OTHER INFORMATION: Synthetic Construct

<400> SEQUENCE: 31

Arg Lys Arg Arg Ser His Asp Val Leu Thr Val Gln Phe Leu Ile Leu
1               5                   10                  15

Gly Met Leu Ala Cys Val Gly Ala Ala Thr Val Arg
            20                  25

<210> SEQ ID NO 32
<211> LENGTH: 84
<212> TYPE: DNA
<213> ORGANISM: Artificial Sequence
<220> FEATURE:
<223> OTHER INFORMATION: Synthetic Construct

<400> SEQUENCE: 32
aggaaacgcc gttcccatga tgttctgact gtgcaattcc taattttggg catgctggct    60
tgtgtcggag cagctaccgt gcga                                          84

<210> SEQ ID NO 33
<211> LENGTH: 84
<212> TYPE: DNA
<213> ORGANISM: Artificial Sequence
<220> FEATURE:
<223> OTHER INFORMATION: Synthetic Construct

<400> SEQUENCE: 33
tcctttgcgg caagggtact acaagactga cacgttaagg attaaaaccc gtacgaccga    60
acacagcctc gtcgatggca cgct                                          84

<210> SEQ ID NO 34
<211> LENGTH: 28
<212> TYPE: PRT
<213> ORGANISM: Artificial Sequence
<220> FEATURE:
<223> OTHER INFORMATION: Synthetic Construct

<400> SEQUENCE: 34

Gln Lys Lys Arg Gly Gly Thr Asp Trp Met Ser Trp Leu Leu Val Ile
1               5                   10                  15

Gly Met Leu Gly Met Thr Ile Ala Ala Thr Val Arg
            20                  25

<210> SEQ ID NO 35
<211> LENGTH: 84
<212> TYPE: DNA
<213> ORGANISM: Artificial Sequence
<220> FEATURE:
<223> OTHER INFORMATION: Synthetic Construct

<400> SEQUENCE: 35
caaaagaaac gggggggaac agactggatg agctggctgc tcgtaatcgg catgctgggc    60
atgacaatcg cagctacggt tcgc                                          84

<210> SEQ ID NO 36
<211> LENGTH: 84
<212> TYPE: DNA
<213> ORGANISM: Artificial Sequence
<220> FEATURE:
<223> OTHER INFORMATION: Synthetic Construct
```

```
<400> SEQUENCE: 36
gttttctttg ccccccttg tctgacctac tcgaccgacg agcattagcc gtacgacccg      60
tactgttagc gtcgatgcca agcg                                            84

<210> SEQ ID NO 37
<211> LENGTH: 26
<212> TYPE: PRT
<213> ORGANISM: Artificial Sequence
<220> FEATURE:
<223> OTHER INFORMATION: Synthetic Construct

<400> SEQUENCE: 37

Gln Lys Lys Arg Gly Gly Lys Thr Gly Ile Ala Val Met Ile Gly Met
1               5                   10                  15

Leu Ala Cys Val Gly Ala Ala Thr Val Arg
            20                  25

<210> SEQ ID NO 38
<211> LENGTH: 78
<212> TYPE: DNA
<213> ORGANISM: Artificial Sequence
<220> FEATURE:
<223> OTHER INFORMATION: Synthetic Construct

<400> SEQUENCE: 38
caaaagaaac gcgggggaaa gacaggcata gctgtgatga taggcatgct ggcttgtgtc      60
ggagcagcta ccgtgcga                                                    78

<210> SEQ ID NO 39
<211> LENGTH: 78
<212> TYPE: DNA
<213> ORGANISM: Artificial Sequence
<220> FEATURE:
<223> OTHER INFORMATION: Synthetic Construct

<400> SEQUENCE: 39
gttttctttg cgcccccttt ctgtccgtat cgacactact atccgtacga ccgaacacag      60
cctcgtcgat ggcacgct                                                    78

<210> SEQ ID NO 40
<211> LENGTH: 793
<212> TYPE: PRT
<213> ORGANISM: Artificial Sequence
<220> FEATURE:
<223> OTHER INFORMATION: Synthetic Construct

<400> SEQUENCE: 40

Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Val Ser Leu Met Arg Gly Leu Ser Ser
                85                  90                  95
```

```
Arg Lys Arg Arg Ser His Asp Val Leu Thr Val Gln Phe Leu Ile Leu
                100                 105                 110

Gly Met Leu Gly Met Thr Ile Ala Ala Thr Val Arg Lys Glu Arg Asp
        115                 120                 125

Gly Ser Thr Val Ile Arg Ala Glu Gly Lys Asp Ala Ala Thr Gln Val
    130                 135                 140

Arg Val Glu Asn Gly Thr Cys Val Ile Leu Ala Thr Asp Met Gly Ser
145                 150                 155                 160

Trp Cys Asp Asp Ser Leu Ser Tyr Glu Cys Val Thr Ile Asp Gln Gly
                165                 170                 175

Glu Glu Pro Val Asp Val Asp Cys Phe Cys Arg Asn Val Asp Gly Val
            180                 185                 190

Tyr Leu Glu Tyr Gly Arg Cys Gly Lys Gln Glu Gly Ser Arg Thr Arg
        195                 200                 205

Arg Ser Val Leu Ile Pro Ser His Ala Gln Gly Glu Leu Thr Gly Arg
210                 215                 220

Gly His Lys Trp Leu Glu Gly Asp Ser Leu Arg Thr His Leu Thr Arg
225                 230                 235                 240

Val Glu Gly Trp Val Trp Lys Asn Arg Leu Leu Ala Leu Ala Met Val
                245                 250                 255

Thr Val Val Trp Leu Thr Leu Glu Ser Val Val Thr Arg Val Ala Val
            260                 265                 270

Leu Val Val Leu Leu Cys Leu Ala Pro Val Tyr Ala Ser Arg Cys Thr
        275                 280                 285

His Leu Glu Asn Arg Asp Phe Val Thr Gly Thr Gln Gly Thr Thr Arg
    290                 295                 300

Val Thr Leu Val Leu Glu Leu Gly Gly Cys Val Thr Ile Thr Ala Glu
305                 310                 315                 320

Gly Lys Pro Ser Met Asp Val Trp Leu Asp Ala Ile Tyr Gln Glu Asn
                325                 330                 335

Pro Ala Gln Thr Arg Glu Tyr Cys Leu His Ala Lys Leu Ser Asp Thr
            340                 345                 350

Lys Val Ala Ala Arg Cys Pro Thr Met Gly Pro Ala Thr Leu Ala Glu
        355                 360                 365

Glu His Gln Gly Gly Thr Val Cys Lys Arg Asp Gln Ser Asp Arg Gly
    370                 375                 380

Trp Gly Asn His Cys Gly Leu Phe Gly Lys Gly Ser Ile Val Ala Cys
385                 390                 395                 400

Val Lys Ala Ala Cys Glu Ala Lys Lys Ala Thr Gly His Val Tyr
                405                 410                 415

Asp Ala Asn Lys Ile Val Tyr Thr Val Lys Val Glu Pro His Thr Gly
            420                 425                 430

Asp Tyr Val Ala Ala Asn Glu Thr His Ser Gly Arg Lys Thr Ala Ser
        435                 440                 445

Phe Thr Val Ser Ser Glu Lys Thr Ile Leu Thr Met Gly Glu Tyr Gly
    450                 455                 460

Asp Val Ser Leu Leu Cys Arg Val Ala Ser Gly Val Asp Leu Ala Gln
465                 470                 475                 480

Thr Val Ile Leu Glu Leu Asp Lys Thr Val Glu His Leu Pro Thr Ala
                485                 490                 495

Trp Gln Val His Arg Asp Trp Phe Asn Asp Leu Ala Leu Pro Trp Lys
            500                 505                 510

His Glu Gly Ala Arg Asn Trp Asn Asn Ala Glu Arg Leu Val Glu Phe
```

```
       515                 520                 525
Gly Ala Pro His Ala Val Lys Met Asp Val Tyr Asn Leu Gly Asp Gln
    530                 535                 540

Thr Gly Val Leu Leu Lys Ala Leu Ala Gly Val Pro Val Ala His Ile
545                 550                 555                 560

Glu Gly Thr Lys Tyr His Leu Lys Ser Gly His Val Thr Cys Glu Val
                565                 570                 575

Gly Leu Glu Lys Leu Lys Met Lys Gly Leu Thr Tyr Thr Met Cys Asp
                580                 585                 590

Lys Thr Lys Phe Thr Trp Lys Arg Ala Pro Thr Asp Ser Gly His Asp
                595                 600                 605

Thr Val Val Met Glu Val Thr Phe Ser Gly Thr Lys Pro Cys Arg Ile
                610                 615                 620

Pro Val Arg Ala Val Ala His Gly Ser Pro Asp Val Asn Val Ala Met
625                 630                 635                 640

Leu Ile Thr Pro Asn Pro Thr Ile Glu Asn Asn Gly Gly Phe Ile
                645                 650                 655

Glu Met Gln Leu Pro Pro Gly Asp Asn Ile Ile Tyr Val Gly Glu Leu
                660                 665                 670

Ser Tyr Gln Trp Phe Gln Lys Gly Ser Ser Ile Gly Arg Val Phe Gln
                675                 680                 685

Lys Thr Lys Lys Gly Ile Glu Arg Leu Thr Val Ile Gly Glu His Ala
                690                 695                 700

Trp Asp Phe Gly Ser Ala Gly Gly Phe Leu Ser Ser Ile Gly Lys Ala
705                 710                 715                 720

Leu His Thr Val Leu Gly Gly Ala Phe Asn Ser Ile Phe Gly Val
                725                 730                 735

Gly Phe Leu Pro Lys Leu Leu Leu Gly Val Ala Leu Ala Trp Leu Gly
                740                 745                 750

Leu Asn Met Arg Asn Pro Thr Met Ser Met Ser Phe Leu Leu Ala Gly
                755                 760                 765

Val Leu Val Leu Ala Met Thr Leu Gly Val Gly Ala Asp Gln Gly Cys
                770                 775                 780

Ala Ile Asn Phe Gly Lys Arg Glu Leu
785                 790

<210> SEQ ID NO 41
<211> LENGTH: 2500
<212> TYPE: DNA
<213> ORGANISM: Artificial Sequence
<220> FEATURE:
<223> OTHER INFORMATION: Synthetic Construct

<400> SEQUENCE: 41
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa aacaaaaaac aaaacaaatt ggaaacagac ctggaccttc     240
aagaggtgtt caaggattta tcttttttctt tttgttcaac attttgactg aaaaaagat     300 cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aatttttgggc atgctgggca tgacaatcgc     480
```

```
agctacggtt cgcaaggaaa gagacggcag tacggtcata cgcgcggaag gtaaggatgc     540
cgctacccaa gtgagagtgg aaaatggtac ctgcgtcatt ctggccaccg acatgggctc     600
ttggtgtgat gatagccttt cttatgagtg cgtaaccata gatcaaggtg aggaacctgt     660
tgacgttgat tgcttctgcc gaaacgtgga tggggtgtat ctcgaatatg acggtgtgg      720
taaacaagaa ggaagcagaa ccagacgctc agtgcttata ccctcccacg ctcaaggaga     780
gctgaccgga cggggacata aatggttgga gggcgactca ctccgaacac atttgacccg     840
cgtcgagggc tgggtctgga aaaatcggct gttggccctc gctatggtga cagtcgtttg     900
gctcacgctg gagtctgtgg ttactcgcgt ggcagtgctg gtggtgctcc tctgtcttgc     960
ccctgtctac gcgtccaggt gtactcattt ggaaaacaga gattttgtca ccggcaccca    1020
ggggacgact cgggtaaccc tggtgcttga actgggtggt tgcgttacta ttaccgctga    1080
gggcaaaccc tctatggatg tgtggctgga tgcaatctat caggagaatc ccgcacaaac    1140
cagggaatat tgccttcacg caaagctgtc cgatacaaag gtcgcggcta ggtgcccaac    1200
aatgggaccg gccaccctgg cggaggaaca tcagggaggt acagtgtgca aacgggacca    1260
gagtgataga ggctggggta atcactgcgg cctgttcggc aaaggaagta ttgtcgcttg    1320
cgtcaaggca gcctgtgagg ccaaaaagaa ggctactggg cacgtctatg acgccaacaa    1380
gatcgtttat acagtgaaag tggaaccaca cacaggggat tacgtggcgg ccaacgagac    1440
tcattccggt cgcaaaacgg ccagcttcac cgtgtcatcc gaaaagacca tcctcactat    1500
gggggagtat ggcgacgttt ctctgctctg ccgggtggct agcggagtcg acctggccca    1560
gacagtcatc ctggaactgg ataaaacagt tgagcatctg cctaccgctt ggcaggtgca    1620
cagggattgg tttaacgacc ttgccctgcc atggaaacat gaaggagcga gaaactggaa    1680
taatgcagag cgactcgtag aattcggtgc ccctcatgcc gtgaagatgg acgtctacaa    1740
tctgggtgat cagaccggcg ttctccttaa agctctcgct ggcgtaccag ttgcccacat    1800
cgaaggaacg aagtaccacc tgaagtcagg ccatgtaact tgcgaggtgg gcctggagaa    1860
gttgaaaatg aaaggtctta cgtacacaat gtgtgacaag accaagttca catggaagag    1920
ggcccccaca gatagcggcc acgatactgt ggtgatggag gtgacctttt ctggaacaaa    1980
accctgcaga ataccccgtgc gggctgtagc tcacggatct cccgatgtca atgttgctat    2040
gctgattaca cctaacccta ccatcgagaa taacggtggt ggtttttattg agatgcagct    2100
tccgccaggc gataacatca tctacgtggg cgaactctct taccagtggt tcagaaagg    2160
gagttcaatt gggcgggtct tccaaaaaac gaagaaggga atcgaacgat tgacggttat    2220
cggcgagcac gcatgggatt ttggttccgc aggggggattc ctgtcttcta ttggtaaggc    2280
actgcatacc gtgctggggg gcgcattcaa ttctattttc gggggcgtgg ggttcctgcc    2340
taaactcctg ctgggagtag ccctggcctg gttgggactg aatatgcgga atccgacgat    2400
gtccatgtca ttcctcttgg ccggcgtgct tgtactggcc atgacactgg gcgttggcgc    2460
cgatcaagga tgcgccatca actttggcaa gagagagctc              2500
```

<210> SEQ ID NO 42
<211> LENGTH: 2496
<212> TYPE: DNA
<213> ORGANISM: Artificial Sequence
<220> FEATURE:
<223> OTHER INFORMATION: Synthetic Construct

<400> SEQUENCE: 42

```
tcatttagga cacacgatta actccacgta accagacgtt tagctcaacg atccgttatt      60
```

```
tgtgtaaacc taattaaaat tagcaagcaa ctcgctaatc gtctcttgac tggtcttgta    120
cagaccagca tttcgagtcc cttttttggga cccgcagtta taccatgctg ctcctcaagc    180
gaggaacagt ttgttttatt ttgttttttg ttttgtttaa cctttgtctg gacctggaag    240
ttctccacaa gttcctaaat agaaaaagaa aaacaagttg taaaactgac cttttttcta    300
gtgtcgggtg gatttctcca acaccttta cgacctgggt tctgttccga accgacaaga    360
ttcctttcag ttctctcacc accggtcaaa ctactctcct aacaggagtt cctttgcggc    420
aagggtacta caagactgac acgttaagga ttaaacccg tacgacccgt actgttagcg    480
tcgatgccaa gcgttccttt ctctgccgtc atgccagtat gcgcgccttc cattcctacg    540
gcgatgggtt cactctcacc ttttaccatg gacgcagtaa gaccggtggc tgtacccgag    600
aaccacacta ctatcggaaa gaatactcac gcattggtat ctagttccac tccttggaca    660
actgcaacta acgaagacgg ctttgcacct accccacata gagcttatac ctgccacacc    720
atttgttctt ccttcgtctt ggtctgcgag tcacgaatat gggagggtgc gagttcctct    780
cgactggcct gccctgtat ttaccaacct cccgctgagt gaggcttgtg taaactgggc    840
gcagctcccg acccagacct ttttagccga caacccgggag cgataccact gtcagcaaac    900
cgagtgcgac ctcagacacc aatgagcgca ccgtcacgac caccacgagg agacagaacg    960
gggacagatg cgcaggtcca catgagtaaa ccttttgtct ctaaaacagt ggccgtgggt   1020
cccctgctga gcccattggg accacgaact tgacccacca acgcaatgat aatggcgact   1080
cccgtttggg agatacctac acaccgacct acgttagata gtcctcttag ggcgtgtttg   1140
gtcccttata acggaagtgc gtttcgacag gctatgtttc cagcgccgat ccacgggttg   1200
ttaccctggc cggtgggacc gcctccttgt agtccctcca tgtcacacgt ttgccctggt   1260
ctcactatct ccgaccccat tagtgacgcc ggacaagccg tttccttcat aacagcgaac   1320
gcagttccgt cggacactcc ggtttttctt ccgatgaccc gtgcagatac tgcggttgtt   1380
ctagcaaata tgtcactttc accttggtgt gtgtccccta atgcaccgcc ggttgctctg   1440
agtaaggcca gcgttttgcc ggtcgaagtg gcacagtagg cttttctggt aggagtgata   1500 cccccctcata ccgctgcaaa gagacagac ggcccaccga tcgcctcagc tggaccgggt   1560
ctgtcagtag gaccttgacc tattttgtca actcgtagac ggatggcgaa ccgtccacgt   1620
gtccctaacc aaattgctgg aacgggacgg tacctttgta cttcctcgct ctttgacctt   1680
attacgtctc gctgagcatc ttaagccacg gggagtacgg cacttctacc tgcagatgtt   1740
agacccacta gtctggccgc aagaggaatt tcgagagcga ccgcatggtc aacgggtgta   1800
gcttccttgc ttcatggtgg acttcagtcc ggtacattga acgctccacc cggacctctt   1860 caactttac tttccagaat gcatgtgtta cacactgttc tggttcaagt gtaccttctc   1920
ccgggggtgt ctatcgccgg tgctatgaca ccactacctc cactggaaaa gaccttgttt   1980
tgggacgtct tatgggcacg cccgacatcg agtgcctaga gggctacagt tacaacgata   2040
cgactaatgt ggattgggat ggtagctctt attgccacca ccaaaataac tctacgtcga   2100
aggcggtccg ctattgtagt agatgcaccc gcttgagaga atggtcacca aagtctttcc   2160
ctcaagttaa cccgcccaga aggttttttg cttcttccct tagcttgcta actgccaata   2220
gccgctcgtg cgtaccctaa aaccaaggcg tccccctaag gacagaagat aaccattccg   2280
tgacgtatgg cacgaccccc cgcgtaagtt aagataaaag ccccgcacc ccaaggacgg   2340 atttgaggac gaccctcatc gggaccggac caaccctgac ttatacgcct taggctgcta   2400
```

```
tacagtaagg agaaccggcc gcacgaacat gaccggtact gtgacccgca accgcggcta    2460
gttcctacgc ggtagttgaa accgttctct ctcgag                              2496
```

<210> SEQ ID NO 43
<211> LENGTH: 793
<212> TYPE: PRT
<213> ORGANISM: Artificial Sequence
<220> FEATURE:
<223> OTHER INFORMATION: Synthetic Construct

<400> SEQUENCE: 43

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Ala Cys Val Gly Ala Ala Thr Val Arg Lys Glu Arg
        115                 120                 125

Asp Gly Ser Thr Val Ile Arg Ala Glu Gly Lys Asp Ala Ala Thr Gln
    130                 135                 140

Val Arg Val Glu Asn Gly Thr Cys Val Ile Leu Ala Thr Asp Met Gly
145                 150                 155                 160

Ser Trp Cys Asp Asp Ser Leu Ser Tyr Glu Cys Val Thr Ile Asp Gln
                165                 170                 175

Gly Glu Glu Pro Val Asp Val Asp Cys Phe Cys Arg Asn Val Asp Gly
            180                 185                 190

Val Tyr Leu Glu Tyr Gly Arg Cys Gly Lys Gln Glu Gly Ser Arg Thr
        195                 200                 205

Arg Arg Ser Val Leu Ile Pro Ser His Ala Gln Gly Glu Leu Thr Gly
    210                 215                 220

Arg Gly His Lys Trp Leu Glu Gly Asp Ser Leu Arg Thr His Leu Thr
225                 230                 235                 240

Arg Val Glu Gly Trp Val Trp Lys Asn Arg Leu Leu Ala Leu Ala Met
                245                 250                 255

Val Thr Val Val Trp Leu Thr Leu Glu Ser Val Val Thr Arg Val Ala
            260                 265                 270

Val Leu Val Val Leu Leu Cys Leu Ala Pro Val Tyr Ala Ser Arg Cys
        275                 280                 285

Thr His Leu Glu Asn Arg Asp Phe Val Thr Gly Thr Gln Gly Thr Thr
    290                 295                 300

Arg Val Thr Leu Val Leu Glu Leu Gly Gly Cys Val Thr Ile Thr Ala
305                 310                 315                 320

Glu Gly Lys Pro Ser Met Asp Val Trp Leu Asp Ala Ile Tyr Gln Glu
                325                 330                 335

Asn Pro Ala Gln Thr Arg Glu Tyr Cys Leu His Ala Lys Leu Ser Asp
            340                 345                 350
```

```
Thr Lys Val Ala Ala Arg Cys Pro Thr Met Gly Pro Ala Thr Leu Ala
        355                 360                 365

Glu Glu His Gln Gly Gly Thr Val Cys Lys Arg Asp Gln Ser Asp Arg
        370                 375                 380

Gly Trp Gly Asn His Cys Gly Leu Phe Gly Lys Gly Ser Ile Val Ala
385                 390                 395                 400

Cys Val Lys Ala Ala Cys Glu Ala Lys Lys Ala Thr Gly His Val
                    405                 410                 415

Tyr Asp Ala Asn Lys Ile Val Tyr Thr Val Lys Glu Pro His Thr Gly
                420                 425                 430

Asp Tyr Val Ala Ala Asn Glu Thr His Ser Gly Arg Lys Thr Ala Ser
                435                 440                 445

Phe Thr Val Ser Ser Glu Lys Thr Ile Leu Thr Met Gly Glu Tyr Gly
        450                 455                 460

Asp Val Ser Leu Leu Cys Arg Val Ala Ser Gly Val Asp Leu Ala Gln
465                 470                 475                 480

Thr Val Ile Leu Glu Leu Asp Lys Thr Val Glu His Leu Pro Thr Ala
                485                 490                 495

Trp Gln Val His Arg Asp Trp Phe Asn Asp Leu Ala Leu Pro Trp Lys
                500                 505                 510

His Glu Gly Ala Arg Asn Trp Asn Asn Ala Glu Arg Leu Val Glu Phe
        515                 520                 525

Gly Ala Pro His Ala Val Lys Met Asp Val Tyr Asn Leu Gly Asp Gln
        530                 535                 540

Thr Gly Val Leu Leu Lys Ala Leu Ala Gly Val Pro Val Ala His Ile
545                 550                 555                 560

Glu Gly Thr Lys Tyr His Leu Lys Ser Gly His Val Thr Cys Glu Val
                565                 570                 575

Gly Leu Glu Lys Leu Lys Met Lys Gly Leu Thr Tyr Thr Met Cys Asp
            580                 585                 590

Lys Thr Lys Phe Thr Trp Lys Arg Ala Pro Thr Asp Ser Gly His Asp
        595                 600                 605

Thr Val Val Met Glu Val Thr Phe Ser Gly Thr Lys Pro Cys Arg Ile
        610                 615                 620

Pro Val Arg Ala Val Ala His Gly Ser Pro Asp Val Asn Val Ala Met
625                 630                 635                 640

Leu Ile Thr Pro Asn Pro Thr Ile Glu Asn Asn Gly Gly Phe Ile
                645                 650                 655

Glu Met Gln Leu Pro Pro Gly Asp Asn Ile Ile Tyr Val Gly Glu Leu
                660                 665                 670

Ser Tyr Gln Trp Phe Gln Lys Gly Ser Ser Ile Gly Arg Val Phe Gln
        675                 680                 685

Lys Thr Lys Lys Gly Ile Glu Arg Leu Thr Val Ile Gly Glu His Ala
        690                 695                 700

Trp Asp Phe Gly Ser Ala Gly Gly Phe Leu Ser Ile Gly Lys Ala
705                 710                 715                 720

Leu His Thr Val Leu Gly Gly Ala Phe Asn Ser Ile Phe Gly Gly Val
                725                 730                 735

Gly Phe Leu Pro Lys Leu Leu Gly Val Ala Leu Ala Trp Leu Gly
            740                 745                 750

Leu Asn Met Arg Asn Pro Thr Met Ser Met Ser Phe Leu Leu Ala Gly
        755                 760                 765
```

| Val | Leu | Val | Leu | Ala | Met | Thr | Leu | Gly | Val | Gly | Ala | Asp | Gln | Gly | Cys |
|---|---|---|---|---|---|---|---|---|---|---|---|---|---|---|---|
| 770 | | | | | 775 | | | | | 780 | | | | | |

| Ala | Ile | Asn | Phe | Gly | Lys | Arg | Glu | Leu |
|---|---|---|---|---|---|---|---|---|
| 785 | | | | | 790 | | | |

<210> SEQ ID NO 44
<211> LENGTH: 2500
<212> TYPE: DNA
<213> ORGANISM: Artificial Sequence
<220> FEATURE:
<223> OTHER INFORMATION: Synthetic Construct

<400> SEQUENCE: 44

```
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa aacaaaaaac aaaacaaatt ggaaacagac ctggaccttc     240
aagaggtgtt caaggattta tctttttctt tttgttcaac attttgactg gaaaaaagat     300
cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aattttgggc atgctggctt gtgtcggagc     480
agctaccgtg cgaaaagaac gcgacggaag caccgtgata agggctgagg gtaaggatgc     540
ggctacgcag gtgagagtag agaatggcac ttgcgtaata ctcgcgactg atatgggatc     600
ctggtgtgac gatagcctca gttatgaatg cgtaacaata gaccagggcg aagaacctgt     660
ggacgttgac tgtttctgta gaaatgtgga tggcgtttat ctggagtacg ccgctgtgg     720
aaaacaggag ggctcacgaa ctcgaagatc tgtgctgatt ccaagtcacg cgcaaggaga     780
gttgaccggt agaggccaca agtggcttga aggggactca ttgaggaccc acctgactag     840
ggtggagggt tgggtttgga agaatcggtt gctcgcgctc gctatggtca ccgtcgtgtg     900
gctgacactg gagagtgtcg tgactcgggt tgctgtgttg gttgtcctcc tctgtttggc     960
cccagtgtac gcgtccaggt gtactcattt ggaaaaacaga gattttgtca ccggcaccca    1020
ggggacgact cgggtaaccc tggtgcttga actgggtggt tgcgttacta ttaccgctga    1080
gggcaaaccc tctatggatg tgtggctgga tgcaatctat caggagaatc ccgcacaaac    1140
cagggaatat tgccttcacg caaagctgtc cgatacaaag gtcgcggcta ggtgcccaac    1200
aatgggaccg gccaccctgg cggaggaaca tcagggaggg acagtgtgca acgggaccaa    1260
gagtgataga ggctggggta atcactgcgg cctgttcggc aaaggaagta ttgtcgcttg    1320
cgtcaaggca gcctgtgagg ccaaaaagaa ggcactggg cacgtctatg acgccaacaa    1380
gatcgtttat acagtgaaag tggaaccaca cacagggat tacgtggcgg ccaacgagac    1440
tcattccggt cgcaaaacgg ccagcttcac cgtgtcatcc gaaaagacca tcctcactat    1500
gggggagtat ggcgacgttt ctctgctctg ccgggtggct agcggagtcg acctggccca    1560
gacagtcatc ctggaactgg ataaaacagt tgagcatctg cctaccgctt ggcaggtgca    1620
cagggattgg tttaacgacc ttgccctgcc atggaaacat gaaggagcga gaaactggaa    1680
taatgcagag cgactcgtag aattcggtgc ccctcatgcc gtgaagatgg acgtctacaa    1740
tctgggtgat cagaccggcg ttctccttaa agctctcgct ggcgtaccag ttgcccacat    1800
cgaaggaacg aagtaccacc tgaagtcagg ccatgtaact tgcgaggtgg gcctggaaaa    1860
gttgaaaatg aaaggtctta cgtacacaat gtgtgacaag accaagttca catggaagag    1920
```

| ggcccccaca gatagcggcc acgatactgt ggtgatggag gtgacctttt ctggaacaaa | 1980 |
| accctgcaga atacccgtgc gggctgtagc tcacggatct cccgatgtca atgttgctat | 2040 |
| gctgattaca cctaaccta ccatcgagaa taacggtggt ggttttattg agatgcagct | 2100 |
| tccgccaggc gataacatca tctacgtggg cgaactctct taccagtggt ttcagaaagg | 2160 |
| gagttcaatt gggcgggtct tccaaaaaac gaagaaggga atcgaacgat tgacggttat | 2220 |
| cggcgagcac gcatgggatt ttggttccgc aggggattc ctgtcttcta ttggtaaggc | 2280 |
| actgcatacc gtgctggggg gcgcattcaa ttctattttc ggggcgtgg ggttcctgcc | 2340 |
| taaactcctg ctgggagtag ccctggcctg gttgggactg aatatgcgga atccgacgat | 2400 |
| gtccatgtca ttcctcttgg ccggcgtgct tgtactggcc atgacactgg gcgttggcgc | 2460 |
| cgatcaagga tgcgccatca actttggcaa gagagagctc | 2500 |

<210> SEQ ID NO 45
<211> LENGTH: 2500
<212> TYPE: DNA
<213> ORGANISM: Artificial Sequence
<220> FEATURE:
<223> OTHER INFORMATION: Synthetic Construct

<400> SEQUENCE: 45

| tcatttagga cacacgatta actccacgta accagacgtt tagctcaacg atccgttatt | 60 |
| tgtgtaaacc taattaaaat tagcaagcaa ctcgctaatc gtctcttgac tggtcttgta | 120 |
| cagaccagca tttcgagtcc cttttggga cccgcagtta taccatgctg ctcctcaagc | 180 |
| gaggaacagt ttgttttatt tgttttttg ttttgtttaa cctttgtctg gacctggaag | 240 |
| ttctccacaa gttcctaaat agaaaaagaa aaacaagttg taaaactgac cttttttcta | 300 |
| gtgtcgggtg gatttctcca acaccttta cgacctgggt tctgttccga accgacaaga | 360 |
| ttcctttcag ttctctcacc accggtcaaa ctactctcct aacaggagtt cctttgcggc | 420 |
| aagggtacta caagactgac acgttaagga ttaaaacccg tacgaccgaa cacagcctcg | 480 |
| tcgatggcac gcttttcttg cgctgccttc gtggcactat tcccgactcc cattcctacg | 540 |
| ccgatgcgtc cactctcatc tcttaccgtg aacgcattat gagcgctgac tataccctag | 600 |
| gaccacactg ctatcggagt caatacttac gcattgttat ctggtcccgc ttcttggaca | 660 |
| cctgcaactg acaaagacat ctttacacct accgcaaata gacctcatgc cggcgacacc | 720 |
| ttttgtcctc ccgagtgctt gagcttctag acacgactaa ggttcagtgc gcgttcctct | 780 |
| caactggcca tctccggtgt tcaccgaact tcccctgagt aactcctggg tggactgatc | 840 |
| ccacctccca acccaaacct tcttagccaa cgagcgcgag cgataccagt ggcagcacac | 900 |
| cgactgtgac ctctcacagc actgagccca acgacacaac caacaggagg agacaaaccg | 960 |
| gggtcacatg cgcaggtcca catgagtaaa ccttttgtct ctaaaacagt ggccgtgggt | 1020 |
| cccctgctga gcccattggg accacgaact tgacccacca acgcaatgat aatggcgact | 1080 |
| cccgtttggg agatacctac acaccgacct acgttagata gtcctcttag ggcgtgtttg | 1140 |
| gtcccttata acggaagtgc gtttcgacag gctatgtttc cagcgccgat ccacgggttg | 1200 |
| ttaccctggc cggtgggacc gcctccttgt agtccctcca tgtcacacgt ttgccctggt | 1260 |
| ctcactatct ccgaccccat tagtgacgcc ggacaagccg tttccttcat aacagcgaac | 1320 |
| gcagttccgt cggacactcc ggttttcctt ccgatgaccc gtgcagatac tgcggttgtt | 1380 |
| ctagcaaata tgtcactttc accttggtgt gtgtccccta atgcaccgcc ggttgctctg | 1440 |

```
agtaaggcca gcgttttgcc ggtcgaagtg gcacagtagg cttttctggt aggagtgata   1500
ccccctcata ccgctgcaaa gagacgagac ggcccaccga tcgcctcagc tggaccgggt   1560
ctgtcagtag gaccttgacc tattttgtca actcgtagac ggatggcgaa ccgtccacgt   1620
gtccctaacc aaattgctgg aacgggacgg tacctttgta cttcctcgct ctttgacctt   1680
attacgtctc gctgagcatc ttaagccacg gggagtacgg cacttctacc tgcagatgtt   1740
agacccacta gtctggccgc aagaggaatt tcgagagcga ccgcatggtc aacgggtgta   1800
gcttccttgc ttcatggtgg acttcagtcc ggtacattga acgctccacc cggacctctt   1860
caacttttac tttccagaat gcatgtgtta cacactgttc tggttcaagt gtaccttctc   1920
ccgggggtgt ctatcgccgg tgctatgaca ccactacctc cactggaaaa gaccttgttt   1980
tgggacgtct tatgggcacg cccgacatcg agtgcctaga gggctacagt tacaacgata   2040
cgactaatgt ggattgggat ggtagctctt attgccacca ccaaaataac tctacgtcga   2100
aggcggtccg ctattgtagt agatgcaccc gcttgagaga atggtcacca aagtctttcc   2160
ctcaagttaa cccgcccaga aggttttttg cttcttccct tagcttgcta actgccaata   2220
gccgctcgtg cgtaccctaa aaccaaggcg tcccctaag gacagaagat aaccattccg   2280
tgacgtatgg cacgaccccc cgcgtaagtt aagataaaag cccccgcacc ccaaggacgg   2340
atttgaggac gaccctcatc gggaccggac caaccctgac ttatacgcct taggctgcta   2400
caggtacagt aaggagaacc ggccgcacga acatgaccgg tactgtgacc cgcaaccgcg   2460
gctagttcct acgcggtagt tgaaaccgtt ctctctcgag                          2500
```

<210> SEQ ID NO 46
<211> LENGTH: 794
<212> TYPE: PRT
<213> ORGANISM: Artificial Sequence
<220> FEATURE:
<223> OTHER INFORMATION: Synthetic Construct

<400> SEQUENCE: 46

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Gly Met Thr Ile Ala Ala Thr Val Arg Glu Arg
        115                 120                 125

Asp Gly Ser Met Val Ile Arg Ala Glu Gly Arg Asp Ala Ala Thr Gln
    130                 135                 140

Val Arg Val Glu Asn Gly Thr Cys Val Ile Leu Ala Thr Asp Met Gly
145                 150                 155                 160

Ser Trp Cys Asp Asp Ser Leu Ala Tyr Glu Cys Val Thr Ile Asp Gln
                165                 170                 175
```

```
Gly Glu Glu Pro Val Asp Val Asp Cys Phe Cys Arg Gly Val Glu Lys
            180                 185                 190

Val Thr Leu Glu Tyr Gly Arg Cys Gly Arg Arg Glu Gly Ser Arg Ser
        195                 200                 205

Arg Arg Ser Val Leu Ile Pro Ser His Ala Gln Arg Asp Leu Thr Gly
    210                 215                 220

Arg Gly His Gln Trp Leu Glu Gly Glu Ala Val Lys Ala His Leu Thr
225                 230                 235                 240

Arg Val Glu Gly Trp Val Trp Lys Asn Lys Leu Phe Thr Leu Ser Leu
                245                 250                 255

Val Met Val Ala Trp Leu Met Val Asp Gly Leu Leu Pro Arg Ile Leu
        260                 265                 270

Ile Val Val Ala Leu Ala Leu Ala Pro Ala Tyr Ala Ser Arg Cys
    275                 280                 285

Thr His Leu Glu Asn Arg Asp Phe Val Thr Gly Val Gln Gly Thr Thr
    290                 295                 300

Arg Leu Thr Leu Val Leu Glu Leu Gly Gly Cys Val Thr Val Thr Ala
305                 310                 315                 320

Asp Gly Lys Pro Ser Leu Asp Val Trp Leu Asp Ser Ile Tyr Gln Glu
                325                 330                 335

Ser Pro Ala Gln Thr Arg Glu Tyr Cys Leu His Ala Lys Leu Thr Gly
        340                 345                 350

Thr Lys Val Ala Ala Arg Cys Pro Thr Met Gly Pro Ala Thr Leu Pro
    355                 360                 365

Glu Glu His Gln Ser Gly Thr Val Cys Lys Arg Asp Gln Ser Asp Arg
    370                 375                 380

Gly Trp Gly Asn His Cys Gly Leu Phe Gly Lys Gly Ser Ile Val Thr
385                 390                 395                 400

Cys Val Lys Val Thr Cys Glu Asp Lys Lys Ala Thr Gly His Val
                405                 410                 415

Tyr Asp Val Asn Lys Ile Thr Tyr Thr Ile Lys Val Glu Pro His Thr
                420                 425                 430

Gly Glu Phe Val Ala Ala Asn Glu Thr His Ser Gly Arg Lys Ser Ala
        435                 440                 445

Ser Phe Thr Val Ser Ser Glu Lys Thr Ile Leu Thr Leu Gly Asp Tyr
    450                 455                 460

Gly Asp Val Ser Leu Leu Cys Arg Val Ala Ser Gly Val Asp Leu Ala
465                 470                 475                 480

Gln Thr Val Val Leu Ala Leu Asp Lys Thr His Glu His Leu Pro Thr
                485                 490                 495

Ala Trp Gln Val His Arg Asp Trp Phe Asn Asp Leu Ala Leu Pro Trp
        500                 505                 510

Lys His Asp Gly Ala Glu Ala Trp Asn Glu Ala Gly Arg Leu Val Glu
    515                 520                 525

Phe Gly Thr Pro His Ala Val Lys Met Asp Val Phe Asn Leu Gly Asp
    530                 535                 540

Gln Thr Gly Val Leu Leu Lys Ser Leu Ala Gly Val Pro Val Ala Ser
545                 550                 555                 560

Ile Glu Gly Thr Lys Tyr His Leu Lys Ser Gly His Val Thr Cys Glu
                565                 570                 575

Val Gly Leu Glu Lys Leu Lys Met Lys Gly Leu Thr Tyr Thr Val Cys
        580                 585                 590

Asp Lys Thr Lys Phe Thr Trp Lys Arg Ala Pro Thr Asp Ser Gly His
```

```
              595                 600                 605
Asp Thr Val Val Met Glu Val Gly Phe Ser Gly Thr Arg Pro Cys Arg
    610                 615                 620

Ile Pro Val Arg Ala Val Ala His Gly Val Pro Glu Val Asn Val Ala
625                 630                 635                 640

Met Leu Ile Thr Pro Asn Pro Thr Met Glu Asn Asn Gly Gly Gly Phe
                645                 650                 655

Ile Glu Met Gln Leu Pro Pro Gly Asp Asn Ile Ile Tyr Val Gly Asp
                660                 665                 670

Leu Asp His Gln Trp Phe Gln Lys Gly Ser Ser Ile Gly Arg Val Leu
                675                 680                 685

Gln Lys Thr Arg Lys Gly Ile Glu Arg Leu Thr Val Leu Gly Glu His
                690                 695                 700

Ala Trp Asp Phe Gly Ser Val Gly Gly Val Met Thr Ser Ile Gly Arg
705                 710                 715                 720

Ala Met His Thr Val Leu Gly Gly Ala Phe Asn Thr Leu Leu Gly Gly
                725                 730                 735

Val Gly Phe Leu Pro Lys Ile Leu Leu Gly Val Ala Met Ala Trp Leu
                740                 745                 750

Gly Leu Asn Met Arg Asn Pro Thr Leu Ser Met Gly Phe Leu Leu Ser
                755                 760                 765

Gly Gly Leu Val Leu Ala Met Thr Leu Gly Val Gly Ala Asp Gln Gly
                770                 775                 780

Cys Ala Ile Asn Phe Gly Lys Arg Glu Leu
785                 790

<210> SEQ ID NO 47
<211> LENGTH: 2500
<212> TYPE: DNA
<213> ORGANISM: Artificial Sequence
<220> FEATURE:
<223> OTHER INFORMATION: Synthetic Construct

<400> SEQUENCE: 47
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa acaaaaaaac aaaacaaatt ggaaacagac ctggaccttc     240
aagaggtgtt caaggattta tcttttttctt tttgttcaac attttgactg gaaaaaagat     300
cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aattttgggc atgctgggga tgacgatcgc     480
agctactgtg cgaagggaga gagacggctc tatggtgatc agagccgaag gtagggacgc     540
tgcgacccag gtgagggtcg aaaatggcac ctgtgttatt ctggcgaccg acatgggctc     600
ctggtgtgat gattctctgg cttatgaatg tgttactatt gatcagggtg aagagcctgt     660
ggacgtggac tgtttctgta gaggcgtcga gaaagtgacc ctggaatatg acgatgtgg     720 ccggcgagaa ggctccagga gtcggagatc cgtgttgatc ccttcacatg cgcagcgcga     780
tctgacaggg agggtcacc agtggctcga aggcgaagca gtcaaggccc atctgactcg     840
cgttgaaggc tgggtgtgga aaacaaaact ctttaccctt agcctggtga tggtcgcgtg     900
gctgatggta gacggactcc ttccccgcat tctcattgtt gtggtggctc tcgcgctcgc     960
```

```
ccctgcatac gcgtccaggt gtacgcacct cgaaaatcga gatttcgtca caggcgtcca    1020
aggtactacc cggctcaccc tcgtgctgga gctgggaggc tgtgtcactg ttacagccga    1080
cggaaaacct agtctggatg tgtggctgga ctccatctat caggagagcc cggcacagac    1140
cagggagtac tgcctccacg ctaagctgac tgggacaaag gtagccgcaa gatgtcccac    1200 aatgggcct gccaccttgc ccgaggaaca ccaatccggt acggtatgca agcgagatca    1260
gtctgatcgc ggatggggga atcattgcgg cctcttcggt aaaggcagca ttgtcacttg    1320
cgtgaaggtg acatgcgagg acaagaagaa ggccacaggt catgtatatg atgtgaacaa    1380
aatcacatat accattaagg tagaaccaca tacaggggaa ttcgtggcag caaacgagac    1440
tcatagcgga cgaaagtccg cctccttcac cgtctcctcc gagaaaacaa tcctgaccct    1500
cggagactac ggcgacgtat ctttgctgtg cagggtggcc agcggcgtgg accttgctca    1560
gacagtcgtg ttggccctgg acaagacaca tgagcacttg ccaacagcct ggcaggtgca    1620
cagggactgg tttaacgacc tggcgctccc gtggaaacat gacggcgctg aagcatggaa    1680
tgaggcaggg agactggtgg aatttggaac cccacacgcc gtaaagatgg acgttttcaa    1740
tcttggtgac cagacagggg tgctcctgaa atcactggcg ggcgtgcctg tagccagcat    1800
cgagggcaca aagtatcacc tgaagtctgg gcatgtaacc tgcgaagtgg gcctggaaaa    1860
gctgaagatg aaaggactta cgtacactgt ttgtgataag accaagttta catggaagcg    1920
agccccaacg gattccggcc atgataccgt cgtgatggag gttggtttct ccggcaccag    1980
accatgtaga ataccagtga gagctgtcgc ccacggtgta cccgaggtaa acgtggccat    2040
gctgattaca ccgaatccca ctatggagaa caatggcgga gggttcatcg aaatgcagct    2100
gccgcctgga gacaacatca tttatgtcgg cgacctcgat catcaatggt tccagaaagg    2160
gtcttccatc ggccgcgtcc ttcagaagac acgaaaaggc attgaaagac ttacagtcct    2220
gggcgaacat gcctgggact tcgggtcagt tggcggggta atgacaagca taggcagagc    2280
tatgcacacc gttctcggtg gggcatttaa tactctgttg ggtggcgtgg gttttcttcc    2340
gaaaatcctg ctcggtgtcg caatggcctg gcttggactg aatatgcgca atcctacact    2400
gagtatgggg tttcttctgt caggaggcct ggtcctggca atgactctgg gagtgggcgc    2460
cgatcaagga tgcgccatca actttggcaa gagagagctc                          2500
```

<210> SEQ ID NO 48
<211> LENGTH: 2500
<212> TYPE: DNA
<213> ORGANISM: Artificial Sequence
<220> FEATURE:
<223> OTHER INFORMATION: Synthetic Construct

<400> SEQUENCE: 48

```
tcatttagga cacacgatta actccacgta accagacgtt tagctcaacg atccgttatt      60
tgtgtaaacc taattaaaat tagcaagcaa ctcgctaatc gtctcttgac tggtcttgta     120
cagaccagca tttcgagtcc ctttttggga cccgcagtta taccatgctg ctcctcaagc     180
gaggaacagt tgttttatt ttgttttttg ttttgtttaa cctttgtctg gacctggaag      240
ttctccacaa gttcctaaat agaaaaagaa aaacaagttg taaaactgac cttttttcta     300
gtgtcgggtg gatttctcca acaccttttta cgacctgggt tctgttccga accgacaaga    360
ttcctttcag ttctctcacc accggtcaaa ctactctcct aacaggagtt cctttgcggc     420
aagggtacta caagactgac acgttaagga ttaaaacccg tacgacccct actgctagcg     480
```

```
tcgatgacac gcttccctct ctctgccgag ataccactag tctcggcttc catccctgcg    540
acgctgggtc cactcccagc ttttaccgtg acacaataa gaccgctggc tgtacccgag     600
gaccacacta ctaagagacc gaatacttac acaatgataa ctagtcccac ttctcggaca    660
cctgcacctg acaaagacat ctccgcagct ctttcactgg gaccttatac ctgctacacc    720
ggccgctctt ccgaggtcct cagcctctag gcacaactag ggaagtgtac gcgtcgcgct    780
agactgtccc tccccagtgg tcaccgagct tccgcttcgt cagttccggg tagactgagc    840
gcaacttccg acccacacct ttttgtttga gaaatgggaa tcggaccact accagcgcac    900
cgactaccat ctgcctgagg aagggcgta agagtaacaa caccaccgag agcgcgagcg     960
gggacgtatg cgcaggtcca catgcgtgga gcttttagct ctaaagcagt gtccgcaggt   1020
tccatgatgg gccgagtggg agcacgacct cgaccctccg acacagtgac aatgtcggct   1080
gccttttgga tcagacctac acaccgacct gaggtagata gtcctctcgg gccgtgtctg   1140
gtccctcatg acggaggtgc gattcgactg accctgtttc catcggcgtt ctacagggtg   1200
ttaccccgga cggtggaacg ggctccttgt ggttaggcca tgccatacgt tcgctctagt   1260
cagactagcg cctacccct tagtaacgcc ggagaagcca tttccgtcgt aacagtgaac    1320
gcacttccac tgtacgctcc tgttcttctt ccggtgtcca gtacatatac tacacttgtt   1380
ttagtgtata tggtaattcc atcttggtgt atgtccccct aagcaccgtc gtttgctctg   1440
agtatcgcct gctttcaggc ggaggaagtg gcagaggagg ctcttttgtt aggactggga   1500
gcctctgatg ccgctgcata gaaacgacac gtcccaccgg tcgccgcacc tggaacgagt   1560
ctgtcagcac aaccgggacc tgttctgtgt actcgtgaac ggttgtcgga ccgtccacgt   1620
gtccctgacc aaattgctgg accgcgaggg cacctttgta ctgccgcgac ttcgtacctt   1680
actccgtccc tctgaccacc ttaaaccttg gggtgtgcgg catttctacc tgcaaaagtt   1740
agaaccactg gtctgtcccc acgaggactt tagtgaccgc ccgcacggac atcggtcgta   1800
gctcccgtgt ttcatagtgg acttcagacc cgtacattgg acgcttcacc cggaccttt    1860 cgacttctac tttcctgaat gcatgtgaca aacactattc tggttcaaat gtaccttcgc   1920
tcggggttgc ctaaggccgg tactatggca gcactacctc caaccaaaga ggccgtggtc   1980
tggtacatct tatggtcact ctcgacagcg ggtgccacat gggctccatt tgcaccggta   2040
cgactaatgt ggcttagggt gatacctctt gttaccgcct cccaagtagc tttacgtcga   2100
cggcggacct ctgttgtagt aaatacagcc gctggagcta gtagttacca aggtctttcc   2160
cagaaggtag ccggcgcagg aagtcttctg tgcttttccg taactttctg aatgtcagga   2220
cccgcttgta cggaccctga agcccagtca accgccccat tactgttcgt atccgtctcg   2280
atacgtgtgg caagagccac cccgtaaatt atgagacaac ccaccgcacc caaaagaagg   2340
cttttaggac gagccacagc gttaccggac cgaacctgac ttatacgcgt taggatgtga   2400 ctcataccc aaagaagaca gtcctccgga ccaggaccgt tactgagacc ctcacccgcg    2460
gctagttcct acgcggtagt tgaaaccgtt ctctctcgag                         2500
```

<210> SEQ ID NO 49
<211> LENGTH: 791
<212> TYPE: PRT
<213> ORGANISM: Artificial Sequence
<220> FEATURE:
<223> OTHER INFORMATION: Synthetic Construct

<400> SEQUENCE: 49

Met Ser Gly Arg Lys Ala Gln Gly Lys Thr Leu Gly Val Asn Met Val

```
  1               5                  10                 15
Arg Arg Gly Val Arg Ser Leu Ser Asn Lys Ile Lys Gln Lys Thr Lys
             20                  25                 30

Gln Ile Gly Asn Arg Pro Gly Gly Val Gln Gly Phe Ile Phe Phe Phe
             35                  40                 45

Leu Phe Asn Ile Leu Thr Gly Lys Lys Ile Thr Ala His Leu Lys Arg
 50                      55                 60

Leu Trp Lys Met Leu Asp Pro Arg Gln Gly Leu Ala Val Leu Arg Lys
 65                  70                  75                 80

Val Lys Arg Val Val Ala Ser Leu Met Arg Gly Leu Ser Ser Arg Lys
                 85                  90                 95

Arg Arg Ser His Asp Val Leu Thr Val Gln Phe Leu Ile Leu Gly Met
                100                 105                110

Leu Gly Met Thr Ile Ala Ala Thr Val Arg Lys Glu Arg Asp Gly Ser
             115                 120                 125

Thr Val Ile Arg Ala Glu Gly Lys Asp Ala Ala Thr Gln Val Arg Val
         130                 135                 140

Glu Asn Gly Thr Cys Val Ile Leu Ala Thr Asp Met Gly Ser Trp Cys
145                 150                 155                160

Asp Asp Ser Leu Ser Tyr Glu Cys Val Thr Ile Asp Gln Gly Glu Glu
                 165                 170                 175

Pro Val Asp Val Asp Cys Phe Cys Arg Asn Val Asp Gly Val Tyr Leu
             180                 185                 190

Glu Tyr Gly Arg Cys Gly Lys Gln Glu Gly Ser Arg Thr Arg Arg Ser
         195                 200                 205

Val Leu Ile Pro Ser His Ala Gln Gly Glu Leu Thr Gly Arg Gly His
 210                 215                 220

Lys Trp Leu Glu Gly Asp Ser Leu Arg Thr His Leu Thr Arg Val Glu
225                 230                 235                240

Gly Trp Val Trp Lys Asn Arg Leu Leu Ala Leu Ala Met Val Thr Val
                 245                 250                 255

Val Trp Leu Thr Leu Glu Ser Val Val Thr Arg Val Ala Val Leu Val
             260                 265                 270

Val Leu Leu Cys Leu Ala Pro Val Tyr Ala Ser Arg Cys Thr His Leu
         275                 280                 285

Glu Asn Arg Asp Phe Val Thr Gly Thr Gln Gly Thr Thr Arg Val Thr
         290                 295                 300

Leu Val Leu Glu Leu Gly Gly Cys Val Thr Ile Thr Ala Glu Gly Lys
305                 310                 315                320

Pro Ser Met Asp Val Trp Leu Asp Ala Ile Tyr Gln Glu Asn Pro Ala
                 325                 330                 335

Gln Thr Arg Glu Tyr Cys Leu His Ala Lys Leu Ser Asp Thr Lys Val
             340                 345                 350

Ala Ala Arg Cys Pro Thr Met Gly Pro Ala Thr Leu Ala Glu Glu His
         355                 360                 365

Gln Gly Gly Thr Val Cys Lys Arg Asp Gln Ser Asp Arg Gly Trp Gly
         370                 375                 380

Asn His Cys Gly Leu Phe Gly Lys Gly Ser Ile Val Ala Cys Val Lys
385                 390                 395                400

Ala Ala Cys Glu Ala Lys Lys Lys Ala Thr Gly His Val Tyr Asp Ala
                 405                 410                 415

Asn Lys Ile Val Tyr Thr Val Lys Val Glu Pro His Thr Gly Asp Tyr
             420                 425                 430
```

```
Val Ala Ala Asn Glu Thr His Ser Gly Arg Lys Thr Ala Ser Phe Thr
            435                 440                 445

Val Ser Ser Glu Lys Thr Ile Leu Thr Met Gly Glu Tyr Gly Asp Val
450                 455                 460

Ser Leu Leu Cys Arg Val Ala Ser Gly Val Asp Leu Ala Gln Thr Val
465                 470                 475                 480

Ile Leu Glu Leu Asp Lys Thr Val Glu His Leu Pro Thr Ala Trp Gln
                485                 490                 495

Val His Arg Asp Trp Phe Asn Asp Leu Ala Leu Pro Trp Lys His Glu
                500                 505                 510

Gly Ala Arg Asn Trp Asn Asn Ala Glu Arg Leu Val Glu Phe Gly Ala
                515                 520                 525

Pro His Ala Val Lys Met Asp Val Tyr Asn Leu Gly Asp Gln Thr Gly
                530                 535                 540

Val Leu Leu Lys Ala Leu Ala Gly Val Pro Val Ala His Ile Glu Gly
545                 550                 555                 560

Thr Lys Tyr His Leu Lys Ser Gly His Val Thr Cys Glu Val Gly Leu
                565                 570                 575

Glu Lys Leu Lys Met Lys Gly Leu Thr Tyr Thr Met Cys Asp Lys Thr
                580                 585                 590

Lys Phe Thr Trp Lys Arg Ala Pro Thr Asp Ser Gly His Asp Thr Val
                595                 600                 605

Val Met Glu Val Thr Phe Ser Gly Thr Lys Pro Cys Arg Ile Pro Val
                610                 615                 620

Arg Ala Val Ala His Gly Ser Pro Asp Val Asn Val Ala Met Leu Ile
625                 630                 635                 640

Thr Pro Asn Pro Thr Ile Glu Asn Asn Gly Gly Phe Ile Glu Met
                645                 650                 655

Gln Leu Pro Pro Gly Asp Asn Ile Ile Tyr Val Gly Glu Leu Ser Tyr
                660                 665                 670

Gln Trp Phe Gln Lys Gly Ser Ser Ile Gly Arg Val Phe Gln Lys Thr
                675                 680                 685

Lys Lys Gly Ile Glu Arg Leu Thr Val Ile Gly Glu His Ala Trp Asp
690                 695                 700

Phe Gly Ser Ala Gly Gly Phe Leu Ser Ser Ile Gly Lys Ala Leu His
705                 710                 715                 720

Thr Val Leu Gly Gly Ala Phe Asn Ser Ile Phe Gly Gly Val Gly Phe
                725                 730                 735

Leu Pro Lys Leu Leu Leu Gly Val Ala Leu Ala Trp Leu Gly Leu Asn
                740                 745                 750

Met Arg Asn Pro Thr Met Ser Met Ser Phe Leu Leu Ala Gly Val Leu
                755                 760                 765

Val Leu Ala Met Thr Leu Gly Val Gly Ala Asp Gln Gly Cys Ala Ile
770                 775                 780

Asn Phe Gly Lys Arg Glu Leu
785                 790
```

<210> SEQ ID NO 50
<211> LENGTH: 2491
<212> TYPE: DNA
<213> ORGANISM: Artificial Sequence
<220> FEATURE:
<223> OTHER INFORMATION: Synthetic Construct

<400> SEQUENCE: 50

```
agtaaatcct gtgtgctaat tgaggtgcat tggtctgcaa atcgagttgc taggcaataa    60
acacatttgg attaatttta atcgttcgtt gagcgattag cagagaactg accagaacat   120
gtctggtcgt aaagctcagg gaaaaaccct gggcgtcaat atggtacgac gaggagttcg   180
ctccttgtca aacaaaataa aacaaaaaac aaaacaaatt ggaaacagac ctggaggtgt   240
tcaaggattt atcttttttct ttttgttcaa cattttgact ggaaaaaaga tcacagccca   300
cctaaagagg ttgtggaaaa tgctggaccc aagacaaggc ttggctgttc taaggaaagt   360
caagagagtg gtggccagtt tgatgagagg attgtcctca aggaaacgcc gttcccatga   420
tgttctgact gtgcaattcc taattttggg catgctgggc atgacaatcg cagctacggt   480
tcgcaaggaa agagacggca gtacggtcat acgcgcggaa ggtaaggatg ccgctaccca   540
agtgagagtg gaaaatggta cctgcgtcat tctggccacc gacatgggct cttggtgtga   600
tgatagcctt tcttatgagt gcgtaaccat agatcaaggt gaggaacctg ttgacgttga   660
ttgcttctgc cgaaacgtgg atggggtgta tctcgaatat ggacggtgtg gtaaacaaga   720
aggaagcaga accagacgct cagtgcttat accctcccac gctcaaggag agctgaccgg   780
acggggacat aaatggttgg agggcgactc actccgaaca catttgaccc cgtcgaggg   840
ctgggtctgg aaaaatcggc tgttggccct cgctatggtg acagtcgttt ggctcacgct   900
ggagtctgtg gttactcgcg tggcagtgct ggtggtgctc ctctgtcttg ccctgtcta    960
cgcgtccagg tgtactcatt tggaaaacag agattttgtc accggcaccc aggggacgac  1020
tcgggtaacc ctggtgcttg aactgggtgg ttgcgttact attaccgctg agggcaaacc  1080
ctctatggat gtgtggctgg atgcaatcta tcaggagaat cccgcacaaa ccagggaata  1140
ttgccttcac gcaaagctgt ccgatacaaa ggtcgcggct aggtgcccaa caatgggacc  1200
ggccaccctg gcggaggaac atcagggagg tacagtgtgc aaacgggacc agagtgatag  1260
aggctggggt aatcactgcg gcctgttcgg caaaggaagt attgtcgctt gcgtcaaggc  1320
agcctgtgag gccaaaaaga aggctactgg gcacgtctat gacgccaaca agatcgttta  1380
tacagtgaaa gtggaaccac acacagggga ttacgtggcg ccaacgagac tcattccgg  1440
tcgcaaaacg gccagcttca ccgtgtcatc cgaaaagacc atcctcacta tggggagta   1500
tggcgacgtt tctctgctct gccgggtggc tagcggagtc gacctggccc agacagtcat  1560
cctgaactg gataaaacag ttgagcatct gcctaccgct tggcaggtgc acagggattg   1620
gtttaacgac cttgccctgc catggaaaca tgaaggagcg agaaactgga ataatgcaga  1680
gcgactcgta gaattcggtg cccctcatgc cgtgaagatg gacgtctaca atctgggtga  1740
tcagaccggc gttctcctta aagctctcgc tggcgtacca gttgcccaca tcgaaggaac  1800
gaagtaccac ctgaagtcag gccatgtaac ttgcgaggtg ggcctggaga agttgaaaat  1860
gaaaggtctt acgtacacaa tgtgtgacaa gaccaagttc acatggaaga gggcccccac  1920
agatagcgg cacgatactg tggtgatgga ggtgacttt tctggaacaa aaccctgcag  1980
aatacccgtg cgggctgtag ctcacggatc tcccgatgtc aatgttgcta tgctgattac  2040
acctaacccct accatcgaga ataacggtgg tggttttatt gagatgcagc ttccgccagg  2100
cgataacatc atctacgtgg gcgaactctc ttaccagtgg tttcagaaag ggagttcaat  2160
tgggcgggtc ttccaaaaaa cgaagaaggg aatcgaacga ttgacggtta tcggcgagca  2220
cgcatgggat tttggttccg caggggatt cctgtcttct attggtaagg cactgcatac  2280
cgtgctgggg ggcgcattca attctatttt cggggggcgtg gggttcctgc taaaactcct  2340
```

```
gctgggagta gccctggcct ggttgggact gaatatgcgg aatccgacga tgtccatgtc    2400
attcctcttg gccggcgtgc ttgtactggc catgacactg ggcgttggcg ccgatcaagg    2460
atgcgccatc aactttggca agagagagct c                                   2491

<210> SEQ ID NO 51
<211> LENGTH: 2491
<212> TYPE: DNA
<213> ORGANISM: Artificial Sequence
<220> FEATURE:
<223> OTHER INFORMATION: Synthetic Construct

<400> SEQUENCE: 51
tcatttagga cacacgatta actccacgta accagacgtt tagctcaacg atccgttatt      60
tgtgtaaacc taattaaaat tagcaagcaa ctcgctaatc gtctcttgac tggtcttgta     120
cagaccagca tttcgagtcc ttttttggga cccgcagtta taccatgctg ctcctcaagc     180
gaggaacagt tgttttatt ttgtttttg ttttgtttaa cctttgtctg gacctccaca       240
agttcctaaa tagaaaaaga aaacaagtt gtaaaactga cctttttct agtgtcgggt       300 ggatttctcc aacaccttt acgacctggg ttctgttccg aaccgacaag attcctttca     360
gttctctcac caccggtcaa actactctcc taacaggagt tcctttgcgg caagggtact     420
acaagactga cacgttaagg attaaaaccc gtacgacccg tactgttagc gtcgatgcca     480
agcgttcctt tctctgccgt catgccagta tgcgcgcctt ccattcctac ggcgatgggt     540
tcactctcac cttttaccat ggacgcagta agaccggtgg ctgtacccga gaaccacact     600
actatcggaa agaatactca cgcattggta tctagttcca ctccttggac aactgcaact     660
aacgaagacg gctttgcacc taccccacat agagcttata cctgccacac catttgttct     720
tccttcgtct tggtctgcga gtcacgaata tgggaggtg cgagttcctc tcgactggcc       780 tgccctgta tttaccaacc tcccgctgag tgaggcttgt gtaaactggg cgcagctccc       840
gacccagacc tttttagccg acaaccggga gcgataccac tgtcagcaaa ccagtgcga       900 cctcagacac caatgagcgc accgtcacga ccaccacgag gagacagaac ggggacagat     960
gcgcaggtcc acatgagtaa acctttttgtc tctaaaacag tggccgtggg tccctgctg    1020 agcccattgg gaccacgaac ttgacccacc aacgcaatga taatggcgac tcccgtttgg    1080
gagataccta cacaccgacc tacgttagat agtcctctta gggcgtgttt ggtcccttat    1140
aacggaagtg cgtttcgaca ggctatgttt ccagcgccga tccacgggtt gttaccctgg    1200
ccggtgggac cgcctccttg tagtccctcc atgtcacacg tttgccctgg tctcactatc    1260
tccgacccca ttagtgacgc cggacaagcc gtttccttca taacagcgaa cgcagttccg    1320
tcggacactc cggtttttct tccgatgacc cgtgcagata ctgcggttgt tctagcaaat    1380
atgtcacttt caccttggtg tgtgtcccct aatgcaccgc cggttgctct gagtaaggcc    1440
agcgttttgc cggtcgaagt ggcacagtag gctttctgg taggagtgat accccctcat    1500
accgctgcaa agagacgaga cggcccaccg atcgcctcag ctggaccggg tctgtcagta    1560
ggaccttgac ctatttttgtc aactcgtaga cggatggcga accgtccacg tgtccctaac    1620
caaattgctg gaacgggacg gtacctttgt acttcctcgc tctttgacct tattacgtct    1680
cgctgagcat cttaagccac ggggagtacg gcacttctac ctgcagatgt tagacccact    1740
agtctggccg caagaggaat tcgagagcg accgcatggt caacgggtgt agcttccttg    1800
cttcatggtg gacttcagtc cggtacattg aacgctccac ccggaccttct tcaactttta    1860 cttttccagaa tgcatgtgtt acacactgtt ctggttcaag tgtaccttct cccggggtg    1920
```

-continued

```
tctatcgccg gtgctatgac accactacct ccactggaaa agaccttgtt tgggacgtc    1980
ttatgggcac gcccgacatc gagtgcctag agggctacag ttacaacgat acgactaatg   2040
tggattggga tggtagctct tattgccacc accaaaataa ctctacgtcg aaggcggtcc   2100
gctattgtag tagatgcacc cgcttgagag aatggtcacc aaagtctttc cctcaagtta   2160
acccgcccag aaggtttttt gcttcttccc ttagcttgct aactgccaat agccgctcgt   2220
gcgtaccta aaaccaaggc gtcccccta ggacagaaga taaccattcc gtgacgtatg    2280
gcacgacccc ccgcgtaagt taagataaaa gcccccgcac cccaaggacg gatttgagga   2340
cgaccctcat cgggaccgga ccaaccctga cttatacgcc ttaggctgct acaggtacag   2400
taaggagaac cggccgcacg aacatgaccg gtactgtgac ccgcaaccgc ggctagttcc   2460
tacgcggtag ttgaaaccgt tctctctcga g                                  2491
```

<210> SEQ ID NO 52
<211> LENGTH: 730
<212> TYPE: PRT
<213> ORGANISM: Artificial Sequence
<220> FEATURE:
<223> OTHER INFORMATION: Synthetic Construct

<400> SEQUENCE: 52

```
Met Ser Lys Lys Pro Gly Gly Pro Gly Lys Ser Arg Ala Val Tyr Leu
1               5                   10                  15

Leu Lys Arg Gly Met Pro Arg Val Leu Ser Leu Ile Gly Leu Lys Arg
            20                  25                  30

Ser Ser Lys Gln Lys Lys Arg Gly Gly Thr Asp Trp Met Ser Trp Leu
        35                  40                  45

Leu Val Ile Gly Met Leu Gly Met Thr Ile Ala Ala Thr Val Arg Lys
    50                  55                  60

Glu Arg Asp Gly Ser Thr Val Ile Arg Ala Glu Gly Lys Asp Ala Ala
65                  70                  75                  80

Thr Gln Val Arg Val Glu Asn Gly Thr Cys Val Ile Leu Ala Thr Asp
                85                  90                  95

Met Gly Ser Trp Cys Asp Asp Ser Leu Ser Tyr Glu Cys Val Thr Ile
            100                 105                 110

Asp Gln Gly Glu Glu Pro Val Asp Val Asp Cys Phe Cys Arg Asn Val
        115                 120                 125

Asp Gly Val Tyr Leu Glu Tyr Gly Arg Cys Gly Lys Gln Glu Gly Ser
    130                 135                 140

Arg Thr Arg Arg Ser Val Leu Ile Pro Ser His Ala Gln Gly Glu Leu
145                 150                 155                 160

Thr Gly Arg Gly His Lys Trp Leu Glu Gly Asp Ser Leu Arg Thr His
                165                 170                 175

Leu Thr Arg Val Glu Gly Trp Val Trp Lys Asn Arg Leu Leu Ala Leu
            180                 185                 190

Ala Met Val Thr Val Val Trp Leu Thr Leu Glu Ser Val Val Thr Arg
        195                 200                 205

Val Ala Val Leu Val Val Leu Leu Cys Leu Ala Pro Val Tyr Ala Ser
    210                 215                 220

Arg Cys Thr His Leu Glu Asn Arg Asp Phe Val Thr Gly Thr Gln Gly
225                 230                 235                 240

Thr Thr Arg Val Thr Leu Val Leu Glu Leu Gly Gly Cys Val Thr Ile
                245                 250                 255
```

```
Thr Ala Glu Gly Lys Pro Ser Met Asp Val Trp Leu Asp Ala Ile Tyr
            260                 265                 270

Gln Glu Asn Pro Ala Gln Thr Arg Glu Tyr Cys Leu His Ala Lys Leu
        275                 280                 285

Ser Asp Thr Lys Val Ala Ala Arg Cys Pro Thr Met Gly Pro Ala Thr
    290                 295                 300

Leu Ala Glu Glu His Gln Gly Gly Thr Val Cys Lys Arg Asp Gln Ser
305                 310                 315                 320

Asp Arg Gly Trp Gly Asn His Cys Gly Leu Phe Gly Lys Gly Ser Ile
                325                 330                 335

Val Ala Cys Val Lys Ala Ala Cys Glu Ala Lys Lys Lys Ala Thr Gly
            340                 345                 350

His Val Tyr Asp Ala Asn Lys Ile Val Tyr Thr Val Lys Val Glu Pro
        355                 360                 365

His Thr Gly Asp Tyr Val Ala Ala Asn Glu Thr His Ser Gly Arg Lys
    370                 375                 380

Thr Ala Ser Phe Thr Val Ser Ser Glu Lys Thr Ile Leu Thr Met Gly
385                 390                 395                 400

Glu Tyr Gly Asp Val Ser Leu Leu Cys Arg Val Ala Ser Gly Val Asp
                405                 410                 415

Leu Ala Gln Thr Val Ile Leu Glu Leu Asp Lys Thr Val Glu His Leu
            420                 425                 430

Pro Thr Ala Trp Gln Val His Arg Asp Trp Phe Asn Asp Leu Ala Leu
        435                 440                 445

Pro Trp Lys His Glu Gly Ala Arg Asn Trp Asn Asn Ala Glu Arg Leu
    450                 455                 460

Val Glu Phe Gly Ala Pro His Ala Val Lys Met Asp Val Tyr Asn Leu
465                 470                 475                 480

Gly Asp Gln Thr Gly Val Leu Leu Lys Ala Leu Ala Gly Val Pro Val
                485                 490                 495

Ala His Ile Glu Gly Thr Lys Tyr His Leu Lys Ser Gly His Val Thr
            500                 505                 510

Cys Glu Val Gly Leu Glu Lys Leu Lys Met Lys Gly Leu Thr Tyr Thr
        515                 520                 525

Met Cys Asp Lys Thr Lys Phe Thr Trp Lys Arg Ala Pro Thr Asp Ser
    530                 535                 540

Gly His Asp Thr Val Val Met Glu Val Thr Phe Ser Gly Thr Lys Pro
545                 550                 555                 560

Cys Arg Ile Pro Val Arg Ala Val Ala His Gly Ser Pro Asp Val Asn
                565                 570                 575

Val Ala Met Leu Ile Thr Pro Asn Pro Thr Ile Glu Asn Asn Gly Gly
            580                 585                 590

Gly Phe Ile Glu Met Gln Leu Pro Pro Gly Asp Asn Ile Ile Tyr Val
        595                 600                 605

Gly Glu Leu Ser Tyr Gln Trp Phe Gln Lys Gly Ser Ser Ile Gly Arg
    610                 615                 620

Val Phe Gln Lys Thr Lys Lys Gly Ile Glu Arg Leu Thr Val Ile Gly
625                 630                 635                 640

Glu His Ala Trp Asp Phe Gly Ser Ala Gly Gly Phe Leu Ser Ser Ile
                645                 650                 655

Gly Lys Ala Leu His Thr Val Leu Gly Gly Ala Phe Asn Ser Ile Phe
            660                 665                 670

Gly Gly Val Gly Phe Leu Pro Lys Leu Leu Leu Gly Val Ala Leu Ala
```

```
                    675                 680                 685
Trp Leu Gly Leu Asn Met Arg Asn Pro Thr Met Ser Met Ser Phe Leu
        690                 695                 700

Leu Ala Gly Val Leu Val Leu Ala Met Thr Leu Gly Val Gly Ala Asp
705                 710                 715                 720

Thr Gly Cys Ala Ile Asp Ile Ser Arg Gln
                725                 730

<210> SEQ ID NO 53
<211> LENGTH: 2286
<212> TYPE: DNA
<213> ORGANISM: Artificial Sequence
<220> FEATURE:
<223> OTHER INFORMATION: Synthetic Construct

<400> SEQUENCE: 53
agtagttcgc ctgtgtgagc tgacaaactt agtagtgttt gtgaggatta acaacaatta       60
acacagtgcg agctgtttct tagcacgaag atctcgatgt ctaagaaacc aggagggccc      120
ggcaagagcc gggctgtcta tttgctaaaa cgcggaatgc ccgcgtgtt gtccttgatt      180 ggacttaagc ggagctccaa acaaaagaaa cgggggggaa cagactggat gagctggctg      240
ctcgtaatcg gcatgctggg catgacaatc gcagctacgg ttcgcaagga agagacggc      300 agtacggtca tacgcgcgga aggtaaggat gccgctaccc aagtgagagt ggaaaatggt      360
acctgcgtca ttctggccac cgacatgggc tcttggtgtg atgatagcct ttcttatgag      420
tgcgtaacca tagatcaagg tgaggaacct gttgacgttg attgcttctg ccgaaacgtg      480 gatgggtgt atctcgaata tggacggtgt ggtaaacaag aaggaagcag aaccagacgc      540
tcagtgctta taccctccca cgctcaagga gagctgaccg gacggggaca taaatggttg      600
gagggcgact cactccgaac acatttgacc cgcgtcgagg gctgggtctg gaaaaatcgg      660
ctgttggccc tcgctatggt gacagtcgtt tggctcacgc tggagtctgt ggttactcgc      720
gtggcagtgc tggtggtgct cctctgtctt gcccctgtct acgcgtccag gtgtactcat      780
ttggaaaaca gagattttgt caccggcacc caggggacga ctcgggtaac cctggtgctt      840
gaactgggtg gttgcgttac tattaccgct gagggcaaac cctctatgga tgtgtggctg      900
gatgcaatct atcaggagaa tcccgcacaa accagggaat attgccttca cgcaaagctg      960
tccgatacaa aggtcgcggc taggtgccca acaatggacc cggccaccct ggcggaggaa     1020
catcagggag gtacagtgtg caaacgggac cagagtgata gaggctgggg taatcactgc     1080
ggcctgttcg gcaaaggaag tattgtcgct tgcgtcaagg cagcctgtga ggccaaaaag     1140
aaggctactg gcacgtctca tgacgccaac aagatcgttt atacagtgaa agtggaacca     1200
cacacagggg attacgtggc ggccaacgag actcattccg gtcgcaaaac ggccagcttc     1260
accgtgtcat ccgaaaagac catcctcact atggggagt atggcgacgt ttctctgctc     1320 tgccggtgg ctagcggagt cgacctggcc cagacagtca tcctggaact ggataaaaca     1380
gttgagcatc tgcctaccgc ttggcaggtg cacagggatt ggtttaacga ccttgccctg     1440
ccatggaaac atgaaggagc gagaaactgg aataatgcag agcgactcgt agaattcggt     1500 gccccctcatg ccgtgaagat ggacgtctac aatctgggtg atcagaccgg cgttctcctt     1560
aaagctctcg ctggcgtacc agttgcccac atcgaaggaa cgaagtacca cctgaagtca     1620
ggccatgtaa cttgcgaggt gggcctggag aagttgaaaa tgaaggtct acgtacaca     1680 atgtgtgaca agaccaagtt cacatggaag agggcccca cagatagcgg ccacgatact     1740
```

-continued

| | |
|---|---|
| gtggtgatgg aggtgacctt ttctggaaca aaaccctgca gaataccegt geggectgta | 1800 |
| gctcacggat ctcccgatgt caatgttgct atgctgatta cacctaaccc taccatcgag | 1860 |
| aataacggtg gtggttttat tgagatgcag cttccgccag gcgataacat catctacgtg | 1920 |
| ggcgaactct cttaccagtg gtttcagaaa gggagttcaa ttgggcgggt cttccaaaaa | 1980 |
| acgaagaagg gaatcgaacg attgacggtt atcggcgagc acgcatggga ttttggttcc | 2040 |
| gcaggggat tcctgtcttc tattggtaag gcactgcata ccgtgctggg gggcgcattc | 2100 |
| aattctatttt tcggggcgt ggggttcctg cctaaactcc tgctgggagt agccctggcc | 2160 |
| tggttgggac tgaatatgcg gaatccgacg atgtccatgt cattcctctt ggccggcgtg | 2220 |
| cttgtactgg ccatgacact gggcgttggc gccgacactg ggtgtgccat agacatcagc | 2280 |
| cggcaa | 2286 |

<210> SEQ ID NO 54
<211> LENGTH: 2286
<212> TYPE: DNA
<213> ORGANISM: Artificial Sequence
<220> FEATURE:
<223> OTHER INFORMATION: Synthetic Construct

<400> SEQUENCE: 54

| | |
|---|---|
| tcatcaagcg gacacactcg actgtttgaa tcatcacaaa cactcctaat tgttgttaat | 60 |
| tgtgtcacgc tcgacaaaga atcgtgcttc tagagctaca gattctttgg tcctcccggg | 120 |
| ccgttctcgg cccgacagat aaacgatttt gcgccttacg gggcgcacaa caggaactaa | 180 |
| cctgaattcg cctcgaggtt tgtttctctt gccccccctt gtctgaccta ctcgaccgac | 240 |
| gagcattagc cgtacgaccc gtactgttag cgtcgatgcc aagcgttcct ttctctgccg | 300 |
| tcatgccagt atgcgcgcct tccattccta cggcgatggg ttcactctca ccttttacca | 360 |
| tggacgcagt aagaccggtg gctgtacccg agaaccacac tactatcgga agaatactc | 420 |
| acgcattggt atctagttcc actccttgga caactgcaac taacgaagac ggcttttgcac | 480 |
| ctaccccaca tagagcttat acctgccaca ccatttgttc ttccttcgtc ttggtctgcg | 540 |
| agtcacgaat atgggagggt gcgagttcct ctcgactggc ctgcccctgt atttaccaac | 600 |
| ctcccgctga gtgaggcttg tgtaaactgg gcgcagctcc cgacccagac cttttagcc | 660 |
| gacaaccggg agcgatacca ctgtcagcaa accgagtgcg acctcagaca ccaatgagcg | 720 |
| caccgtcacg accaccacga ggagacagaa cggggacaga tgcgcaggtc cacatgagta | 780 |
| aacctttgt ctctaaaaca gtggccgtgg gtccctgct gagcccattg ggaccacgaa | 840 |
| cttgacccac caacgcaatg ataatggcga ctcccgtttg ggagatacct acacaccgac | 900 |
| ctacgttaga tagtcctctt agggcgtgtt tggtccctta taacggaagt gcgtttcgac | 960 |
| aggctatgtt tccagcgccg atccacgggt tgttaccctg gccggtggga ccgcctcctt | 1020 |
| gtagtccctc catgtcacac gtttgccctg gtctcactat ctccgacccc attagtgacg | 1080 |
| ccggacaagc cgtttccttc ataacagcga acgcagttcc gtcggacact ccggttttc | 1140 |
| ttccgatgac ccgtgcagat actgcggttg ttctagcaaa tatgtcactt tcaccttggt | 1200 |
| gtgtgtcccc taatgcaccg ccggttgctc tgagtaaggc cagcgttttg ccggtcgaag | 1260 |
| tggcacagta ggcttttctg gtaggagtga tacccctca taccgctgca aagagacgag | 1320 |
| acggcccacc gatcgcctca gctggaccgg gtctgtcagt aggaccttga cctatttgt | 1380 |
| caactcgtag acgatggcg aaccgtccac gtgtccctaa ccaaattgct ggaacggac | 1440 |
| ggtacctttg tacttcctcg ctctttgacc ttattacgtc tcgctgagca tcttaagcca | 1500 |

-continued

```
cggggagtac ggcacttcta cctgcagatg ttagacccac tagtctggcc gcaagaggaa    1560
tttcgagagc gaccgcatgg tcaacgggtg tagcttcctt gcttcatggt ggacttcagt    1620
ccggtacatt gaacgctcca cccggacctc ttcaactttt actttccaga atgcatgtgt    1680
tacacactgt tctggttcaa gtgtaccttc tcccgggggt gtctatcgcc ggtgctatga    1740
caccactacc tccactggaa aagaccttgt tttgggacgt cttatgggca cgcccgacat    1800
cgagtgccta gagggctaca gttacaacga tacgactaat gtggattggg atggtagctc    1860
ttattgccac caccaaaata actctacgtc gaaggcggtc cgctattgta gtagatgcac    1920
ccgcttgaga gaatggtcac caaagtcttt ccctcaagtt aacccgccca gaaggttttt    1980
tgcttcttcc cttagcttgc taactgccaa tagccgctcg tgcgtaccct aaaaccaagg    2040
cgtcccccta aggacagaag ataaccattc cgtgacgtat ggcacgaccc cccgcgtaag    2100
ttaagataaa agcccccgca ccccaaggac ggatttgagg acgaccctca tcgggaccgg    2160
accaaccctg acttatacgc cttaggctgc tacaggtaca gtaaggagaa ccggccgcac    2220
gaacatgacc ggtactgtga cccgcaaccg cggctgtgac ccacacggta tctgtagtcg    2280
gccgtt                                                               2286
```

<210> SEQ ID NO 55
<211> LENGTH: 727
<212> TYPE: PRT
<213> ORGANISM: Artificial Sequence
<220> FEATURE:
<223> OTHER INFORMATION: Synthetic Construct

<400> SEQUENCE: 55

```
Met Ser Lys Lys Pro Gly Gly Pro Gly Lys Ser Arg Ala Val Tyr Leu
1               5                   10                  15

Leu Lys Arg Gly Met Pro Arg Val Leu Ser Leu Ile Gly Leu Lys Arg
            20                  25                  30

Ser Ser Lys Gln Lys Lys Arg Gly Gly Lys Thr Gly Ile Ala Val Met
        35                  40                  45

Ile Gly Met Leu Ala Cys Val Gly Ala Ala Thr Val Arg Lys Glu Arg
    50                  55                  60

Asp Gly Ser Thr Val Ile Arg Ala Glu Gly Lys Asp Ala Ala Thr Gln
65                  70                  75                  80

Val Arg Val Glu Asn Gly Thr Cys Val Ile Leu Ala Thr Asp Met Gly
                85                  90                  95

Ser Trp Cys Asp Asp Ser Leu Ser Tyr Glu Cys Val Thr Ile Asp Gln
            100                 105                 110

Gly Glu Glu Pro Val Asp Val Asp Cys Phe Cys Arg Asn Val Asp Gly
        115                 120                 125

Val Tyr Leu Glu Tyr Gly Arg Cys Gly Lys Gln Glu Gly Ser Arg Thr
    130                 135                 140

Arg Arg Ser Val Leu Ile Pro Ser His Ala Gln Gly Glu Leu Thr Gly
145                 150                 155                 160

Arg Gly His Lys Trp Leu Glu Gly Asp Ser Leu Arg Thr His Leu Thr
                165                 170                 175

Arg Val Glu Gly Trp Val Trp Lys Asn Arg Leu Leu Ala Leu Ala Met
            180                 185                 190

Val Thr Val Val Trp Leu Thr Leu Glu Ser Val Thr Arg Val Ala
        195                 200                 205

Val Leu Val Val Leu Leu Cys Leu Ala Pro Val Tyr Ala Ser Arg Cys
```

```
                210                 215                 220
Thr His Leu Glu Asn Arg Asp Phe Val Thr Gly Thr Gln Gly Thr Thr
225                 230                 235                 240

Arg Val Thr Leu Val Leu Glu Leu Gly Gly Cys Val Thr Ile Thr Ala
                245                 250                 255

Glu Gly Lys Pro Ser Met Asp Val Trp Leu Asp Ala Ile Tyr Gln Glu
                260                 265                 270

Asn Pro Ala Gln Thr Arg Glu Tyr Cys Leu His Ala Lys Leu Ser Asp
                275                 280                 285

Thr Lys Val Ala Ala Arg Cys Pro Thr Met Gly Pro Ala Thr Leu Ala
        290                 295                 300

Glu Glu His Gln Gly Gly Thr Val Cys Lys Arg Asp Gln Ser Asp Arg
305                 310                 315                 320

Gly Trp Gly Asn His Cys Gly Leu Phe Gly Lys Gly Ser Ile Val Ala
                325                 330                 335

Cys Val Lys Ala Ala Cys Glu Ala Lys Lys Lys Ala Thr Gly His Val
                340                 345                 350

Tyr Asp Ala Asn Lys Ile Val Tyr Thr Val Lys Val Glu Pro His Thr
        355                 360                 365

Gly Asp Tyr Val Ala Ala Asn Glu Thr His Ser Gly Arg Lys Thr Ala
        370                 375                 380

Ser Phe Thr Val Ser Ser Glu Lys Thr Ile Leu Thr Met Gly Glu Tyr
385                 390                 395                 400

Gly Asp Val Ser Leu Leu Cys Arg Val Ala Ser Gly Val Asp Leu Ala
                405                 410                 415

Gln Thr Val Ile Leu Glu Leu Asp Lys Thr Val Glu His Leu Pro Thr
                420                 425                 430

Ala Trp Gln Val His Arg Asp Trp Phe Asn Asp Leu Ala Leu Pro Trp
        435                 440                 445

Lys His Glu Gly Ala Arg Asn Trp Asn Asn Ala Glu Arg Leu Val Glu
        450                 455                 460

Phe Gly Ala Pro Ala Val Lys Met Asp Val Tyr Asn Leu Gly Asp Gln
465                 470                 475                 480

Thr Gly Val Leu Leu Lys Ala Leu Ala Gly Val Pro Val Ala His Ile
                485                 490                 495

Glu Gly Thr Lys Tyr His Leu Lys Ser Gly His Val Thr Cys Glu Val
                500                 505                 510

Gly Leu Glu Lys Leu Lys Met Lys Gly Leu Thr Tyr Thr Met Cys Asp
                515                 520                 525

Lys Thr Lys Phe Thr Trp Lys Arg Ala Pro Thr Asp Ser Gly His Asp
        530                 535                 540

Thr Val Val Met Glu Val Thr Phe Ser Gly Thr Lys Pro Cys Arg Ile
545                 550                 555                 560

Pro Val Arg Ala Val Ala His Gly Ser Pro Asp Val Asn Val Ala Met
                565                 570                 575

Leu Ile Thr Pro Asn Pro Thr Ile Glu Asn Asn Gly Gly Gly Phe Ile
                580                 585                 590

Glu Met Gln Leu Pro Pro Gly Asp Asn Ile Ile Tyr Val Gly Glu Leu
        595                 600                 605

Ser Tyr Gln Trp Phe Gln Lys Gly Ser Ser Ile Gly Arg Val Phe Gln
        610                 615                 620

Lys Thr Lys Lys Gly Ile Glu Arg Leu Thr Val Ile Gly Glu His Ala
625                 630                 635                 640
```

```
Trp Asp Phe Gly Ser Ala Gly Gly Phe Leu Ser Ile Gly Lys Ala
                645                 650                 655

Leu His Thr Val Leu Gly Gly Ala Phe Asn Ser Ile Phe Gly Gly Val
            660                 665                 670

Gly Phe Leu Pro Lys Leu Leu Leu Gly Val Ala Leu Ala Trp Leu Gly
        675                 680                 685

Leu Asn Met Arg Asn Pro Thr Met Ser Met Ser Phe Leu Leu Ala Gly
    690                 695                 700

Val Leu Val Leu Ala Met Thr Leu Gly Val Gly Ala Asp Thr Gly Cys
705                 710                 715                 720

Ala Ile Asp Ile Ser Arg Gln
                725

<210> SEQ ID NO 56
<211> LENGTH: 2280
<212> TYPE: DNA
<213> ORGANISM: Artificial Sequence
<220> FEATURE:
<223> OTHER INFORMATION: Synthetic Construct

<400> SEQUENCE: 56
```

| | | | | |
|---|---|---|---|---|
| agtagttcgc | ctgtgtgagc | tgacaaactt | agtagtgttt | gtgaggatta | acaacaatta | 60 |
| acacagtgcg | agctgtttct | tagcacgaag | atctcgatgt | ctaagaaacc | aggagggccc | 120 |
| ggcaagagcc | gggctgtcta | tttgctaaaa | cgcggaatgc | cccgcgtgtt | gtccttgatt | 180 |
| ggacttaagc | ggagctccaa | gcaaaagaaa | cgcgggggaa | agacaggcat | agctgtgatg | 240 |
| ataggcatgc | tggcttgtgt | cggagcagct | accgtgcgaa | agaacgcga | cggaagcacc | 300 |
| gtgataaggg | ctgagggtaa | ggatgcggct | acgcaggtga | gagtagagaa | tggcacttgc | 360 |
| gtaatactcg | cgactgatat | gggatcctgg | tgtgacgata | gcctcagtta | tgaatgcgta | 420 |
| acaatagacc | agggcgaaga | acctgtggac | gttgactgtt | tctgtagaaa | tgtggatggc | 480 |
| gtttatctgg | agtacggccg | ctgtggaaaa | caggagggct | cacgaactcg | aagatctgtg | 540 |
| ctgattccaa | gtcacgcgca | aggagagttg | accggtagag | gccacaagtg | gcttgaaggg | 600 |
| gactcattga | ggacccacct | gactagggtg | agggttggg | tttggaagaa | tcggttgctc | 660 |
| gcgctcgcta | tggtcaccgt | cgtgtggctg | acactggaga | gtgtcgtgac | tcgggttgct | 720 |
| gtgttggttg | tcctcctctg | tttggcccca | gtgtacgcgt | ccaggtgtac | tcatttggaa | 780 |
| aacagagatt | tgtcaccgg | cacccagggg | acgactcggg | taaccctggt | gcttgaactg | 840 |
| ggtggttgcg | ttactattac | cgctgagggc | aaaccctcta | tggatgtgtg | gctggatgca | 900 |
| atctatcagg | agaatcccgc | acaaaccagg | gaatattgcc | ttcacgcaaa | gctgtccgat | 960 |
| acaaaggtcg | cggctaggtg | cccaacaatg | ggaccggcca | ccctggcgga | ggaacatcag | 1020 |
| ggaggtacag | tgtgcaaacg | ggaccagagt | gatagaggct | ggggtaatca | ctgcggcctg | 1080 |
| ttcggcaaag | gaagtattgt | cgcttgcgtc | aaggcagcct | gtgaggccaa | aaagaaggct | 1140 |
| actggacacg | tctatgacgc | caacaagatc | gtttatacag | tgaaagtgga | accacacaca | 1200 |
| ggggattacg | tggcggccaa | cgagactcat | tccggtcgca | aaacggccag | cttcaccgtg | 1260 |
| tcatccgaaa | agaccatcct | cactatgggg | gagtatggcg | acgtttctct | gctctgccgg | 1320 |
| gtggctagcg | gagtcgacct | ggcccagaca | gtcatcctgg | aactggataa | acagttgag | 1380 |
| catctgccta | ccgcttggca | ggtgcacagg | gattggttta | acgaccttgc | cctgccatgg | 1440 |
| aaacatgaag | gagcgagaaa | ctggaataat | gcagagcgac | tcgtagaatt | cggtgcccct | 1500 |

| | |
|---|---|
| catgccgtga agatggacgt ctacaatctg ggtgatcaga ccggcgttct ccttaaagct | 1560 |
| ctcgctggcg taccagttgc ccacatcgaa ggaacgaagt accacctgaa gtcaggccat | 1620 |
| gtaacttgcg aggtgggcct ggagaagttg aaaatgaaag gtcttacgta cacaatgtgt | 1680 |
| gacaagacca agttcacatg gaagagggcc cccacagata gcggccacga tactgtggtg | 1740 |
| atggaggtga cctttctgg aacaaaaccc tgcagaatac ccgtgcgggc tgtagctcac | 1800 |
| ggatctcccg atgtcaatgt tgctatgctg attacaccta accctaccat cgagaataac | 1860 |
| ggtggtggtt ttattgagat gcagcttccg ccaggcgata acatcatcta cgtgggcgaa | 1920 |
| ctctcttacc agtggtttca gaagggagt tcaattgggc gggtcttcca aaaaacgaag | 1980 |
| aagggaatcg aacgattgac ggttatcggc gagcacgcat gggattttgg ttccgcaggg | 2040 |
| ggattcctgt cttctattgg taaggcactg cataccgtgc tggggggcgc attcaattct | 2100 |
| attttcgggg gcgtggggtt cctgcctaaa ctcctgctgg gagtagccct ggcctggttg | 2160 |
| ggactgaata tgcggaatcc gacgatgtcc atgtcattcc tcttggccgg cgtgcttgta | 2220 |
| ctggccatga cactgggcgt tggcgccgac actgggtgtg ccatagacat cagccggcaa | 2280 |

<210> SEQ ID NO 57
<211> LENGTH: 2280
<212> TYPE: DNA
<213> ORGANISM: Artificial Sequence
<220> FEATURE:
<223> OTHER INFORMATION: Synthetic Construct

<400> SEQUENCE: 57

| | |
|---|---|
| tcatcaagcg gacacactcg actgtttgaa tcatcacaaa cactcctaat tgttgttaat | 60 |
| tgtgtcacgc tcgacaaaga atcgtgcttc tagagctaca gattctttgg tcctcccggg | 120 |
| ccgttctcgg cccgacagat aaacgatttt gcgccttacg gggcgcacaa caggaactaa | 180 |
| cctgaattcg cctcgaggtt cgttttcttt gcgcccccctt tctgtccgta tcgacactac | 240 |
| tatccgtacg accgaacaca gcctcgtcga tggcacgctt tcttgcgct gccttcgtgg | 300 |
| cactattccc gactcccatt cctacgccga tgcgtccact ctcatctctt accgtgaacg | 360 |
| cattatgagc gctgactata ccctaggacc acactgctat cggagtcaat acttacgcat | 420 |
| tgttatctgg tcccgcttct tggacacctg caactgacaa agacatcttt acacctaccg | 480 |
| caaatagacc tcatgccggc gacaccttt gtcctcccga gtgcttgagc ttctagacac | 540 |
| gactaaggtt cagtgcgcgt tcctctcaac tggccatctc cggtgttcac cgaacttccc | 600 |
| ctgagtaact cctgggtgga ctgatcccac ctcccaaccc aaaccttctt agccaacgag | 660 |
| cgcgagcgat accagtggca gcacaccgac tgtgacctct cacagcactg agcccaacga | 720 |
| cacaaccaac aggaggagac aaaccgggt cacatgcgca ggtccacatg agtaaacctt | 780 |
| ttgtctctaa aacagtggcc gtgggtcccc tgctgagccc attgggacca cgaacttgac | 840 |
| ccaccaacgc aatgataatg gcgactcccg tttgggagat acctacacac cgacctacgt | 900 |
| tagatagtcc tcttagggcg tgtttggtcc cttataacgg aagtgcgttt cgacaggcta | 960 |
| tgtttccagc gccgatccac gggttgttac cctggccggt gggaccgcct ccttgtagtc | 1020 |
| cctccatgtc acacgtttgc cctggtctca ctatctccga ccccattagt gacgccggac | 1080 |
| aagccgtttc cttcataaca gcgaacgcag ttccgtcgga cactccggtt tttcttccga | 1140 |
| tgacccgtga agatactgcg gttgttctag caaatatgtc actttcacct tggtgtgtgt | 1200 |
| cccctaatgc accgccggtt gctctgagta aggccagcgt tttgccggtc gaagtggcac | 1260 |
| agtaggcttt tctggtagga gtgataccc ctcataccgc tgcaaagaga cgagacggcc | 1320 |

-continued

```
caccgatcgc ctcagctgga ccgggtctgt cagtaggacc ttgacctatt ttgtcaactc   1380
gtagacggat ggcgaaccgt ccacgtgtcc ctaaccaaat tgctggaacg ggacggtacc   1440
tttgtacttc ctcgctcttt gaccttatta cgtctcgctg agcatcttaa gccacgggga   1500
gtacggcact tctacctgca gatgttagac ccactagtct ggccgcaaga ggaatttcga   1560
gagcgaccgc atggtcaacg ggtgtagctt ccttgcttca tggtggactt cagtccggta   1620
cattgaacgc tccacccgga cctcttcaac ttttactttc cagaatgcat gtgttacaca   1680
ctgttctggt tcaagtgtac cttctcccgg gggtgtctat cgccggtgct atgacaccac   1740
tacctccact ggaaaagacc ttgttttggg acgtcttatg ggcacgcccg acatcgagtg   1800
cctagagggc tacagttaca acgatacgac taatgtggat tgggatggta gctcttattg   1860
ccaccaccaa ataactcta cgtcgaaggc ggtccgctat tgtagtagat gcacccgctt   1920
gagagaatgg tcaccaaagt ctttccctca agttaacccg cccagaaggt tttttgcttc   1980
ttcccttagc ttgctaactg ccaatagccg ctcgtgcgta ccctaaaacc aaggcgtccc   2040
cctaaggaca gaagataacc attccgtgac gtatggcacg accccccgcg taagttaaga   2100
taaaagcccc cgcaccccaa ggacggattt gaggacgacc ctcatcggga ccggaccaac   2160
cctgacttat acgccttagg ctgctacagg tacagtaagg agaaccggcc gcacgaacat   2220
gaccggtact gtgacccgca accgcggctg tgacccacac ggtatctgta gtcggccgtt   2280
```

<210> SEQ ID NO 58  
<211> LENGTH: 635  
<212> TYPE: PRT  
<213> ORGANISM: Artificial Seqeunce  
<220> FEATURE:  
<223> OTHER INFORMATION: Synthetic Construct

<400> SEQUENCE: 58

```
Met Ser Lys Lys Pro Gly Gly Pro Gly Lys Ser Arg Ala Val Tyr Leu
1               5                   10                  15

Leu Lys Arg Gly Met Pro Arg Val Leu Ser Leu Ile Gly Leu Lys Gln
            20                  25                  30

Lys Lys Arg Gly Gly Lys Thr Gly Ile Ala Val Ile Val Pro Gln Ala
        35                  40                  45

Leu Leu Phe Val Pro Leu Leu Val Phe Pro Leu Cys Phe Gly Lys Phe
    50                  55                  60

Pro Ile Tyr Thr Ile Pro Asp Lys Leu Gly Pro Trp Ser Pro Ile Asp
65                  70                  75                  80

Ile His His Leu Ser Cys Pro Asn Asn Leu Val Val Glu Asp Glu Gly
                85                  90                  95

Cys Thr Asn Leu Ser Gly Phe Ser Tyr Met Glu Leu Lys Val Gly Tyr
            100                 105                 110

Ile Ser Ala Ile Lys Met Asn Gly Phe Thr Cys Thr Gly Val Val Thr
        115                 120                 125

Glu Ala Glu Thr Tyr Thr Asn Phe Val Gly Tyr Val Thr Thr Thr Phe
    130                 135                 140

Lys Arg Lys His Phe Arg Pro Thr Pro Asp Ala Cys Arg Ala Ala Tyr
145                 150                 155                 160

Asn Trp Lys Met Ala Gly Asp Pro Arg Tyr Glu Glu Ser Leu His Asn
                165                 170                 175

Pro Tyr Pro Asp Tyr His Trp Leu Arg Thr Val Lys Thr Thr Lys Glu
            180                 185                 190
```

```
Ser Leu Val Ile Ile Ser Pro Ser Val Ala Asp Leu Asp Pro Tyr Asp
            195                 200                 205

Arg Ser Leu His Ser Arg Val Phe Pro Gly Gly Asn Cys Ser Gly Val
    210                 215                 220

Ala Val Ser Ser Thr Tyr Cys Ser Thr Asn His Asp Tyr Thr Ile Trp
225                 230                 235                 240

Met Pro Glu Asn Pro Arg Leu Gly Met Ser Cys Asp Ile Phe Thr Asn
                245                 250                 255

Ser Arg Gly Lys Arg Ala Ser Lys Gly Ser Glu Thr Cys Gly Phe Val
            260                 265                 270

Asp Glu Arg Gly Leu Tyr Lys Ser Leu Lys Gly Ala Cys Lys Leu Lys
        275                 280                 285

Leu Cys Gly Val Leu Gly Leu Arg Leu Met Asp Gly Thr Trp Val Ala
    290                 295                 300

Met Gln Thr Ser Asn Glu Thr Lys Trp Cys Pro Pro Gly Gln Leu Val
305                 310                 315                 320

Asn Leu His Asp Phe Arg Ser Asp Glu Ile Glu His Leu Val Val Glu
                325                 330                 335

Glu Leu Val Lys Lys Arg Glu Glu Cys Leu Asp Ala Leu Glu Ser Ile
            340                 345                 350

Met Thr Thr Lys Ser Val Ser Phe Arg Arg Leu Ser His Leu Arg Lys
        355                 360                 365

Leu Val Pro Gly Phe Gly Lys Ala Tyr Thr Ile Phe Asn Lys Thr Leu
    370                 375                 380

Met Glu Ala Asp Ala His Tyr Lys Ser Val Arg Thr Trp Asn Glu Ile
385                 390                 395                 400

Ile Pro Ser Lys Gly Cys Leu Arg Val Gly Gly Arg Cys His Pro His
                405                 410                 415

Val Asn Gly Val Phe Phe Asn Gly Ile Ile Leu Gly Pro Asp Gly Asn
            420                 425                 430

Val Leu Ile Pro Glu Met Gln Ser Ser Leu Leu Gln Gln His Met Glu
        435                 440                 445

Leu Leu Val Ser Ser Val Ile Pro Leu Met His Pro Leu Ala Asp Pro
    450                 455                 460

Ser Thr Val Phe Lys Asn Gly Asp Glu Ala Glu Asp Phe Val Glu Val
465                 470                 475                 480

His Leu Pro Asp Val His Glu Arg Ile Ser Gly Val Asp Leu Gly Leu
                485                 490                 495

Pro Asn Trp Gly Lys Tyr Val Leu Leu Ser Ala Gly Ala Leu Thr Ala
            500                 505                 510

Leu Met Leu Ile Ile Phe Leu Met Thr Cys Trp Arg Arg Val Asn Arg
        515                 520                 525

Ser Glu Pro Thr Gln His Asn Leu Arg Gly Thr Gly Arg Glu Val Ser
530                 535                 540

Val Thr Pro Gln Ser Gly Lys Ile Ile Ser Ser Trp Glu Ser Tyr Lys
545                 550                 555                 560

Ser Gly Gly Glu Thr Gly Leu Asn Phe Asp Leu Leu Lys Leu Ala Gly
                565                 570                 575

Asp Val Glu Ser Asn Pro Gly Pro Ala Arg Asp Arg Ser Ile Ala Leu
            580                 585                 590

Thr Phe Leu Ala Val Gly Gly Val Leu Leu Phe Leu Ser Val Asn Val
        595                 600                 605

His Ala Asp Thr Gly Cys Ala Ile Asp Ile Ser Arg Gln Glu Leu Arg
```

```
            610             615             620
Cys Gly Ser Gly Val Phe Ile His Asn Asp Val
625             630             635

<210> SEQ ID NO 59
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 59
```

| | | | | | |
|---|---|---|---|---|---|
| agtagttcgc | ctgtgtgagc | tgacaaactt | agtagtgttt | gtgaggatta | acaacaatta | 60 |
| acacagtgcg | agctgtttct | tagcacgaag | atctcgatgt | ctaagaaacc | aggagggccc | 120 |
| ggcaagagcc | gggctgtcta | tttgctaaaa | cgcggaatgc | cccgcgtgtt | gtccttgatt | 180 |
| ggacttaagc | aaaagaagcg | aggggcaag | actggtatag | ctgtgatcgt | tcctcaggct | 240 |
| cttttgtttg | tacccttgct | ggtatttccc | ctttgctttg | gtaaatttcc | tatctatacc | 300 |
| atccctgata | agctcgggcc | ttggagtccc | attgatattc | accatttgag | ctgcccaaac | 360 |
| aacctcgtcg | ttgaggatga | agggtgcact | aatctttctg | gattttccta | catggagttg | 420 |
| aaagtgggct | atatttcagc | cattaagatg | aacggcttta | cttgtacagg | agtcgtgacc | 480 |
| gaagccgaga | catatacaaa | tttcgtggga | tacgtcacca | ccaccttcaa | gagaaaacac | 540 |
| ttccgcccaa | cgcctgacgc | ttgtcgggcc | gcttacaact | ggaagatggc | aggagatcct | 600 |
| cgatatgaag | aatctctgca | caacccgtat | cctgattacc | attggctgcg | acagtcaag | 660 |
| actaccaagg | agagtctggt | cattatatca | ccaagcgtgg | ccgatcttga | tccttatgat | 720 |
| agatccctgc | acagtagggt | ttttcctggc | gggaattgta | gcggtgttgc | agtatcaagt | 780 |
| acctactgct | ccactaacca | cgactacact | atatggatgc | ctgagaaccc | tcgactcggt | 840 |
| atgagttgcg | acatttttac | gaactcacgg | ggcaagcggg | catctaaggg | gtctgaaaca | 900 |
| tgcgggtttg | ttgatgagcg | ggggttgtat | aaatctctta | aaggcgcctg | taagctgaaa | 960 |
| ctctgtggcg | tactgggggct | gcgcctgatg | gacggcacat | gggtggctat | gcagacaagc | 1020 |
| aatgaaacaa | gtggtgtcc | ccctggtcag | ctggttaatc | tgcacgactt | taggtctgac | 1080 |
| gaaatcgagc | accttgtggt | ggaggaactg | gtgaagaaac | gcgaagagtg | cctggacgca | 1140 |
| cttgagagta | ttatgaccac | caaatccgtt | tccttcagaa | gactgagcca | cctgcgaaag | 1200 |
| ctggtgccag | ggttcgggaa | ggcttatact | attttcaaca | agactcttat | ggaggcggat | 1260 |
| gcccattata | agtcagttag | gacttggaat | gagataattc | cctccaaagg | atgtctgaga | 1320 |
| gtcggtggga | gatgccaccc | ccatgtcaat | ggggtgttct | ttaacggaat | catcctggga | 1380 |
| cctgacggga | acgtgctgat | tcccgagatg | caatcttccc | ttctgcagca | acacatggaa | 1440 |
| ctcctggtgt | cttcagtgat | acccctgatg | cacccactgg | ccgacccccag | cactgtgttc | 1500 |
| aaaaatggcg | atgaggccga | agactttgtg | aagttcacc | tgcccgatgt | acacgaaagg | 1560 |
| atatctggag | tagacctggg | ccttcctaat | tggggtaagt | acgtgctcct | gagtgcgggt | 1620 |
| gccttgaccg | ctttgatgct | gatcattttt | ctgatgacct | gctggcggag | ggtgaatcgc | 1680 |
| tccgagccga | cacagcacaa | tctcagaggg | acaggccggg | aagtaagtgt | gactccgcaa | 1740 |
| tctggcaaga | ttattagtag | ttgggagagt | tacaagtctg | gaggagagac | tgggttgaat | 1800 |
| tttgatctgc | tcaaacttgc | aggcgatgta | gaatcaaatc | ctggaccgc | ccgggacagg | 1860 |
| tccatagctc | tcacgtttct | cgcagttgga | ggagttctgc | tcttcctctc | cgtgaacgtg | 1920 |

```
cacgctgaca ctgggtgtgc catagacatc agccggcaag agctgagatg tggaagtgga   1980
gtgttcatac acaatgatgt                                                2000

<210> SEQ ID NO 60
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 60
tcatcaagcg acacactcg actgtttgaa tcatcacaaa cactcctaat tgttgttaat     60
tgtgtcacgc tcgacaaaga atcgtgcttc tagagctaca gattctttgg tcctcccggg   120
ccgttctcgg cccgacagat aaacgatttt gcgccttacg gggcgcacaa caggaactaa   180
cctgaattcg ttttcttcgc tcccccgttc tgaccatatc gacactagca aggagtccga   240
gaaaacaaac atgggaacga ccataaaggg gaaacgaaac catttaaagg atagatatgg   300
tagggactat tcgagcccgg aacctcaggg taactataag tggtaaactc gacgggtttg   360
ttggagcagc aactcctact tcccacgtga ttagaaagac ctaaaaggat gtacctcaac   420
tttcacccga tataaagtcg gtaattctac ttgccgaaat gaacatgtcc tcagcactgg   480
cttcggctct gtatatgttt aaagcaccct atgcagtggt ggtggaagtt ctcttttgtg   540
aaggcgggtt gcggactgcg aacagcccgg cgaatgttga ccttctaccg tcctctagga   600
gctatacttc ttagagacgt gttgggcata ggactaatgg taaccgacgc tgtcagttc    660 tgatggttcc tctcagacca gtaatatagt ggttcgcacc ggctagaact aggaatacta   720
tctagggacg tgtcatccca aaaaggaccg cccttaacat cgccacaacg tcatagttca   780
tggatgacga ggtgattggt gctgatgtga tatacctacg gactcttggg agctgagcca   840
tactcaacgc tgtaaaaatg cttgagtgcc ccgttcgccc gtagattccc cagactttgt   900
acgcccaaac aactactcgc ccccaacata tttagagaat ttccgcggac attcgacttt   960
gagacaccgc atgaccccga cgcggactac ctgccgtgta cccaccgata cgtctgttcg  1020
ttactttgtt tcaccacagg gggaccagtc gaccaattag acgtgctgaa atccagactg  1080
ctttagctcg tggaacacca cctccttgac cacttctttg cgcttctcac ggacctgcgt  1140
gaactctcat aatactggtg gtttaggcaa aggaagtctt ctgactcggt ggacgctttc  1200
gaccacggtc ccaagccctt ccgaatatga taaaagttgt tctgagaata cctccgccta  1260
cgggtaatat tcagtcaatc ctgaacctta ctctattaag ggaggtttcc tacagactct  1320
cagccaccct ctacggtggg ggtacagtta ccccacaaga aattgccttt gtaggaccct  1380
ggactgccct tgcacgacta agggctctac gttagaaggg aagacgtcgt tgtgtacctt  1440
gaggaccaca gaagtcacta tggggactac gtgggtgacc ggctggggtc gtgacacaag  1500
tttttaccgc tactccggct tctgaaacac cttcaagtgg acgggctaca tgtgctttcc  1560
tatagacctc atctggaccc ggaaggatta acccccattca tgcacgagga ctcacgccca  1620
cggaactggc gaaactacga ctagtaaaaa gactactgga cgaccgcctc ccacttagcg  1680
aggctcggct gtgtcgtgtt agagtctccc tgtccggccc ttcattcaca ctgaggcgtt  1740
agaccgttct aataatcatc aaccctctca atgttcagac ctcctctctg acccaactta  1800
aaactagacg agtttgaacg tccgctacat cttagtttag gacctgggcg ggccctgtcc  1860
aggtatcgag agtgcaaaga gcgtcaacct cctcaagacg agaaggagag gcacttgcac  1920
gtgcgactgt gacccacacg gtatctgtag tcggccgttc tcgactctac accttcacct  1980
```
cacaagtatg tgttactaca                                                    2000

<210> SEQ ID NO 61
<211> LENGTH: 1303
<212> TYPE: PRT
<213> ORGANISM: Artificial Sequence
<220> FEATURE:
<223> OTHER INFORMATION: Synthetic Construct

<400> SEQUENCE: 61

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Gln
            20                  25                  30

Lys Lys Arg Gly Gly Lys Thr Gly Ile Ala Val Ile Val Pro Gln Ala
        35                  40                  45

Leu Leu Phe Val Pro Leu Leu Val Phe Pro Leu Cys Phe Gly Lys Phe
    50                  55                  60

Pro Ile Tyr Thr Ile Pro Asp Lys Leu Gly Pro Trp Ser Pro Ile Asp
65                  70                  75                  80

Ile His His Leu Ser Cys Pro Asn Asn Leu Val Val Glu Asp Glu Gly
                85                  90                  95

Cys Thr Asn Leu Ser Gly Phe Ser Tyr Met Glu Leu Lys Val Gly Tyr
            100                 105                 110

Ile Ser Ala Ile Lys Met Asn Gly Phe Thr Cys Thr Gly Val Val Thr
        115                 120                 125

Glu Ala Glu Thr Tyr Thr Asn Phe Val Gly Tyr Val Thr Thr Thr Phe
    130                 135                 140

Lys Arg Lys His Phe Arg Pro Thr Pro Asp Ala Cys Arg Ala Ala Tyr
145                 150                 155                 160

Asn Trp Lys Met Ala Gly Asp Pro Arg Tyr Glu Glu Ser Leu His Asn
                165                 170                 175

Pro Tyr Pro Asp Tyr His Trp Leu Arg Thr Val Lys Thr Thr Lys Glu
            180                 185                 190

Ser Leu Val Ile Ile Ser Pro Ser Val Ala Asp Leu Asp Pro Tyr Asp
        195                 200                 205

Arg Ser Leu His Ser Arg Val Phe Pro Gly Gly Asn Cys Ser Gly Val
    210                 215                 220

Ala Val Ser Ser Thr Tyr Cys Ser Thr Asn His Asp Tyr Thr Ile Trp
225                 230                 235                 240

Met Pro Glu Asn Pro Arg Leu Gly Met Ser Cys Asp Ile Phe Thr Asn
                245                 250                 255

Ser Arg Gly Lys Arg Ala Ser Lys Gly Ser Glu Thr Cys Gly Phe Val
            260                 265                 270

Asp Glu Arg Gly Leu Tyr Lys Ser Leu Lys Gly Ala Cys Lys Leu Lys
        275                 280                 285

Leu Cys Gly Val Leu Gly Leu Arg Leu Met Asp Gly Thr Trp Val Ala
    290                 295                 300

Met Gln Thr Ser Asn Glu Thr Lys Trp Cys Pro Pro Gly Gln Leu Val
305                 310                 315                 320

Asn Leu His Asp Phe Arg Ser Asp Glu Ile Glu His Leu Val Val Glu
                325                 330                 335

Glu Leu Val Lys Lys Arg Glu Glu Cys Leu Asp Ala Leu Glu Ser Ile
            340                 345                 350
```

-continued

```
Met Thr Thr Lys Ser Val Ser Phe Arg Arg Leu Ser His Leu Arg Lys
            355                 360                 365

Leu Val Pro Gly Phe Gly Lys Ala Tyr Thr Ile Phe Asn Lys Thr Leu
    370                 375                 380

Met Glu Ala Asp Ala His Tyr Lys Ser Val Arg Thr Trp Asn Glu Ile
385                 390                 395                 400

Ile Pro Ser Lys Gly Cys Leu Arg Val Gly Arg Cys His Pro His
                405                 410                 415

Val Asn Gly Val Phe Phe Asn Gly Ile Ile Leu Gly Pro Asp Gly Asn
            420                 425                 430

Val Leu Ile Pro Glu Met Gln Ser Ser Leu Leu Gln Gln His Met Glu
        435                 440                 445

Leu Leu Val Ser Ser Val Ile Pro Leu Met His Pro Leu Ala Asp Pro
    450                 455                 460

Ser Thr Val Phe Lys Asn Gly Asp Glu Ala Glu Asp Phe Val Glu Val
465                 470                 475                 480

His Leu Pro Asp Val His Glu Arg Ile Ser Gly Val Asp Leu Gly Leu
                485                 490                 495

Pro Asn Trp Gly Lys Tyr Val Leu Leu Ser Ala Gly Ala Leu Thr Ala
            500                 505                 510

Leu Met Leu Ile Ile Phe Leu Met Thr Cys Trp Arg Arg Val Asn Arg
        515                 520                 525

Ser Glu Pro Thr Gln His Asn Leu Arg Gly Thr Gly Arg Glu Val Ser
    530                 535                 540

Val Thr Pro Gln Ser Gly Lys Ile Ile Ser Ser Trp Glu Ser Tyr Lys
545                 550                 555                 560

Ser Gly Gly Glu Thr Gly Leu Asn Phe Asp Leu Leu Lys Leu Ala Gly
                565                 570                 575

Asp Val Glu Ser Asn Pro Gly Pro Gly Gly Lys Thr Gly Ile Ala Val
            580                 585                 590

Met Ile Gly Leu Ile Ala Cys Val Gly Ala Val Thr Leu Ser Asn Phe
        595                 600                 605

Gln Gly Lys Val Met Met Thr Val Asn Ala Thr Asp Val Thr Asp Val
    610                 615                 620

Ile Thr Ile Pro Thr Ala Ala Gly Lys Asn Leu Cys Ile Val Arg Ala
625                 630                 635                 640

Met Asp Val Gly Tyr Met Cys Asp Asp Thr Ile Thr Tyr Glu Cys Pro
                645                 650                 655

Val Leu Ser Ala Gly Asn Asp Pro Glu Asp Ile Asp Cys Trp Cys Thr
            660                 665                 670

Lys Ser Ala Val Tyr Val Arg Tyr Gly Arg Cys Thr Lys Thr Arg His
        675                 680                 685

Ser Arg Arg Ser Arg Arg Ser Leu Thr Val Gln Thr His Gly Glu Ser
    690                 695                 700

Thr Leu Ala Asn Lys Lys Gly Ala Trp Met Asp Ser Thr Lys Ala Thr
705                 710                 715                 720

Arg Tyr Leu Val Lys Thr Glu Ser Trp Ile Leu Arg Asn Pro Gly Tyr
                725                 730                 735

Ala Leu Val Ala Ala Val Ile Gly Trp Met Leu Gly Ser Asn Thr Met
            740                 745                 750

Gln Arg Val Val Phe Val Val Leu Leu Leu Leu Val Ala Pro Ala Tyr
        755                 760                 765

Ser Phe Asn Cys Leu Gly Met Ser Asn Arg Asp Phe Leu Glu Gly Val
```

```
                770             775             780
Ser Gly Ala Thr Trp Val Asp Leu Val Leu Glu Gly Asp Ser Cys Val
785             790             795             800

Thr Ile Met Ser Lys Asp Lys Pro Thr Ile Asp Val Lys Met Met Asn
            805             810             815

Met Glu Ala Ala Asn Leu Ala Glu Val Arg Ser Tyr Cys Tyr Leu Ala
            820             825             830

Thr Val Ser Asp Leu Ser Thr Lys Ala Ala Cys Pro Ala Met Gly Glu
            835             840             845

Ala His Asn Asp Lys Arg Ala Asp Pro Ala Phe Val Cys Arg Gln Gly
        850             855             860

Val Val Asp Arg Gly Trp Gly Asn Gly Cys Gly Leu Phe Gly Lys Gly
865             870             875             880

Ser Ile Asp Thr Cys Ala Lys Phe Ala Cys Ser Thr Lys Ala Ile Gly
            885             890             895

Arg Thr Ile Leu Lys Glu Asn Ile Lys Tyr Glu Val Ala Ile Phe Val
            900             905             910

His Gly Pro Thr Thr Val Glu Ser His Gly Asn Tyr Ser Thr Gln Val
        915             920             925

Gly Ala Thr Gln Ala Gly Arg Phe Ser Ile Thr Pro Ala Ala Pro Ser
930             935             940

Tyr Thr Leu Lys Leu Gly Glu Tyr Gly Glu Val Thr Val Asp Cys Glu
945             950             955             960

Pro Arg Ser Gly Ile Asp Thr Asn Ala Tyr Tyr Val Met Thr Val Gly
            965             970             975

Thr Lys Thr Phe Leu Val His Arg Glu Trp Phe Met Asp Leu Asn Leu
            980             985             990

Pro Trp Ser Ser Ala Gly Ser Thr Val Trp Arg Asn Arg Glu Thr Leu
            995             1000            1005

Met Glu Phe Glu Glu Pro His Ala Thr Lys Gln Ser Val Ile Ala
    1010            1015            1020

Leu Gly Ser Gln Glu Gly Ala Leu His Gln Ala Leu Ala Gly Ala
    1025            1030            1035

Ile Pro Val Glu Phe Ser Ser Asn Thr Val Lys Leu Thr Ser Gly
    1040            1045            1050

His Leu Lys Cys Arg Val Lys Met Glu Lys Leu Gln Leu Lys Gly
    1055            1060            1065

Thr Thr Tyr Gly Val Cys Ser Lys Ala Phe Lys Phe Leu Gly Thr
    1070            1075            1080

Pro Ala Asp Thr Gly His Gly Thr Val Val Leu Glu Leu Gln Tyr
    1085            1090            1095

Thr Gly Thr Asp Gly Pro Cys Lys Val Pro Ile Ser Ser Val Ala
    1100            1105            1110

Ser Leu Asn Asp Leu Thr Pro Val Gly Arg Leu Val Thr Val Asn
    1115            1120            1125

Pro Phe Val Ser Val Ala Thr Ala Asn Ala Lys Val Leu Ile Glu
    1130            1135            1140

Leu Glu Pro Pro Phe Gly Asp Ser Tyr Ile Val Val Gly Arg Gly
    1145            1150            1155

Glu Gln Gln Ile Asn His His Trp His Lys Ser Gly Ser Ser Ile
    1160            1165            1170

Gly Lys Ala Phe Thr Thr Thr Leu Lys Gly Ala Gln Arg Leu Ala
    1175            1180            1185
```

```
Ala Leu Gly Asp Thr Ala Trp Asp Phe Gly Ser Val Gly Gly Val
    1190            1195                1200

Phe Thr Ser Val Gly Lys Ala Val His Gln Val Phe Gly Gly Ala
    1205            1210                1215

Phe Arg Ser Leu Phe Gly Gly Met Ser Trp Ile Thr Gln Gly Leu
    1220            1225                1230

Leu Gly Ala Leu Leu Leu Trp Met Gly Ile Asn Ala Arg Asp Arg
    1235            1240                1245

Ser Ile Ala Leu Thr Phe Leu Ala Val Gly Gly Val Leu Leu Phe
    1250            1255                1260

Leu Ser Val Asn Val Glu His Ala Asp Thr Gly Cys Ala Ile Asp
    1265            1270                1275

Ile Ser Arg Gln Glu Leu Arg Cys Gly Ser Gly Val Phe Ile His
    1280            1285                1290

Asn Asp Val Glu Ala Trp Met Asp Arg Tyr
    1295            1300
```

<210> SEQ ID NO 62
<211> LENGTH: 4000
<212> TYPE: DNA
<213> ORGANISM: Artificial Sequence
<220> FEATURE:
<223> OTHER INFORMATION: Synthetic Construct

<400> SEQUENCE: 62

```
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcaa tatgctaaaa cgcggaatgc cccgcgtgtt gtccttgatt     180
ggacttaagc aaaagaagcg agggggcaag actggtatag ctgtgatcgt tcctcaggct     240
cttttgtttg taccttgct ggtatttccc ctttgctttg gtaaatttcc tatctatacc      300
atccctgata agctcgggcc ttggagtccc attgatattc ccatttgag ctgcccaaac      360
aacctcgtcg ttgaggatga agggtgcact aatctttctg gatttttccta catggagttg    420
aaagtgggct atatttcagc cattaagatg aacggcttta cttgtacagg agtcgtgacc    480
gaagccgaga catatacaaa tttcgtggga tacgtcacca ccaccttcaa gagaaaacac    540
ttccgcccaa cgcctgacgc ttgtcgggcc gcttacaact ggaagatggc aggagatcct    600
cgatatgaag aatctctgca caacccgtat cctgattacc attggctgcg acagtcaag    660
actaccaagg agagtctggt cattatatca ccaagcgtgg ccgatcttga tccttatgat    720
agatccctgc acagtagggt ttttcctggc gggaattgta gcggtgttgc agtatcaagt    780
acctactgct ccactaacca cgactacact atatggatgc ctgagaaccc tcgactcggt    840
atgagttgcg acatttttac gaactcacgg ggcaagcggg catctaaggg gtctgaaaca    900
tgcgggtttg ttgatgagcg ggggttgtat aaatctctta aggcgcctg taagctgaaa    960
ctctgtggcg tactggggct cgcctgatg gacggcacat gggtggctat gcagacaagc   1020
aatgaaacaa agtggtgtcc ccctggtcag ctggttaatc tgcacgactt taggtctgac   1080
gaaatcgagc accttgtggt ggaggaactg gtgaagaaac gcgaagagtg cctggacgca   1140
cttgagagta ttatgaccac caaatccgtt tccttcagaa gactgagcca cctgcgaaag   1200
ctggtgccag ggtccgggaa ggcttatact atttttcaaca agactcttat ggaggcggat   1260
gcccattata agtcagttag gacttggaat gagataattc cctccaaagg atgtctgaga   1320
```

```
gtcggtggga gatgccaccc ccatgtcaat ggggtgttct ttaacggaat catcctggga   1380
cctgacggga acgtgctgat tcccgagatg caatcttccc ttctgcagca acacatggaa   1440
ctcctggtgt cttcagtgat accoctgatg cacccactgg ccgaccccag cactgtgttc   1500
aaaaatggcg atgaggccga agactttgtg aagttcacc tgcccgatgt acacgaaagg   1560
atatctggag tagacctggg ccttcctaat tggggtaagt acgtgctcct gagtgcgggt   1620
gccttgaccg cttttgatgct gatcattttt ctgatgacct gctggcggag ggtgaatcgc   1680
tccgagccga cacagcacaa tctcagaggg acaggccggg aagtaagtgt gactccgcaa   1740
tctggcaaga ttattagtag ttgggagagt tacaagtctg gaggagagac tgggttgaat   1800
tttgatctgc tcaaacttgc aggcgatgta gaatcaaatc ctggaccegg aggaaagacc   1860 ggtattgcag tcatgattgg cctgatcgcc tgcgtaggag cagttaccct ctctaacttc   1920
caagggaagg tgatgatgac ggtaaatgct actgacgtca cagatgtcat cacgattcca   1980
acagctgctg gaaagaacct atgcattgtc agagcaatgg atgtgggata catgtgcgat   2040
gatactatca cttatgaatg cccagtgctg tcggctggta atgatccaga agacatcgac   2100
tgttggtgca caaagtcagc agtctacgtc aggtatggaa gatgcaccaa gacacgccac   2160
tcaagacgca gtcggaggtc actgacagtg cagacacacg gagaaagcac tctagcgaac   2220
aagaaggggg cttggatgga cagcaccaag ccacaaggt atttggtaaa acagaatca   2280 tggatcttga gaaccctgg atatgccctg gtggcagccg tcattggttg gatgcttggg   2340
agcaacacca tgcagagagt tgtgtttgtc gtgctattgc ttttggtggc cccagcttac   2400
agctttaact gccttggaat gagcaacaga gacttcttgg aaggagtgtc tggagcaaca   2460
tgggtggatt tggttctcga aggcgacagc tgcgtgacta tcatgtctaa ggacaagcct   2520
accatcgatg tgaagatgat gaatatggag gcggccaacc tggcagaggt ccgcagttat   2580
tgctatttgg ctaccgtcag cgatctctcc accaaagctg cgtgcccggc catgggagaa   2640
gctcacaatg acaaacgtgc tgacccagct tttgtgtgca gacaaggagt ggtggacagg   2700
ggctggggca acggctgcgg actatttggc aaaggaagca ttgacacatg cgccaaattt   2760
gcctgctcta ccaaggcaat aggaagaacc attttgaaag agaatatcaa gtacgaagtg   2820 gccattttg tccatggacc aactactgtg gagtcgcacg gaaactactc cacacaggtt   2880
ggagccactc aggcagggag attcagcatc actcctgcgg cgccttcata cactactaaag   2940 cttggagaat atggagaggt gacagtggac tgtgaaccac ggtcagggat tgacaccaat   3000
gcatactacg tgatgactgt tggaacaaag acgttcttgg tccatcgtga gtggttcatg   3060
gacctcaacc tcccttggag cagtgctgga agtactgtgt ggaggaacag agagacgtta   3120
atggagtttg aggaaccaca cgccacgaag cagtctgtga tagcattggg ctcacaagag   3180
ggagctctgc atcaagcttt ggctggagcc attcctgtgg aattttcaag caacactgtc   3240
aagttgacgt cgggtcattt gaagtgtaga gtgaagatgg aaaaattgca gttgaaggga   3300
acaacctatg gcgtctgttc aaaggctttc aagtttcttg ggactcccgc agacacaggt   3360
cacggcactg tggtgttgga attgcagtac actggcacgg atggaccttg caaagttcct   3420
atctcgtcag tggcttcatt gaacgaccta acgccagtgg gcagattggt cactgtcaac   3480
ccttttgttt cagtggccac ggccaacgct aaggtcctga ttgaattgga accacccttt   3540
ggagactcat acatagtggt gggcagagga gaacaacaga tcaatcacca ctggcacaag   3600
tctgaagcca gcattggcaa agcctttaca accacctca aaggagcgca gagactagcc   3660
gctctaggag acacagcttg ggactttgga tcagttggag gggtgttcac ctcagttggg   3720
```

```
aaggctgtcc atcaagtgtt cggaggagca ttccgctcac tgttcggagg catgtcctgg   3780
ataacgcaag gattgctggg ggctctcctg ttgtggatgg gcatcaatgc tcgtgacagg   3840
tccatagctc tcacgtttct cgcagttgga ggagttctgc tcttcctctc cgtgaacgtg   3900
cacgctgaca ctgggtgtgc catagacatc agccggcaag agctgagatg tggaagtgga   3960
gtgttcatac acaatgatgt ggaggcttgg atggaccggt                         4000

<210> SEQ ID NO 63
<211> LENGTH: 4000
<212> TYPE: DNA
<213> ORGANISM: Artificial Sequence
<220> FEATURE:
<223> OTHER INFORMATION: Synthetic Construct

<400> SEQUENCE: 63
tcatcaagcg gacacactcg actgtttgaa tcatcacaaa cactcctaat tgttgttaat     60
tgtgtcacgc tcgacaaaga atcgtgcttc tagagctaca gattctttgg tcctcccggg    120
ccgttctcgg cccgacagtt atacgatttt gcgccttacg gggcgcacaa caggaactaa    180
cctgaattcg tttctcttcgc tcccccgttc tgaccatatc gacactagca aggagtccga    240
gaaaacaaac atgggaacga ccataaaggg gaaacgaaac catttaaagg atagatatgg    300
tagggactat tcgagcccgg aacctcaggg taactataag tggtaaactc gacgggtttg    360
ttggagcagc aactcctact tcccacgtga ttagaaagac ctaaaaggat gtacctcaac    420
tttcacccga tataaagtcg gtaattctac ttgccgaaat gaacatgtcc tcagcactgg    480
cttcggctct gtatatgttt aaagcaccct atgcagtggt ggtggaagtt ctcttttgtg    540
aaggcgggtt gcggactgcg aacagcccgg cgaatgttga ccttctaccg tcctctagga    600
gctatacttc ttagagacgt gttgggcata ggactaatgg taaccgacgc ctgtcagttc    660
tgatggttcc tctcagacca gtaatatagt ggttcgcacc ggctagaact aggaatacta    720
tctagggacg tgtcatccca aaaaggaccg cccttaacat cgccacaacg tcatagttca    780
tggatgacga ggtgattggt gctgatgtga tatacctacg gactcttggg agctgagcca    840
tactcaacgc tgtaaaaatg cttgagtgcc ccgttcgccc gtagattccc cagactttgt    900
acgcccaaac aactactcgc ccccaacata tttagagaat ttccgcggac attcgacttt    960
gagacaccgc atgaccccga cgcggactac ctgccgtgta cccaccgata cgtctgttcg   1020
ttactttgtt tcaccacagg gggaccagtc gaccaattag acgtgctgaa atccagactg   1080
ctttagctcg tggaacacca cctccttgac cacttctttg cgcttctcac ggacctgcgt   1140
gaactctcat aatactggtg gtttaggcaa aggaagtctt ctgactcggt ggacgctttc   1200
gaccacggtc ccaagccctt ccgaatatga taaagttgt tctgagaata cctccgccta   1260
cgggtaatat tcagtcaatc ctgaacctta ctctattaag ggaggtttcc tacagactct   1320
cagccaccct ctacggtggg ggtacagtta ccccacaaga aattgcctta gtaggaccct   1380
ggactgccct tgcacgacta agggctctac gttagaaggg aagacgtcgt tgtgtacctt   1440
gaggaccaca gaagtcacta tggggactac gtgggtgacc ggctggggtc gtgacacaag   1500
tttttaccgc tactccggct tctgaaacac cttcaagtgg acgggctaca tgtgctttcc   1560
tatagacctc atctggaccc ggaaggatta accccattca tgcacgagga ctcacgccca   1620
cggaactggc gaaactacga ctagtaaaaa gactactgga cgaccgcctc ccacttagcg   1680
aggctcggct gtgtcgtgtt agagtctccc tgtccggccc ttcattcaca ctgaggcgtt   1740
```

```
agaccgttct aataatcatc aaccctctca atgttcagac ctcctctctg acccaactta    1800
aaactagacg agtttgaacg tccgctacat cttagtttag gacctgggcc tcctttctgg    1860
ccataacgtc agtactaacc ggactagcgg acgcatcctc gtcaatggga gagattgaag    1920
gttcccttcc actactactg ccatttacga tgactgcagt gtctacagta gtgctaaggt    1980
tgtcgacgac ctttcttgga tacgtaacag tctcgttacc tacaccctat gtacacgcta    2040
ctatgatagt gaatacttac gggtcacgac agccgaccat tactaggtct tctgtagctg    2100
acaaccacgt gtttcagtcg tcagatgcag tccatacctt ctacgtggtt ctgtgcggtg    2160
agttctgcgt cagcctccag tgactgtcac gtctgtgtgc ctctttcgtg agatcgcttg    2220
ttcttccccc gaacctacct gtcgtggttc cggtgttcca taaaccattt ttgtcttagt    2280
acctagaact ccttgggacc tatacgggac caccgtcggc agtaaccaac ctacgaaccc    2340
tcgttgtggt acgtctctca acacaaacag cacgataacg aaaaccaccg gggtcgaatg    2400
tcgaaattga cggaacctta ctcgttgtct ctgaagaacc ttcctcacag acctcgttgt    2460
acccacctaa accaagagct tccgctgtcg acgcactgat agtacagatt cctgttcgga    2520
tggtagctac acttctacta cttatacctc cgccggttgg accgtctcca ggcgtcaata    2580
acgataaacc gatggcagtc gctagagagg tggtttcgac gcacgggccg gtaccctctt    2640
cgagtgttac tgtttgcacg actgggtcga aaacacacgt ctgttcctca ccacctgtcc    2700 ccgacccgt tgccgacgcc tgataaaccg tttccttcgt aactgtgtac gcggtttaaa    2760
cggacgagat ggttccgtta tccttcttgg taaaactttc tcttatagtt catgcttcac    2820
cggtaaaaac aggtacctgg ttgatgacac ctcagcgtgc ctttgatgag gtgtgtccaa    2880
cctcggtgag tccgtccctc taagtcgtag tgaggacgcc gcggaagtat gtgtgatttc    2940
gaacctctta tacctctcca ctgtcacctg acacttggtg ccagtcccta actgtggtta    3000
cgtatgatgc actactgaca accttgtttc tgcaagaacc aggtagcact caccaagtac    3060
ctggagttgg agggaacctc gtcacgacct tcatgacaca cctccttgtc tctctgcaat    3120
tacctcaaac tccttggtgt gcggtgcttc gtcagacact atcgtaaccc gagtgttctc    3180
cctcgagacg tagttcgaaa ccgacctcgg taaggacacc ttaaaagttc gttgtgacag    3240
ttcaactgca gcccagtaaa cttcacatct cacttctacc tttttaacgt caacttccct    3300
tgttggatac cgcagacaag tttccgaaag ttcaaagaac cctgagggcg tctgtgtcca    3360
gtgccgtgac accacaacct taacgtcatg tgaccgtgcc tacctggaac gtttcaagga    3420
tagagcagtc accgaagtaa cttgctggat tgccggtcacc cgtctaacca gtgacagttg    3480
ggaaaacaaa gtcaccggtg ccggttgcga ttccaggact aacttaacct tggtgggaaa    3540
cctctgagta tgtatcacca cccgtctcct cttgttgtct agttagtggt gaccgtgttc    3600
agaccttcgt cgtaaccgtt tcggaaatgt tggtgggagt ttcctcgcgt ctctgatcgg    3660
cgagatcctc tgtgtcgaac cctgaaacct agtcaacctc cccacaagtg gagtcaaccc    3720
ttccgacagg tagttcacaa gcctcctcgt aaggcgagtg acaagcctcc gtacaggacc    3780
tattgcgttc ctaacgaccc ccgagaggac aacacctacc cgtagttacg agcactgtcc    3840
aggtatcgag agtgcaaaga gcgtcaacct cctcaagacg agaaggagag gcacttgcac    3900
gtgcgactgt gacccacacg gtatctgtag tcggccgttc tcgactctac accttcacct    3960
cacaagtatg tgttactaca cctccgaacc tacctggcca                          4000
```

<210> SEQ ID NO 64
<211> LENGTH: 702

```
<212> TYPE: PRT
<213> ORGANISM: Artificial Sequence
<220> FEATURE:
<223> OTHER INFORMATION: Synthetic Construct

<400> SEQUENCE: 64
```

| | | | | | | | | | | | | | | |
|---|---|---|---|---|---|---|---|---|---|---|---|---|---|---|
| Met | Ser | Lys | Lys | Pro | Gly | Gly | Pro | Gly | Lys | Ser | Arg | Ala | Val | Tyr | Leu |
| 1 | | | | 5 | | | | | 10 | | | | | 15 | |
| Leu | Lys | Arg | Gly | Met | Pro | Arg | Val | Leu | Ser | Leu | Ile | Gly | Leu | Lys | Arg |
| | | | 20 | | | | | 25 | | | | | 30 | | |
| Ala | Met | Leu | Ser | Leu | Ile | Asp | Gly | Lys | Gly | Pro | Ile | Arg | Phe | Val | Leu |
| | | | 35 | | | | 40 | | | | | 45 | | | |
| Ala | Leu | Leu | Ala | Phe | Phe | Arg | Phe | Thr | Ala | Ile | Ala | Pro | Thr | Arg | Ala |
| 50 | | | | | 55 | | | | | 60 | | | | | |
| Val | Leu | Asp | Arg | Trp | Arg | Gly | Val | Asn | Lys | Gln | Thr | Ala | Met | Lys | His |
| 65 | | | | 70 | | | | | 75 | | | | | 80 | |
| Leu | Leu | Ser | Phe | Lys | Lys | Glu | Leu | Gly | Thr | Leu | Thr | Ser | Ala | Ile | Asn |
| | | | | 85 | | | | | 90 | | | | | 95 | |
| Arg | Arg | Ser | Ser | Lys | Gln | Lys | Lys | Arg | Gly | Gly | Lys | Thr | Gly | Ile | Ala |
| | | | 100 | | | | | 105 | | | | | 110 | | |
| Val | Ile | Val | Pro | Gln | Ala | Leu | Leu | Phe | Val | Pro | Leu | Leu | Val | Phe | Pro |
| | | | 115 | | | | | 120 | | | | | 125 | | |
| Leu | Cys | Phe | Gly | Lys | Phe | Pro | Ile | Tyr | Thr | Ile | Pro | Asp | Lys | Leu | Gly |
| | 130 | | | | | 135 | | | | | 140 | | | | |
| Pro | Trp | Ser | Pro | Ile | Asp | Ile | His | His | Leu | Ser | Cys | Pro | Asn | Asn | Leu |
| 145 | | | | | 150 | | | | | 155 | | | | | 160 |
| Val | Val | Glu | Asp | Glu | Gly | Cys | Thr | Asn | Leu | Ser | Gly | Phe | Ser | Tyr | Met |
| | | | | 165 | | | | | 170 | | | | | 175 | |
| Glu | Leu | Lys | Val | Gly | Tyr | Ile | Ser | Ala | Ile | Lys | Met | Asn | Gly | Phe | Thr |
| | | | 180 | | | | | 185 | | | | | 190 | | |
| Cys | Thr | Gly | Val | Val | Thr | Glu | Ala | Glu | Thr | Tyr | Thr | Asn | Phe | Val | Gly |
| | | | 195 | | | | | 200 | | | | | 205 | | |
| Tyr | Val | Thr | Thr | Thr | Phe | Lys | Arg | Lys | His | Phe | Arg | Pro | Thr | Pro | Asp |
| | 210 | | | | | 215 | | | | | 220 | | | | |
| Ala | Cys | Arg | Ala | Ala | Tyr | Asn | Trp | Lys | Met | Ala | Gly | Asp | Pro | Arg | Tyr |
| 225 | | | | | 230 | | | | | 235 | | | | | 240 |
| Glu | Glu | Ser | Leu | His | Asn | Pro | Tyr | Pro | Asp | Tyr | His | Trp | Leu | Arg | Thr |
| | | | | 245 | | | | | 250 | | | | | 255 | |
| Val | Lys | Thr | Thr | Lys | Glu | Ser | Leu | Val | Ile | Ile | Ser | Pro | Ser | Val | Ala |
| | | | 260 | | | | | 265 | | | | | 270 | | |
| Asp | Leu | Asp | Pro | Tyr | Asp | Arg | Ser | Leu | His | Ser | Arg | Val | Phe | Pro | Gly |
| | | | 275 | | | | | 280 | | | | | 285 | | |
| Gly | Asn | Cys | Ser | Gly | Val | Ala | Val | Ser | Ser | Thr | Tyr | Cys | Ser | Thr | Asn |
| | 290 | | | | | 295 | | | | | 300 | | | | |
| His | Asp | Tyr | Thr | Ile | Trp | Met | Pro | Glu | Asn | Pro | Arg | Leu | Gly | Met | Ser |
| 305 | | | | | 310 | | | | | 315 | | | | | 320 |
| Cys | Asp | Ile | Phe | Thr | Asn | Ser | Arg | Gly | Lys | Arg | Ala | Ser | Lys | Gly | Ser |
| | | | | 325 | | | | | 330 | | | | | 335 | |
| Glu | Thr | Cys | Gly | Phe | Val | Asp | Glu | Arg | Gly | Leu | Tyr | Lys | Ser | Leu | Lys |
| | | | 340 | | | | | 345 | | | | | 350 | | |
| Gly | Ala | Cys | Lys | Leu | Lys | Leu | Cys | Gly | Val | Leu | Gly | Leu | Arg | Leu | Met |
| | | | 355 | | | | | 360 | | | | | 365 | | |
| Asp | Gly | Thr | Trp | Val | Ala | Met | Gln | Thr | Ser | Asn | Glu | Thr | Lys | Trp | Cys |
| | 370 | | | | | 375 | | | | | 380 | | | | |

Pro Pro Gly Gln Leu Val Asn Leu His Asp Phe Arg Ser Asp Glu Ile
385                 390                 395                 400

Glu His Leu Val Val Glu Glu Leu Val Lys Lys Arg Glu Glu Cys Leu
            405                 410                 415

Asp Ala Leu Glu Ser Ile Met Thr Thr Lys Ser Val Ser Phe Arg Arg
        420                 425                 430

Leu Ser His Leu Arg Lys Leu Val Pro Gly Phe Gly Lys Ala Tyr Thr
    435                 440                 445

Ile Phe Asn Lys Thr Leu Met Glu Ala Asp Ala His Tyr Lys Ser Val
450                 455                 460

Arg Thr Trp Asn Glu Ile Ile Pro Ser Lys Gly Cys Leu Arg Val Gly
465                 470                 475                 480

Gly Arg Cys His Pro His Val Asn Gly Val Phe Phe Asn Gly Ile Ile
            485                 490                 495

Leu Gly Pro Asp Gly Asn Val Leu Ile Pro Glu Met Gln Ser Ser Leu
        500                 505                 510

Leu Gln Gln His Met Glu Leu Leu Val Ser Ser Val Ile Pro Leu Met
    515                 520                 525

His Pro Leu Ala Asp Pro Ser Thr Val Phe Lys Asn Gly Asp Glu Ala
530                 535                 540

Glu Asp Phe Val Glu Val His Leu Pro Asp Val His Glu Arg Ile Ser
545                 550                 555                 560

Gly Val Asp Leu Gly Leu Pro Asn Trp Gly Lys Tyr Val Leu Leu Ser
            565                 570                 575

Ala Gly Ala Leu Thr Ala Leu Met Leu Ile Ile Phe Leu Met Thr Cys
        580                 585                 590

Trp Arg Arg Val Asn Arg Ser Glu Pro Thr Gln His Asn Leu Arg Gly
    595                 600                 605

Thr Gly Arg Glu Val Ser Val Thr Pro Gln Ser Gly Lys Ile Ile Ser
610                 615                 620

Ser Trp Glu Ser Tyr Lys Ser Gly Gly Glu Thr Gly Leu Asn Phe Asp
625                 630                 635                 640

Leu Leu Lys Leu Ala Gly Asp Val Glu Ser Asn Pro Gly Pro Ala Arg
            645                 650                 655

Asp Arg Ser Ile Ala Leu Thr Phe Leu Ala Val Gly Gly Val Leu Leu
        660                 665                 670

Phe Leu Ser Val Asn Val His Ala Asp Thr Gly Cys Ala Ile Asp Ile
    675                 680                 685

Ser Arg Gln Glu Leu Arg Cys Gly Ser Gly Val Phe Ile His
690                 695                 700

<210> SEQ ID NO 65
<211> LENGTH: 2200
<212> TYPE: DNA
<213> ORGANISM: Artificial Sequence
<220> FEATURE:
<223> OTHER INFORMATION: Synthetic Construct

<400> SEQUENCE: 65
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcta tttgctaaaa cgcggaatgc cccgcgtgtt gtccttgatt     180
ggacttaaga gggctatgtt gagcctgatc gacggcaagg ggccaatacg atttgtgttg     240
gctctcttgg cgttcttcag gttcacagca attgctccga cccgagcagt gctggatcga     300

```
tggagaggtg tgaacaaaca aacagcgatg aaacaccttc tgagtttcaa gaaggaacta     360
gggaccttga ccagtgctat caatcggcgg agctcaaagc aaaagaagcg aggggggcaag    420 actggtatag ctgtgatcgt tcctcaggct cttttgtttg tacccttgct ggtatttccc    480
ctttgctttg gtaaatttcc tatctatacc atccctgata agctcgggcc ttggagtccc    540
attgatattc accatttgag ctgcccaaac aacctcgtcg ttgaggatga agggtgcact    600
aatctttctg gattttccta catggagttg aaagtgggct atatttcagc cattaagatg    660
aacggcttta cttgtacagg agtcgtgacc gaagccgaga catatacaaa tttcgtggga    720
tacgtcacca ccaccttcaa gagaaaacac ttccgcccaa cgcctgacgc ttgtcgggcc    780
gcttacaact ggaagatggc aggagatcct cgatatgaag aatctctgca acccgtat    840 cctgattacc attggctgcg acagtcaag actaccaagg agtctggt cattatatca    900 ccaagcgtgg ccgatcttga tccttatgat agatccctgc acagtagggt ttttcctggc    960
gggaattgta gcggtgttgc agtatcaagt acctactgct ccactaacca cgactacact   1020
atatggatgc ctgagaaccc tcgactcggt atgagttgcg cattttttac gaactcacgg   1080
ggcaagcggg catctaaggg gtctgaaaca tgcgggtttg ttgatgagcg gggttgtat   1140 aaatctctta aggcgcctg taagctgaaa ctctgtggcg tactggggct gcgcctgatg   1200
gacggcacat gggtggctat gcagacaagc aatgaaacaa agtggtgtcc ccctggtcag   1260
ctggttaatc tgcacgactt taggtctgac gaaatcgagc accttgtggt ggaggaactg   1320
gtgaagaaac gcgaagagtg cctggacgca cttgagagta ttatgaccac caaatccgtt   1380
tccttcagaa gactgagcca cctgcgaaag ctggtgccag ggttcgggaa ggcttatact   1440
attttcaaca agactcttat ggaggcggat gcccattata agtcagttag acttggaat   1500 gagataattc cctccaaagg atgtctgaga gtcggtggga gatgccaccc ccatgtcaat   1560
ggggtgttct ttaacggaat catcctggga cctgacggga acgtgctgat tcccgagatg   1620
caatcttccc ttctgcagca acacatggaa ctcctggtgt cttcagtgat acccctgatg   1680 caccccactgg ccgaccccag cactgtgttc aaaatggcg atgaggccga agactttgtg   1740
gaagttcacc tgcccgatgt acacgaaagg atatctggag tagacctggg ccttcctaat   1800
tggggtaagt acgtgctcct gagtgcgggt gccttgaccg cttgatgct gatcattttt   1860 ctgatgacct gctggcggag ggtgaatcgc tccgagccga cacagcacaa tctcagaggg   1920
acaggccggg aagtaagtgt gactccgcaa tctggcaaga ttattagtag ttgggagagt   1980
tacaagtctg gaggagagac tgggttgaat tttgatctgc tcaaacttgc aggcgatgta   2040
gaatcaaatc ctggacccgc ccgggacagg tccatagctc tcacgtttct cgcagttgga   2100
ggagttctgc tcttcctctc cgtgaacgtg cacgctgaca ctgggtgtgc catagacatc   2160
agccggcaag agctgagatg tggaagtgga gtgttcatac                          2200

<210> SEQ ID NO 66
<211> LENGTH: 2200
<212> TYPE: DNA
<213> ORGANISM: Artificial Sequence
<220> FEATURE:
<223> OTHER INFORMATION: Synthetic Construct

<400> SEQUENCE: 66
tcatcaagcg gacacactcg actgtttgaa tcatcacaaa cactcctaat tgttgttaat      60
tgtgtcacgc tcgacaaaga atcgtgcttc tagagctaca gattctttgg tcctcccggg    120
```

```
ccgttctcgg cccgacagat aaacgatttt gcgccttacg gggcgcacaa caggaactaa      180
cctgaattct cccgatacaa ctcggactag ctgccgttcc ccggttatgc taaacacaac      240
cgagagaacc gcaagaagtc caagtgtcgt taacgaggct gggctcgtca cgacctagct      300
acctctccac acttgtttgt ttgtcgctac tttgtggaag actcaaagtt cttccttgat      360
ccctggaact ggtcacgata gttagccgcc tcgagtttcg ttttcttcgc tcccccgttc      420
tgaccatatc gacactagca aggagtccga gaaacaaac atgggaacga ccataaaggg       480
gaaacgaaac catttaaagg atagatatgg tagggactat tcgagcccgg aacctcaggg      540
taactataag tggtaaactc gacgggtttg ttggagcagc aactcctact tcccacgtga      600
ttagaaagac ctaaaggat gtacctcaac tttcacccga tataaagtcg gtaattctac       660
ttgccgaaat gaacatgtcc tcagcactgg cttcggctct gtatatgttt aaagcaccct      720
atgcagtggt ggtggaagtt ctcttttgtg aaggcgggtt gcggactgcg aacagcccgg     780
cgaatgttga ccttctaccg tcctctagga gctatacttc ttagacgt gttgggcata        840 ggactaatgg taaccgacgc ctgtcagttc tgatggttcc tctcagacca gtaatatagt      900
ggttcgcacc ggctagaact aggaatacta tctagggacg tgtcatccca aaaaggaccg      960
cccttaacat cgccacaacg tcatagttca tggatgacga ggtgattggt gctgatgtga     1020
tatacctacg gactcttggg agctgagcca tactcaacgc tgtaaaaatg cttgagtgcc     1080
ccgttcgccc gtagattccc cagactttgt acgcccaaac aactactcgc ccccaacata     1140
tttagagaat ttccgcggac attcgacttt gagacaccgc atgaccccga cgcggactac     1200
ctgccgtgta cccaccgata cgtctgttcg ttactttgtt tcaccacagg gggaccagtc     1260
gaccaattag acgtgctgaa atccagactg ctttagctcg tggaacacca cctccttgac     1320
cacttctttg cgcttctcac ggacctgcgt gaactctcat aatactggtg gtttaggcaa     1380
aggaagtctt ctgactcggt ggacgctttc gaccacggtc ccaagccctt ccgaatatga     1440
taaaagttgt tctgagaata cctccgccta cgggtaatat tcagtcaatc ctgaaccttta    1500 ctctattaag ggaggtttcc tacagactct cagccaccct ctacggtggg ggtacagtta     1560
ccccacaaga aattgcctta gtaggaccct ggactgcccc tgcacgacta agggctctac     1620
gttagaaggg aagacgtcgt tgtgtacctt gaggaccaca gaagtcacta tgggggactac    1680 gtgggtgacc ggctggggtc gtgacacaag ttttttaccgc tactccggct tctgaaacac    1740
cttcaagtgg acgggctaca tgtgctttcc tatagacctc atctggaccc ggaaggatta     1800 acccccattca tgcacgagga ctcacgccca cggaactggc gaaactacga ctagtaaaaa    1860
gactactgga cgaccgcctc ccacttagcg aggctcggct gtgtcgtgtt agagtctccc     1920
tgtccggccc ttcattcaca ctgaggcgtt agaccgttct aataatcatc aaccctctca     1980
atgttcagac ctcctctctg acccaactta aaactagacg agtttgaacg tccgctacat     2040
cttagtttag gacctgggcg ggccctgtcc aggtatcgag agtgcaaaga gcgtcaacct     2100
cctcaagacg agaaggagag gcacttgcac gtgcgactgt gacccacacg gtatctgtag    2160
tcggccgttc tcgactctac accttcacct cacaagtatg                          2200
```

<210> SEQ ID NO 67
<211> LENGTH: 868
<212> TYPE: PRT
<213> ORGANISM: Artificial Sequence
<220> FEATURE:
<223> OTHER INFORMATION: Synthetic Construct

<400> SEQUENCE: 67

```
Met Ser Lys Lys Pro Gly Gly Pro Gly Lys Ser Arg Ala Val Asn Met
1               5                   10                  15
Leu Lys Arg Gly Met Pro Arg Val Leu Ser Leu Ile Gly Leu Lys Arg
            20                  25                  30
Ala Met Leu Ser Leu Ile Asp Gly Lys Gly Pro Ile Arg Phe Val Leu
        35                  40                  45
Ala Leu Leu Ala Phe Phe Arg Phe Thr Ala Ile Ala Pro Thr Arg Ala
    50                  55                  60
Val Leu Asp Arg Trp Arg Gly Val Asn Lys Gln Thr Ala Met Lys His
65                  70                  75                  80
Leu Leu Ser Phe Lys Lys Glu Leu Gly Thr Leu Thr Ser Ala Ile Asn
            85                  90                  95
Arg Arg Ser Ser Lys Gln Lys Lys Arg Gly Gly Lys Thr Gly Ile Ala
        100                 105                 110
Val Met Ile Gly Leu Ile Ala Ser Val Gly Ala Val Thr Leu Ser Asn
    115                 120                 125
Phe Gln Gly Lys Val Met Met Thr Val Asn Ala Thr Asp Val Thr Asp
    130                 135                 140
Val Ile Thr Ile Pro Thr Ala Ala Gly Lys Asn Leu Cys Ile Val Arg
145                 150                 155                 160
Ala Met Asp Val Gly Tyr Met Cys Asp Asp Thr Ile Thr Tyr Glu Cys
            165                 170                 175
Pro Val Leu Ser Ala Gly Asn Asp Pro Glu Asp Ile Asp Cys Trp Cys
        180                 185                 190
Thr Lys Ser Ala Val Tyr Val Arg Tyr Gly Arg Cys Thr Lys Thr Arg
    195                 200                 205
His Ser Arg Arg Ser Arg Arg Ser Leu Thr Val Gln Thr His Gly Glu
    210                 215                 220
Ser Thr Leu Ala Asn Lys Lys Gly Ala Trp Met Asp Ser Thr Lys Ala
225                 230                 235                 240
Thr Arg Tyr Leu Val Lys Thr Glu Ser Trp Ile Leu Arg Asn Pro Gly
            245                 250                 255
Tyr Ala Leu Val Ala Ala Val Ile Gly Trp Met Leu Gly Ser Asn Thr
        260                 265                 270
Met Gln Arg Val Val Phe Val Val Leu Leu Leu Leu Val Ala Pro Ala
    275                 280                 285
Tyr Ser Phe Asn Cys Leu Gly Met Ser Asn Arg Asp Phe Leu Glu Gly
    290                 295                 300
Val Ser Gly Ala Thr Trp Val Asp Leu Val Leu Glu Gly Asp Ser Cys
305                 310                 315                 320
Val Thr Ile Met Ser Lys Asp Lys Pro Thr Ile Asp Val Lys Met Met
            325                 330                 335
Asn Met Glu Ala Ala Asn Leu Ala Glu Val Arg Ser Tyr Cys Tyr Leu
        340                 345                 350
Ala Thr Val Ser Asp Leu Ser Thr Lys Ala Ala Cys Pro Ala Met Gly
    355                 360                 365
Glu Ala His Asn Asp Lys Arg Ala Asp Pro Ala Phe Val Cys Arg Gln
    370                 375                 380
Gly Val Val Asp Arg Gly Trp Gly Asn Gly Cys Gly Leu Phe Gly Lys
385                 390                 395                 400
Gly Ser Ile Asp Thr Cys Ala Lys Phe Ala Cys Ser Thr Lys Ala Ile
            405                 410                 415
```

```
Gly Arg Thr Ile Leu Lys Glu Asn Ile Lys Tyr Glu Val Ala Ile Phe
            420                 425                 430

Val His Gly Pro Thr Thr Val Glu Ser His Gly Asn Tyr Ser Thr Gln
            435                 440                 445

Val Gly Ala Thr Gln Ala Gly Arg Phe Ser Ile Thr Pro Ala Ala Pro
            450                 455                 460

Ser Tyr Thr Leu Lys Leu Gly Glu Tyr Gly Glu Val Thr Val Asp Cys
465                 470                 475                 480

Glu Pro Arg Ser Gly Ile Asp Thr Asn Ala Tyr Tyr Val Met Thr Val
                485                 490                 495

Gly Thr Lys Thr Phe Leu Val His Arg Glu Trp Phe Met Asp Leu Asn
            500                 505                 510

Leu Pro Trp Ser Ser Ala Gly Ser Thr Val Trp Arg Asn Arg Glu Thr
            515                 520                 525

Leu Met Glu Phe Glu Glu Pro His Ala Thr Lys Gln Ser Val Ile Ala
            530                 535                 540

Leu Gly Ser Gln Glu Gly Ala Leu His Gln Ala Leu Ala Gly Ala Ile
545                 550                 555                 560

Pro Val Glu Phe Ser Ser Asn Thr Val Lys Leu Thr Ser Gly His Leu
                565                 570                 575

Lys Cys Arg Val Lys Met Glu Lys Leu Gln Leu Lys Gly Thr Thr Tyr
            580                 585                 590

Gly Val Cys Ser Lys Ala Phe Lys Phe Leu Gly Thr Pro Ala Asp Thr
            595                 600                 605

Gly His Gly Thr Val Val Leu Glu Leu Gln Tyr Thr Gly Thr Asp Gly
            610                 615                 620

Pro Cys Lys Val Pro Ile Ser Ser Val Ala Ser Leu Asn Asp Leu Thr
625                 630                 635                 640

Pro Val Gly Arg Leu Val Thr Val Asn Pro Phe Val Ser Val Ala Thr
                645                 650                 655

Ala Asn Ala Lys Val Leu Ile Glu Leu Glu Pro Pro Phe Gly Asp Ser
            660                 665                 670

Tyr Ile Val Val Gly Arg Gly Glu Gln Gln Ile Asn His His Trp His
            675                 680                 685

Lys Ser Gly Ser Ser Ile Gly Lys Ala Phe Thr Thr Thr Leu Lys Gly
            690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
                725                 730                 735

Gly Gly Ala Phe Arg Ser Leu Phe Gly Gly Met Ser Trp Ile Thr Gln
            740                 745                 750

Gly Leu Leu Gly Ala Leu Leu Leu Trp Met Gly Ile Asn Ala Arg Asp
            755                 760                 765

Arg Ser Ile Ala Leu Thr Phe Leu Ala Val Gly Gly Val Leu Leu Phe
            770                 775                 780

Leu Ser Val Asn Val His Ala Asp Thr Gly Ile His Arg Gly Pro Ala
785                 790                 795                 800

Thr Arg Thr Thr Thr Glu Ser Gly Lys Leu Ile Thr Asp Trp Cys Cys
                805                 810                 815

Arg Ser Cys Thr Leu Pro Pro Leu Arg Tyr Gln Thr Asp Ser Gly Cys
            820                 825                 830

Trp Tyr Gly Met Glu Ile Arg Pro Gln Arg His Asp Glu Lys Thr Leu
```

```
                835                 840                 845
Val Gln Ser Gln Val Asn Ala Tyr Asn Ala Asp Met Ile Asp Pro Phe
        850                 855                 860

Gln Leu Gly Leu
865

<210> SEQ ID NO 68
<211> LENGTH: 2700
<212> TYPE: DNA
<213> ORGANISM: Artificial Sequence
<220> FEATURE:
<223> OTHER INFORMATION: Synthetic Construct

<400> SEQUENCE: 68
```

| | | | | | |
|---|---|---|---|---|---|
| agtagttcgc | ctgtgtgagc | tgacaaactt | agtagtgttt | gtgaggatta | acaacaatta | 60 |
| acacagtgcg | agctgtttct | tagcacgaag | atctcgatgt | ctaagaaacc | aggagggccc | 120 |
| ggcaagagcc | gggctgtcaa | tatgctaaaa | cgcggaatgc | cccgcgtgtt | gtccttgatt | 180 |
| ggacttaaga | gggctatgtt | gagcctgatc | acggcaagg | ggccaatacg | atttgtgttg | 240 |
| gctctcttgg | cgttcttcag | gttcacagca | attgctccga | cccgagcagt | gctggatcga | 300 |
| tggagaggtg | tgaacaaaca | aacagcgatg | aaacaccttc | tgagtttcaa | gaaggaacta | 360 |
| gggaccttga | ccagtgctat | caatcggcgg | agctcaaaac | aaaagaaaag | aggaggaaag | 420 |
| accggaattg | cagtcatgat | tggcctgatc | gccagcgtag | gagcagttac | cctctctaac | 480 |
| ttccaaggga | aggtgatgat | gacggtaaat | gctactgacg | tcacagatgt | catcacgatt | 540 |
| ccaacagctg | ctgaaagaa | cctatgcatt | gtcagagcaa | tggatgtggg | atacatgtgc | 600 |
| gatgatacta | tcacttatga | atgcccagtg | ctgtcggctg | gtaatgatcc | agaagacatc | 660 |
| gactgttggt | gcacaaagtc | agcagtctac | gtcaggtatg | aagatgcac | caagacacgc | 720 |
| cactcaagac | gcagtcggag | gtcactgaca | gtgcagacac | acggagaaag | cactctagcg | 780 |
| aacaagaagg | gggcttggat | ggacagcacc | aaggccacaa | ggtatttggt | aaaaacagaa | 840 |
| tcatggatct | tgaggaaccc | tggatatgcc | ctggtggcag | ccgtcattgg | ttggatgctt | 900 |
| gggagcaaca | ccatgcagag | agttgtgttt | gtcgtgctat | tgcttttggt | ggccccagct | 960 |
| tacagcttta | actgccttgg | aatgagcaac | agagacttct | ggaaggagt | gtctggagca | 1020 |
| acatgggtgg | atttggttct | cgaaggcgac | agctgcgtga | ctatcatgtc | taaggacaag | 1080 |
| cctaccatcg | atgtgaagat | gatgaatatg | gaggcggcca | acctggcaga | ggtccgcagt | 1140 |
| tattgctatt | tggctaccgt | cagcgatctc | tccaccaaag | ctgcgtgccc | ggccatggga | 1200 |
| gaagctcaca | atgacaaacg | tgctgaccca | gcttttgtgt | gcagacaagg | agtggtggac | 1260 |
| aggggctggg | gcaacggctg | cggactattt | ggcaaaggaa | gcattgacac | atgcgccaaa | 1320 |
| tttgcctgct | ctaccaaggc | aataggaaga | accatttga | aagagaatat | caagtacgaa | 1380 |
| gtggccattt | ttgtccatgg | accaactact | gtggagtcgc | acggaaacta | ctccacacag | 1440 |
| gttggagcca | ctcaggcagg | agattcagc | atcactcctg | cggcgccttc | atacacacta | 1500 |
| aagcttggag | aatatggaga | ggtgacagtg | gactgtgaac | cacggtcagg | gattgacacc | 1560 |
| aatgcatact | acgtgatgac | tgttggaaca | aagacgttct | ggtccatcg | tgagtggttc | 1620 |
| atggacctca | acctcccttg | gagcagtgct | ggaagtactg | tgtggaggaa | cagagagacg | 1680 |
| ttaatggagt | ttgaggaacc | acacgccacg | aagcagtctg | tgatagcatt | gggctcacaa | 1740 |
| gagggagctc | tgcatcaagc | tttggctgga | gccattcctg | tggaattttc | aagcaacact | 1800 |
| gtcaagttga | cgtcgggtca | tttgaagtgt | agagtgaaga | tggaaaaatt | gcagttgaag | 1860 |

```
ggaacaacct atggcgtctg ttcaaaggct ttcaagtttc ttgggactcc cgcagacaca   1920
ggtcacggca ctgtggtgtt ggaattgcag tacactggca cggatggacc ttgcaaagtt   1980
cctatctcgt cagtggcttc attgaacgac ctaacgccag tgggcagatt ggtcactgtc   2040
aacccttttg tttcagtggc cacgccaac gctaaggtcc tgattgaatt ggaaccaccc    2100
tttggagact catacatagt ggtgggcaga ggagaacaac agatcaatca ccactggcac   2160
aagtctggaa gcagcattgg caaagccttt acaaccaccc tcaaaggagc cagagacta    2220 gccgctctag agacacagc ttgggacttt ggatcagttg gaggggtgtt cacctcagtt    2280
gggaaggctg tccatcaagt gttcggagga gcattccgct cactgttcgg aggcatgtcc   2340
tggataacgc aaggattgct gggggctctc ctgttgtgga tgggcatcaa tgctcgtgac   2400
aggtccatag ctctcacgtt tctcgcagtt ggaggagttc tgctcttcct ctccgtgaac   2460
gtgcacgctg acactgggat ccaccgtgga cctgccactc gcaccaccac agagagcgga   2520
aagttgataa cagattggtg ctgcaggagc tgcaccttac caccactgcg ctaccaaact   2580
gacagcggct gttggtatgg tatggagatc agaccacaga gacatgatga aaagaccctc   2640
gtgcagtcac aagtgaatgc ttataatgct gatatgattg accctttca gttgggcctt    2700

<210> SEQ ID NO 69
<211> LENGTH: 2700
<212> TYPE: DNA
<213> ORGANISM: Artificial Sequence
<220> FEATURE:
<223> OTHER INFORMATION: Synthetic Construct

<400> SEQUENCE: 69
tcatcaagcg acacactcg actgtttgaa tcatcacaaa cactcctaat tgttgttaat      60
tgtgtcacgc tcgacaaaga atcgtgcttc tagagctaca gattctttgg tcctcccggg    120
ccgttctcgg cccgacagtt atacgatttt gcgccttacg gggcgcacaa caggaactaa    180
cctgaattct cccgatacaa ctcggactag ctgccgttcc ccggttatgc taaacacaac    240
cgagagaacc gcaagaagtc caagtgtcgt taacgaggct gggctcgtca cgacctagct    300
acctctccac acttgtttgt ttgtcgctac tttgtggaag actcaaagtt cttccttgat    360
ccctggaact ggtcacgata gttagccgcc tcgagttttg ttttcttttc tcctcctttc    420
tggccttaac gtcagtacta accggactag cggtcgcatc ctcgtcaatg ggagagattg    480
aaggttccct tccactacta ctgccattta cgatgactgc agtgtctaca gtagtgctaa    540
ggttgtcgac gacctttctt ggatacgtaa cagtctcgtt acctacaccc tatgtacacg    600
ctactatgat agtgaatact tacgggtcac gacagccgac cattactagg tcttctgtag    660
ctgacaacca cgtgtttcag tcgtcagatg cagtccatac cttctacgtg gttctgtgcg    720
gtgagttctg cgtcagcctc cagtgactgt cacgtctgtg tgcctctttc gtgagatcgc    780
ttgttcttcc cccgaaccta cctgtcgtgg ttccggtgtt ccataaacca ttttgtctt     840 agtacctaga actccttggg acctatacgg gaccaccgtc ggcagtaacc aacctacgaa    900
ccctcgttgt ggtacgtctc tcaacacaaa cagcacgata acgaaaacca ccggggtcga    960
atgtcgaaat tgacggaacc ttactcgttg tctctgaaga accttcctca cagacctcgt   1020
tgtacccacc taaaccaaga gcttccgctg tcgacgcact gatagtacag attcctgttc   1080
ggatggtagc tacacttcta ctacttatac ctccgccggt tggaccgtct ccaggcgtca   1140
ataacgataa accgatggca gtcgctagag aggtggttc gacgcacggg ccggtaccct    1200
```

-continued

```
cttcgagtgt tactgtttgc acgactgggt cgaaaacaca cgtctgttcc tcaccacctg    1260
tccccgaccc cgttgccgac gcctgataaa ccgtttcctt cgtaactgtg tacgcggttt    1320
aaacggacga gatggttccg ttatccttct tggtaaaact ttctcttata gttcatgctt    1380
caccggtaaa aacaggtacc tggttgatga cacctcagcg tgcctttgat gaggtgtgtc    1440
caacctcggt gagtccgtcc tctaagtcg tagtgaggac gccgcggaag tatgtgtgat     1500
ttcgaacctc ttatacctct ccactgtcac ctgacacttg gtgccagtcc taactgtgg     1560 ttacgtatga tgcactactg acaaccttgt ttctgcaaga accaggtagc actcaccaag    1620
tacctggagt tggagggaac ctcgtcacga ccttcatgac acacctcctt gtctctctgc    1680
aattacctca aactccttgg tgtgcggtgc ttcgtcagac actatcgtaa cccgagtgtt    1740
ctccctcgag acgtagttcg aaaccgacct cggtaaggac accttaaaag ttcgttgtga    1800
cagttcaact gcagcccagt aaacttcaca tctcacttct acctttttaa cgtcaacttc    1860
ccttgttgga taccgcagac aagtttccga aagttcaaag aaccctgagg cgtctgtgt    1920 ccagtgccgt gacaccacaa ccttaacgtc atgtgaccgt gcctacctgg aacgtttcaa    1980
ggatagagca gtcaccgaag taacttgctg gattgcggtc accgtctaa ccagtgacag     2040 ttgggaaaac aaagtcaccg gtgccggttg cgattccagg actaacttaa ccttggtggg    2100
aaacctctga gtatgtatca ccacccgtct cctcttgttg tctagttagt ggtgaccgtg    2160
ttcagacctt cgtcgtaacc gtttcggaaa tgttggtggg agtttcctcg cgtctctgat    2220
cggcgagatc ctctgtgtcg aaccctgaaa cctagtcaac ctccccacaa gtggagtcaa    2280
cccttccgac aggtagttca caagcctcct cgtaaggcga gtgacaagcc tccgtacagg    2340
acctattgcg ttcctaacga ccccgagag  gacaacacct acccgtagtt acgagcactg    2400
tccaggtatc gagagtgcaa agagcgtcaa cctcctcaag acgagaagga gaggcacttg    2460
cacgtgcgac tgtgaccc ta ggtggcacct ggacggtgag cgtggtggtg tctctcgcct    2520
ttcaactatt gtctaaccac gacgtcctcg acgtggaatg gtggtgacgc gatggtttga    2580
ctgtcgccga caaccatacc atacctctag tctggtgtct ctgtactact tttctgggag    2640
cacgtcagtg ttcacttacg aatattacga ctatactaac tgggaaaagt caacccggaa    2700
```

<210> SEQ ID NO 70
<211> LENGTH: 734
<212> TYPE: PRT
<213> ORGANISM: Artificial Sequence
<220> FEATURE:
<223> OTHER INFORMATION: Synthetic Construct

<400> SEQUENCE: 70

```
Met Ser Lys Lys Pro Gly Gly Pro Gly Lys Ser Arg Ala Val Tyr Leu
1               5                   10                  15

Leu Lys Arg Gly Met Pro Arg Val Leu Ser Leu Ile Gly Leu Lys Arg
                20                  25                  30

Ala Met Leu Ser Leu Ile Asp Gly Lys Gly Pro Ile Arg Phe Val Leu
            35                  40                  45

Ala Leu Leu Ala Phe Phe Arg Phe Thr Ala Ile Ala Pro Thr Arg Ala
        50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Glu Leu Leu Ile Leu
```

```
                100                 105                 110
Lys Ala Asn Ala Ile Thr Thr Ile Leu Thr Ala Val Thr Phe Cys Phe
            115                 120                 125
Ala Ser Gly Gln Asn Ile Thr Glu Glu Phe Tyr Gln Ser Thr Cys Ser
            130                 135                 140
Ala Val Ser Lys Gly Tyr Leu Ser Ala Leu Arg Thr Gly Trp Tyr Thr
145                 150                 155                 160
Ser Val Ile Thr Ile Glu Leu Ser Asn Ile Lys Glu Asn Lys Cys Asn
                165                 170                 175
Gly Thr Asp Ala Lys Val Lys Leu Ile Lys Gln Glu Leu Asp Lys Tyr
            180                 185                 190
Lys Asn Ala Val Thr Glu Leu Gln Leu Leu Met Gln Ser Thr Pro Pro
            195                 200                 205
Thr Asn Asn Arg Ala Arg Arg Glu Leu Pro Arg Phe Met Asn Tyr Thr
            210                 215                 220
Leu Asn Asn Ala Lys Lys Thr Asn Val Thr Leu Ser Lys Lys Arg Lys
225                 230                 235                 240
Arg Arg Phe Leu Gly Phe Leu Leu Gly Val Gly Ser Ala Ile Ala Ser
                245                 250                 255
Gly Val Ala Val Ser Lys Val Leu His Leu Glu Gly Glu Val Asn Lys
            260                 265                 270
Ile Lys Ser Ala Leu Leu Ser Thr Asn Lys Ala Val Val Ser Leu Ser
            275                 280                 285
Asn Gly Val Ser Val Leu Thr Ser Lys Val Leu Asp Leu Lys Asn Tyr
            290                 295                 300
Ile Asp Lys Gln Leu Leu Pro Ile Val Asn Lys Gln Ser Cys Ser Ile
305                 310                 315                 320
Ser Asn Ile Glu Thr Val Ile Glu Phe Gln Gln Lys Asn Asn Arg Leu
                325                 330                 335
Leu Glu Ile Thr Arg Glu Phe Ser Val Asn Ala Gly Val Thr Thr Pro
            340                 345                 350
Val Ser Thr Tyr Met Leu Thr Asn Ser Glu Leu Leu Ser Leu Ile Asn
            355                 360                 365
Asp Met Pro Ile Thr Asn Asp Gln Lys Lys Leu Met Ser Asn Asn Val
            370                 375                 380
Gln Ile Val Arg Gln Gln Ser Tyr Ser Ile Met Ser Ile Ile Lys Glu
385                 390                 395                 400
Glu Val Leu Ala Tyr Val Val Gln Leu Pro Leu Tyr Gly Val Ile Asp
                405                 410                 415
Thr Pro Cys Trp Lys Leu His Thr Ser Pro Leu Cys Thr Thr Asn Thr
            420                 425                 430
Lys Glu Gly Ser Asn Ile Cys Leu Thr Arg Thr Asp Arg Gly Trp Tyr
            435                 440                 445
Cys Asp Asn Ala Gly Ser Val Ser Phe Phe Pro Gln Ala Glu Thr Cys
            450                 455                 460
Lys Val Gln Ser Asn Arg Val Phe Cys Asp Thr Met Asn Ser Leu Thr
465                 470                 475                 480
Leu Pro Ser Glu Ile Asn Leu Cys Asn Val Asp Ile Phe Asn Pro Lys
                485                 490                 495
Tyr Asp Cys Lys Ile Met Thr Ser Lys Thr Asp Val Ser Ser Ser Val
            500                 505                 510
Ile Thr Ser Leu Gly Ala Ile Val Ser Cys Tyr Gly Lys Thr Lys Cys
            515                 520                 525
```

```
Thr Ala Ser Asn Lys Asn Arg Gly Ile Ile Lys Thr Phe Ser Asn Gly
        530                 535                 540
Cys Asp Tyr Val Ser Asn Lys Gly Met Asp Thr Val Ser Val Gly Asn
545                 550                 555                 560
Thr Leu Tyr Tyr Val Asn Lys Gln Glu Gly Lys Ser Leu Tyr Val Lys
                565                 570                 575
Gly Glu Pro Ile Ile Asn Phe Tyr Asp Pro Leu Val Phe Pro Ser Asp
            580                 585                 590
Glu Phe Asp Ala Ser Ile Ser Gln Val Asn Glu Lys Ile Asn Gln Ser
        595                 600                 605
Leu Ala Phe Ile Arg Lys Ser Asp Glu Leu Leu His Asn Val Asn Ala
    610                 615                 620
Gly Lys Ser Thr Thr Asn Ile Met Ile Thr Thr Ile Ile Ile Val Ile
625                 630                 635                 640
Ile Val Ile Leu Leu Ser Leu Ile Ala Val Gly Leu Leu Leu Tyr Cys
                645                 650                 655
Lys Ala Arg Ser Thr Pro Val Thr Leu Ser Lys Asp Gln Leu Ser Gly
            660                 665                 670
Ile Asn Asn Ile Ala Phe Ser Asn Asn Phe Asp Leu Leu Lys Leu Ala
        675                 680                 685
Gly Asp Val Glu Ser Asn Pro Gly Pro Ala Arg Asp Arg Ser Ile Ala
    690                 695                 700
Leu Thr Phe Leu Ala Val Gly Gly Val Leu Leu Phe Leu Ser Val Asn
705                 710                 715                 720
Val His Ala Asp Thr Gly Cys Ala Ile Asp Ile Ser Arg Gln
                725                 730

<210> SEQ ID NO 71
<211> LENGTH: 2298
<212> TYPE: DNA
<213> ORGANISM: Artificial Sequence
<220> FEATURE:
<223> OTHER INFORMATION: Synthetic Construct

<400> SEQUENCE: 71
agtagttcgc ctgtgtgagc tgacaaactt agtagtgttt gtgaggatta acaacaatta    60
acacagtgcg agctgtttct tagcacgaag atctcgatgt ctaagaaacc aggagggccc   120
ggcaagagcc gggctgtcta tttgctaaaa cgcggaatgc cccgcgtgtt gtccttgatt   180
ggacttaaga gggctatgtt gagcctgatc gacggcaagg ggccaatacg atttgtgttg   240
gctctcttgg cgttcttcag gttcacagca attgctccga cccgagcagt gctggatcga   300
tggagaggtg tgaacaaaca aacagcgatg aaacaccttc tgagtttcaa gaaggaacta   360
gggaccttga ccagtgctat caatcggcgg agctcaaagc aaaagaagcg aggggcgag   420 ttgctaatcc tcaaagcaaa tgcaattacc acaatcctca ctgcagtcac attttgtttt   480
gcttctggtc aaaacatcac tgaagaattt tatcaatcaa catgcagtgc agttagcaaa   540
ggctatctta gtgctctgag aactggttgg tataccagtg ttataactat agaattaagt   600
aatatcaagg aaaataagtg taatggaaca gatgctaagg taaaattgat aaaacaagaa   660
ttagataaat ataaaaatgc tgtaacagaa ttgcagttgc tcatgcaaag cacaccacca   720
acaaacaatc gagccagaag agaactacca aggtttatga attatacact caacaatgcc   780
aaaaaaacca atgtaacatt aagcaagaaa aggaaaagaa gatttcttgg ttttttgtta   840
ggtgttggat ctgcaatcgc cagtggcgtt gctgtatcta aggtcctgca cctagaaggg   900
```

```
gaagtgaaca agatcaaaag tgctctacta tccacaaaca aggctgtagt cagcttatca      960
aatggagtta gtgtcttaac cagcaaagtg ttagacctca aaaactatat agataaacaa     1020
ttgttaccta ttgtgaacaa gcaaagctgc agcatatcaa atatagaaac tgtgatagag     1080
ttccaacaaa agaacaacag actactagag attaccaggg aatttagtgt taatgcaggt     1140
gtaactacac ctgtaagcac ttacatgtta actaatagtg aattattgtc attaatcaat     1200
gatatgccta taacaaatga tcagaaaaag ttaatgtcca acaatgttca aatagttaga     1260
cagcaaagtt actctatcat gtccataata aaagaggaag tcttagcata tgtagtacaa     1320
ttaccactat atggtgttat agatacaccc tgttggaaac tacacacatc ccctctatgt     1380
acaaccaaca caaagaagg gtccaacatc tgtttaacaa gaactgacag aggatggtac      1440
tgtgacaatg caggatcagt atctttcttc ccacaagctg aaacatgtaa agttcaatca     1500
aatcgagtat tttgtgacac aatgaacagt ttaacattac caagtgaaat aaatctctgc     1560
aatgttgaca tattcaaccc caaatatgat tgtaaaatta tgacttcaaa aacagatgta     1620
agcagctccg ttatcacatc tctaggagcc attgtgtcat gctatggcaa aactaaatgt     1680
acagcatcca ataaaaatcg tggaatcata agacattttt ctaacgggtg cgattatgta     1740
tcaaataaag ggatggacac tgtgtctgta ggtaacacat tatattatgt aaataagcaa     1800
gaaggtaaaa gtctctatgt aaaaggtgaa ccaataataa atttctatga cccattagta     1860
ttcccctctg atgaatttga tgcatcaata tctcaagtca acgagaagat taaccagagc     1920
ctagcattta ttcgtaaatc cgatgaatta ttacataatg taaatgctgg taaatccacc     1980
acaaatatca tgataactac tataattata gtgattatag taatattgtt atcattaatt     2040
gctgttggac tgctcttata ctgtaaggcc agaagcacac cagtcacact aagcaaagat     2100
caactgagtg gtataaataa tattgcattt agtaacaatt ttgatctgct caaacttgca     2160
ggcgatgtag aatcaaatcc tggacccgcc cgggacaggt ccatagctct cacgtttctc     2220
gcagttggag gagttctgct cttcctctcc gtgaacgtgc acgctgacac tgggtgtgcc     2280
atagacatca gccggcaa                                                   2298
```

<210> SEQ ID NO 72
<211> LENGTH: 2298
<212> TYPE: DNA
<213> ORGANISM: Artificial Sequence
<220> FEATURE:
<223> OTHER INFORMATION: Synthetic Construct

<400> SEQUENCE: 72

```
tcatcaagcg acacactcg actgtttgaa tcatcacaaa cactcctaat tgttgttaat       60
tgtgtcacgc tcgacaaaga atcgtgcttc tagagctaca gattctttgg tcctcccggg    120
ccgttctcgg cccgacagat aaacgatttt gcgccttacg gggcgcacaa caggaactaa    180
cctgaattct cccgatacaa ctcggactag ctgccgttcc ccggttatgc taaacacaac    240
cgagagaacc gcaagaagtc caagtgtcgt taacgaggct gggctcgtca cgacctagct    300
acctctccac acttgtttgt ttgtcgctac tttgtggaag actcaaagtt cttccttgat    360
ccctggaact ggtcacgata gttagccgcc tcgagtttcg ttttcttcgc tccccgctc     420 aacgattagg agtttcgttt acgttaatgg tgttaggagt gacgtcagtg taaaacaaaa    480
cgaagaccag ttttgtagtg acttcttaaa atagttagtt gtacgtcacg tcaatcgttt    540
ccgatagaat cacgagactc ttgaccaacc atatggtcac aatattgata tcttaattca    600
```

-continued

```
ttatagttcc ttttattcac attaccttgt ctacgattcc attttaacta ttttgttctt        660
aatctattta tattttacg acattgtctt aacgtcaacg agtacgtttc gtgtggtggt         720
tgtttgttag ctcggtcttc tcttgatggt tccaaatact aatatgtga gttgttacgg        780 ttttttggt tacattgtaa ttcgttcttt ccttttctt ctaaagaacc aaaaaacaat         840
ccacaaccta gacgttagcg gtcaccgcaa cgacatagat tccaggacgt ggatcttccc      900
cttcacttgt tctagttttc acgagatgat aggtgtttgt tccgacatca gtcgaatagt      960
ttacctcaat cacagaattg gtcgtttcac aatctggagt ttttgatata tctatttgtt    1020
aacaatggat aacacttgtt cgtttcgacg tcgtatagtt tatatctttg acactatctc     1080
aaggttgttt tcttgttgtc tgatgatctc taatggtccc ttaaatcaca attacgtcca    1140
cattgatgtg gacattcgtg aatgtacaat tgattatcac ttaataacag taattagtta    1200
ctatacggat attgtttact agtctttttc aattacaggt tgttacaagt ttatcaatct    1260
gtcgtttcaa tgagatagta caggtattat tttctccttc agaatcgtat acatcatgtt    1320
aatggtgata taccacaata tctatgtggg acaaccttg atgtgtgtag gggagataca    1380
tgttggttgt gtttcttcc caggttgtag acaaattgtt cttgactgtc tcctaccatg     1440
acactgttac gtcctagtca tagaaagaag ggtgttcgac tttgtacatt tcaagttagt    1500
ttagctcata aaacactgtg ttacttgtca aattgtaatg gttcactta tttagagacg      1560 ttacaactgt ataagttggg gtttatacta acatttaat actgaagttt ttgtctacat     1620
tcgtcgaggc aatagtgtag agatcctcgg taacacagta cgataccgtt tgatttaca     1680 tgtcgtaggt tattttagc acctagtat ttctgtaaaa gattgcccac gctaatacat      1740
agtttatttc cctacctgtg acacagacat ccattgtgta atataataca tttattcgtt    1800 cttccattt cagagataca ttttccactt ggttattatt taaagatact gggtaatcat     1860
aaggggagac tacttaaact acgtagttat agagttcagt tgctcttcta attggtctcg    1920
gatcgtaaat aagcatttag gctacttaat aatgtattac atttcgacc atttaggtgg     1980 tgtttatagt actattgatg atattaatat cactaatatc attataacaa tagtaattaa     2040
cgacaacctg acgagaatat gacattccgg tcttcgtgtg gtcagtgtga ttcgtttcta     2100
gttgactcac catatttatt ataacgtaaa tcattgttaa aactagacga gtttgaacgt     2160
ccgctacatc ttagtttagg acctgggcgg gccctgtcca ggtatcgaga gtgcaaagag     2220
cgtcaacctc ctcaagacga gaaggagagg cacttgcacg tgcgactgtg acccacacgg     2280
tatctgtagt cggccgtt                                                    2298
```

<210> SEQ ID NO 73
<211> LENGTH: 667
<212> TYPE: PRT
<213> ORGANISM: Artificial Sequence
<220> FEATURE:
<223> OTHER INFORMATION: Synthetic Construct

<400> SEQUENCE: 73

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Gln
            20                  25                  30

Lys Lys Arg Gly Gly Glu Leu Leu Ile Leu Lys Ala Asn Ala Ile Thr
        35                  40                  45

Thr Ile Leu Thr Ala Val Thr Phe Cys Phe Ala Ser Gly Gln Asn Ile
    50                  55                  60
```

```
Thr Glu Glu Phe Tyr Gln Ser Thr Cys Ser Ala Val Ser Lys Gly Tyr
 65                  70                  75                  80

Leu Ser Ala Leu Arg Thr Gly Trp Tyr Thr Ser Val Ile Thr Ile Glu
                 85                  90                  95

Leu Ser Asn Ile Lys Glu Asn Lys Cys Asn Gly Thr Asp Ala Lys Val
            100                 105                 110

Lys Leu Ile Lys Gln Glu Leu Asp Lys Tyr Lys Asn Ala Val Thr Glu
        115                 120                 125

Leu Gln Leu Leu Met Gln Ser Thr Pro Pro Thr Asn Asn Arg Ala Arg
    130                 135                 140

Arg Glu Leu Pro Arg Phe Met Asn Tyr Thr Leu Asn Asn Ala Lys Lys
145                 150                 155                 160

Thr Asn Val Thr Leu Ser Lys Lys Arg Lys Arg Arg Phe Leu Gly Phe
                165                 170                 175

Leu Leu Gly Val Gly Ser Ala Ile Ala Ser Gly Val Ala Val Ser Lys
            180                 185                 190

Val Leu His Leu Glu Gly Glu Val Asn Lys Ile Lys Ser Ala Leu Leu
        195                 200                 205

Ser Thr Asn Lys Ala Val Val Ser Leu Ser Asn Gly Val Ser Val Leu
210                 215                 220

Thr Ser Lys Val Leu Asp Leu Lys Asn Tyr Ile Asp Lys Gln Leu Leu
225                 230                 235                 240

Pro Ile Val Asn Lys Gln Ser Cys Ser Ile Ser Asn Ile Glu Thr Val
                245                 250                 255

Ile Glu Phe Gln Gln Lys Asn Asn Arg Leu Leu Glu Ile Thr Arg Glu
            260                 265                 270

Phe Ser Val Asn Ala Gly Val Thr Thr Pro Val Ser Thr Tyr Met Leu
        275                 280                 285

Thr Asn Ser Glu Leu Leu Ser Leu Ile Asn Asp Met Pro Ile Thr Asn
    290                 295                 300

Asp Gln Lys Lys Leu Met Ser Asn Asn Val Gln Ile Val Arg Gln Gln
305                 310                 315                 320

Ser Tyr Ser Ile Met Ser Ile Ile Lys Glu Glu Val Leu Ala Tyr Val
                325                 330                 335

Val Gln Leu Pro Leu Tyr Gly Val Ile Asp Thr Pro Cys Trp Lys Leu
            340                 345                 350

His Thr Ser Pro Leu Cys Thr Thr Asn Thr Lys Glu Gly Ser Asn Ile
        355                 360                 365

Cys Leu Thr Arg Thr Asp Arg Gly Trp Tyr Cys Asp Asn Ala Gly Ser
    370                 375                 380

Val Ser Phe Phe Pro Gln Ala Glu Thr Cys Lys Val Gln Ser Asn Arg
385                 390                 395                 400

Val Phe Cys Asp Thr Met Asn Ser Leu Thr Leu Pro Ser Glu Ile Asn
                405                 410                 415

Leu Cys Asn Val Asp Ile Phe Asn Pro Lys Tyr Asp Cys Lys Ile Met
            420                 425                 430

Thr Ser Lys Thr Asp Val Ser Ser Val Ile Thr Ser Leu Gly Ala
        435                 440                 445

Ile Val Ser Cys Tyr Gly Lys Thr Lys Cys Thr Ala Ser Asn Lys Asn
    450                 455                 460

Arg Gly Ile Ile Lys Thr Phe Ser Asn Gly Cys Asp Tyr Val Ser Asn
465                 470                 475                 480
```

| | | | | | | | | | | | |
|---|---|---|---|---|---|---|---|---|---|---|---|
|Lys|Gly|Met|Asp|Thr 485|Val|Ser|Val|Gly 490|Asn|Thr|Leu Tyr Tyr Val Asn 495|

Lys Gln Glu Gly Lys Ser Leu Tyr Val Lys Gly Glu Pro Ile Ile Asn
            500                 505                 510

Phe Tyr Asp Pro Leu Val Phe Pro Ser Asp Glu Phe Asp Ala Ser Ile
            515                 520                 525

Ser Gln Val Asn Glu Lys Ile Asn Gln Ser Leu Ala Phe Ile Arg Lys
            530                 535                 540

Ser Asp Glu Leu Leu His Asn Val Asn Ala Gly Lys Ser Thr Thr Asn
545                 550                 555                 560

Ile Met Ile Thr Thr Ile Ile Ile Val Ile Ile Val Ile Leu Leu Ser
                    565                 570                 575

Leu Ile Ala Val Gly Leu Leu Leu Tyr Cys Lys Ala Arg Ser Thr Pro
                580                 585                 590

Val Thr Leu Ser Lys Asp Gln Leu Ser Gly Ile Asn Asn Ile Ala Phe
            595                 600                 605

Ser Asn Asn Phe Asp Leu Leu Lys Leu Ala Gly Asp Val Glu Ser Asn
            610                 615                 620

Pro Gly Pro Ala Arg Asp Arg Ser Ile Ala Leu Thr Phe Leu Ala Val
625                 630                 635                 640

Gly Gly Val Leu Leu Phe Leu Ser Val Asn Val His Ala Asp Thr Gly
                    645                 650                 655

Cys Ala Ile Asp Ile Ser Arg Gln Glu Leu Arg
                660                 665

```
<210> SEQ ID NO 74
<211> LENGTH: 2097
<212> TYPE: DNA
<213> ORGANISM: Artificial Sequence
<220> FEATURE:
<223> OTHER INFORMATION: Synthetic Construct

<400> SEQUENCE: 74
agtagttcgc ctgtgtgagc tgacaaactt agtagtgttt gtgaggatta acaacaatta     60
acacagtgcg agctgtttct tagcacgaag atctcgatgt ctaagaaacc aggagggccc    120
ggcaagagcc gggctgtcaa tatgctaaaa cgcggaatgc cccgcgtgtt gtccttgatt    180
ggacttaagc aaaagaagcg aggggggcgag ttgctaatcc tcaaagcaaa tgcaattacc    240
acaatcctca ctgcagtcac atttttgtttt gcttctggtc aaaacatcac tgaagaattt    300
tatcaatcaa catgcagtgc agttagcaaa ggctatctta gtgctctgag aactggttgg    360
tataccagtg ttataactat agaattaagt aatatcaagg aaaataagtg taatggaaca    420
gatgctaagg taaaattgat aaaacaagaa ttagataaat ataaaaatgc tgtaacagaa    480
ttgcagttgc tcatgcaaag cacaccacca acaaacaatc gagccagaag agaactacca    540
aggtttatga attatacact caacaatgcc aaaaaaacca atgtaacatt aagcaagaaa    600
aggaaaagaa gatttcttgg ttttttgtta ggtgttggat ctgcaatcgc cagtggcgtt    660
gctgtatcta aggtcctgca cctagaaggg gaagtgaaca agatcaaaag tgctctacta    720
tccacaaaca aggctgtagt cagcttatca aatggagtta gtgtcttaac cagcaaagtg    780
ttagacctca aaaactatat agataaacaa ttgttaccta ttgtgaacaa gcaaagctgc    840
agcatatcaa atatagaaac tgtgatagag ttccaacaaa agaacaacag actactagag    900
attaccaggg aatttagtgt taatgcaggt gtaactacac tgtaagcac ttacatgtta    960 actaatagtg aattattgtc attaatcaat gatatgccta taacaaatga tcagaaaaag   1020
```

```
ttaatgtcca acaatgttca aatagttaga cagcaaagtt actctatcat gtccataata    1080
aaagaggaag tcttagcata tgtagtacaa ttaccactat atggtgttat agatacaccc    1140
tgttggaaac tacacacatc ccctctatgt acaaccaaca caaaagaagg gtccaacatc    1200
tgtttaacaa gaactgacag aggatggtac tgtgacaatg caggatcagt atctttcttc    1260
ccacaagctg aaacatgtaa agttcaatca aatcgagtat tttgtgacac aatgaacagt    1320
ttaacattac caagtgaaat aaatctctgc aatgttgaca tattcaaccc caaatatgat    1380
tgtaaaatta tgacttcaaa aacagatgta agcagctccg ttatcacatc tctaggagcc    1440
attgtgtcat gctatggcaa aactaaatgt acagcatcca ataaaaatcg tggaatcata    1500
aagacatttt ctaacgggtg cgattatgta tcaaataaag ggatggacac tgtgtctgta    1560
ggtaacacat tatattatgt aaataagcaa gaaggtaaaa gtctctatgt aaaaggtgaa    1620
ccaataataa atttctatga cccattagta ttcccctctg atgaatttga tgcatcaata    1680
tctcaagtca acgagaagat taaccagagc ctagcattta ttcgtaaatc cgatgaatta    1740
ttacataatg taaatgctgg taaatccacc acaaatatca tgataactac tataattata    1800
gtgattatag taatattgtt atcattaatt gctgttggac tgctcttata ctgtaaggcc    1860
agaagcacac cagtcacact aagcaaagat caactgagtg gtataaataa tattgcattt    1920
agtaacaatt ttgatctgct caaacttgca ggcgatgtag aatcaaatcc tggacccgcc    1980
cgggacaggt ccatagctct cacgtttctc gcagttggag gagttctgct cttcctctcc    2040
gtgaacgtgc acgctgacac tgggtgtgcc atagacatca gccggcaaga gctgaga      2097

<210> SEQ ID NO 75
<211> LENGTH: 2097
<212> TYPE: DNA
<213> ORGANISM: Artificial Sequence
<220> FEATURE:
<223> OTHER INFORMATION: Synthetic Construct

<400> SEQUENCE: 75
tcatcaagcg gacacactcg actgtttgaa tcatcacaaa cactcctaat tgttgttaat      60
tgtgtcacgc tcgacaaaga atcgtgcttc tagagctaca gattctttgg tcctcccggg     120
ccgttctcgg cccgacagtt atacgatttt gcgccttacg gggcgcacaa caggaactaa     180
cctgaattcg ttttcttcgc tcccccgctc aacgattagg agtttcgttt acgttaatgg     240
tgttaggagt gacgtcagtg taaaacaaaa cgaagaccag ttttgtagtg acttcttaaa     300
atagttagtt gtacgtcacg tcaatcgttt ccgatagaat cacgagactc ttgaccaacc     360
atatggtcac aatattgata tcttaattca ttatagttcc ttttattcac attaccttgt     420
ctacgattcc attttaacta ttttgttctt aatctattta tattttacg acattgtctt      480 aacgtcaacg agtacgtttc gtgtggtggt tgtttgttag ctcggtcttc tcttgatggt     540
tccaaatact aatatgtgac gttgttacgg tttttttggt tacattgtaa ttcgttcttt     600
tccttttctt ctaaagaacc aaaaaacaat ccacaaccta gacgttagcg gtcaccgcaa     660
cgacatagat tccaggacgt ggatcttccc cttcacttgt tctagttttc acgagatgat     720
aggtgtttgt tccgacatca gtcgaatagt ttacctcaat cacagaattg gtcgtttcac     780
aatctggagt ttttgatata tctatttgtt aacaatggat aacacttgtt cgtttcgacg     840
tcgtatagtt tatatctttg acactatctc aaggttgttt tcttgttgtc tgatgatctc     900
taatggtccc ttaaatcaca attacgtcca cattgatgtg gacattcgtg aatgtacaat     960
```

```
tgattatcac ttaataacag taattagtta ctatacggat attgtttact agtcttttc      1020 aattacaggt tgttacaagt ttatcaatct gtcgtttcaa tgagatagta caggtattat      1080
tttctccttc agaatcgtat acatcatgtt aatggtgata taccacaata tctatgtggg      1140
acaacctttg atgtgtgtag gggagataca tgttggttgt gttttcttcc caggttgtag      1200
acaaattgtt cttgactgtc tcctaccatg acactgttac gtcctagtca tagaaagaag      1260
ggtgttcgac tttgtacatt tcaagttagt ttagctcata aaacactgtg ttacttgtca      1320
aattgtaatg gttcacttta tttagagacg ttacaactgt ataagttggg gtttatacta      1380
acattttaat actgaagttt ttgtctacat tcgtcgaggc aatagtgtag agatcctcgg      1440
taacacagta cgataccgtt ttgatttaca tgtcgtaggt tatttttagc accttagtat      1500
ttctgtaaaa gattgcccac gctaatacat agtttatttc cctacctgtg acacagacat      1560
ccattgtgta atataataca tttattcgtt cttccatttt cagagataca ttttccactt      1620
ggttattatt taaagatact gggtaatcat aaggggagac tacttaaact acgtagttat      1680
agagttcagt tgctcttcta attggtctcg gatcgtaaat aagcatttag gctacttaat      1740
aatgtattac atttcgacc atttaggtgg tgtttatagt actattgatg atattaatat      1800
cactaatatc attataacaa tagtaattaa cgacaacctg acgagaatat gacattccgg      1860
tcttcgtgtg gtcagtgtga ttcgtttcta gttgactcac catatttatt ataacgtaaa      1920
tcattgttaa aactagacga gtttgaacgt ccgctacatc ttagtttagg acctgggcgg      1980
gccctgtcca ggtatcgaga gtgcaaagag cgtcaacctc ctcaagacga aaggagagg      2040 cacttgcacg tgcgactgtg acccacacgg tatctgtagt cggccgttct cgactct         2097
```

<210> SEQ ID NO 76
<211> LENGTH: 1327
<212> TYPE: PRT
<213> ORGANISM: Artificial Sequence
<220> FEATURE:
<223> OTHER INFORMATION: Synthetic Construct

<400> SEQUENCE: 76

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Gln
            20                  25                  30

Lys Lys Arg Gly Gly Glu Leu Leu Ile Leu Lys Ala Asn Ala Ile Thr
        35                  40                  45

Thr Ile Leu Thr Ala Val Thr Phe Cys Phe Ala Ser Gly Gln Asn Ile
    50                  55                  60

Thr Glu Glu Phe Tyr Gln Ser Thr Cys Ser Ala Val Ser Lys Gly Tyr
65                  70                  75                  80

Leu Ser Ala Leu Arg Thr Gly Trp Tyr Thr Ser Val Ile Thr Ile Glu
                85                  90                  95

Leu Ser Asn Ile Lys Glu Asn Lys Cys Asn Gly Thr Asp Ala Lys Val
            100                 105                 110

Lys Leu Ile Lys Gln Glu Leu Asp Lys Tyr Lys Asn Ala Val Thr Glu
        115                 120                 125

Leu Gln Leu Leu Met Gln Ser Thr Pro Pro Thr Asn Asn Arg Ala Arg
    130                 135                 140

Arg Glu Leu Pro Arg Phe Met Asn Tyr Thr Leu Asn Asn Ala Lys Lys
145                 150                 155                 160

```
Thr Asn Val Thr Leu Ser Lys Lys Arg Lys Arg Phe Leu Gly Phe
            165                 170                 175

Leu Leu Gly Val Gly Ser Ala Ile Ala Ser Gly Val Ala Val Ser Lys
        180                 185                 190

Val Leu His Leu Glu Gly Glu Val Asn Lys Ile Lys Ser Ala Leu Leu
        195                 200                 205

Ser Thr Asn Lys Ala Val Val Ser Leu Ser Asn Gly Val Ser Val Leu
        210                 215                 220

Thr Ser Lys Val Leu Asp Leu Lys Asn Tyr Ile Asp Lys Gln Leu Leu
225                 230                 235                 240

Pro Ile Val Asn Lys Gln Ser Cys Ser Ile Ser Asn Ile Glu Thr Val
                245                 250                 255

Ile Glu Phe Gln Gln Lys Asn Asn Arg Leu Leu Glu Ile Thr Arg Glu
                260                 265                 270

Phe Ser Val Asn Ala Gly Val Thr Thr Pro Val Ser Thr Tyr Met Leu
            275                 280                 285

Thr Asn Ser Glu Leu Leu Ser Leu Ile Asn Asp Met Pro Ile Thr Asn
        290                 295                 300

Asp Gln Lys Lys Leu Met Ser Asn Asn Val Gln Ile Val Arg Gln Gln
305                 310                 315                 320

Ser Tyr Ser Ile Met Ser Ile Ile Lys Glu Glu Val Leu Ala Tyr Val
                325                 330                 335

Val Gln Leu Pro Leu Tyr Gly Val Ile Asp Thr Pro Cys Trp Lys Leu
            340                 345                 350

His Thr Ser Pro Leu Cys Thr Thr Asn Thr Lys Glu Gly Ser Asn Ile
            355                 360                 365

Cys Leu Thr Arg Thr Asp Arg Gly Trp Tyr Cys Asp Asn Ala Gly Ser
        370                 375                 380

Val Ser Phe Phe Pro Gln Ala Glu Thr Cys Lys Val Gln Ser Asn Arg
385                 390                 395                 400

Val Phe Cys Asp Thr Met Asn Ser Leu Thr Leu Pro Ser Glu Ile Asn
                405                 410                 415

Leu Cys Asn Val Asp Ile Phe Asn Pro Lys Tyr Asp Cys Lys Ile Met
            420                 425                 430

Thr Ser Lys Thr Asp Val Ser Ser Ser Val Ile Thr Ser Leu Gly Ala
        435                 440                 445

Ile Val Ser Cys Tyr Gly Lys Thr Lys Cys Thr Ala Ser Asn Lys Asn
        450                 455                 460

Arg Gly Ile Ile Lys Thr Phe Ser Asn Gly Cys Asp Tyr Val Ser Asn
465                 470                 475                 480

Lys Gly Met Asp Thr Val Ser Val Gly Asn Thr Leu Tyr Tyr Val Asn
                485                 490                 495

Lys Gln Glu Gly Lys Ser Leu Tyr Val Lys Gly Glu Pro Ile Ile Asn
            500                 505                 510

Phe Tyr Asp Pro Leu Val Phe Pro Ser Asp Glu Phe Asp Ala Ser Ile
            515                 520                 525

Ser Gln Val Asn Glu Lys Ile Asn Gln Ser Leu Ala Phe Ile Arg Lys
        530                 535                 540

Ser Asp Glu Leu Leu His Asn Val Asn Ala Gly Lys Ser Thr Thr Asn
545                 550                 555                 560

Ile Met Ile Thr Thr Ile Ile Ile Val Ile Ile Val Ile Leu Leu Ser
                565                 570                 575
```

```
Leu Ile Ala Val Gly Leu Leu Tyr Cys Lys Ala Arg Ser Thr Pro
                580             585             590

Val Thr Leu Ser Lys Asp Gln Leu Ser Gly Ile Asn Asn Ile Ala Phe
    595             600             605

Ser Asn Asn Phe Asp Leu Leu Lys Leu Ala Gly Asp Val Glu Ser Asn
610             615             620

Pro Gly Pro Gly Gly Lys Thr Gly Ile Ala Val Met Ile Gly Leu Ile
625             630             635             640

Ala Cys Val Gly Ala Val Thr Leu Ser Asn Phe Gln Gly Lys Val Met
                645             650             655

Met Thr Val Asn Ala Thr Asp Val Thr Asp Val Ile Thr Ile Pro Thr
                660             665             670

Ala Ala Gly Lys Asn Leu Cys Ile Val Arg Ala Met Asp Val Gly Tyr
                675             680             685

Met Cys Asp Asp Thr Ile Thr Tyr Glu Cys Pro Val Leu Ser Ala Gly
    690             695             700

Asn Asp Pro Glu Asp Ile Asp Cys Trp Cys Thr Lys Ser Ala Val Tyr
705             710             715             720

Val Arg Tyr Gly Arg Cys Thr Lys Thr Arg His Ser Arg Arg Ser Arg
                725             730             735

Arg Ser Leu Thr Val Gln Thr His Gly Glu Ser Thr Leu Ala Asn Lys
                740             745             750

Lys Gly Ala Trp Met Asp Ser Thr Lys Ala Thr Arg Tyr Leu Val Lys
                755             760             765

Thr Glu Ser Trp Ile Leu Arg Asn Pro Gly Tyr Ala Leu Val Ala Ala
    770             775             780

Val Ile Gly Trp Met Leu Gly Ser Asn Thr Met Gln Arg Val Val Phe
785             790             795             800

Val Val Leu Leu Leu Leu Val Ala Pro Ala Tyr Ser Phe Asn Cys Leu
                805             810             815

Gly Met Ser Asn Arg Asp Phe Leu Glu Gly Val Ser Gly Ala Thr Trp
                820             825             830

Val Asp Leu Val Leu Glu Gly Asp Ser Cys Val Thr Ile Met Ser Lys
    835             840             845

Asp Lys Pro Thr Ile Asp Val Lys Met Met Asn Met Glu Ala Ala Asn
850             855             860

Leu Ala Glu Val Arg Ser Tyr Cys Tyr Leu Ala Thr Val Ser Asp Leu
865             870             875             880

Ser Thr Lys Ala Ala Cys Pro Ala Met Gly Glu Ala His Asn Asp Lys
                885             890             895

Arg Ala Asp Pro Ala Phe Val Cys Arg Gln Gly Val Val Asp Arg Gly
                900             905             910

Trp Gly Asn Gly Cys Gly Leu Phe Gly Lys Gly Ser Ile Asp Thr Cys
    915             920             925

Ala Lys Phe Ala Cys Ser Thr Lys Ala Ile Gly Arg Thr Ile Leu Lys
930             935             940

Glu Asn Ile Lys Tyr Glu Val Ala Ile Phe Val His Gly Pro Thr Thr
945             950             955             960

Val Glu Ser His Gly Asn Tyr Ser Thr Gln Val Gly Ala Thr Gln Ala
                965             970             975

Gly Arg Phe Ser Ile Thr Pro Ala Ala Pro Ser Tyr Thr Leu Lys Leu
                980             985             990
```

Gly Glu Tyr Gly Glu Val Thr Val Asp Cys Glu Pro Arg Ser Gly Ile
            995                 1000                1005

Asp Thr Asn Ala Tyr Val Met Thr Val Gly Thr Lys Thr Phe
    1010                1015                1020

Leu Val His Arg Glu Trp Phe Met Asp Leu Asn Leu Pro Trp Ser
    1025                1030                1035

Ser Ala Gly Ser Thr Val Trp Arg Asn Arg Glu Thr Leu Met Glu
    1040                1045                1050

Phe Glu Glu Pro His Ala Thr Lys Gln Ser Val Ile Ala Leu Gly
    1055                1060                1065

Ser Gln Glu Gly Ala Leu His Gln Ala Leu Ala Gly Ala Ile Pro
    1070                1075                1080

Val Glu Phe Ser Ser Asn Thr Val Lys Leu Thr Ser Gly His Leu
    1085                1090                1095

Lys Cys Arg Val Lys Met Glu Lys Leu Gln Leu Lys Gly Thr Thr
    1100                1105                1110

Tyr Gly Val Cys Ser Lys Ala Phe Lys Phe Leu Gly Thr Pro Ala
    1115                1120                1125

Asp Thr Gly His Gly Thr Val Val Leu Glu Leu Gln Tyr Thr Gly
    1130                1135                1140

Thr Asp Gly Pro Cys Lys Val Pro Ile Ser Ser Val Ala Ser Leu
    1145                1150                1155

Asn Asp Leu Thr Pro Val Gly Arg Leu Val Thr Val Asn Pro Phe
    1160                1165                1170

Val Ser Val Ala Thr Ala Asn Ala Lys Val Leu Ile Glu Leu Glu
    1175                1180                1185

Pro Pro Phe Gly Asp Ser Tyr Ile Val Val Gly Arg Gly Glu Gln
    1190                1195                1200

Gln Ile Asn His His Trp His Lys Ser Gly Ser Ser Ile Gly Lys
    1205                1210                1215

Ala Phe Thr Thr Thr Leu Lys Gly Ala Gln Arg Leu Ala Ala Leu
    1220                1225                1230

Gly Asp Thr Ala Trp Asp Phe Gly Ser Val Gly Gly Val Phe Thr
    1235                1240                1245

Ser Val Gly Lys Ala Val His Gln Val Phe Gly Gly Ala Phe Arg
    1250                1255                1260

Ser Leu Phe Gly Gly Met Ser Trp Ile Thr Gln Gly Leu Leu Gly
    1265                1270                1275

Ala Leu Leu Leu Trp Met Gly Ile Asn Ala Arg Asp Arg Ser Ile
    1280                1285                1290

Ala Leu Thr Phe Leu Ala Val Gly Gly Val Leu Leu Phe Leu Ser
    1295                1300                1305

Val Asn Val His Ala Asp Thr Gly Cys Ala Ile Asp Ile Ser Arg
    1310                1315                1320

Gln Glu Leu Arg
    1325

<210> SEQ ID NO 77
<211> LENGTH: 4100
<212> TYPE: DNA
<213> ORGANISM: Artificial Sequence
<220> FEATURE:
<223> OTHER INFORMATION: Synthetic Construct

```
<400> SEQUENCE: 77
gatcctaata cgactcacta tagagtagtt cgcctgtgtg agctgacaaa cttagtagtg      60
tttgtgagga ttaacaacaa ttaacacagt gcgagctgtt tcttagcacg aagatctcga     120
tgtctaagaa accaggaggg cccggcaaga gccgggctgt caatatgcta aaacgcggaa     180
tgccccgcgt gttgtccttg attggactta agcaaaagaa gcgaggggc gagttgctaa      240 tcctcaaagc aaatgcaatt accacaatcc tcactgcagt cacattttgt tttgcttctg     300
gtcaaaacat cactgaagaa ttttatcaat caacatgcag tgcagttagc aaaggctatc     360
ttagtgctct gagaactggt tggtatacca gtgttataac tatagaatta agtaatatca     420
aggaaaataa gtgtaatgga acagatgcta aggtaaaatt gataaaacaa gaattagata     480
aatataaaaa tgctgtaaca gaattgcagt tgctcatgca aagcacacca ccaacaaaca     540
atcgagccag aagagaacta ccaaggttta tgaattatac actcaacaat gccaaaaaaa     600
ccaatgtaac attaagcaag aaaaggaaaa gaagatttct tggtttttg ttaggtgttg      660 gatctgcaat cgccagtggc gttgctgtat ctaaggtcct gcacctagaa ggggaagtga     720
acaagatcaa aagtgctcta ctatccacaa acaaggctgt agtcagctta tcaaatggag     780
ttagtgtctt aaccagcaaa gtgttagacc tcaaaaacta tatagataaa caattgttac     840
ctattgtgaa caagcaaagc tgcagcatat caaatataga aactgtgata gagttccaac     900
aaaagaacaa cagactacta gagattacca gggaatttag tgttaatgca ggtgtaacta     960
cacctgtaag cacttacatg ttaactaata gtgaattatt gtcattaatc aatgatatgc    1020
ctataacaaa tgatcagaaa aagttaatgt ccaacaatgt tcaaatagtt agacagcaaa    1080
gttactctat catgtccata ataaagagg aagtcttagc atatgtagta caattccac     1140 tatatgtgt tatagataca ccctgttgga aactacacac atcccctcta tgtacaacca    1200
acacaaaaga agggtccaac atctgtttaa caagaactga cagaggatgg tactgtgaca    1260
atgcaggatc agtatctttc ttcccacaag ctgaaacatg taaagttcaa tcaaatcgag    1320
tattttgtga cacaatgaac agtttaacat taccagtga aataaatctc tgcaatgttg     1380
acatattcaa ccccaaatat gattgtaaaa ttatgacttc aaaaacagat gtaagcagct    1440
ccgttatcac atctctagga gccattgtgt catgctatgg caaaactaaa tgtacagcat    1500
ccaataaaaa tcgtggaatc ataaagacat tttctaacgg gtgcgattat gtatcaaata    1560
aagggatgga cactgtgtct gtaggtaaca cattatatta tgtaaataag caagaaggta    1620
aaagtctcta tgtaaaaggt gaaccaataa taaatttcta tgacccatta gtattcccct    1680
ctgatgaatt tgatgcatca atatctcaag tcaacgagaa gattaaccag agcctagcat    1740
ttattcgtaa atccgatgaa ttattacata atgtaaatgc tggtaaatcc accacaaata    1800
tcatgataac tactataatt atagtgatta tagtaatatt gttatcatta attgctgttg    1860
gactgctctt atactgtaag gccagaagca caccagtcac actaagcaaa gatcaactga    1920
gtggtataaa taatattgca tttagtaaca atttgatct gctcaaactt gcaggcgatg     1980
tagaatcaaa tcctggaccc ggaggaaaga ccggtattgc agtcatgatt ggcctgatcg    2040
cctgcgtagg agcagttacc ctctctaact tccaagggaa ggtgatgatg acggtaaatg    2100
ctactgacgt cacagatgtc atcacgattc caacagctgc tggaaagaac ctatgcattg    2160
tcagagcaat ggatgtggga tacatgtgcg atgatactat cacttatgaa tgcccagtgc    2220
tgtcggctgg taatgatcca gaagacatcg actgttggtg cacaaagtca gcagtctacg    2280
tcaggtatgg aagatgcacc aagacacgcc actcaagacg cagtcggagg tcactgacag    2340
```

```
tgcagacaca cggagaaagc actctagcga acaagaaggg ggcttggatg acagcacca     2400 aggccacaag gtatttggta aaaacagaat catggatctt gaggaaccct ggatatgccc    2460
tggtggcagc cgtcattggt tggatgcttg ggagcaacac catgcagaga gttgtgtttg    2520
tcgtgctatt gcttttggtg gccccagctt acagctttaa ctgccttgga atgagcaaca    2580
gagacttctt ggaaggagtg tctggagcaa catgggtgga tttggttctc gaaggcgaca    2640
gctgcgtgac tatcatgtct aaggacaagc ctaccatcga tgtgaagatg atgaatatgg    2700
aggcggccaa cctggcagag gtccgcagtt attgctattt ggctaccgtc agcgatctct    2760
ccaccaaagc tgcgtgcccg gccatgggag aagctcacaa tgacaaacgt gctgacccag    2820
cttttgtgtg cagacaagga gtggtggaca ggggctgggg caacggctgc ggactatttg    2880
gcaaaggaag cattgacaca tgcgccaaat ttgcctgctc taccaaggca ataggaagaa    2940
ccattttgaa agagaatatc aagtacgaag tggccatttt tgtccatgga ccaactactg    3000
tggagtcgca cggaaactac tccacacagg ttggagccac tcaggcaggg agattcagca    3060
tcactcctgc ggcgccttca tacacactaa agcttggaga atatggagag gtgacagtgg    3120
actgtgaacc acggtcaggg attgacacca atgcatacta cgtgatgact gttggaacaa    3180
agacgttctt ggtccatcgt gagtggttca tggacctcaa cctcccttgg agcagtgctg    3240
gaagtactgt gtggaggaac agagagacgt taatggagtt tgaggaacca cacgccacga    3300
agcagtctgt gatagcattg ggctcacaag agggagctct gcatcaagct ttggctggag    3360
ccattcctgt ggaattttca agcaacactg tcaagttgac gtcgggtcat ttgaagtgta    3420
gagtgaagat ggaaaaattg cagttgaagg gaacaaccta tggcgtctgt tcaaaggctt    3480
tcaagtttct tgggactccc gcagacacag tcacggcac tgtggtgttg gaattgcagt    3540
acactggcac ggatgggcct tgcaaagttc ctatctcgtc agtggcttca ttgaacgacc    3600
taacgccagt gggcagattg gtcactgtca acccttttgt ttcagtggcc acggccaacg    3660
ctaaggtcct gattgaattg gaaccaccct ttggagactc atacatagtg gtgggcagag    3720
gagaacaaca gatcaatcac cactggcaca gtctggaag cagcattggc aaagccttta    3780
caaccaccct caaaggagcg cagagactag ccgtctagg agacacagct gggactttg    3840 gatcagttgg aggggtgttc acctcagttg gaaggctgt ccatcaagtg ttcggaggag    3900
cattccgctc actgttcgga ggcatgtcct ggataacgca aggattgctg ggggctctcc    3960
tgttgtggat gggcatcaat gctcgtgaca ggtccatagc tctcacgttt ctcgcagttg    4020
gaggagttct gctcttcctc tccgtgaacg tgcacgctga cactgggtgt gccatagaca    4080
tcagccggca agagctgaga                                                4100

<210> SEQ ID NO 78
<211> LENGTH: 4100
<212> TYPE: DNA
<213> ORGANISM: Artificial Sequence
<220> FEATURE:
<223> OTHER INFORMATION: Synthetic Construct

<400> SEQUENCE: 78
ctaggattat gctgagtgat atctcatcaa gcggacacac tcgactgttt gaatcatcac      60
aaacactcct aattgttgtt aattgtgtca cgctcgacaa agaatcgtgc ttctagagct     120
acagattctt tggtcctccc gggccgttct cggcccgaca gttatacgat tttgcgcctt     180
acggggcgca caacaggaac taacctgaat tcgtttctt cgctccccg ctcaacgatt      240 aggagtttcg tttacgttaa tggtgttagg agtgacgtca gtgtaaaaca aaacgaagac     300
```

```
cagttttgta gtgacttctt aaaatagtta gttgtacgtc acgtcaatcg tttccgatag    360
aatcacgaga ctcttgacca accatatggt cacaatattg atatcttaat tcattatagt    420 tcctttttatt cacattacct tgtctacgat tccattttaa ctattttgtt cttaatctat    480
ttatattttt acgacattgt cttaacgtca acgagtacgt ttcgtgtggt ggttgtttgt    540
tagctcggtc ttctcttgat ggttccaaat acttaatatg tgagttgtta cggttttttt    600
ggttacattg taattcgttc ttttcctttt cttctaaaga accaaaaaac aatccacaac    660
ctagacgtta gcggtcaccg caacgacata gattccagga cgtggatctt ccccttcact    720
tgttctagtt ttcacgagat gataggtgtt gttccgaca tcagtcgaat agtttacctc    780
aatcacagaa ttggtcgttt cacaatctgg agtttttgat atatctattt gttaacaatg    840
gataacactt gttcgtttcg acgtcgtata gtttatatct ttgacactat ctcaaggttg    900
ttttcttgtt gtctgatgat ctctaatggt cccttaaatc acaattacgt ccacattgat    960
gtggacattc gtgaatgtac aattgattat cacttaataa cagtaattag ttactatacg   1020
gatattgttt actagtctttt tcaattaca ggttgttaca agtttatcaa tctgtcgttt   1080
caatgagata gtacaggtat tattttctcc ttcagaatcg tatacatcat gttaatggtg   1140
atataccaca atatctatgt gggacaacct ttgatgtgtg taggggagat acatgttggt   1200
tgtgttttct tcccaggttg tagacaaatt gttcttgact gtctcctacc atgacactgt   1260
tacgtcctag tcatagaaag aagggtgttc gactttgtac atttcaagtt agtttagctc   1320
ataaaacact gtgttacttg tcaaattgta atggttcact ttatttagag acgttacaac   1380
tgtataagtt ggggttttata ctaacatttt aatactgaag tttttgtcta cattcgtcga   1440
ggcaatagtg tagagatcct cggtaacaca gtacgatacc gttttgattt acatgtcgta   1500 ggttatttttt agcaccttag tatttctgta aaagattgcc cacgctaata catagtttat   1560
ttccctacct gtgacacaga catccattgt gtaatataat acatttattc gttcttccat   1620
tttcagagat acattttcca cttggttatt atttaaagat actgggtaat cataagggga   1680
gactacttaa actacgtagt tatagagttc agttgctctt ctaattggtc tcggatcgta   1740
aataagcatt taggctactt aataatgtat tacatttacg accatttagg tggtgtttat   1800
agtactattg atgatattaa tatcactaat atcattataa caatagtaat taacgacaac   1860
ctgacgagaa tatgacattc cggtcttcgt gtggtcagtg tgattcgttt ctagttgact   1920
caccatattt attataacgt aaatcattgt taaaactaga cgagtttgaa cgtccgctac   1980
atcttagttt aggacctggg cctccttcct ggccataacg tcagtactaa ccggactagc   2040
ggacgcatcc tcgtcaatgg gagagattga aggttcccctt ccactactac tgccatttac   2100
gatgactgca gtgtctacag tagtgctaag gttgtcgacg accttctctg gatacgtaac   2160
agtctcgtta cctacaccct atgtacacgc tactatgata gtgaatactt acgggtcacg   2220
acagccgacc attactaggt cttctgtagc tgacaaccac gtgtttcagt cgtcagatgc   2280
agtccatacc ttctacgtgg ttctgtgcgg tgagttctgc gtcagcctcc agtgactgtc   2340
acgtctgtgt gcctctttcg tgagatcgct tgttcttccc ccgaacctac ctgtcgtggt   2400
tccggtgttc cataaaccat ttttgtctta gtacctagaa ctccttggga cctatacggg   2460
accaccgtcg gcagtaacca acctacgaac cctcgttgtg gtacgtctct caacacaaac   2520
agcacgataa cgaaaaccac cggggtcgaa tgtcgaaatt gacggaacct tactcgttgt   2580
ctctgaagaa ccttcctcac agacctcgtt gtacccacct aaaccaagag cttccgctgt   2640
cgacgcactg atagtacaga ttcctgttcg gatggtagct acacttctac tacttatacc   2700
```

```
tccgccggtt ggaccgtctc caggcgtcaa taacgataaa ccgatggcag tcgctagaga    2760
ggtggtttcg acgcacgggc cggtaccctc ttcgagtgtt actgtttgca cgactgggtc    2820
gaaaacacac gtctgttcct caccacctgt ccccgacccc gttgccgacg cctgataaac    2880
cgtttccttc gtaactgtgt acgcggttta aacggacgag atggttccgt tatccttctt    2940
ggtaaaactt tctcttatag ttcatgcttc accggtaaaa acaggtacct ggttgatgac    3000
acctcagcgt gcctttgatg aggtgtgtcc aacctcggtg agtccgtccc tctaagtcgt    3060
agtgaggacg ccgcggaagt atgtgtgatt tcgaacctct tatacctctc cactgtcacc    3120
tgacacttgg tgccagtccc taactgtggt tacgtatgat gcactactga caaccttgtt    3180
tctgcaagaa ccaggtagca ctcaccaagt acctggagtt ggagggaacc tcgtcacgac    3240
cttcatgaca cacctccttg tctctctgca attacctcaa actccttggt gtgcggtgct    3300
tcgtcagaca ctatcgtaac ccgagtgttc tccctcgaga cgtagttcga aaccgacctc    3360
ggtaaggaca ccttaaaagt tcgttgtgac agttcaactg cagcccagta aacttcacat    3420
ctcacttcta ccttttttaac gtcaacttcc cttgttggat accgcagaca agtttccgaa    3480
agttcaaaga accctgaggg cgtctgtgtc cagtgccgtg acaccacaac cttaacgtca    3540
tgtgaccgtg cctacctgga acgtttcaag gatagagcag tcaccgaagt aacttgctgg    3600
attgcggtca cccgtctaac cagtgacagt tgggaaaaca aagtcaccgg tgccggttgc    3660
gattccagga ctaacttaac cttggtggga aacctctgag tatgtatcac cacccgtctc    3720
ctcttgttgt ctagttagtg gtgaccgtgt tcagaccttc gtcgtaaccg tttcggaaat    3780
gttggtggga gtttcctcgc gtctctgatc ggcgagatcc tctgtgtcga accctgaaac    3840
ctagtcaacc tccccacaag tggagtcaac ccttccgaca ggtagttcac aagcctcctc    3900
gtaaggcgag tgacaagcct ccgtacagga cctattgcgt tcctaacgac ccccgagagg    3960
acaacaccta cccgtagtta cgagcactgt ccaggtatcg agagtgcaaa gagcgtcaac    4020
ctcctcaaga cgagaaggag aggcacttgc acgtgcgact gtgacccaca cggtatctgt    4080
agtcggccgt tctcgactct                                                 4100
```

What is claimed is:

1. A replication-deficient pseudoinfectious flavivirus comprising (i) a flavivirus genome comprising sequences encoding West Nile virus capsid and non-structural proteins and tick-borne encephalitis virus pre-membrane and envelope sequences, and (ii) a capsid/pre-membrane signal sequence of tick-borne encephalitis virus, wherein the sequences encoding the West Nile virus capsid protein comprises one or more deletions or mutations.

2. The replication-deficient pseudoinfectious flavivirus of claim 1, further comprising a capsid protein provided in trans.

3. The replication-deficient pseudoinfectious flavivirus of claim 2, wherein the capsid protein is a West Nile virus capsid protein.

4. The replication-deficient pseudoinfectious flavivirus of claim 2, wherein the capsid protein is produced in a packaging cell line.

5. The replication-deficient pseudoinfectious flavivirus of claim 1, wherein the capsid protein is encoded on a second flavivirus genome comprising one or more deletions or mutations.

6. The replication-deficient pseudoinfectious flavivirus of claim 1, wherein said tick-borne encephalitis virus is the Hypr strain.

7. A pharmaceutical composition comprising the replication-deficient pseudoinfectious flavivirus of claim 1.

* * * * *